United States Patent
Visnick et al.

(10) Patent No.: US 12,060,340 B2
(45) Date of Patent: Aug. 13, 2024

(54) CYSTEINE-DEPENDENT INVERSE AGONISTS OF NUCLEAR RECEPTORS ROR-GAMMA/ROR-GAMMA-T AND METHODS OF TREATING DISEASES OR DISORDERS THEREWITH

(71) Applicant: REATA PHARMACEUTICALS, INC., Irving, TX (US)

(72) Inventors: Melean Visnick, Irving, TX (US); Xin Jiang, Coppell, TX (US)

(73) Assignee: REATA PHARMACEUTICALS, INC, Irving, TX (US)

( * ) Notice: Subject to any disclaimer, the term of this patent is extended or adjusted under 35 U.S.C. 154(b) by 354 days.

(21) Appl. No.: 17/252,841

(22) PCT Filed: Jun. 20, 2019

(86) PCT No.: PCT/US2019/038337
§ 371 (c)(1),
(2) Date: Dec. 16, 2020

(87) PCT Pub. No.: WO2019/246461
PCT Pub. Date: Dec. 26, 2019

(65) Prior Publication Data
US 2021/0147380 A1     May 20, 2021

Related U.S. Application Data

(60) Provisional application No. 62/687,782, filed on Jun. 20, 2018.

(51) Int. Cl.
*C07D 401/04* (2006.01)
*C07D 403/04* (2006.01)

(52) U.S. Cl.
CPC ......... *C07D 401/04* (2013.01); *C07D 403/04* (2013.01)

(58) Field of Classification Search
CPC .. C07D 239/70; C07D 239/72; C07D 403/04; A61K 31/517
See application file for complete search history.

(56) References Cited

U.S. PATENT DOCUMENTS

| | | | |
|---|---|---|---|
| 4,395,423 A | 7/1983 | Neumann | |
| 5,064,823 A | 11/1991 | Lee et al. | |
| 6,326,507 B1 | 12/2001 | Gribble et al. | |
| 6,369,101 B1 | 4/2002 | Carlson et al. | |
| 6,503,913 B1 | 1/2003 | Goldmann et al. | |
| 6,552,075 B2 | 4/2003 | Gribble et al. | |
| 6,642,217 B2 | 11/2003 | Krasutsky et al. | |
| 6,649,654 B1 | 11/2003 | Karin et al. | |
| 6,951,847 B2 | 10/2005 | Gibson et al. | |
| 6,974,801 B2 | 12/2005 | Honda et al. | |
| 7,053,119 B2 | 5/2006 | Karin et al. | |
| 7,144,875 B2 | 12/2006 | Gibson et al. | |
| 7,176,237 B2 | 2/2007 | Honda et al. | |
| 7,288,568 B2 | 10/2007 | Gribble et al. | |
| 7,399,606 B2 | 7/2008 | Karin et al. | |
| 7,410,958 B2 | 8/2008 | Krasutsky et al. | |
| 7,435,755 B2 | 10/2008 | Konopleva et al. | |
| 7,678,830 B2 | 3/2010 | Honda et al. | |
| 7,714,012 B2 | 5/2010 | Honda et al. | |
| 7,795,305 B2 | 9/2010 | Konopleva et al. | |
| 7,863,327 B2 | 1/2011 | Gribble et al. | |
| 7,915,402 B2 | 3/2011 | Anderson et al. | |
| 7,943,778 B2 | 5/2011 | Jiang et al. | |
| 8,034,955 B2 | 10/2011 | Gribble et al. | |
| 8,067,394 B2 | 11/2011 | Honda et al. | |
| 8,067,465 B2 | 11/2011 | Honda et al. | |
| 8,071,632 B2 | 12/2011 | Jiang et al. | |
| 8,088,824 B2 | 1/2012 | Walling et al. | |
| 8,124,656 B2 | 2/2012 | Anderson et al. | |
| 8,124,799 B2 | 2/2012 | Anderson et al. | |
| 8,129,429 B2 | 3/2012 | Sporn et al. | |
| 8,258,329 B2 | 9/2012 | Anderson et al. | |
| 8,299,046 B2 | 10/2012 | Sporn et al. | |
| 8,309,601 B2 | 11/2012 | Walling et al. | |
| 8,314,137 B2 | 11/2012 | Honda et al. | |

(Continued)

FOREIGN PATENT DOCUMENTS

| CN | 101298466 | 11/2008 |
|---|---|---|
| CN | 103665087 | 3/2014 |

(Continued)

OTHER PUBLICATIONS

Simone, Oncology: Introduction, Cecil Textbook of Medicine, 20th Edition, vol. 1, pp. 1004-1010, 1996.*
Acute Leukemia, Merck Manual (Online Edition) 6 pages, pp. 1-6 (2013).*
Pearce et al., Failure modes in anticancer drug discovery and development, Cancer Drug Design and Discovery Edited by Stephen Neidle, Chapter 18, pp. 424-435 (2008).*
Gura et al., Systems for identifying new drugs are often faulty, Science, 278:1041-1042, 1997.*
Johnson et al., Relationships between drug activity in NCI preclinical in vitro and in vivo models and early clinical trials, British Journal of Cancer, 84(10):1424-1431, 2001.*
Damasio, Alzheimer's Disease and related dementias, Cecil Textbook of Medicine, 20th Edition, vol. 2, pp. 1992-1996, 1996.*

(Continued)

*Primary Examiner* — Deepak R Rao
(74) *Attorney, Agent, or Firm* — Parker Highlander PLLC

(57) ABSTRACT

Provided herein are compounds, compositions and methods for treating and preventing diseases and disorders, comprising administering to patients therapeutically effective amounts of cysteine-dependent inverse agonists of the nuclear receptor RORγ/RORγt. In some such embodiments, the inverse agonists bind to cysteine 476 of a nuclear receptor RORγ in the patient. Also provided are methods, as well as compounds and compositions, for modulating the activity of RORγ and RORγt by binding to the allosteric binding site through a covalent bond. In some aspects, the present disclosure relates to using compounds containing Michael acceptor groups which bind to a cysteine residue in the allosteric binding site such as cysteine 476 in RORγ.

20 Claims, 4 Drawing Sheets

Specification includes a Sequence Listing.

(56) References Cited

U.S. PATENT DOCUMENTS

| | | |
|---|---|---|
| 8,338,618 B2 | 12/2012 | Jiang et al. |
| 8,394,967 B2 | 3/2013 | Jiang et al. |
| 8,440,820 B2 | 5/2013 | Anderson et al. |
| 8,440,854 B2 | 5/2013 | Anderson et al. |
| 8,455,544 B2 | 6/2013 | Sporn et al. |
| 8,513,436 B2 | 8/2013 | Anderson et al. |
| 8,586,775 B2 | 11/2013 | Gribble et al. |
| RE45,288 E | 12/2014 | Anderson et al. |
| 8,921,340 B2 | 12/2014 | Sporn et al. |
| 8,921,419 B2 | 12/2014 | Gribble et al. |
| RE45,325 E | 1/2015 | Anderson et al. |
| 8,993,640 B2 | 3/2015 | Anderson et al. |
| 9,000,188 B2 | 4/2015 | Honda et al. |
| 9,090,574 B2 | 7/2015 | Anderson et al. |
| 9,102,681 B2 | 8/2015 | Anderson et al. |
| 9,174,941 B2 | 11/2015 | Anderson et al. |
| 9,233,998 B2 | 1/2016 | Anderson et al. |
| 9,249,089 B2 | 2/2016 | Jiang et al. |
| 9,278,912 B2 | 3/2016 | Jiang et al. |
| 9,278,913 B2 | 3/2016 | Gribble et al. |
| 9,290,536 B2 | 3/2016 | Anderson et al. |
| 9,464,082 B2 | 10/2016 | Donner et al. |
| 9,512,094 B2 | 12/2016 | Jiang et al. |
| 9,556,222 B2 | 1/2017 | Anderson et al. |
| 9,593,074 B2 | 3/2017 | Bender et al. |
| 9,670,147 B2 | 6/2017 | Anderson et al. |
| 9,701,709 B2 | 7/2017 | Anderson et al. |
| 9,757,359 B2 | 9/2017 | Sporn et al. |
| 9,796,668 B2 | 10/2017 | Anderson et al. |
| 9,856,286 B2 | 1/2018 | Sheikh et al. |
| 9,884,809 B2 | 2/2018 | Anderson et al. |
| 9,889,143 B2 | 2/2018 | Jiang et al. |
| 10,093,614 B2 | 10/2018 | Anderson et al. |
| 10,105,372 B2 | 10/2018 | Meyer et al. |
| 10,398,711 B2 | 9/2019 | Jiang et al. |
| 10,501,489 B2 | 12/2019 | Bender et al. |
| 10,556,858 B2 | 2/2020 | Anderson et al. |
| 11,292,781 B2 * | 4/2022 | Jiang ............ C07D 413/14 |
| 2002/0042535 A1 | 4/2002 | Gribble et al. |
| 2002/0115856 A1 | 8/2002 | Sakya |
| 2003/0119732 A1 | 1/2003 | Konopleva et al. |
| 2003/0125361 A1 | 7/2003 | Clare et al. |
| 2003/0232786 A1 | 12/2003 | Honda et al. |
| 2003/0236303 A1 | 12/2003 | Gribble et al. |
| 2004/0002463 A1 | 1/2004 | Honda et al. |
| 2004/0097436 A1 | 5/2004 | Krasutsky et al. |
| 2005/0208151 A1 | 9/2005 | Hurez et al. |
| 2005/0288363 A1 | 12/2005 | Gribble et al. |
| 2006/0258752 A1 | 11/2006 | Vander Jagt et al. |
| 2007/0155742 A1 | 7/2007 | Honda et al. |
| 2007/0232577 A1 | 10/2007 | Xu et al. |
| 2007/0244081 A1 | 10/2007 | Krasutsky et al. |
| 2007/0249561 A1 | 10/2007 | Taylor |
| 2007/0259839 A1 | 11/2007 | Krasutsky et al. |
| 2007/0259842 A1 | 11/2007 | Krasutsky et al. |
| 2008/0220057 A1 | 9/2008 | Gribble et al. |
| 2008/0233195 A1 | 9/2008 | Sporn et al. |
| 2008/0261985 A1 | 10/2008 | Honda et al. |
| 2009/0048204 A1 | 2/2009 | Walling et al. |
| 2009/0048205 A1 | 2/2009 | Meyer et al. |
| 2009/0060873 A1 | 3/2009 | Sporn et al. |
| 2009/0093447 A1 | 4/2009 | Konopleva et al. |
| 2009/0270364 A1 | 10/2009 | Liu et al. |
| 2009/0326063 A1 | 12/2009 | Sporn et al. |
| 2010/0041904 A1 | 2/2010 | Jiang et al. |
| 2010/0048887 A1 | 2/2010 | Anderson et al. |
| 2010/0048892 A1 | 2/2010 | Anderson et al. |
| 2010/0048911 A1 | 2/2010 | Jiang et al. |
| 2010/0056777 A1 | 3/2010 | Anderson et al. |
| 2010/0261930 A1 | 10/2010 | Honda et al. |
| 2011/0009363 A1 | 1/2011 | Honda et al. |
| 2011/0196007 A1 | 8/2011 | Honda et al. |
| 2011/0245206 A1 | 10/2011 | Jiang et al. |
| 2011/0245233 A1 | 10/2011 | Anderson et al. |
| 2011/0281955 A1 | 11/2011 | Meyer et al. |
| 2012/0022156 A1 | 1/2012 | Zhang et al. |
| 2012/0071684 A1 | 3/2012 | Walling et al. |
| 2012/0101149 A1 | 4/2012 | Honda et al. |
| 2012/0196880 A1 | 8/2012 | Anderson et al. |
| 2012/0214814 A1 | 8/2012 | Anderson et al. |
| 2012/0220652 A1 | 8/2012 | Sporn et al. |
| 2012/0238767 A1 | 9/2012 | Jiang et al. |
| 2012/0245374 A1 | 9/2012 | Anderson et al. |
| 2012/0252776 A1 | 10/2012 | Anderson et al. |
| 2012/0283450 A1 | 11/2012 | Anderson et al. |
| 2012/0330050 A1 | 12/2012 | Walling et al. |
| 2013/0089526 A1 | 4/2013 | Sporn et al. |
| 2013/0122053 A1 | 5/2013 | Sporn et al. |
| 2013/0237721 A1 | 9/2013 | Gribble et al. |
| 2013/0274480 A1 | 10/2013 | Honda et al. |
| 2013/0303607 A1 | 11/2013 | Gribble et al. |
| 2013/0317007 A1 | 11/2013 | Anderson et al. |
| 2013/0324599 A1 | 12/2013 | Anderson et al. |
| 2013/0345276 A1 | 12/2013 | Sporn et al. |
| 2014/0051739 A1 | 2/2014 | Anderson et al. |
| 2014/0066408 A1 | 3/2014 | Jiang et al. |
| 2014/0073700 A1 | 3/2014 | Wagner et al. |
| 2014/0088163 A1 | 3/2014 | Jiang et al. |
| 2014/0088188 A1 | 3/2014 | Jiang et al. |
| 2014/0100227 A1 | 4/2014 | Bender et al. |
| 2014/0179928 A1 | 6/2014 | Anderson et al. |
| 2014/0275618 A1 | 9/2014 | Gribble et al. |
| 2014/0323579 A1 | 10/2014 | Sheikh et al. |
| 2014/0377235 A1 | 12/2014 | Sporn et al. |
| 2015/0080465 A1 | 3/2015 | Chin et al. |
| 2015/0148384 A1 | 5/2015 | Anderson et al. |
| 2015/0152071 A1 | 6/2015 | Jiang et al. |
| 2015/0225397 A1 | 8/2015 | Donner et al. |
| 2015/0259377 A1 | 9/2015 | Anderson et al. |
| 2015/0376121 A1 | 12/2015 | Anderson et al. |
| 2016/0130220 A1 | 5/2016 | Anderson et al. |
| 2016/0145200 A1 | 5/2016 | Anderson et al. |
| 2017/0165278 A1 | 6/2017 | Jiang et al. |
| 2017/0260227 A1 | 9/2017 | Bender et al. |
| 2018/0002277 A1 | 1/2018 | Anderson et al. |
| 2018/0009839 A1 | 1/2018 | Anderson et al. |
| 2018/0111931 A1 | 4/2018 | Barlaam et al. |
| 2018/0127380 A1 | 5/2018 | Jiang et al. |
| 2018/0161311 A1 | 6/2018 | Sporn et al. |
| 2018/0170908 A1 | 6/2018 | Aspnes et al. |
| 2018/0170931 A1 | 6/2018 | Koudriakova et al. |
| 2018/0235981 A1 | 8/2018 | Jiang et al. |
| 2018/0237383 A1 | 8/2018 | Anderson et al. |
| 2019/0153022 A1 | 5/2019 | Visnick et al. |
| 2019/0322665 A1 | 10/2019 | Bacani et al. |
| 2019/0350941 A1 | 11/2019 | Meyer |
| 2020/0077658 A1 | 3/2020 | Sambasivan et al. |
| 2020/0131148 A1 | 4/2020 | Jiang et al. |
| 2021/0040142 A1 | 2/2021 | Jiang et al. |

FOREIGN PATENT DOCUMENTS

| | | |
|---|---|---|
| CN | 104861027 | 8/2015 |
| EP | 2787002 | 10/2014 |
| JP | 2005-314381 | 11/2005 |
| WO | WO 1999/065478 | 12/1999 |
| WO | WO 2000/073253 | 12/2000 |
| WO | WO 2002/003996 | 1/2002 |
| WO | WO 2002/026761 | 4/2002 |
| WO | WO 2002/026762 | 4/2002 |
| WO | WO 2002/032410 | 4/2002 |
| WO | WO 2002/047611 | 6/2002 |
| WO | WO 2003/059339 | 7/2003 |
| WO | WO 2003/062260 | 7/2003 |
| WO | WO 2004/064723 | 8/2004 |
| WO | WO 2004/089357 | 10/2004 |
| WO | WO 2005/042002 | 5/2005 |
| WO | WO 2005/046732 | 5/2005 |
| WO | WO 2006/029221 | 3/2006 |
| WO | WO 2002/092768 | 6/2006 |
| WO | WO 2006/089406 | 8/2006 |
| WO | WO 2007/005879 | 1/2007 |
| WO | WO 2007/112043 | 10/2007 |
| WO | WO 2007/127791 | 11/2007 |

(56) References Cited

FOREIGN PATENT DOCUMENTS

| WO | WO 2008/000068 | 1/2008 |
|---|---|---|
| WO | WO 2008/000070 | 1/2008 |
| WO | WO 2008/016095 | 2/2008 |
| WO | WO 2008/064132 | 5/2008 |
| WO | WO 2008/064133 | 5/2008 |
| WO | WO 2008/097596 | 8/2008 |
| WO | WO 2008/111497 | 9/2008 |
| WO | WO 2008/136838 | 11/2008 |
| WO | WO 2009/023232 | 2/2009 |
| WO | WO 2009/023845 | 2/2009 |
| WO | WO 2009/058849 | 5/2009 |
| WO | WO 2009/089545 | 7/2009 |
| WO | WO 2009/129545 | 10/2009 |
| WO | WO 2009/129546 | 10/2009 |
| WO | WO 2009/129548 | 10/2009 |
| WO | WO 2009/146216 | 12/2009 |
| WO | WO 2009/146218 | 12/2009 |
| WO | WO 2010/011782 | 1/2010 |
| WO | WO 2010/053817 | 5/2010 |
| WO | WO 2010/093944 | 8/2010 |
| WO | WO 2011/130302 | 10/2011 |
| WO | WO 2012/083306 | 6/2012 |
| WO | WO 2012/096718 | 7/2012 |
| WO | WO 2012/106190 | 8/2012 |
| WO | WO 2012/125488 | 9/2012 |
| WO | WO 2013/163344 | 10/2013 |
| WO | WO 2013/169740 | 11/2013 |
| WO | WO 2013/188818 | 12/2013 |
| WO | WO 2014/040052 | 3/2014 |
| WO | WO 2014/040056 | 3/2014 |
| WO | WO 2014/040060 | 3/2014 |
| WO | WO 2014/040073 | 3/2014 |
| WO | WO 2014/176415 | 10/2014 |
| WO | WO 2015/027206 | 2/2015 |
| WO | WO 2015/112792 | 7/2015 |
| WO | WO 2016/033132 | 3/2016 |
| WO | WO 2016/130927 | 8/2016 |
| WO | WO 2017/053868 | 3/2017 |
| WO | WO 2018/089539 | 5/2018 |
| WO | WO 2018/111315 | 6/2018 |
| WO | WO 2021/016191 | 1/2021 |

OTHER PUBLICATIONS

Layzer, Degenerative diseases of the nervous system, Cecil Textbook of Medicine, 20th Edition, vol. 2, pp. 2050-2057, 1996.*
Douglas, Jr., Introduction to Viral Diseases, Cecil Textbook of Medicine, 20th Edition, vol. 2, pp. 1739-1747, 1996.*
Bosseray et al., PubMed Abstract (Pathol Biol (Paris) 50(8):483-92), 2002.*
Razonable et al., PubMed Abstract (Herpes 10(3):60-5), 2003.*
Goff, PubMed Abstract (J Gene Med. 3(6):517-28), 2001.*
"RTA 402, Therapeutic Properties I", slides/handouts presented by Reata Pharmaceuticals, Inc. at private partnering meetings at BioSquare 2006 conference, Mar. 8-10, 2006, Geneva, Switzerland.
"RTA 402, Therapeutic Properties II", slides/handouts presented by Reata Pharmaceuticals, Inc. at private partnering meetings at BIO 2006 conference, Apr. 9-12, 2006, Chicago, Illinois.
"RTA 402, Therapeutic Properties III", slides presented by Reata Pharmaceuticals, Inc. as a podium presentation at BIO 2006 conference, Apr. 9-12, 2006, Chicago, Illinois.
"RTA 402, Therapeutic Properties IV", slides/handouts presented by Reata Pharmaceuticals, Inc. at private partnering meetings at BioPartnering Europe 2006 conference, Oct. 8-10, 2006, London, England.
"RTA 402, Therapeutic Properties IX", slides/handouts presented by Reata Pharmaceuticals, Inc. at a private partnering meeting at BIO Europe 2007 conference, Nov. 12-14, 2007, Hamburg, Germany.
"RTA 402, Therapeutic Properties V", slides/handouts presented by Reata Pharmaceuticals, Inc. at private partnering meetings at BIO 2007 conference, May 6-9, 2007, Boston Massachusetts.
"RTA 402, Therapeutic Properties VI", slides/handouts presented by Reata Pharmaceuticals, Inc. at private partnering meetings at BIO 2007 conference, May 6-9, 2007, Boston, Massachusetts.

"RTA 402, Therapeutic Properties VII", slides presented by Reata Pharmaceuticals, Inc. as a podium presentation at BIO 2007 conference, May 6-9, 2007, Boston, Massachusetts.
"RTA 402, Therapeutic Properties VIII", slides/handouts presented by Reata Pharmaceuticals, Inc. at private partnering meetings at BIO Europe 2007 conference, Nov. 12-14, 2007, Hamburg, Germany.
Ahmad et al., "Triterpenoid CDDO-Me blocks the NF-kappaB pathway by direct inhibition of IKKbeta on Cys-179," J. Biol. Chem., 281:35764-35769, 2006.
Ahmad et al., "Triterpenoid CDDO-methyl ester inhibits the Janus-activated kinase-1 (JAK1)àsignal transducer and activator of transcription-3 (STAT3) pathway by direct inhibition of JAK1 and STAT3," Cancer Res., 68 (8): 2920-2926, 2008.
Akiyama et al., "Cell mediators of inflammation in the Alzheimer disease brain," Alzheimer Dis. Assoc. Disord., 14 (1): S47-S53, 2000.
Albini and Sporn, "Opinion: the tumour microenvironment as a target for chemoprevention," Nature Reviews Cancer, 7: 13-147, 2007.
Andreef et al., "PPARgamma nuclear resceptor as a novel molecular target in leukemias," 2002 Keystone Symposia, Abstract 501:149, 2002.
Andresen and Margaretha, "Preparation of dialkyl 2-cyanocycloalk-2-en-1-ones," J. Chem. Research (S), 1:332, 1994.
Auletta et al., "The synthetic triterpenoid, CDDO-Me, modulates the proinflammatory response to in vivo lipopolysaccharide challenge," J. Interferon Cytokine Res., 30(7):497-508, 2010.
Ballesta-Acosta et al., "A new 24-nor-oleanane triterpenoid from Salvia carduacea," J. Nat. Prod., 65(10): 1513-1515, 2002.
Banerjee et al., "JAK-STAT Signaling as a Target for Inflammatory and Autoimmune Diseases: Current and Future Prospects", *Drugs*, 77:521-546, 2017.
Bore et al., "The anti-inflammatory triterpenoid methyl 2-cyano-3,12-dioxoolean 1,9(11)-dien-28-oate methanol solvate hydrate," Acta Crystallorg C., 58(Pt 3):0199-0200, 2002.
Bowden et al., "Constituents of the fruit of pseudopanax arboretum (Araliaceae)," Australian Journal of Chemistry, 28(1): 91-107, 1975.
Brookes et al., "The triterpenoid 2-cyano-3,12-dioxooleana-1,9-dien-28-oic acid and its derivatives elicit human lymphoid cell apoptosis through a novel pathway involving the unregulated mitochondrial permeability transition pore," Cancer Res., 67:1793-1802, 2007.
Buchanan et al., "The conversion of turraeanthin and turraeanthin A into simple melaiacins by a route involving an oxidative rearrangement of probable biogenetic importance," J Chem. Soc C, 17:2280-2284, 1970.
Caron and Deslongchamps, "Versatile Strategy to Access Tricycles Related to Quassinoids and Triterpenes," Org Lett., 12(3):508-511, 2010.
Chadalapaka et al., "Structure-dependent inhibition of bladder and pancreatic cancer cell growth by 2-substituted glycyrrhetinic and ursolic acid derivatives," Bioorganic & Medicinal Chemistry Letters, 18:2633-2639, 2008.
Chauhan et al., "The bortezomib/proteasome inhibitor PS-341 and triterpenoid CDDO-Im induce synergistic anti-multiple myeloma (MM) activity and overcome bortezomib resistance," Blood, 103:3158-3166, 2004.
Chen et al., "FOXP3 and RORγt: transcriptional regulation of Treg and Th17," Int. Immunopharmacol., 11(5):536-542, 2011.
Cheung et al., "Structures of Triterpenes from Dryobalanops Aromatica," Phytochemistry, 11:1771-1780, 1972.
Chintharlapalli et al., "2-Cyano-3,12-dioxoolean-1,9-dien-28-oic acid and related compounds inhibit growth of colon cancer cells through peroxisome proliferator-activated receptor gamma-dependent and -independent pathways," Mol. Pharmacol., 68:119-128, 2005.
Chintharlapalli et al., "2-Cyano-lup-1-en-3-oxo-20-oic acid, a cyano derivative of betulinic acid, activates peroxisome proliferator-activated receptor [gamma] in colon and pancreatic cancer cells.," Carcinogenesis, 28 (11): 2337-2346, 2007.

(56) References Cited

OTHER PUBLICATIONS

Chintharlapalli et al., "Structure-dependent activity of glycyrrhetinic acid derivatives as peroxisome proliferator-activated receptor {gamma} agonists in colon cancer cells," Molecular Cancer Therapeutics, 6 (5): 1588-1598, 2007.
Clinicaltrial.gov Study NCT00322140, "CDDO to Treat Solid Tumors and Lymphomas," and associated updates, first published May 5, 2006.
Clinicaltrial.gov Study NCT00508807, "RTA 402 in Advanced Solid Tumors or Lymphoid Malignancies," and associated updates, first published Jul. 30, 2007.
Clinicaltrial.gov Study NCT00529113, "Study With Gemcitabine and RTA 402 for Patients With Unresectable Pancreatic Cancer," and associated updates, first published Sep. 14, 2007.
Clinicaltrial.gov Study NCT00529438, "RTA 402 in Patients With Advanced Solid Tumors or Lymphoid Malignancies," and associated updates, first published Sep. 14, 2007.
Clinicaltrial.gov Study NCT00535314, "Study of Two Dose Levels of RTA 402 in Patients With Advanced Malignant Melanoma," and associated updates, first published Sep. 26, 2007.
Clinicaltrial.gov Study NCT00550849, "Study to Assess the Safety, Tolerability, and Pharmacodynamics of RTA 402 in Patients With Hepatic Dysfunction," and associated updates, first published Oct. 30, 2007.
Clinicaltrial.gov Study NCT00664027, "Phase IIa Trial to Determine the Effects of Bardoxolone Methyl on Renal Function in Patients With Diabetic Nephropathy," and associated updates, first published Apr. 22, 2008.
Clinicaltrial.gov Study NCT00811889, "Trial to Determine the Effects of Bardoxolone Methyl on eGFR in Patients With Type 2 Diabetes and Chronic Kidney Disease," and associated updates, first published Dec. 19, 2008.
Clinicaltrial.gov Study NCT01053936, "Phase II Pharmacodynamic Trial to Determine the Effects of Bardoxolone Methyl on eGFR in Patients With Type 2 Diabetes and Chronic Kidney Disease," and associated updates, first published Jan. 22, 2010.
Clinicaltrial.gov Study NCT01351675, "Bardoxolone Methyl Evaluation in Patients With Chronic Kidney Disease and Type 2 Diabetes," and associated updates, first published May 11, 2011.
Clinicaltrial.gov Study NCT01461161, "A Single-Dose, Open-Label, Randomized, Food Effect and Blinded, Randomized, Dose Proportionality Study in Healthy Volunteers With Bardoxolone Methyl," and associated updates, first published Oct. 27, 2011.
Clinicaltrial.gov Study NCT01500798, "A Pharmacodynamic Study of Measured Glomerular Filtration Rate in Patients With Chronic Kidney Disease and Type 2 Diabetes," and associated updates, first published Dec. 28, 2011.
Clinicaltrial.gov Study NCT01503866, "A Phase I Study to Investigate the Absorption, Metabolism and Excretion in Healthy Male Subjects," and associated updates, first published Jan. 4, 2012.
Clinicaltrial.gov Study NCT01549769, "Pharmacokinetic and Pharmacodynamic Study of Bardoxolone Methyl in Patients With Chronic Kidney Disease and Type 2 Diabetes," and associated updates, first published Mar. 9, 2012.
Clinicaltrial.gov Study NCT01551446, "Pilot Assessment of the Effects of Bardoxolone Methyl on Renal Perfusion, Systemic Haemodynamics and Cardiac Function in Patients With Chronic Kidney Disease and Type 2 Diabetes," and associated updates, first published Mar. 12, 2012.
Clinicaltrial.gov Study NCT01563562, "Single-Dose, Open-Label Pharmacokinetic Study of Bardoxolone Methyl in Subjects With Mild, Moderate, and Severe Hepatic Impairment and Normal Hepatic Function," and associated updates, first published Mar. 27, 2012.
Clinicaltrial.gov Study NCT01572610, "A Glomerular Filtration Rate (GFR) Measuring Study of RTA 402 in Chronic Kidney Disease (CKD) Patients With Type 2 Diabetes Mellitus," and associated updates, first published Apr. 6, 2012.
Clinicaltrial.gov Study NCT01574365, "A Study of RTA 402 in Chronic Kidney Disease (CKD) Patients With Type 2 Diabetes Mellitus," and associated updates, first published Apr. 10, 2012.
Clinicaltrial.gov Study NCT01576887, "A Double-Blind, Randomized, Placebo-Controlled Safety Study Evaluating the Effects of Residual Renal Function (RFF) in Patients With End-Stage Renal Disease and Type 2 Diabetes Mellitus on Peritoneal Dialysis," and associated updates, first published Apr. 13, 2012.
Clinicaltrial.gov Study NCT01598363, "An Open-Label Study of the Effect of Bardoxolone Methyl on the Single Dose Pharmacokinetics of Digoxin and Rosuvastatin in Healthy Volunteers," and associated updates, first published May 15, 2012.
Clinicaltrial.gov Study NCT01655186, "A Double-Blind, Randomized, Placebo-Controlled Study Evaluating the Effects of Bardoxolone Methyl on Body Composition in Patients With Stage 4 Chronic Kidney Disease and Type 2 Diabetes Mellitus," and associated updates, first published Aug. 1, 2012.
Clinicaltrial.gov Study NCT01689116, "Multiple-Dose Study of Effect of Bardoxolone Methyl on QT/QTC Interval Volunteers," and associated updates, first published Sep. 21, 2012.
Clinicaltrial.gov Study NCT02029716, "RTA 408 Lotion in Healthy Volunteers," and associated updates, first published Jan. 8, 2014.
Clinicaltrial.gov Study NCT02029729, "RTA 408 in the Treatment of Advanced Solid Tumors (NSCLC & Melanoma)—DISCOVER," and associated updates, first published Jan. 8, 2014.
Clinicaltrial.gov Study NCT02036970, "Bardoxolone Methyl Evaluation in Patients With Pulmonary Hypertension (PH)—LARIAT," and associated updates, first published Jan. 15, 2014.
Clinicaltrial.gov Study NCT02065375, "RTA 408 Ophthalmic Suspension for the Treatment of Ocular Inflammation and Pain Following Ocular Surgery," and associated updates, first published Feb. 19, 2014.
Clinicaltrial.gov Study NCT02128113, "RTA 408 Ophthalmic Suspension for the Prevention of Corneal Endothelial Cell Loss Following Cataract Surgery—GUARD," and associated updates, first published May 1, 2014.
Clinicaltrial.gov Study NCT02142959, "RTA 408 Lotion in Patients at Risk for Radiation Dermatitis—PRIMROSE," and associated updates, first published May 20, 2014.
Clinicaltrial.gov Study NCT02255422, "RTA 408 Capsules in Patients With Mitochondrial Myopathy—MOTOR," and associated updates, first published Oct. 2, 2014.
Clinicaltrial.gov Study NCT02255435, "RTA 408 Capsules in Patients With Friedreich's Ataxia—MOXIe," and associated updates, first published Oct. 2, 2014.
Clinicaltrial.gov Study NCT02259231, "RTA 408 Capsules in Patients With Melanoma—REVEAL," and associated updates, first published Oct. 8, 2014.
Clinicaltrial.gov Study NCT02316821, "The Phase II Study of Bardoxolone Methyl in Patients With Chronic Kidney Disease and Type 2 Diabetes; TSUBAKI Study," and associated updates, first published Dec. 15, 2014.
Clinicaltrial.gov Study NCT02657356, "Bardoxolone Methyl in Patients With Connective Tissue Disease-associated Pulmonary Arterial Hypertension—CATALYST," and associated updates, first published Jan. 15, 2016.
Clinicaltrial.gov Study NCT03019185, "A Phase 2/3 Trial of the Efficacy and Safety of Bardoxolone Methyl in Patients With Alport Syndrome—CARDINAL," and associated updates, first published Jan. 12, 2017.
Clinicaltrial.gov Study NCT03068130, "Extended Access Program to Assess Long-term Safety of Bardoxolone Methyl in Patients With Pulmonary Hypertension RANGER," and associated updates, first published Mar. 1, 2017.
Clinicaltrial.gov Study NCT03264079, "Effect of Itraconazole on the Pharmacokinetics of Bardoxolone Methyl in Healthy Adults," and associated updates, first published Aug. 28, 2017.
Clinicaltrial.gov Study NCT03366337, "A Phase 2 Trial of the Safety and Efficacy of Bardoxolone Methyl in Patients With Rare Chronic Kidney Diseases—PHOENIX," and associated updates, first published Dec. 8, 2017.
Clinicaltrial.gov Study NCT03550443, "A Phase 3 Study of Bardoxolone Methyl in Patients With Diabetic Kidney Disease; AYAME Study," and associated updates, first published Jun. 8, 2018.

(56) References Cited

OTHER PUBLICATIONS

Clinicaltrial.gov Study NCT03579030, "Safety and PK/PD of RTA 1701 in Healthy Adults," and associated updates, first published Jul. 6, 2018.
Clinicaltrial.gov Study NCT03593499, "Expanded Access to Omaveloxolone for Melanoma for Patients Previously Enrolled in 408-C-1401," and associated updates, first published Jul. 20, 2018.
Clinicaltrial.gov Study NCT03664453, "A Pharmacokinetic Study of Omaveloxolone in Healthy Volunteers," and associated updates, first published Sep. 10, 2018.
Clinicaltrial.gov Study NCT03749447, "An Extended Access Program for Bardoxolone Methyl in Patients With CKD (EAGLE)," and associated updates, first published Nov. 21, 2018.
Clinicaltrial.gov Study NCT03902002, "A Pharmacokinetic Study of Omaveloxolone in Subjects With Hepatic Impairment and Normal Hepatic Function," and associated updates, first published Apr. 3, 2019.
Clinicaltrial.gov Study NCT03918447, "A Trial of Bardoxolone Methyl in Patients With ADPKD—FALCON," and associated updates, first published Apr. 17, 2019.
Clinicaltrial.gov Study NCT03931590, "A Human AME Study for Omaveloxolone," and associated updates, first published Apr. 30, 2019.
Clinicaltrial.gov Study NCT04008186, "A Clinical Drug-Drug Interaction (DDI) Study With Omaveloxolone," and associated updates, first published Jul. 4, 2019.
Clinicaltrial.gov Study NCT04018339, "A Study of RTA 402 in Obese Adults," and associated updates, first published Jul. 12, 2019.
Clinicaltrial.gov Study NCT04023903, "A Clinical Pharmacology Study of Bardoxolone Methyl in Healthy Adults," and associated updates, first published Jul. 18, 2019.
Clinicaltrial.gov Study NCT04494646, "BARCONA: A Study of Effects of Bardoxolone Methyl in Participants With SARS-Corona Virus-2 (COVID-19)," and associated updates, first published Jul. 31, 2020.
Clinicaltrial.gov Study NCT04702997, "A Trial of Bardoxolone Methyl in Patients With CKD at Risk of Rapid Progression (MERLIN)," and associated updates, first published Jan. 11, 2021.
Clinton et al., "Steroidal[3,2-c]pyrazoles. II. Androstanes, 19-norandrostanes and their unsaturated analogs," J. Am Chem Soc., 83:1478-1491, 1961.
Cohen et al., "A general method for removal of a 4-methyl group from triterpenoids. Synthesis of 4beta-demethylglycyrrhetinic acid," J Chem. Soc, Perkin Trans 1, (19): 2076-2082, 1973.
Connolly et al., "Grandiofoliene: a novel tetranortriterpenoid," Chemical Communications, 23:867-568, 1966.
Couch et al., "Studies on the reactivity of CDDO, a promising new chemopreventive and chemotherapeutic agent: implications for a molecular mechanism of action ," Bioorganic and Medicinal Chemistry Letters, 15 (9): 2215-2219, 2005.
Damsté et al., "A sedimentary tetrahydrophenanthrene derivative of tetrahymanol," Tetrahedron Letters, 40(20: 3949-3952, 1999.
De Mico et al., "A Versatile and Highly Selective Hypervalent Iodine (III)/2,2,6,6-Tetramethyl-1-piperidinyloxyl-Mediated Oxidation of Alcohols to Carbonyl Compounds," J. Org. Chem., 62: 6974, 1997.
De Ruggieri et al., "Deidrogenazione e bromurazione di beta-chetonitrili steroidali," Il Farmaco, 20: 358-388, 1964. (English summary).
Dean et al., "Halogenolysis of methyl glycyrrhetate with lithium iodidedimethylformamide," J. Chem. Soc., 6655-6659, 1965.
Deng and Snyder, "Preparation of a 24-Nor-1,4-dien-3-one triterpene derivative from betulin: a new route to 24-nortriterpene analogues," J. of Organic Chemistry, 67 (9): 2864-2873, 2002.
Dezube et al., "Interim results of a phase I trial with a novel orally administered synthetic triterpenoid RTA 402 (CDDO-Me) in patients with solid tumors and lymphoid malignancies," J. Clin. Oncol., 2007 ASCO Annual Meeting Proceedings, 25(18S):14101, 2007.

Dinkova-Kostova et al., "Direct evidence that sulfhydryl groups of Keap1 are the sensors regulating induction of phase 2 enzymes that protect against carcinogens and oxidants," Proc. Natl. Acad. Sci., 99(18): 11908-11913, 2002.
Dinkova-Kostova et al., "Extremely potent triterpenoid inducers of the phase 2 response: correlations of protection against oxidant and inflammatory stress," Proc. Natl. Acad. Sci., 102(12): 4584-4589, 2005.
Dirsch et al., "The triterpenoid quinonemethide pristimerin inhibits induction of inducible nitric oxide synthase in murine macrophages," Eur J Pharmacol., 336(2-3): 211-217, 1997.
Dracinsky et al., "Preparation and Conformational Study of 19β,28-Epoxy-18α-olean-5-ene Derivatives," Collection of Czechoslovak Chemical Communications, 71(3): 387-410, 2006.
Dragnev et al., "Specific chemopreventive agents trigger proteasomal degradation of G1 cyclins: implications for combination therapy," Clin. Cancer Research, 10 (7): 2570-2577, 2004.
Duan et al., "Di- and triterpenoids from Triptergium hypoglaucum," Phytochemistry, 46(3): 535-543, 1997.
Duan et al., "Immunosuppressive terpenoids from extracts of tripterygium wilfordii," Tetrahedron, 57 (40): 8413-8424, 2001.
Dulubova et al., "RTA 1701 is an orally-bioavailable, potent, and selective ROR65 t inhibitor that suppresses Th17 differentiation in vitro and is efficacious in mouse models of autoimmune disease," J. Immunol., 200(1 Suppl.):121.14, 2018.
Elliot et al., "The triterpenoid CDDO inhibits expression of matrix metalloproteinase-1, matrix metalloproteinase-13 and Bcl-3 in primary human chondrocytes," Arthritis Res. Ther., 5:R285-R291, 2003.
Elsawa et al., "Preferential Inhibition of Malignant Cell Growth by CDDO in Waldenstrom Macroglobulinemia," Blood, 108(11):2528, 2006.
Favaloro et al., "Design and synthesis of tricyclic compounds with enone functionalities in rings A and C: a novel class of highly active inhibitors of nitric oxide production in mouse macrophages," J. Med. Chem., 45:4801-4805, 2002.
Feehan and Gilroy, "Is Resolution the End of Inflammation?", Trends Mol. Med., 25(3): 198-214, 2019.
Ferreira et al., "Phytochemistry of the mopane, Colophosperum mopane," Phytochemistry, 64 (1): 31-51, 2003.
Finlay et al., "Novel A-ring cleaved analogs of oleanolic and ursolic acids which affect growth regulation in NRP.152 prostate cells," Biorg. Med. Chem. Lett., 7(13): 1769-1772, 1997.
Finlay et al., "The Effect of A and C Ring Modification of Oleanolic and Ursolic Acid on the Inhibition of Nitric Oxide Formation in Mouse Macrophages," 213th American Chemical Society National Meeting, Abstract: 084, 1997.
Fitzpatrick et al., "The synthetic triterpenoid (CDDO-Im) inhibits STAT3, as well as IL-17, and improves DSS-induced colitis in mice", Inflammopharmacology, 22:341-349, 2014.
Gaffen et al., "IL-23-IL-17 immune axis: discovery, mechanistic understanding, and clinical testing", Nat. Rev. Immunol., 14(9):585-600, 2014.
Gao et al., "Synthetic triterpenoids inhibit growth and induce apoptosis in human glioblastoma and neuroblastoma cells through inhibition of prosurvival Akt, NF-κB and Notch1 signaling," J. of Neuro-oncology, 84 (2): 147-157, 2007.
Grant et al., "Boron trifluoride catalyzed rearrangements of novel epoxide derivatives of manool and manoyl oxide," Australian Journal of Chemistry, 46 (8): 1125-1145, 1993.
Grieco and Speake, "Synthetic Studies on Quassinoids: Total Synthesis and Biological Evaluation of (+)-Des-D-chaparrinone," J. Org. Chem., 63:5929-5936, 1998.
Guix et al., "The physiology and pathophysiology of nitric oxide in the brain", Prog. Neurobiol., 76:126-152, 2005.
Hail et al., "Evidence supporting a role for calcium in apoptosis induction by the synthetic triterpenoid 2-cyano-3,12-dioxooleana-1,9-dien-28-oic acid (Cddo)," J. Biol. Chem., 279:11179-11187, 2004.
Han et al., "CDDO-Imidazolide inhibits growth and survival of c-Myc-induced mouse B cell and plasma cell neoplasms," Molecular Cancer, 5:22, 2006.

(56) References Cited

OTHER PUBLICATIONS

Hatcher et al., "Curcumin: from ancient medicine to current clinical trials," CMLS Cellular and Molecular Life Sciences, 65 (11): 1631-1652, 2008.
Hill et al., "Synthetical approaches to the pristimerin chromophore," J. of the Chemical Society, 361-375, 1965.
Hirota et al., "Suppression of tumor promoter-induced inflammation of mouse ear by ursolic acid and 4,4-dimethycholestane derivatives" Agric. Biol. Chem., 54:1073-1075, 1990.
Hirota et al., "Total synthesis of (±)-amarolide, a quassinoid bitter principle," J. Org. Chem., 56:1119-1127, 1991.
Honda et al., "An Efficient Synthesis of Tricyclic Compounds, (±)-(4aβ8aβ10aα)-1,2,3,4,4a,6,7,8,8a,9,10,10a-dodecahydro-1,1,4a-trimethyl-2-oxophenanthrene-8a-carboxylic acid, its methyl ester, and (±)-(4aβ,8aβ10aα)-3,4,4a,6,7,8,8a,9,10,10a-decahydro-8a-hydroxymethyl-1,1,4a-trimethylphenanthren-2(1H)-one", Org. Prep. Proced. Int., 37(6):546-550, 2005.
Honda et al., "A novel dicyanotriterpenoid, 2-cyano-3,12-dioxooleana-1,9(11)-dien-28-onitrile, active at picomolar concentrations for inhibition of nitric oxide production," Bioorg. Med. Chem. Lett., 12:1027-1030, 2002.
Honda et al., "Design and synthesis of 23,24-dinoroleanolic acid derivatives, novel triterpenoid-steroid hybrid molecules," J. Org. Chem., 63:4846-4849, 1998.
Honda et al., "Design and synthesis of 2-cyano-3,12-dioxoolean-1,9-dien-28-oic acid, a novel and highly active inhibitor of nitric oxide production in mouse macrophages," Bioorg Med Chem Lett., 8(19):2711-2714, 1998.
Honda et al., "Design, synthesis, and biological evaluation of biotin conjugates of 2-cyano-3,12-dioxooleana-1,9(11)-dien-28-oic acid for the isolation of the protein targets," J. Med. Chem., 47 (20): 4923-4932, 2004.
Honda et al., "Efficient synthesis of (−)- and (+)-tricyclic compounds with enone functionalities in rings A and C. A novel class of orally active anti-inflammatory and cancer chemopreventive agents," Org Biomol Chem., 1:4384-4391, 2003.
Honda et al., "New enone derivatives of oleanolic acid and ursolic acid as inhibitors of nitric oxide production in mouse macrophages," Bioorg. Med. Chem. Lett., 7:1623-1628, 1997.
Honda et al., "New synthetic oleanane and ursane triterpenoids as inhibitors of nitric oxide production in mouse macrophages," The Fifth Chemical Congress of North America, Cancun, Mexico, Abstract 552 and slides for oral presentation, Nov. 1997.
Honda et al., "Novel synthetic oleanane and ursane triterpenoids with various enone functionalities in ring A as inhibitors of nitric oxide production in mouse macrophages," J. Med. Chem., 43:1866-1877, 2000.
Honda et al., "Novel synthetic oleanane triterpenoids: a series of highly active inhibitors of nitric oxide production in mouse macrophages," Bioorg Med Chem Lett, 9(24):3429-3434, 1999.
Honda et al., "Novel tricyclic compounds having acetylene groups at C-8a and cyano enones in rings A and C: highly potent anti-inflammatory and cytoprotective agents," J. Med. Chem., 50:1731-1734, 2007.
Honda et al., "Revision and confirmation of the regiochemistry of isoxazoles derived from methyl oleanonate and lanost-8-en-3-one. Synthesis of a new lanostane triterpenoid with a cyano-enone functionality in ring A," J. Org. Chem., 68:4991-4993, 2003.
Honda et al., "Synthesis of (±)-3,3-ethylenedioxy-14a-hydroxy-5-picrasene-11,16-dione, a 14aH-picrasane derivative," Chem. Lett., 299-302, 1981.
Honda et al., "Synthesis of a novel dicyano abietane analogue: a potential antiinflammatory agent," J. Org. Chem., 71:3314-3316, 2006.
Honda et al., "Synthetic oleanane and ursane triterpenoids with modified rings A and C: A series of highly active inhibitors of nitric oxide production in mouse macrophages," J. Med. Chem., 43:4233-4246, 2000.
Honda et al., "Tricyclic Compounds Containing Nonenolizable Cyano Enones. A Novel Class of Highly Potent Anti-Inflammatory and Cytoprotective Agents," J. Med. Chem., 54(6):1762-1778, 2011.
Hong et al., "Phase I trial of a novel oral NF-κB/pSTAT3 inhibitor RTA-402 in patients with solid tumors and lymphoid malignancies," 44th Annual Meeting of the American Society of Clinical Oncology, 2008.
Hu et al., "The IL-17 pathway as a major therapeutic target in autoimmune diseases", Ann. N.Y. Acad. Sci., 1217:60-76, 2011.
Huerta et al., "Characterization of novel small-molecule NRF2 activators: Structural and biochemical validation of stereospecific KEAP1 binding," Biochim. Biophys. Acta, 1860:2537-2552, 2016.
Hybertson et al., "Oxidative Stress in health and disease: The therapeutic potential of Nrf2 activation," Molecular Aspects of Medicine, 32:234-246, 2011.
Hyer et al., "Synthetic triterpenoids cooperate with tumor necrosis factor-related apoptosis-inducing ligand to induce apoptosis of breast cancer cells," Cancer Res., 65:4799-4808, 2005.
Iizuka et al., "Nrf2-deficient mice are highly susceptible to cigarette smoke-induced emphysema", Genes Cells, 10:1113-1125, 2005.
Ikeda et al., "Induction of redox imbalance and apoptosis in multiple myeloma cells by the novel triterpenoid 2-cyano-3,12-dioxoolean-1,9-dien-28-oic acid," Mol. Cancer Ther., 3:39-45, 2004.
Ikeda et al., "The novel triterpenoid CDDO and its derivatives induce apoptosis by disruption of intracellular redox balance," Cancer Res., 63:5551-5558, 2003.
Ikeda et al., "Triterpenoid CDDO-Im downregulates PML/RAR αexpression in acute promyelocytic leukemia cell," Cell Death and Differentiation, 12 (5): 523-531, 2005.
Inoue et al., "CDDO induces apoptosis via the intrinsic pathway in lymphoid cells," Leukemia, 18 (5): 948-952, 2004.
International Preliminary Report on Patentability issued in corresponding PCT Application No. PCT/US2019/038337, mailed on Dec. 30, 2020.
International Search Report and Written Opinion issued in corresponding PCT Application No. PCT/US2019/038337, mailed on Oct. 8, 2019.
Ishii et al. "Transcription factor Nrf2 plays a pivotal role in protection against elastase-induced pulmonary inflammation and emphysema", J. Immunol., 175, 6968-6975, 2005.
Ito et al., "Involvement of caspase-8 in the induction of osteosarcoma cell apoptosis by the novel triterpenoid CDDO," 47th Annual Meeting, Orthopaedic Research Society, Feb. 25-28, 2001, San Francisco, California, p. 0863, Poster Session, 2001.
Ito et al., "The novel triterpenoid 2-cyano-3, 12-dioxoolean-1,9-dien-28-oic acid induces apoptosis of human myeloid leukemia cells by a caspase-8-dependent mechanism," Cell Growth & Differentiation, 11(5):261-267, 2000.
Ito et al., "The novel triterpenoid CDDO induces apoptosis and differentiation of human osteosarcoma cells by a caspase-8 dependent mechanism," Mol. Pharmacol., 59:1094-1099, 2001.
Ivanov et al., "The orphan nuclear receptor RORγt directs the differentiation program of proinflammatory IL-17+ T helper cells", Cell, 126:1121-1133, 2006.
Iwakura and Ishigame, "The IL-23/IL-17 axis in inflammation", 116(5):1218-1222, 2006.
Jang et al., "24-nor-ursane type triterpenoids from the stems of Rumex japonicus," Chem. Pharm Bull (Tokyo), 53(12): 1594-1596, 2005.
Ji et al., "The synthetic triterpenoid CDDO-imidazolide induces monocytic differentiation by activating the Smad and ERK signaling pathways in HL60 leukemia cells," Molecular Cancer Therapeutics, 5 (6): 1452-1458, 2006.
Johansen et al., "Pharmacology and preclinical pharmacokinetics of the triterpenoid CDDO methyl ester," Proc. Amer. Assoc. Cancer Res., 44:1728, 2003.
Johns et al., "Triterpenes of Lanatana Tiliafolia. 24-hydroxy-3-oxours-12-en-28-oic acid, a new triterpene," Australian J. Chem. 36:2537-2547, 1983.
Kahne and Collum, "Kinetic cyanations of ketone enolates," Tetrahedron Lett., 22:5011-5014, 1981.

(56) References Cited

OTHER PUBLICATIONS

Kamal et al., "23-oxoisopristimerin III: an new natural phenolic (9→8)-24-nor-D:A-friedo-oleanane triterpene," Tetrahedron Letters, 24(27):2799-2800, 1983.
Kamal et al., "Structures of two new phenolic 24-nor-D: A-friedoleananes related to zeylasterone: a partial synthesis of trimethylzeylasterone," Tetrahetron Letters, 24(19):2025-2028, 1983.
Kamal et al., "The structure of zeylasterone, the first of a new series of phenolic 24-nor-D: A friedo-oleanane triterpenes," Tetrahedron Letters, 21(49): 4749-4752, 1980.
Kansanen et al., "Regulation of Nrf2-dependent gene expression by 15-deoxy-Delta12,14-prostaglandin J2," Free Radic. Biol. Med., 47(9):1310-7, 2009.
Khalid et al., "Isolation and characterization of pristimerin as the antiplasmodial and antileishmanial agent of maytenus senegalensis (Lam.) Exell," ARKIVOC, 129-134, 2007.
Kim et al., "An inducible pathway for degradation of FLIP protein sensitizes tumor cells to TRAIL-induced apoptosis," J. of Biological Chemistry, 277 (25): 22320-22329, 2002.
Kim et al., "Capasase-3 activation is involved in apoptosis induced by a synthetic triterpenoid in Non-small cell lung cancer (NSCLC) cells," Proc. Amer. Assoc. Cancer Res., 41:770, Abstract #4894, 2000.
Kim et al., "Identification of a novel synthetic triterpenoid, methyl-2-cyano-3,12-dioxooleana-1,9-dien-28-oate, that potently induces caspace-mediated apoptosis in human lung cancer cells," Molecular Cancer Therapeutics, 1:177-184, 2002.
Kincl et al., "Pituitary gonadotropin inhibitory action of neutral steroids," Acta. Endocrinologica, 46: 300-306, 1964.
Kircher, "Triterpenes, in organ pipe cactus," Phytochemistry, 19:2707-2712, 1980; Database CAPLUS on STN AN:1981:550946.
Klyne et al., "The molecular rotations of polyclyclic compounds. III. Polyclyclic alcohols and their derivatives," J Chem Soc., 1979-1988, 1954.
Kobayashi and Yamamoto, "Molecular mechanisms activating the Nrf2-Keap 1 pathway of antioxidant gene regulation," Antioxid. Redox. Signal., 7:385-394, 2005.
Kobayashi et al., "Nrf2 suppresses macrophage inflammatory response by blocking proinflammatory cytokine transcription", Nat Commun., 7:11624, 2016.
Kobayashi et al., "The antioxidant defense system Keap1-Nrf2 comprises a multiple sensing mechanism for responding to a wide range of chemical compounds," Mol. Cell Biol., 29(2):493-502, 2009.
Kolak et al., "Antioxidant and anticholinesterase constituents of Salvia poculata," Turkish Journal of Chemistry, 33(6): 813-823, 2009.
Konopleva et al., "Activation of nuclear transcription factor PPARgamma by the novel triterpenoid CDDO as targeted therapy in breast cancer," 2002 Keystone Symposium, Abstract No. 539, 2002.
Konopleva et al., "Mechanisms and Activity of PPARgamma-Active Triterpenoids CDDO and CDDO-Me in Leukemias," Blood, 106:2460, 2005.
Konopleva et al., "Novel synthetic triterpenoid CDDO-Me: potent antiproliferative, proapoptotic and differentiating agent in AML," Blood, 96(11), Part 1: 121A, abstract # 522, 2000.
Konopleva et al., "Novel synthetic triterpenoid, CDDO, and its methyl ester: Potent antiproliferative, proapoptotic and differentiating agents in AML," Blood, 94(Suppl 1):479a, Abstract #2140, 1999.
Konopleva et al., "Novel triterpenoid CDDO-Me is a potent inducer of apoptosis and differentiation in acute myelogenous leukemia," Blood, 99(1):326-335, 2002.
Konopleva et al., "Peroxisome proliferator-activated receptor gamma and retinoid X receptor ligands are potent inducers of differentiation and apoptosis in leukemias," Mol. Cancer Ther., 3:1249-1262, 2004.
Konopleva et al., "PPARg nuclear receptor as a novel therapeutic target in AML," Blood, 96(11):460a, Abstract #1982, 2000.

Konopleva et al., "PPARg nuclear receptor as a novel therapeutic target in AML," Proc. of the AACR, ,42, Abstract #4458, 2001.
Konopleva et al., "PPARgamma Ligand CDDO Induces Apoptosis in Leukemias via Multiple Apoptosis Pathways," Abstracts of the 44th Annual Meeting of the American Society of Hematology, Abstract No. 2209, 2002.
Konopleva et al., "PPARgamma Ligands Are Potent Inducers of Apoptosis in Leukemias and Lymphomas," American Society of Hematology 43rd Annual Meeting and Exposition, Abstract No. 501, 2001.
Konopleva et al., "PPARgamma Nuclear Receptor as a Novel Molecular Target in Leukemia Therapy," Proc. Amer. Assoc. Cancer Res., 43:4730, 2002.
Konopleva et al., "Suppression of ERK Activation is Required for Triterpenoid Methyl-CDDO-Induced Apoptosis in AML," Blood, 102(11):1404, 2003.
Konopleva et al., "Synthetic triterpenoid 2-cyano-3,12-dioxooleana-1,9-dien-28-oic acid induces growth arrest in HER2-overexpressing breast cancer cells," Mol. Cancer Ther., 5:317-328, 2006.
Konopleva et al., "Synthetic triterpenoid CDDO as a novel therapy for resistant breast cancer," Proc. Amer. Assoc. Cancer Res., 44:2726, 2003.
Konopleva et al., "The novel triterpenoid CDDO-Me suppresses MAPK pathways and promotes p38 activation in acute myeloid leukemia cells," Leukemia, 19:1350-1354, 2005.
Konopleva et al., "The synthetic triterpenoid 2-cyano-3,12-dioxooleana-1,9-dien-28-oic acid induces caspase-dependent and -independent apoptosis in acute myelogenous leukemia," Cancer Res., 64:7927-7935, 2004.
Korovin and Tkachev, "Synthesis of quinoxalines fused with triterpenes, ursolic acid and betulin derivatives," Russian Chemical Bulletin, (Translation of Izvestiya Akademii Nauk, Seriya Khimicheskaya), 20 (2): 304-310, 2001.
Koschmieder et al. "CDDO induces granulocytic differentiation of myeloid leukemic blasts through translational up-regulation of p42 CCAAT enhancer-binding protein alpha," Blood, 110 (10): 3695-3705, 2007.
Kress et al., "Triterpenoids display single agent activity in a mouse model of CLL/SBL," Blood, 108(11):2530, 2006.
Kress et al., "Triterpenoids display single agent anti-tumor activity in a transgenic mouse model of chronic lymphocytic leukemia and small B cell lymphoma," PLOS ONE, 6(e559):1-11, 2007.
Kurinna et al., "The novel triterpenoid CDDO-Me promotes apoptosis in Gleevec-resistant chronic myeloid leukemia cells by caspase-independent mechanisms," Proc. Amer. Assoc. Cancer Res., 46:2240, 2005.
Kutschabsky et al., "Natural products from Vietnamese plants. Part XV. Molecular and crystal structure of a new 24-nor triperpenoid carboxylic acid from Acanthopanax trifoliatus," Croatica Chemica Acta, 58(4): 427-434, 1986.
Lapillonne et al., "Activation of peroxisome proliferator-activated receptor gamma by a novel synthetic triterpenoid 2-cyano-3,12-dioxooleana-1,9-dien-28-oic acid induces growth arrest and apoptosis in breast cancer cells," Cancer Res., 63:5926-5939, 2003.
Larock et al., "Carbocycle synthesis via carbopalladation of nitriles," J. of the American Chemical Society, 121 (13): 3238-3239, 1999.
Lavie et al., "Studies on epoxides. IV. Rearrangements in triterpenoids," Tetrahedron Letters, 17: 2097-2100, 1968.
Lavie et al., "Tetranortriterpenoids from Melia azadirachta," Chemical Communcations, 6:278-280, 1967.
Lawrence, "The Nuclear Factor NF-kB Pathway in Inflammation", Cold Spring Harb. Perspect. Biol., 1:a001651, 2009.
Lei et al., "Regulatory T cell-mediated anti-inflammatory effects promote successful tissue repair in both indirect and direct manners," Front. Pharmacol., 6(184):1-10, 2015.
Li and Förstermann, "Nitric oxide in the pathogenesis of vascular disease", J. Pathol., 190:244-254, 2000.
Li et al., "Nrf2 Lowers the Risk of Lung Injury via Modulating the Airway Innate Immune Response Induced by Diesel Exhaust in Mice", Biomedicines, 8, 2020.
Li et al., "Terpenoids from tripterygium wilfordii," Phytochemistry, 45(4): 791-796, 1997.

(56) References Cited

OTHER PUBLICATIONS

Liby et al., "A novel acetylenic tricyclic bis-(cyano enone) potently induces phase 2 cytoprotective pathways and blocks liver carcinogenesis induced by aflatoxin," Cancer Res., 68:6727-6733, 2008.
Liby et al., "Novel semisynthetic analogues of betulinic acid with diverse cytoprotective, antiproliferative, and proapoptotic activities," Mol. Cancer. Ther., 6(7): 2113-2119, 2007.
Liby et al., "The rexinoid LG100268 and the synthetic triterpenoid CDDO-methyl amide are more potent than erlotinib for prevention of mouse lung carcinogenesis," Mol. Cancer Ther., 7:1251-1257, 2008.
Liby et al., "The synthetic triterpenoid CDDO-Imidazolide suppresses STAT phosphorylation and induces apoptosis in myeloma and lung cancer cells," Clinical Cancer Research, 12 (14 Part 1): 4288-4293, 2006.
Liby et al., "The synthetic triterpenoids CDDO-Methyl ester and CDDO-ethyl amide prevent lung cancer induced by vinyl carbamate in A/J mice," Cancer Research, 67(6):2414-2419, 2007.
Liby et al., "The synthetic triterpenoids, CDDO and CDDO-imidazolide, are potent inducers of heme oxygenase-1 and Nrf2/ARE signaling," Cancer Res., 65:4789-4798, 2005.
Liby et al., "Triterpenoids and rexinoids as multifunctional agents for the prevention and treatment of cancer," Nat. Rev. Cancer, 7 (5): 357-369, 2007.
Ling et al., "The novel triterpenoid C-28 methyl ester of 2-cyano-3,12-dioxoolen-1,9-dien-28-oic acid inhibits metastatic murine breast tumor growth through inactivation of STAT3 signaling," Cancer Res., 67:4210-4218, 2007.
Ling et al., "The novel triterpenoid CDDO-Me inhibits metastatic murine breast tumor through inhibition of Stat3 signaling," 2007 AACR Annual Meeting, Abstract No. 301, 2007.
Liu et al., "Chemical constituents from root of rubus irenaeus," Zhongcaoyao, 34 (5): 394-396, 2003.
Liu et al., "New lupane-type triterpenoid saponins from leaves of Oplopanax horridus (Devil's Club)," Nat Prod Comm., 5(7): 1019-1022, 2010.
Marples and Spilling, "Ene reactions of unsaturated acyloins," Tetrahedron Letters, 26 (52): 6515-6518, 1985.
Marples and Spilling, "Facile intramolecular ene reactions of steroidal unsaturated acyloins," Tetrahedron, 48 (19): 4017-4026, 1992.
Melichar et al., "Growth-inhibitory effect of a novel synthetic triterpenoid, 2-cyano-3,12-dioxoolean-1,9-dien-28-oic acid, on ovarian carcinoma cell lines not dependent on peroxisome proliferator-activated receptor-gamma expression," Gynecologic Oncology, 93:149-154, 2004.
Mencherini et al., "Triterpenoid constituents from the roots of the Paeonia rockii ssp. rockii," J Nat Prod., 74(10): 2116-2121, 2011.
Minns et al., "A novel triterpenoid induces transforming growth factor beta production by intraepithelial lymphocytes to prevent ileitis," Gastroenterology, 127:119-126, 2004.
Mix et al., "A synthetic triterpenoid selectively inhibits the induction of matrix metalloproteinases 1 and 13 by inflammatory cytokines," Arthritis Rheum., 44:1096-1104, 2001.
Mix et al., "Peroxisome proliferator-activated receptor-gamma-independent repression of collagenase gene expression by 2-cyano-3,12-dioxooleana-1,9-dien-28-oic acid and prostaglandin 15-deoxy-delta(12,14) J2: a role for Smad signaling," Mol. Pharmacol., 65(2):309-318, 2004.
Murphy et al., "Immunomodulatory Effects of the Triterpenoid CDDO after Allogeneic Bone Marrow Transplantation in Mice: Reduction of Acute Graft-Versus-Host Disease Lethality," Blood, 106:1316, 2005.
Murray and Zweifel, "Preparation of Phenyl Cyanate and Its Utilization for the Synthesis of α, β-Unsaturated Nitriles," Synthesis, 150-151, 1980.Synthesis, 150-151, 1980.
Muzart, "Synthesis of unsaturated carbonyl compounds via a chromium-mediated allylic oxidation by 70% tert.butylhydroperoxide," Tetrahedron Lett., 28:4665-4668, 1987.

Na and Surh et al., "Transcriptional regulation via cysteine thiol modification: a novel molecular strategy for chemoprevention and cytoprotection," Mol. Carcinog.,45 (6): 368-380, 2006.
Nair et al., "Triterpenes. XLVII. Oxidation rates of triterpenoid secondary alcohols with chromic acid," Collection of Czechoslovak Chemical Communications, 41(3): 770-779, 1976.
Nanduri et al., "Biological investigation and structure-activity relationship studies on azadirone from azadirachta indica A. juss," Bioorganic and Medicinal Chemistry, 13 (22): 4111-4115, 2003.
Nelson et al., "Oxidative demethylation at C-4 of a steroid via nitroxide photolysis," J. of the American Chemical Society, 97 (3): 648-649, 1975.
Niikura et al., "The effects of synthetic triterpenoids on superficial zone protein synthesis in articular chondrocytes," Abstract, Orthopedic Research Society, San Diego, 2007.
Niikura et al., "The effects of synthetic triterpenoids on szp synthesis in articular chondrocytes," Abstract P197, Osteoarthritis and Cartilage, 14(Suppl B):S112-S113, 2006.
Nishimura et al., "Activity-guided isolation of triterpenoid acyl CoA cholesteryl acyl transferase (ACAT) inhibitors from Ilex kudincha," J Nat Prod., 62(7): 1061-1064, 1999.
Nishino et al., "Inhibition of the tumor-promoting action of 12-O tetradecanoylphorbol-13-acetate by some oleanane-type triterpenoid compounds," Cancer Res., 48:5210-5215, 1988.
Noel et al., "KEAP1 Editing Using CRISPR/Cas9 for Therapeutic NRF2 Activation in Primary Human T Lymphocytes", J. Immunol., 200:1929-1936, 2018.
Orr et al., "Steroids. CCLXV. Studies in cyano steroids. 3. Unsaturated 2-cyano steroids," J. Org. Chem., 29(11): 3300-3303, 1964.
Osburn et al., "Genetic or pharmacologic amplification of Nrf2 signaling inhibits acute inflammatory liver injury in mice," Toxicological Sciences, 104:218-227, 2008.
Overnell and Whitehurts, "Reactions of steroid A-ring lactones with Grignard reagents," J. of the Chemical Society [Section] C: Organic, 2: 378-384, 1971.
Pappas et al., "Photoisomerization of phenalen-1-one oxide. New course of light-induced alpha beta-epoxy ketone rearrangement," J. of the American Chemical Society, 92 (19): 5797-5798, 1970.
Pareek et al., "Triterpenoid modulation of IL-17 and Nrf-2 expression ameliorates neuroinflammation and promotes remyelination in autoimmune encephalomyelitis", Sci. Rep., 1:201, 2011.
Peakman et al., "Characterisation of 24-nor-Triterpenoids Occurring in Sediments and Crude Oils by Comparison with Synthesized Standards," Tetrahedron, 47(23):3779-3786, 1991.
Pedersen et al., "The triterpenoid CDDO induces apoptosis in refractory CLL B cells," Blood, 100:2965-2972, 2002.
Place et al., "The novel synthetic triterpenoid, CDDO-imidazolide, inhibits inflammatory response and tumor growth in vivo," Clin. Cancer Res., 9:2798-2806, 2003.
Rasmusson et al., "Azasteroids: structure-activity relationships for inhibition of 5 alpha-reductase and of androgen receptor binding," J. Med. Chem., 29 (11): 2298, 1986.
Ray et al., "The novel triterpenoid 2-cyano-3,12-dioxooleana-1,9-dien-28-oic acid (CDDO) induces apoptosis of human diffuse large B-cell lymphoma cells through a peroxisome proliferator-activated receptor γ-independent pathway," Exp. Hematology, 34:1202-1211, 2006.
Reisman et al., "RTA 1701 is an oral RORγt inhibitor that suppresses the IL-17A response in non-human primates," J. Immunol., 200(1 Suppl.):175.22, 2018.
Ribo et al., "Synthesis of methyl 1, 11-dioxooleanan-2, 12-dien-30-oate and its 24-nor derivative," Afinidad, 38(373): 197-200, 1981.
Ricciardolo et al., "Nitric oxide in health and disease of the respiratory system", Physiol. Rev., 84:731-765, 2004.
Rossi et al., "Anti-inflammatory cyclopentenone prostaglandins are direct inhibitors of IkappaB kinase," Nature, 403:103-108, 2000.
Rouquette et al., "A ring-D functionalized nor-triterpenoid of the lupane series as a key intermediate in the formation of widespread hydrocarbon derivatives of higher plant origin in petroleum," Organic Geochemistry, 36(9): 1227-1233, 2005.

(56) References Cited

OTHER PUBLICATIONS

Ruvolo et al., "The novel triterpenoid methyl-CDDO inhibits Bcl2 phosphorylation and potently kills U937 cells," Blood, 94(10), Suppl. 1, Part 1: 280A, abstract #1251, 1999.
Ruzicka et al., "Triterpenes. LXXXIX. Decomposition of Hederagenin to the C26-Stage," Helvetica Chimica Acta, 27:1185-1196, 1944.
Samudio et al., "2-cyano-3,12 dioxoolean-1,9 diene-28-imidazolide induces apoptosis in pancreatic cancer via redox-dependent cytoplasmic stress," Proc. Amer. Assoc. Cancer Res., 46: Abstract No. 5899, 2005.
Samudio et al., "2-Cyano-3,12-dioxooleana-1,9-dien-28-imidazolide (CDDO-Im) directly targets mitochondrial glutathione to induce apoptosis in pancreatic cancer," J. Biol. Chem., 280:36273-36282, 2005.
Samudio et al., "A novel mechanism of action of methyl-2-cyano-3,12 dioxoolean-1,9 diene-28-oate (CDDO-Me): Direct permeabilization of the inner mitochondrial membrane to inhibit electron transport and induce apoptosis," Blood, 106(11):4462, 2005.
Samudio et al., "A novel mechanism of action of methyl-2-cyano-3,12 dioxoolean-1,9 diene-28-oate: direct permeabilization of the inner mitochondrial membrane to inhibit electron transport and induce apoptosis," Mol. Pharmacol., 69:1182-1193, 2006.
Samudio et al., "The novel triterpenoid CDDOme potently synergizes with inhibition of bcl-2 function to induce apoptosis in AML via disruption of intracellular redox homeostasis," Proc. Amer. Assoc. Cancer Res., 46: Abstract No. 4955, 2005.
Satoh et al., "Activation of the Keap1/Nrf2 pathway for neuroprotection by electrophillic phase II inducers," PNAS, 103 (3): 768-773, 2006.
Scholz et al., "Sensitive and specific methods for the determination of CDDO methyl ester in mouse, rat, dog, monkey, and human plasma by LC-tandem mass spectrometry," Proc. Amer. Assoc. Cancer Res., 4: Abstract No. 6321, 2003.
Segal et al., "NADPH oxidase limits innate immune responses in the lungs in mice," PLoS One, 5(3), 2010.
Sharpless et al., "Electrophilic and nucleophilic organoselenium reagents. New routes to alpha, beta-unsaturated carbonyl compounds," J. Am. Chem. Soc., 95:6137, 1973.
Shin et al., "Inhibitory roles of NRF2 and an oleanolic triterpenoid on adipocyte differentiation and obesity," dissertation submitted to John Hopkins University in conformity with the requirements for the degree of Doctor of Philosophy, Mar. 2009.
Shin et al., "NRF2 modulates aryl hydrocarbon receptor signaling: influence on adipogenesis," Molecular and Cellular Biology, 27 (20): 7188-7197, 2007.
Shin et al., "Role of Nrf2 in prevention of high-fat diet-induced obesity by synthetic triterpenoid CDDO-imidazolide" Eur. J. Pharmacol., 620(1-3):138-144, 2009.
Shishodia et al., "A synthetic triterpenoid, CDDO-Me, inhibits IkappaBalpha kinase and enhances apoptosis induced by TNF and chemotherapeutic agents through down-regulation of expression of nuclear factor kappaB-regulated gene products in human leukemic cells," Clin. Cancer Res., 12:1828-1838, 2006.
Siddiqui et al., "Kanerin and 12, 13-dihydroursolic acid, two new pentacyclic triterpenes from the leaves of Nerium oleander," J Nat Prod., 52(1): 57-62, 1989.
Simonsen et al., "Tetracyclic hydroxy acids," In the Terpenes, Cambridge University, Cambridge, 5:221-285, 1957.
Singh et al., "Anti-inflammatory activity of oleanolic acid in rats and mice," J. Pharm.Pharmacol., 44:456-458, 1992.
Soufli et al., "Overview of cytokines and nitric oxide involvement in immuno-pathogenesis of inflammatory bowel diseases", World J. Gastrointest. Pharmacol. Ther., 7(3):353-360, 2016.
Sporn and Roberts, "Peptide growth factors and inflammation, tissue repair, and cancer," J. Clin. Invest., 78:329-332, 1986.
Sporn et al., "New synthetic triterpenoids: potent agents for prevention and treatment of tissue injury caused by inflammatory and oxidative stress," J. Nat. Prod., 74(3):537-545, 2011.

Sporn et al., "Prospects for prevention and treatment of cancer with selective PPARg modulators (SPARMs)," Trends in Molecular Medicine, 7(9):395-400, 2001.
Stadheim et al., "The novel triterpenoid 2-cyano-3,12-dioxooleana-1,9-dien-28-oic acid (CDDO) potently enhances apoptosis induced by tumor necrosis factor in human leukemia cells," J. Biol. Chem., 277:16448-16455, 2002.
Subba Rao et al., "Chemical modifications of natural triterpenes—glycyrrhetinic and boswellic acids: evaluation of their biological activity," Tetrahedron, 64(51):11541-11548, 2008.
Suh et al., "A novel synthetic oleanane triterpenoid, 2-cyano-3,12-dioxoolean-1,9-dien-28-oic acid (CDDO), induces cell differentiation in human myeloid leukemias," Proceedings of the American Association for Cancer Research Annual Meeting, 40:300, abstract # 1988, 1999.
Suh et al., "A novel synthetic oleanane triterpenoid, 2-cyano-3,12-dioxoolean-1,9-dien-28-oic acid, with potent differentiating, antiproliferative, and anti-inflammatory activity," Cancer Res., 59(2):336-341, 1999.
Suh et al., "New triterpenoids as cancer preventive and anti-inflammatory agents," Proceedings of the American Association for Cancer Research, Abstract No. 1457, 38: 216, 1997.
Suh et al., "Novel triterpenoids suppress inducible nitric oxide synthase (iNOS) and inducible cyclooxygenase (COX-2) in mouse macrophages," Cancer Res., 58:717-723, 1998.
Suh et al., "Novel triterpenoids suppress inducible nitric oxide synthase (iNOS) and inducible cyclooxygenase (COX-2)," Proceedings of the American Association for Cancer Research Annual Meeting, 39: Abstract No. 1821, 1998.
Suh et al., "Synthetic triterpenoids activate a pathway for apoptosis in AML cells involving downregulation of FLIP and sensitization to TRAIL," Leukemia, 17:2122-2129, 2003.
Suh et al., "Synthetic triterpenoids enhance transforming growth factor β/Smad signaling," Cancer Res., 63:1371-1376, 2003.
Suh et al., "Triterpenoids CDDO and CDDO-Me Down-Regulate FLIP Expression and Sensitize AML Cells to Trail-Induced Apoptosis," American Society of Hematology 43rd Annual Meeting and Exposition, Abstract No. 498, 2001.
Sultana et al., "Phytochemical studies on Alstonia scholaris," Zeitschrift für Naturforschung. B, A Journal of Chemical Sciences, 65(2): 203-210, 2010.
Sun et al., "Structure-activity relationships of olean- and ursane-type triterpenoids," Botanical Studies, 47:339-368, 2006.
Sun et al., "The Synthetic Triterpenoid, CDDO, Suppresses Alloreactive T Cell Responses and Reduces Murine Early Acute Graft-versus-Host Disease Mortality," Biology of Blood and Marrow Transplantation, 13 (5): 521-529, 2007.
Tabe et al., "Chromatin-Mediated Transcriptional Activation with Novel Peroxisome Proliferator-Activated Receptor gamma(P-PARgamma) Ligand 2-cyano-1,9-dien-28-oic Acid (CDDO) in Acute Promyelocytic Leukemia Cells," Abstracts of the 44th Annual Meeting of the American Society of Hematology, Abstract No. 2191, 2002.
Thimmulappa et al., "Nrf2 is a critical regulator of the innate immune response and survival during experimental sepsis," J. Clinical Investigation, 116 (4): 984-995, 2006.
Thimmulappa et al., "Nrf2-dependent protection from LPS induced inflammatory response and mortality by CDDO-imidazolide," Biochem. Biophys. Res. Commun., 351:883-889, 2006.
Thimmulappa et al., "Preclinical evaluation of targeting the Nrf2 pathway by triterpenoids (CDDO-Im and CDDO-Me) for protection from LPS-induced inflammatory response and reactive oxygen species in human peripheral blood mononuclear cells and neutrophils," Antioxidants & Redox Signaling, 9(11):1963-1970, 2007.
Tran et al., "The synthetic triterpenoid CDDO-methyl ester modulates microglial activities, inhibits TNF production, and provides dopaminergic neuroprotection," Journal of Neuroinflammation, 5:1-14, 2008.
Tsao et al., "DRIP205 co-activator overexpression enhances PPARgamma-mediated differentiation of leukemia cells by CDDO," Proc. Amer. Assoc. Cancer Res., 46: Abstract No. 1855, 2005.

(56) References Cited

OTHER PUBLICATIONS

Tsao et al., "Targeted Induction of Apoptosis in Leukemias by PPAR gamma Ligation," American Society of Hematology 43rd Annual Meeting and Exposition, Abstract No. 2381, 2001.
Urban et al., "Influence of esterification and modification of A-ring in a group of lupane acids on their cytotoxicity," Bioorganic and Medicinal Chemistry, 13 (19): 5527-5535, 2005.
Urban et al., "Synthesis of A-seco derivatives of betulinic acid with cytotoxic activity," J. Nat. Prod., 67 (7): 1100-1105, 2004.
Uskoković et al., "D-Homosteroids. I. 3β-Hydroxy-17a,17a-dimethyl-D-homoandrostane-17-one and related compounds," J. Am. Chem. Soc., 81: 4561-4566, 1959.
Vannini et al., "The synthetic oleanane triterpenoid, CDDO-methyl ester, is a potent antiangiogenic agent," Mol. Cancer Ther., 6(12):3139-3146, 2007.
Vilayur and Harris, "Emerging therapies for chronic kidney disease: what is their role?" Nature Reviews, 5: 375-383, 2009.
Vincenti et al., "The synthetic triterpenoid TP-222 inhibits RANKL induction of differentiation and MMP-9 gene expression in osteoclasts," Abstract 1385, American College of Rheumatology Annual Scientific Meeting, 2006.
Wada and Tanaka, "Synthetic lanostane-type triterpenoids as inhibitors of DNA topoisomerase II ," Bioorganic and Medicinal Chemistry Letters, 15 (12): 2966-2969, 2005.
Walsh et al., "Identification and quantification of the basal and inducible Nrf2-dependent proteomes in mouse liver: Biochemical, pharmacological and toxicological implications", J. Proteome, 108:171-187, 2014.
Wang et al., "A novel synthetic triterpenoid, 2-cyano-3,12-dioxoolean-1,9-dien-28-oic acid (CDDO) induces adipocyte differentiation in 3T3-L1 cells," Proceedings of the American Association for Cancer Research Annual Meeting, 40:300, abstract # 1989, 1999.
Wang et al., "A synthetic triterpenoid, 2-cyano-3,12-dioxooleana-1,9-dien-28-oic acid (CDDO), is a ligand for the peroxisome proliferator-activated receptor gamma," Mol. Endocrin., 14(10): 1550-1556, 2000.
Wang et al., "Synthetic triterpenoid CDDO and its derivatives increase ceramides and are cytotoxic to pediatric acute lymphoblastic leukemia cell lines," Proc. Am. Assoc. Cancer Res., 47: 4643, 2006.
Wen et al., "Pentacyclic triterpenes. Part 5: Synthesis and SAR study of corosolic acid derivatives as inhibitors of glycogen phosphorylases," Bioorganic & Medicinal Chemistry Letters, 17:5777-5782, 2007.
Wolff et al., "Novel Monoaromatic Triterpenoids Occuring in Sediments and Crude Oils by Comparison with Synthesized Standards," Tetrahedron, 21:6721-6728, 1989.
Xu et al., "The role of nitric oxide in cancer", Cell Res., 12:311-320, 2002.
Yan et al., "CNS-specific therapy for ongoing EAE by silencing IL-17 pathway in astrocytes", Mol. Ther., 20(7): 1338-1348, 2012.
Yang et al., "Keap1-Nrf2 signaling activation by Bardoxolone-methyl ameliorates high glucose-induced oxidative injury in human umbilical vein endothelial cells", Aging, 12(11):19445-4589, 2020.
Yates et al., "Pharmacodynamic characterization of chemopreventive triterpenoids as exceptionally potent inducers of Nrf2-regulated genes," Mol. Cancer Ther., 6:154-162, 2007.
Yates et al., "Potent protection against aflatoxin-induced tumorigenesis through induction of Nrf2-regulated pathways by the triterpenoid 1-[2-cyano-3-,12-dioxooleana-1,9(11)-dien-28-oyl]imidazole," Cancer Res., 66 (4): 2488-2494, 2006.
Yore et al., "The synthetic triterpenoid 1-[2-cyano-3,12-dioxooleana-1,9(11)-dien-28-oyl]imidazole blocks nuclear factor-kappaB activation through direct inhibition of IkappaB kinase beta," Mol. Cancer Ther., 5(12):3232-3239, 2006.
You et al., "Synthesis and cytotoxic activity of a-ring modified betulinic acid derivatives," Bioorganic and Medicinal Chemistry Letters, 13 (19): 3137-3140, 2003.
Yue et al., "Depletion of intracellular glutathione contributes to JNK-mediated death receptor 5 upregulation and apoptosis induction by the novel synthetic triterpenoid methyl-2-cyano-3, 12-dioxooleana-1, 9-dien-28-oate (CDDO-Me).," Cancer & Biology Therapy, 5(5):492-497, 2006.
Zapata et al., "CDDO and CDDO-Im Reduce Tumor Burden in a Transgenic Mouse Model of CLL," Blood, 104:3477, 2004.
Zapata et al., "Triterpenoids show activity against leukemic cells in a transgenic mouse model of CLL," Proc. Amer. Assoc. Cancer Res., 46: Abstract No. 5179, 2005.
Zhang et al., "Nrf2 Activator RTA-408 Protects Against Ozone-Induced Acute Asthma Exacerbation by Suppressing ROS and γδT17 Cells", Inflammation, 42(5):1843-1856, 2019.
Zhang et al., "Synthetic triterpenoid CDDO as effective therapy for HER2-expressing resistant breast cancer," Proc. Amer. Assoc. Cancer Res., Abstract No. 3799, 2004.
Zhang et al., "The novel synthetic oleanane triterpenoid CDDO (2-cyano-3, 12-dioxoolean-1, 9-dien-28-oic acid) induces apoptosis in Mycosis fungoides/Sézary syndrome cells," J. Invest. Dermatol., 123:380-387, 2004.
Zhao et al., "γδ T cells as a major source of IL-17 production during age-dependent RPE degeneration", Invest. Ophthalmol. Vis. Sci., 55:6580-6589, 2014.
Zhou et al., "A new triterpenoid from the roots of Tripterygium wildfordii," Chinese Chemical Letters, 21(5): 600-602, 2010.
Ziegler et al., "Isolation and structure of eucosterol and 16beta-hydroxyeucosterol, two novel spirocyclic nortriterpenes, and of a new 24-nor-5alpha-chola-8, 16-diene-23-oic acid from bulbs of several Eucomis species," Helv Chim Acta, 59(6):1997-2011, 1976.
Zou et al., "c-Jun NH2-terminal kinase-mediated up-regulation of death receptor 5 contributes to induction of apoptosis by the novel synthetic triterpenoid methyl-2-cyano-3,12-dioxooleana-1, 9-dien-28-oate in human lung cancer cells," Cancer Res., 64:7570-7578, 2004.
Seelige et al., "The ancient cytokine IL-17D is regulated by Nrf2 and mediates tumor and virus surveillance" Cytokine, 91:10-12, 2016.
Office Communication issued in U.S. Appl. No. 17/251,295, dated Feb. 17, 2023.

* cited by examiner

CYSTEINE-DEPENDENT INVERSE AGONISTS OF NUCLEAR RECEPTORS ROR-GAMMA/ROR-GAMMA-T AND METHODS OF TREATING DISEASES OR DISORDERS THEREWITH

This application is a national phase application under 35 U.S.C. § 371 of International Application No. PCT/US2019/038337, filed Jun. 20, 2019, which claims the benefit of United States Provisional Application No. 62/687,782, filed on Jun. 20, 2018, the entire contents of each of which are hereby incorporated by reference.

REFERENCE TO A SEQUENCE LISTING

The instant application contains a Sequence Listing, which has been submitted in ASCII format via EFS-Web and is hereby incorporated by reference in its entirety. Said ASCII copy, created on Dec. 14, 2020, is named REATP0106US_ST25.txt and is 10 kilobytes in size.

BACKGROUND

I. Field

The present invention relates generally to the fields of biology and medicine. More particularly, it concerns compounds, compositions, and methods for the treatment and prevention of diseases such as those associated with RAR-related orphan receptor γ (RORγ) or RORγt and excess production of IL-17.

II. Description of Related Art

Since the discovery of synthetic ligands for the progesterone receptor by Djerassi and colleagues at Syntex in 1950, the field of nuclear receptor (NR) ligand dependent transcription factors has proven fertile territory for drug discovery and development. Not surprisingly, when the lymphocyte specific NR RORγt was shown by Littman to be both necessary and sufficient for IL-17 expression and T helper 17 (Th17) cell differentiation in human CD4+ T cells, a flurry of drug discovery activity ensued. The Th17 cell subset produces several pro-inflammatory cytokines (e.g., IL-17A, IL-17F, GM-CSF and IL-22), and has been shown to be the major pathogenic population in animal models of autoimmune inflammation, such as the experimental autoimmune encephalomyelitis (EAE) model for multiple sclerosis and the collagen-induce arthritis (CIA) model for rheumatoid arthritis. With the FDA approval of several biological agents targeting the IL-17/IL-23 pathway clinical proof of concept for the roles of these cytokines in human autoimmune diseases has been unambiguously established. Vitae Pharmaceuticals was first to enter the clinic with an orally active RORγt inverse agonist, VTP43742, that showed significant efficacy in a Phase 2a psoriasis clinical study. VTP43742 and the majority of orally active agents that modulate RORγt target the classical orthosteric binding pocket in the ligand binding domain (LBD) of RORγt. Recently, Merck Research Laboratories and Eindhoven University have described a series of molecules that antagonize RORγt function through binding to an allosteric site on the LBD through non-covalent interactions. Therefore, methods of modulating the activity of RORγ, especially RORγt, by covalent modulation of the allosteric site in the ligand binding region are of particular interest.

SUMMARY

The present disclosure provides compounds, methods and compositions that may be used, for example, to modulating the activity of RORγ and RORγt by binding to a cysteine residue at an allosteric site.

In one aspect, there are provided methods for treating diseases and disorders in patients in need thereof, comprising administering to the patient a therapeutically effective amount of a cysteine-dependent inverse agonist of the nuclear receptor RORγ/RORγt.

In another aspect, the present disclosure provides pharmaceutical compositions comprising a cysteine-dependent inverse agonist of nuclear receptor RORγ/RORγt in an amount sufficient to modulate the activity of nuclear receptor RORγ/RORγt when administered to a patient.

Either or both of the above methods and pharmaceutical compositions may be combined with any of the following embodiments. In some embodiments, the therapeutically effective amount is sufficient to modulate the activity of the patient's nuclear receptor RORγ/RORγt. In some embodiments, the inverse agonist binds to cysteine 476 of a nuclear receptor RORγ in the patient. In some embodiments, the binding occurs via the formation of a covalent bond between the inverse agonist and the cysteine 476. In some embodiments, the inverse agonist binds selectively to cysteine 476 of a nuclear receptor RORγ in the patient. In some embodiments, the inverse agonist binds preferentially to cysteine 476 of a nuclear receptor RORγ relative to the orthosteric binding pocket (i.e., the cholesterol binding site) in the ligand binding domain (LBD) of RORγ in the patient. In some embodiments, the inverse agonist does not bind to any significant extent to the orthosteric binding pocket in the ligand binding domain (LBD) of RORγ in the patient. In some embodiments, the inverse agonist inhibits the patient's RORγ/RORγt activity without significantly affecting the patient's RORα or RORβ activity.

In some embodiments, the method or pharmaceutical composition results in modulating the function of the patient's RORγ/RORγt. In some embodiments, the method or pharmaceutical composition results in suppressing the patient's interleukin-17A production. In some embodiments, the method or pharmaceutical composition results in selectively inhibiting the patient's T helper 17 (Th17) cell differentiation. In some embodiments, the inverse agonist's RORγt-LBD-GAL4 reporter assay $IC_{50}$ activity is less than 1 µM. In further embodiments, the inverse agonist's RORγt-LBD-GAL4 reporter assay $IC_{50}$ activity is less than 500 nM. In still further embodiments, the inverse agonist's RORγt-LBD-GAL4 reporter assay $IC_{50}$ activity is less than 100 nM. In some embodiments, the inverse agonist's RORγt-LBD-GAL4 reporter assay $IC_{50}$ activity is less than 1,000 nM, 950 nM, 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 75 nM, 50 nM, 25 nM, 20 nM, 15 nM or 10 nM. In some embodiments, the inverse agonist's suppression of IL-17A secretion from human CD4+ T-cells assay $IC_{50}$ activity is less than 500 nM. In further embodiments, the inverse agonist's suppression of IL-17A secretion from human CD4+ T-cells assay $IC_{50}$ activity is less than 100 nM. In still further embodiments, the inverse agonist's suppression of IL-17A secretion from human CD4+ T-cells assay $IC_{50}$ activity is less than 50 nM. In some embodiments, the inverse agonist's suppression of IL-17A secretion from human CD4+ T-cells assay $IC_{50}$ activity is less than 500 nM, 450 nM, 400 nM, 350 nM, 300 nM, 250 nM, 200 nM, 150 nM, 100 nM, 75 nM, 50 nM, 25 nM, 20 nM, 15 nM or 10 nM. In some embodiments, the disease or disorder is an autoimmune disease. In further embodiments, the autoimmune disease is Crohn's disease, rheumatoid arthritis, lupus, or psoriasis. In still further embodiments, the autoimmune disease is rheumatoid arthritis or psoriasis.

In some embodiments, the chemical formula of the inverse agonist comprises a chemical group of the formula:

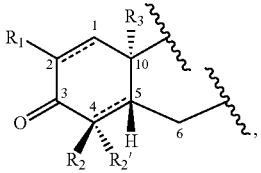

wherein:
 the bond between carbon atoms 1 and 2 is an epoxidized double bond or a double bond;
 the bond between carbon atoms 4 and 5 is a single bond or a double bond;
 $R_1$ is cyano, heteroaryl$_{(C\leq8)}$, substituted heteroaryl$_{(C\leq8)}$, —CF$_3$, or —C(O)R$_a$; wherein:
  $R_a$ is hydroxy, amino, or alkoxy$_{(C\leq8)}$, alkylamino$_{(C\leq8)}$, dialkylamino$_{(C\leq8)}$, alkylsulfonylamino$_{(C\leq8)}$, or a substituted version of any of these groups;
 $R_2$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of any of these groups, or -alkanediyl$_{(C\leq8)}$-cycloalkyl$_{(C\leq12)}$ or a substituted version of this group;
 $R_{2'}$ is absent, hydrogen, or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of these groups; provided that when the bond between carbon atoms 4 and 5 is a double bond then $R_{2'}$ is absent; and
 $R_3$ is alkyl$_{(C\leq12)}$, alkenyl$_{(C\leq12)}$, aryl$_{(C\leq12)}$, aralkyl$_{(C\leq12)}$, or a substituted version of any of these groups.

In some embodiments, the formula is further defined as:

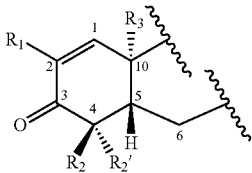

wherein:
 $R_1$ is cyano, heteroaryl$_{(C\leq8)}$, substituted heteroaryl$_{(C\leq8)}$, —CF$_3$, or —C(O)R$_a$; wherein:
  $R_a$ is hydroxy, amino, or alkoxy$_{(C\leq8)}$, alkylamino$_{(C\leq8)}$, dialkylamino$_{(C\leq8)}$, alkylsulfonylamino$_{(C\leq8)}$, or a substituted version of any of these groups;
 $R_2$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of any of these groups, or -alkanediyl$_{(C\leq8)}$-cycloalkyl$_{(C\leq12)}$ or a substituted version of this group;
 $R_{2'}$ is absent, hydrogen, or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of these groups; provided that when the bond between carbon atoms 4 and 5 is a double bond then $R_{2'}$ is absent; and
 $R_3$ is alkyl$_{(C\leq12)}$, alkenyl$_{(C\leq12)}$, aryl$_{(C\leq12)}$, aralkyl$_{(C\leq12)}$, or a substituted version of any of these groups.

In some embodiments, the formula is further defined as:

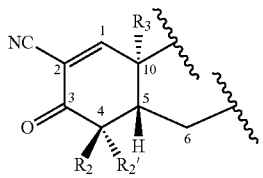

wherein:
 $R_2$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of any of these groups, or -alkanediyl$_{(C\leq8)}$-cycloalkyl$_{(C\leq12)}$ or a substituted version of this group;
 $R_{2'}$ is absent, hydrogen, or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of these groups; provided that when the bond between carbon atoms 4 and 5 is a double bond then $R_{2'}$ is absent; and
 $R_3$ is alkyl$_{(C\leq12)}$, alkenyl$_{(C\leq12)}$, aryl$_{(C\leq12)}$, aralkyl$_{(C\leq12)}$, or a substituted version of any of these groups.

In some embodiments, the formula is further defined as:

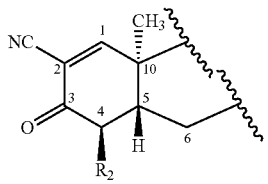

wherein:
 $R_2$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of any of these groups, or -alkanediyl$_{(C\leq8)}$-cycloalkyl$_{(C\leq12)}$ or a substituted version of this group.

In some embodiments, the formula is further defined as:

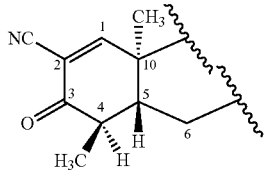

In some embodiments, the inverse agonist is a compound of the formula:

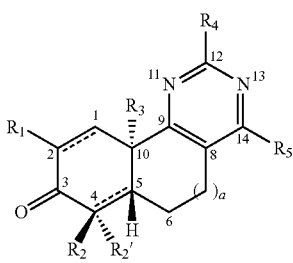

(I)

wherein:
the bond between carbon atoms 1 and 2 is an epoxidized double bond or a double bond;
the bond between carbon atoms 4 and 5 is a single bond or a double bond;
a is 0, 1, or 2;
$R_1$ is cyano, heteroaryl$_{(C\leq 8)}$, substituted heteroaryl$_{(C\leq 8)}$, —CF$_3$, or —C(O)R$_a$; wherein:
$R_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;
$R_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;
$R_{2'}$ is absent, hydrogen, or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of these groups; provided that when the bond between carbon atoms 4 and 5 is a double bond then $R_{2'}$ is absent;
$R_3$ is alkyl$_{(C\leq 12)}$, alkenyl$_{(C\leq 12)}$, aryl$_{(C\leq 12)}$, aralkyl$_{(C\leq 12)}$, or a substituted version of any of these groups;
$R_4$ is hydrogen, amino, alkyl$_{(C\leq 18)}$, substituted alkyl$_{(C\leq 18)}$, cycloalkyl$_{(C\leq 18)}$, substituted cycloalkyl$_{(C\leq 18)}$, aryl$_{(C\leq 18)}$, substituted aryl$_{(C\leq 18)}$, aralkyl$_{(C\leq 18)}$, substituted aralkyl$_{(C\leq 18)}$, heteroaryl$_{(C\leq 18)}$, substituted heteroaryl$_{(C\leq 18)}$, heteroaralkyl$_{(C\leq 18)}$, substituted heteroaralkyl$_{(C\leq 18)}$, heterocycloalkyl$_{(C\leq 18)}$, substituted heterocycloalkyl$_{(C\leq 18)}$, amido$_{(C\leq 18)}$, substituted amido$_{(C\leq 18)}$, or —X$_1$—(CH$_2$)$_m$—R$_{4'}$;

wherein:
$X_1$ is NR$_b$, O, or S; wherein:
$R_b$ is hydrogen, alkyl$_{(C\leq 6)}$, or substituted alkyl$_{(C\leq 6)}$;
m is 0, 1, 2, 3, or 4; and
$R_{4'}$ is alkyl$_{(C\leq 12)}$, cycloalkyl$_{(C\leq 12)}$, aryl$_{(C\leq 18)}$, aralkyl$_{(C\leq 18)}$, heteroaryl$_{(C\leq 18)}$, heteroaralkyl$_{(C\leq 18)}$, heterocycloalkyl$_{(C\leq 18)}$, or a substituted version of any of these groups; or

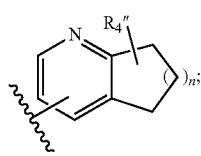

wherein:
n is 0, 1, 2, 3, or 4; and
$R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; or —X$_2$—(CH$_2$)$_p$—R$_{4'''}$;

wherein:
$X_2$ is arenediyl$_{(C\leq 12)}$, substituted arenediyl$_{(C\leq 12)}$, heterocycloalkanediyl$_{(C\leq 12)}$, substituted heterocycloalkanediyl$_{(C\leq 12)}$, heteroarenediyl$_{(C\leq 12)}$, or substituted heteroarenediyl$_{(C\leq 12)}$;
p is 0, 1, 2, 3, or 4; and
$R_{4'''}$ is alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, —C(O)-alkoxy$_{(C\leq 8)}$, —C(O)alkylamino$_{(C\leq 8)}$, —C(O)dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; and
$R_5$ is amino, hydroxy, —OS(O)$_2$C$_6$H$_4$CH$_3$, alkyl$_{(C\leq 12)}$, alkoxy$_{(C\leq 12)}$, cycloalkyl$_{(C\leq 12)}$, cycloalkoxy$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, heterocycloalkyl$_{(C\leq 12)}$, acyl$_{(C\leq 12)}$, acyloxy$_{(C\leq 12)}$, alkylamino$_{(C\leq 12)}$, dialkylamino$_{(C\leq 12)}$, alkylsulfonylamino$_{(C\leq 12)}$, or a substituted version of any of the last fourteen groups, or

—OY$_1$-A$_1$;

wherein:
$Y_1$ is alkanediyl$_{(C\leq 8)}$ or substituted alkanediyl$_{(C\leq 8)}$; and
$A_1$ is cycloalkyl$_{(C\leq 8)}$ or substituted cycloalkyl$_{(C\leq 8)}$; or —Y$_2$—C(O)NR$_c$-A$_2$;

wherein:
$Y_2$ is arenediyl$_{(C\leq 8)}$ or substituted arenediyl$_{(C\leq 8)}$;
$R_c$ is hydrogen, alkyl$_{(C\leq 6)}$, or substituted alkyl$_{(C\leq 6)}$; and
$A_2$ is aralkyl$_{(C\leq 12)}$ or substituted aralkyl$_{(C\leq 12)}$; or -A$_3$R$_d$;

wherein:
$A_3$ is —O— or —NR$_e$—, wherein
$R_e$ is hydrogen, alkyl$_{(C\leq 6)}$, or substituted alkyl$_{(C\leq 6)}$; and
$R_d$ is acyl$_{(C\leq 12)}$, or substituted acyl$_{(C\leq 12)}$;
provided that when carbon atoms 4 and 5 are joined by a double bond, then $R_{2'}$ and the hydrogen atom at carbon atom 5 are absent;
or a pharmaceutically acceptable salt thereof.
In some embodiments, the compound is further defined as:

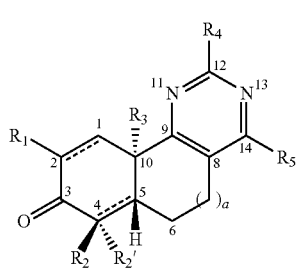

(I)

wherein:
the bond between carbon atoms 1 and 2 is an epoxidized double bond or a double bond;
the bond between carbon atoms 4 and 5 is a single bond or a double bond;
a is 0, 1, or 2;
$R_1$ is cyano, heteroaryl$_{(C\leq 8)}$, substituted heteroaryl$_{(C\leq 8)}$, —CF$_3$, or —C(O)R$_a$; wherein:
$R_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;
$R_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;
$R_{2'}$ is absent, hydrogen, or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of these groups; provided that when the bond between carbon atoms 4 and 5 is a double bond then $R_{2'}$ is absent;
$R_3$ is alkyl$_{(C\leq 12)}$, alkenyl$_{(C\leq 12)}$, aryl$_{(C\leq 12)}$, aralkyl$_{(C\leq 12)}$, or a substituted version of any of these groups;
$R_4$ is hydrogen, amino, alkyl$_{(C2-18)}$, substituted alkyl$_{(C\leq 18)}$, cycloalkyl$_{(C\leq 18)}$, substituted cycloalkyl$_{(C\leq 18)}$, aryl$_{(C\leq 18)}$, substituted aryl$_{(C\leq 18)}$, aralkyl$_{(C\leq 18)}$, substituted aralkyl$_{(C\leq 18)}$, heteroaryl$_{(C\leq 18)}$, substituted heteroaryl$_{(C\leq 18)}$, heteroaralkyl$_{(C\leq 18)}$, substituted heteroaralkyl$_{(C\leq 18)}$, heterocycloalkyl$_{(C\leq 18)}$, substituted heterocycloalkyl$_{(C\leq 18)}$, amido$_{(C\leq 18)}$, substituted amido$_{(C\leq 18)}$, or —X$_1$—(CH$_2$)$_m$—R$_{4'}$;

wherein:
$X_1$ is NR$_b$, O, or S; wherein:
$R_b$ is hydrogen, alkyl$_{(C\leq 6)}$, or substituted alkyl$_{(C\leq 6)}$;
m is 0, 1, 2, 3, or 4; and
$R_{4'}$ is alkyl$_{(C\leq 12)}$, cycloalkyl$_{(C\leq 18)}$, aryl$_{(C\leq 18)}$, aralkyl$_{(C\leq 18)}$, heteroaryl$_{(C\leq 18)}$, heteroaralkyl$_{(C\leq 18)}$, heterocycloalkyl$_{(C\leq 18)}$, or a substituted version of any of these groups, provided that when $X_1$ is O, then $R_{4'}$ is not methyl; or

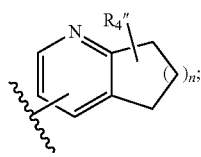

wherein:
n is 0, 1, 2, 3, or 4; and
$R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; or —X$_2$—(CH$_2$)$_p$—R$_{4'''}$;

wherein:
$X_2$ is arenediyl$_{(C\leq 12)}$, substituted arenediyl$_{(C\leq 12)}$, heterocycloalkanediyl$_{(C\leq 12)}$, substituted heterocycloalkanediyl$_{(C\leq 12)}$, heteroarenediyl$_{(C\leq 12)}$, or substituted heteroarenediyl$_{(C\leq 12)}$;
p is 0, 1, 2, 3, or 4; and
$R_{4'''}$ is alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; and
$R_5$ is amino, hydroxy, —OS(O)$_2$C$_6$H$_4$CH$_3$, alkyl$_{(C\leq 12)}$, alkoxy$_{(C\leq 12)}$, cycloalkyl$_{(C\leq 12)}$, cycloalkoxy$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, heterocycloalkyl$_{(C\leq 12)}$, acyl$_{(C\leq 12)}$, acyloxy$_{(C\leq 12)}$, alkylamino$_{(C\leq 12)}$, dialkylamino$_{(C\leq 12)}$, alkylsulfonylamino$_{(C\leq 12)}$, or a substituted version of any of the last fourteen groups, or

—OY$_1$-A$_1$;

wherein:
$Y_1$ is alkanediyl$_{(C\leq 8)}$ or substituted alkanediyl$_{(C\leq 8)}$; and
$A_1$ is cycloalkyl$_{(C\leq 8)}$ or substituted cycloalkyl$_{(C\leq 8)}$; or —Y$_2$—C(O)NR$_c$-A$_2$;

wherein:
$Y_2$ is arenediyl$_{(C\leq 8)}$ or substituted arenediyl$_{(C\leq 8)}$;
$R_c$ is hydrogen, alkyl$_{(C\leq 6)}$, or substituted alkyl$_{(C\leq 6)}$; and
$A_2$ is aralkyl$_{(C\leq 12)}$ or substituted aralkyl$_{(C\leq 12)}$; or -A$_3$R$_d$;

wherein:
$A_3$ is —O— or —NR$_e$—, wherein
$R_e$ is hydrogen, alkyl$_{(C\leq 6)}$, or substituted alkyl$_{(C\leq 6)}$; and
$R_d$ is acyl$_{(C\leq 12)}$, or substituted acyl$_{(C\leq 12)}$;
provided that when carbon atoms 4 and 5 are joined by a double bond, then $R_{2'}$ and the hydrogen atom at carbon atom 5 are absent;
or a pharmaceutically acceptable salt thereof.
In some embodiments, the compound is further defined as:

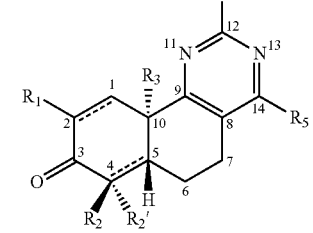

(II)

wherein:
the bond between carbon atoms 1 and 2 is an epoxidized double bond or a double bond;
the bond between carbon atoms 4 and 5 is a single bond or a double bond;
$R_1$ is cyano, heteroaryl$_{(C\leq 8)}$, substituted heteroaryl$_{(C\leq 8)}$, —CF$_3$, or —C(O)R$_a$; wherein:
$R_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;

R$_2$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of any of these groups, or -alkanediyl$_{(C\leq8)}$-cycloalkyl$_{(C\leq12)}$ or a substituted version of this group;

R$_{2'}$ is absent, hydrogen, alkyl$_{(C\leq12)}$, cycloalkyl$_{(C\leq12)}$, alkenyl$_{(C\leq12)}$, alkynyl$_{(C\leq12)}$, or a substituted version of the last four groups; provided that when the bond between carbon atoms 4 and 5 is a double bond then R$_{2'}$ is absent;

R$_3$ is alkyl$_{(C\leq12)}$, alkenyl$_{(C\leq12)}$, aryl$_{(C\leq12)}$, aralkyl$_{(C\leq12)}$, or a substituted version of any of these groups;

R$_4$ is hydrogen, amino, alkyl$_{(C2-18)}$, substituted alkyl$_{(C\leq18)}$, cycloalkyl$_{(C\leq18)}$, substituted cycloalkyl$_{(C\leq18)}$, aryl$_{(C\leq18)}$, substituted aryl$_{(C\leq18)}$, aralkyl$_{(C\leq18)}$, substituted aralkyl$_{(C\leq18)}$, heteroaryl$_{(C\leq18)}$, substituted heteroaryl$_{(C\leq18)}$, heteroaralkyl$_{(C\leq18)}$, substituted heteroaralkyl$_{(C\leq18)}$, heterocycloalkyl$_{(C\leq18)}$, substituted heterocycloalkyl$_{(C\leq18)}$, alkylamino$_{(C\leq18)}$, substituted alkylamino$_{(C\leq18)}$, dialkylamino$_{(C\leq18)}$, substituted dialkylamino$_{(C\leq18)}$, alkylthio$_{(C\leq18)}$, substituted alkylthio$_{(C\leq18)}$, amido$_{(C\leq18)}$, substituted amido$_{(C\leq18)}$, or —X$_1$—(CH$_2$)$_m$—R$_{4'}$;

wherein:
X$_1$ is NR$_b$, O, or S; wherein:
R$_b$ is hydrogen, alkyl$_{(C\leq6)}$, or substituted alkyl$_{(C\leq6)}$;
m is 0, 1, 2, 3, or 4; and
R$_{4'}$ is alkyl$_{(C\leq12)}$, cycloalkyl$_{(C\leq18)}$, aryl$_{(C\leq18)}$, aralkyl$_{(C\leq18)}$, heteroaryl$_{(C\leq18)}$, heteroaralkyl$_{(C\leq18)}$, heterocycloalkyl$_{(C\leq18)}$, or a substituted version of any of these groups, provided that when X$_1$ is O, then R$_{4'}$ is not methyl; or

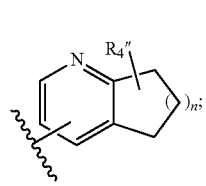

wherein:
n is 0, 1, 2, 3, or 4; and
R$_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C\leq8)}$, cycloalkyl$_{(C\leq8)}$, aryl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, alkylamino$_{(C\leq8)}$, dialkylamino$_{(C\leq8)}$, —C(O)-alkoxy$_{(C\leq8)}$, —C(O)-alkylamino$_{(C\leq8)}$, —C(O)-dialkyl-amino$_{(C\leq8)}$, alkylsulfonyl$_{(C\leq8)}$, arylsulfonyl$_{(C\leq8)}$, alkoxysulfonyl$_{(C\leq8)}$, or a substituted version of any of these groups; or —X$_2$—(CH$_2$)$_p$—R$_{4'''}$;

wherein:
X$_2$ is arenediyl$_{(C\leq12)}$, substituted arenediyl$_{(C\leq12)}$, heterocycloalkanediyl$_{(C\leq12)}$, substituted heterocycloalkanediyl$_{(C\leq12)}$, heteroarenediyl$_{(C\leq12)}$, or substituted heteroarenediyl$_{(C\leq12)}$;
p is 0, 1, 2, 3, or 4; and
R$_{4'''}$ is alkyl$_{(C\leq8)}$, cycloalkyl$_{(C\leq8)}$, aryl$_{(C\leq8)}$, heteroaryl$_{(C\leq8)}$, heterocycloalkyl$_{(C\leq8)}$, acyl$_{(C\leq8)}$, amido$_{(C\leq8)}$, alkoxy$_{(C\leq8)}$, acyloxy$_{(C\leq8)}$, —C(O)-alkoxy$_{(C\leq8)}$, —C(O)-alkylamino$_{(C\leq8)}$, —C(O)-dialkyl-amino$_{(C\leq8)}$, alkylsulfonyl$_{(C\leq8)}$, arylsulfonyl$_{(C\leq8)}$, alkoxysulfonyl$_{(C\leq8)}$, or a substituted version of any of these groups; and R$_5$ is amino, hydroxy, —OS(O)$_2$C$_6$H$_4$CH$_3$, alkyl$_{(C\leq12)}$, alkoxy$_{(C\leq12)}$, cycloalkyl$_{(C\leq12)}$, cycloalkoxy$_{(C\leq12)}$, aryl$_{(C\leq12)}$, aralkyl$_{(C\leq12)}$, heteroaryl$_{(C\leq12)}$, heteroaralkyl$_{(C\leq12)}$, heterocycloalkyl$_{(C\leq12)}$, acyl$_{(C\leq12)}$, acyloxy$_{(C\leq12)}$, alkylamino$_{(C\leq12)}$, dialkylamino$_{(C\leq12)}$, alkylsulfonylamino$_{(C\leq12)}$, or a substituted version of any of the last fourteen groups, or

—OY$_1$-A$_1$;

wherein:
Y$_1$ is alkanediyl$_{(C\leq8)}$ or substituted alkanediyl$_{(C\leq8)}$; and
A$_1$ is cycloalkyl$_{(C\leq8)}$ or substituted cycloalkyl$_{(C\leq8)}$; or —Y$_2$—C(O)NR$_c$-A$_2$;

wherein:
Y$_2$ is arenediyl$_{(C\leq8)}$ or substituted arenediyl$_{(C\leq8)}$;
R$_c$ is hydrogen, alkyl$_{(C\leq6)}$, or substituted alkyl$_{(C\leq6)}$; and
A$_2$ is aralkyl$_{(C\leq12)}$ or substituted aralkyl$_{(C\leq12)}$; or -A$_3$R$_d$;

wherein:
A$_3$ is —O— or —NR$_e$—, wherein
R$_e$ is hydrogen, alkyl$_{(C\leq6)}$, or substituted alkyl$_{(C\leq6)}$; and
R$_d$ is acyl$_{(C\leq12)}$, or substituted acyl$_{(C\leq12)}$;
provided that when carbon atoms 4 and 5 are joined by a double bond, then R$_{2'}$ and the hydrogen atom at carbon atom 5 are absent;
or a pharmaceutically acceptable salt thereof.

In some embodiments, the compound is further defined as:

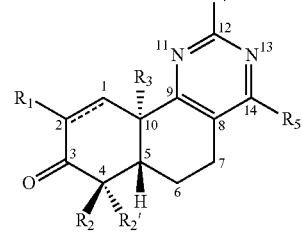

(III)

wherein:
the bond between carbon atoms 1 and 2 is an epoxidized double bond or a double bond;
R$_1$ is cyano, heteroaryl$_{(C\leq8)}$, substituted heteroaryl$_{(C\leq8)}$, —CF$_3$, or —C(O)R$_a$; wherein:
R$_a$ is hydroxy, amino, or alkoxy$_{(C\leq8)}$, alkylamino$_{(C\leq8)}$, dialkylamino$_{(C\leq8)}$, alkylsulfonylamino$_{(C\leq8)}$, or a substituted version of any of these groups;
R$_2$ is hydrogen or alkyl$_{(C\leq12)}$, cycloalkyl$_{(C\leq12)}$, alkenyl$_{(C\leq12)}$, alkynyl$_{(C\leq12)}$, aryl$_{(C\leq12)}$, aralkyl$_{(C\leq12)}$, heteroaryl$_{(C\leq12)}$, heteroaralkyl$_{(C\leq12)}$, acyl$_{(C\leq12)}$, or a substituted version of any of these groups, or -alkanediyl$_{(C\leq8)}$-cycloalkyl$_{(C\leq12)}$ or a substituted version of this group;
R$_{2'}$ is hydrogen, alkyl$_{(C\leq12)}$, cycloalkyl$_{(C\leq12)}$, alkenyl$_{(C\leq12)}$, alkynyl$_{(C\leq12)}$, or a substituted version of the last four groups;
R$_3$ is alkyl$_{(C\leq12)}$, aryl$_{(C\leq12)}$, aralkyl$_{(C\leq12)}$, or a substituted version of any of these groups;

R$_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CH$_2$)$_m$—R$_{4'}$;

wherein:
X$_1$ is NR$_b$, O, or S; wherein:
R$_b$ is hydrogen, alkyl$_{(C≤6)}$, or substituted alkyl$_{(C≤6)}$;
m is 0, 1, 2, 3, or 4; and
R$_{4'}$ is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when X$_1$ is O, then R$_{4'}$ is not methyl; or

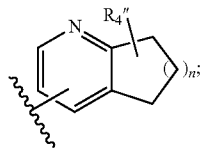

wherein:
n is 0, 1, 2, 3, or 4; and
R$_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_{4'''}$;

wherein:
X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
R$_{4'''}$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and
R$_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$-A$_1$;

wherein:
Y$_1$ is alkanediyl$_{(C≤8)}$ or substituted alkanediyl$_{(C≤8)}$; and
A$_1$ is cycloalkyl$_{(C≤8)}$ or substituted cycloalkyl$_{(C≤8)}$; or
—Y$_2$—C(O)NR$_b$-A$_2$;

wherein:
Y$_2$ is arenediyl$_{(C≤8)}$ or substituted arenediyl$_{(C≤8)}$;
R$_b$ is hydrogen, alkyl$_{(C≤6)}$, or substituted alkyl$_{(C≤6)}$; and
A$_2$ is aralkyl$_{(C≤12)}$ or substituted aralkyl$_{(C≤12)}$; or
-A$_3$R$_d$;

wherein:
A$_3$ is —O— or —NR$_e$—, wherein
R$_e$ is hydrogen, alkyl$_{(C≤6)}$, or substituted alkyl$_{(C≤6)}$; and
R$_d$ is acyl$_{(C≤12)}$, or substituted acyl$_{(C≤12)}$;
or a pharmaceutically acceptable salt thereof.

In some embodiments, the compound is further defined as:

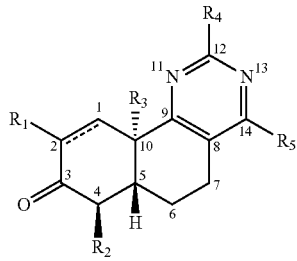

(IV)

wherein:
the bond between carbon atoms 1 and 2 is an epoxidized double bond or a double bond;
R$_1$ is cyano, heteroaryl$_{(C≤8)}$, substituted heteroaryl$_{(C≤8)}$, —CF$_3$, or —C(O)R$_a$; wherein:
R$_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;
R$_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, a substituted version of any of these groups, or -alkanediyl$_{(C≤8)}$-cycloalkyl$_{(C≤12)}$ or a substituted version of this group;
R$_3$ is alkyl$_{(C≤12)}$, aryl$_{(C≤12)}$, aralkyl$_{(C≤12)}$, or a substituted version of any of these groups;
R$_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CH$_2$)$_m$—R$_{4'}$;

wherein:
X$_1$ is NR$_b$, O, or S; wherein:
R$_b$ is hydrogen, alkyl$_{(C≤6)}$, or substituted alkyl$_{(C≤6)}$;
m is 0, 1, 2, 3, or 4; and
R$_{4'}$ is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when X$_1$ is O, then R$_{4'}$ is not methyl; or

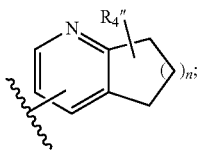

wherein:

n is 0, 1, 2, 3, or 4; and $R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; or —X$_2$—(CH$_2$)$_p$—R$_{4'''}$;

wherein:

X$_2$ is arenediyl$_{(C\leq 12)}$, substituted arenediyl$_{(C\leq 12)}$, heterocycloalkanediyl$_{(C\leq 12)}$, substituted heterocycloalkanediyl$_{(C\leq 12)}$, heteroarenediyl$_{(C\leq 12)}$, or substituted heteroarenediyl$_{(C\leq 12)}$;

p is 0, 1, 2, 3, or 4; and $R_{4'''}$ is alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, —C(O)-alkoxy$_{(C\leq 8)}$, —C(O)-alkylamino$_{(C\leq 8)}$, —C(O)-dialkyl-amino$_{(C\leq 8)}$, alkylsulfonyl$_{(C\leq 8)}$, arylsulfonyl$_{(C\leq 8)}$, alkoxysulfonyl$_{(C\leq 8)}$, or a substituted version of any of these groups; and $R_5$ is amino, hydroxy, —OS(O)$_2$C$_6$H$_4$CH$_3$, alkyl$_{(C\leq 12)}$, alkoxy$_{(C\leq 12)}$, cycloalkyl$_{(C\leq 12)}$, cycloalkoxy$_{(C\leq 12)}$, aryl$_{(C\leq 12)}$, aralkyl$_{(C\leq 12)}$, heteroaryl$_{(C\leq 12)}$, heterocycloalkyl$_{(C\leq 12)}$, acyl$_{(C\leq 12)}$, acyloxy$_{(C\leq 12)}$, alkylamino$_{(C\leq 12)}$, dialkylamino$_{(C\leq 12)}$, alkylsulfonylamino$_{(C\leq 12)}$, or a substituted version of any of the last fourteen groups, or

—OY$_1$-A$_1$;

wherein:

Y$_1$ is alkanediyl$_{(C\leq 8)}$ or substituted alkanediyl$_{(C\leq 8)}$; and

A$_1$ is cycloalkyl$_{(C\leq 8)}$ or substituted cycloalkyl$_{(C\leq 8)}$; or

—Y$_2$—C(O)NR$_b$-A$_2$;

wherein:

Y$_2$ is arenediyl$_{(C\leq 8)}$ or substituted arenediyl$_{(C\leq 8)}$;

R$_b$ is hydrogen, alkyl$_{(C\leq 6)}$, or substituted alkyl$_{(C\leq 6)}$; and

A$_2$ is aralkyl$_{(C\leq 12)}$ or substituted aralkyl$_{(C\leq 12)}$; or

-A$_3$R$_d$;

wherein:

A$_3$ is —O— or —NR$_e$—, wherein

R$_e$ is hydrogen, alkyl$_{(C\leq 6)}$, or substituted alkyl$_{(C\leq 6)}$; and

R$_d$ is acyl$_{(C\leq 12)}$, or substituted acyl$_{(C\leq 12)}$;

or a pharmaceutically acceptable salt thereof.

In some embodiments, the compound is further defined as:

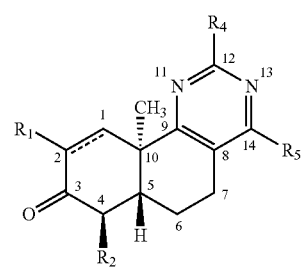

(V)

wherein:

the bond between carbon atoms 1 and 2 is an epoxidized double bond or a double bond;

$R_1$ is cyano, heteroaryl$_{(C\leq 8)}$, substituted heteroaryl$_{(C\leq 8)}$, —CF$_3$, or —C(O)R$_a$; wherein:

R$_a$ is hydroxy, amino, or alkoxy$_{(C\leq 8)}$, alkylamino$_{(C\leq 8)}$, dialkylamino$_{(C\leq 8)}$, alkylsulfonylamino$_{(C\leq 8)}$, or a substituted version of any of these groups;

$R_2$ is hydrogen or alkyl$_{(C\leq 12)}$, cycloalkyl$_{(C\leq 12)}$, alkenyl$_{(C\leq 12)}$, alkynyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, acyl$_{(C\leq 12)}$, or a substituted version of any of these groups, or -alkanediyl$_{(C\leq 8)}$-cycloalkyl$_{(C\leq 12)}$ or a substituted version of this group;

$R_4$ is hydrogen, amino, alkyl$_{(C2-18)}$, substituted alkyl$_{(C\leq 18)}$, cycloalkyl$_{(C\leq 18)}$, substituted cycloalkyl$_{(C\leq 18)}$, aryl$_{(C\leq 18)}$, substituted aryl$_{(C\leq 18)}$, aralkyl$_{(C\leq 18)}$, substituted aralkyl$_{(C\leq 18)}$, heteroaryl$_{(C\leq 18)}$, substituted heteroaryl$_{(C\leq 18)}$, heteroaralkyl$_{(C\leq 18)}$, substituted heteroaralkyl$_{(C\leq 18)}$, heterocycloalkyl$_{(C\leq 18)}$, substituted heterocycloalkyl$_{(C\leq 18)}$, alkylamino$_{(C\leq 18)}$, substituted alkylamino$_{(C\leq 18)}$, dialkylamino$_{(C\leq 18)}$, substituted dialkylamino$_{(C\leq 18)}$, alkylthio$_{(C\leq 18)}$, substituted alkylthio$_{(C\leq 18)}$, amido$_{(C\leq 18)}$, substituted amido$_{(C\leq 18)}$, or —X$_1$—(CH$_2$)$_m$—R$_4$;

wherein:

X$_1$ is NR$_b$, O, or S; wherein:

R$_b$ is hydrogen, alkyl$_{(C\leq 6)}$, or substituted alkyl$_{(C\leq 6)}$;

m is 0, 1, 2, 3, or 4; and $R_{4'}$ is alkyl$_{(C\leq 12)}$, cycloalkyl$_{(C\leq 18)}$, aryl$_{(C\leq 18)}$, aralkyl$_{(C\leq 18)}$, heteroaryl$_{(C\leq 18)}$, heteroaralkyl$_{(C\leq 18)}$, heterocycloalkyl$_{(C\leq 18)}$, or a substituted version of any of these groups, provided that when X$_1$ is O, then R$_{4'}$ is not methyl; or

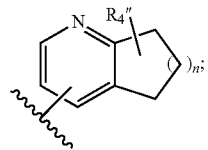

wherein:

n is 0, 1, 2, 3, or 4; and $R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C\leq 8)}$, cycloalkyl$_{(C\leq 8)}$, aryl$_{(C\leq 8)}$, heteroaryl$_{(C\leq 8)}$, heterocycloalkyl$_{(C\leq 8)}$, acyl$_{(C\leq 8)}$, amido$_{(C\leq 8)}$, alkoxy$_{(C\leq 8)}$, acyloxy$_{(C\leq 8)}$, alkylamino$_{(C\leq 8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or $$—X_2—(CH_2)_p—R_{4'''};$$

wherein:
- $X_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
- p is 0, 1, 2, 3, or 4; and
- $R_{4'''}$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and $R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or $$—OY_1-A_1;$$

wherein:
- $Y_1$ is alkanediyl$_{(C≤8)}$ or substituted alkanediyl$_{(C≤8)}$; and
- $A_1$ is cycloalkyl$_{(C≤8)}$ or substituted cycloalkyl$_{(C≤8)}$; or $$—Y_2—C(O)NR_b-A_2;$$

wherein:
- $Y_2$ is arenediyl$_{(C≤8)}$ or substituted arenediyl$_{(C≤8)}$;
- $R_b$ is hydrogen, alkyl$_{(C≤6)}$, or substituted alkyl$_{(C≤6)}$; and
- $A_2$ is aralkyl$_{(C≤12)}$ or substituted aralkyl$_{(C≤12)}$; or $$-A_3R_d;$$

wherein:
- $A_3$ is —O— or —NR$_e$—, wherein
  - $R_e$ is hydrogen, alkyl$_{(C≤6)}$, or substituted alkyl$_{(C≤6)}$; and
- $R_d$ is acyl$_{(C≤12)}$, or substituted acyl$_{(C≤12)}$;

or a pharmaceutically acceptable salt thereof.

In some embodiments, the compound is further defined as:

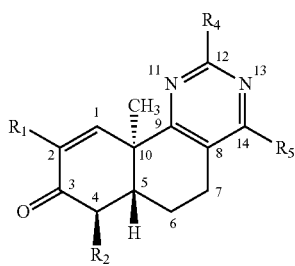

(VI)

wherein:
- $R_1$ is cyano, heteroaryl$_{(C≤8)}$, substituted heteroaryl$_{(C≤8)}$, —CF$_3$, or —C(O)R$_a$; wherein:
  - $R_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;

$R_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;

$R_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or $$—X_1—(CH_2)_m—R_{4'};$$

wherein:
- $X_1$ is NR$_b$, O, or S; wherein:
  - $R_b$ is hydrogen, alkyl$_{(C≤6)}$, or substituted alkyl$_{(C≤6)}$;
- m is 0, 1, 2, 3, or 4; and
- $R_{4'}$ is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when $X_1$ is O, then $R_{4'}$ is not methyl; or

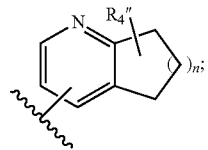

wherein:
- n is 0, 1, 2, 3, or 4; and
- $R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or $$—X_2—(CH_2)_p—R_{4'''};$$

wherein:
- $X_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
- p is 0, 1, 2, 3, or 4; and
- $R_{4'''}$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and $R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$-A$_1$;

wherein:
Y$_1$ is alkanediyl$_{(C≤8)}$ or substituted alkanediyl$_{(C≤8)}$; and
A$_1$ is cycloalkyl$_{(C≤8)}$ or substituted cycloalkyl$_{(C≤8)}$; or —Y$_2$—C(O)NR$_b$-A$_2$;

wherein:
Y$_2$ is arenediyl$_{(C≤8)}$ or substituted arenediyl$_{(C≤8)}$;
R$_b$ is hydrogen, alkyl$_{(C≤6)}$, or substituted alkyl$_{(C≤6)}$; and
A$_2$ is aralkyl$_{(C≤12)}$ or substituted aralkyl$_{(C≤12)}$; or -A$_3$R$_d$;

wherein:
A$_3$ is —O— or —NR$_e$—, wherein
R$_e$ is hydrogen, alkyl$_{(C≤6)}$, or substituted alkyl$_{(C≤6)}$; and
R$_d$ is acyl$_{(C≤12)}$, or substituted acyl$_{(C≤12)}$;
or a pharmaceutically acceptable salt thereof.

In some embodiments, the compound is further defined as:

(VII)

wherein:
R$_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;
R$_4$ is hydrogen, amino, alkyl$_{(C2-18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, alkylamino$_{(C≤18)}$, substituted alkylamino$_{(C≤18)}$, dialkylamino$_{(C≤18)}$, substituted dialkylamino$_{(C≤18)}$, alkylthio$_{(C≤18)}$, substituted alkylthio$_{(C≤18)}$, amido$_{(C≤18)}$, substituted amido$_{(C≤18)}$, or —X$_1$—(CF$_{12}$)$_m$—R$_{4'}$;

wherein:
X$_1$ is NR$_b$, O, or S; wherein:
R$_b$ is hydrogen, alkyl$_{(C≤6)}$, or substituted alkyl$_{(C≤6)}$;
m is 0, 1, 2, 3, or 4; and
R$_{4'}$ is alkyl$_{(C≤12)}$, cycloalkyl$_{(C≤18)}$, aryl$_{(C≤18)}$, aralkyl$_{(C≤18)}$, heteroaryl$_{(C≤18)}$, heteroaralkyl$_{(C≤18)}$, heterocycloalkyl$_{(C≤18)}$, or a substituted version of any of these groups, provided that when X$_1$ is O, then R$_{4'}$ is not methyl; or wherein:
n is 0, 1, 2, 3, or 4; and
R$_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_{4'''}$;

wherein:
X$_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
R$_{4'''}$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and
R$_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of the last fourteen groups, or

—OY$_1$-A$_1$;

wherein:
Y$_1$ is alkanediyl$_{(C≤8)}$ or substituted alkanediyl$_{(C≤8)}$; and
A$_1$ is cycloalkyl$_{(C≤8)}$ or substituted cycloalkyl$_{(C≤8)}$; or —Y$_2$—C(O)NR$_b$-A$_2$;

wherein:
Y$_2$ is arenediyl$_{(C≤8)}$ or substituted arenediyl$_{(C≤8)}$;
R$_b$ is hydrogen, alkyl$_{(C≤6)}$, or substituted alkyl$_{(C≤6)}$; and
A$_2$ is aralkyl$_{(C≤12)}$ or substituted aralkyl$_{(C≤12)}$; or -A$_3$R$_d$;

wherein:
A$_3$ is —O— or —NR$_e$—, wherein
R$_e$ is hydrogen, alkyl$_{(C≤6)}$, or substituted alkyl$_{(C≤6)}$; and
R$_d$ is acyl$_{(C≤12)}$, or substituted acyl$_{(C≤12)}$;
or a pharmaceutically acceptable salt thereof.

In some embodiments, the compound is further defined as:
In still further embodiments, $R_4$ is:

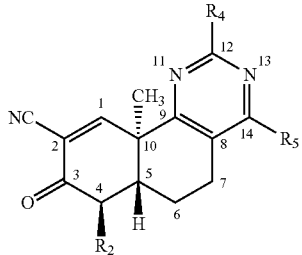

(VII)

wherein:
$R_2$ is hydrogen, alkyl$_{(C \leq 12)}$, or substituted alkyl$_{(C \leq 12)}$;
$R_4$ is heteroaryl$_{(C \leq 18)}$ or substituted heteroaryl$_{(C \leq 18)}$; and
$R_5$ is aryl$_{(C \leq 12)}$ or substituted aryl$_{(C \leq 12)}$;
or a pharmaceutically acceptable salt thereof.
In some embodiments, the compound is further defined as:

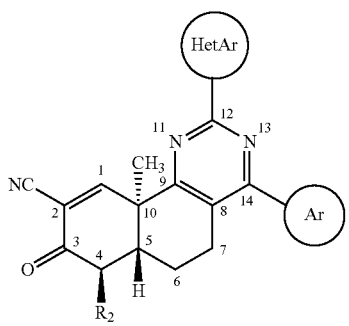

(VIII)

wherein:
$R_2$ is alkyl$_{(C \leq 12)}$ or substituted alkyl$_{(C \leq 12)}$;
HetAr is heteroaryl$_{(C \leq 18)}$ or substituted heteroaryl$_{(C \leq 18)}$; and
Ar is aryl$_{(C \leq 12)}$ or substituted aryl$_{(C \leq 12)}$;
or a pharmaceutically acceptable salt thereof.
In some embodiments, the compound is further defined as:

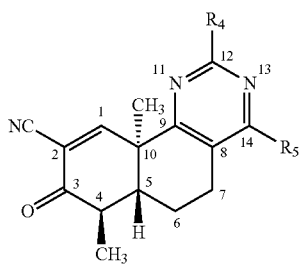

(IX)

wherein:
$R_4$ is heteroaryl$_{(C \leq 18)}$ or substituted heteroaryl$_{(C \leq 18)}$; and
$R_5$ is aryl$_{(C \leq 12)}$ or substituted aryl$_{(C \leq 12)}$;
or a pharmaceutically acceptable salt thereof.

In some embodiments, the inverse agonist is a compound of the formula:

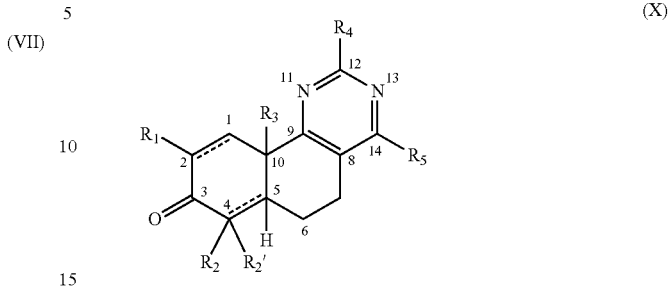

(X)

wherein:
the bond between carbon atoms 1 and 2 is an epoxidized double bond or a double bond;
the bond between carbon atoms 4 and 5 is a single bond or a double bond;
a is 0, 1, or 2;
$R_1$ is cyano, heteroaryl$_{(C \leq 8)}$, substituted heteroaryl$_{(C \leq 8)}$, —CF$_3$, or —C(O)R$_a$; wherein:
  $R_a$ is hydroxy, amino, or alkoxy$_{(C \leq 8)}$, alkylamino$_{(C \leq 8)}$, dialkylamino$_{(C \leq 8)}$, alkylsulfonylamino$_{(C \leq 8)}$, or a substituted version of any of these groups;
$R_2$ is hydrogen, alkyl$_{(C \leq 12)}$, cycloalkyl$_{(C \leq 12)}$, alkenyl$_{(C \leq 12)}$, alkynyl$_{(C \leq 12)}$, or a substituted version of the last four groups, or -alkanediyl$_{(C \leq 12)}$-cycloalkyl$_{(C \leq 12)}$ or a substituted version of this group;
$R_{2'}$ is absent, hydrogen, alkyl$_{(C \leq 12)}$, cycloalkyl$_{(C \leq 12)}$, alkenyl$_{(C \leq 12)}$, alkynyl$_{(C \leq 12)}$, or a substituted version of the last four groups, provided that when the bond between carbon atoms 4 and 5 is a double bond then $R_{2'}$ is absent;
$R_3$ is alkyl$_{(C \leq 12)}$, aryl$_{(C \leq 12)}$, aralkyl$_{(C \leq 12)}$, or a substituted version of any of these groups;
$R_4$ is cycloalkyl$_{(C \leq 18)}$, substituted cycloalkyl$_{(C \leq 18)}$, heteroaryl$_{(C \leq 18)}$, substituted heteroaryl$_{(C \leq 18)}$, heterocycloalkyl$_{(C \leq 18)}$, substituted heterocycloalkyl$_{(C \leq 18)}$, or —X$_1$—(CH$_2$)$_m$—R$_{4'}$;
wherein:
  $X_1$ is NR$_b$, O, or S; wherein:
    $R_b$ is hydrogen, alkyl$_{(C \leq 6)}$, or substituted alkyl$_{(C \leq 6)}$;
  m is 0, 1, 2, 3, or 4; and
  $R_{4'}$ is cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups; or

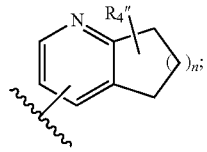

wherein:
n is 0, 1, 2, 3, or 4; and
$R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, alkylamino$_{(C \leq 8)}$, dialkylamino$_{(C \leq 8)}$, —C(O)-alkoxy$_{(C \leq 8)}$, —C(O)-alkylamino$_{(C \leq 8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or $$-X_2-(CH_2)_p-R_{4'''};$$

wherein:
  $X_2$ is arenediyl$_{(C≤12)}$, substituted arenediyl$_{(C≤12)}$, heterocycloalkyldiyl$_{(C≤12)}$, substituted heterocycloalkyldiyl$_{(C≤12)}$, heteroarenediyl$_{(C≤12)}$, or substituted heteroarenediyl$_{(C≤12)}$;
  p is 0, 1, 2, 3, or 4; and
  $R_{4'''}$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and
$R_5$ is cycloalkoxy$_{(C≤12)}$, aryl$_{(C≤12)}$, heteroaryl$_{(C≤12)}$, or a substituted version of any of the last three groups, or $$-OY_1-A_1;$$

wherein:
  $Y_1$ is alkanediyl$_{(C≤8)}$ or substituted alkanediyl$_{(C≤8)}$; and
  $A_1$ is cycloalkyl$_{(C≤8)}$ or substituted cycloalkyl$_{(C≤8)}$; or
  provided that when carbon atoms 4 and 5 are joined by a double bond, then $R_{2'}$ and the hydrogen atom at carbon atom 5 are absent;
or a pharmaceutically acceptable salt thereof.

In some embodiments, the bond between carbon atom 1 and carbon atom 2 is an epoxidized double bond. In other embodiments, the bond between carbon atom 1 and carbon atom 2 is a double bond. In some embodiments, the bond between carbon atom 4 and carbon atom 5 is a single bond. In other embodiments, the bond between carbon atom 4 and carbon atom 5 is a double bond. In some embodiments, a is 1. In other embodiments, a is 0. In still other embodiments, a is 2. In some embodiments, $R_1$ is cyano. In some embodiments, $R_2$ is alkyl$_{(C≤12)}$, alkenyl$_{(C≤12)}$, or a substituted version of either of these groups. In further embodiments, $R_2$ is alkyl$_{(C≤12)}$ or substituted alkyl$_{(C≤12)}$. In still further embodiments, $R_2$ is alkyl$_{(C≤12)}$, such as methyl, ethyl, or propyl. In some embodiments, $R_2$ is methyl. In other embodiments, $R_2$ is substituted alkyl$_{(C≤12)}$, such as 3-hydroxypropyl. In still other embodiments, $R_2$ is alkenyl$_{(C≤12)}$ or substituted alkenyl$_{(C≤12)}$. In further embodiments, $R_2$ is alkenyl$_{(C≤12)}$, such as 2-propenyl or 2-methyl-prop-2-enyl. In some embodiments, $R_{2'}$ is hydrogen. In other embodiments, $R_{2'}$ is alkyl$_{(C≤12)}$ or substituted alkyl$_{(C≤12)}$. In further embodiments, $R_{2'}$ is alkyl$_{(C≤12)}$, such as methyl. In some embodiments, $R_3$ is alkyl$_{(C≤12)}$, aryl$_{(C≤12)}$, or a substituted version of either of these groups. In further embodiments, $R_3$ is alkyl$_{(C≤12)}$ or substituted alkyl$_{(C≤12)}$. In still further embodiments, $R_3$ is alkyl$_{(C≤12)}$, such as methyl, propyl, or isopentyl. In some embodiments, $R_3$ is methyl. In other embodiments, $R_3$ is aryl$_{(C≤12)}$ or substituted aryl$_{(C≤12)}$. In further embodiments, $R_3$ is aryl$_{(C≤12)}$, such as phenyl.

In some embodiments, $R_4$ is alkyl$_{(C2-18)}$ or substituted alkyl$_{(C2-18)}$. In other embodiments, $R_4$ is aryl$_{(C≤18)}$, heteroaryl$_{(C≤18)}$, or a substituted version of either of these groups. In further embodiments, $R_4$ is heteroaryl$_{(C≤18)}$ or substituted heteroaryl$_{(C≤18)}$. In still further embodiments, $R_4$ is a heteroaryl$_{(C≤12)}$ or a substituted heteroaryl$_{(C≤12)}$ group wherein at least one of the heteroatoms in the aromatic ring is a nitrogen atom. In yet further embodiments, $R_4$ is heteroaryl$_{(C≤18)}$, such as 3-pyridinyl, 4-pyridinyl, 4-(2-cyclopropyl)-pyridinyl, 5-(2-cyclopropyl)-pyridinyl, 4-(2-morpholino)-pyridinyl, 4-(2-phenyl)-pyridinyl, 3-(5-methyl)-pyridinyl, 3-(6-methyl)-pyridinyl, 4-(2-methyl)-pyridinyl, 4-(3-methyl)-pyridinyl, 3-pyrazolo[1,5-a]pyridinyl, 3-(N-methyl)-pyrrolo[2,3-b]pyridinyl, 5-isoquinlinyl, 2-isoquinlinyl, 1-isoquinolinyl, 4-(2-phenyl)-pyridinyl, 5-(2-phenyl)-pyridinyl, 3-(5-methyl)-pyridinyl, 4-(3-methyl)-pyridinyl, 4-(3,5-dimethyl)-isoxazolyl, 4-(2-methyl)-pyridinyl, 4-(3-methyl)-pyridinyl, 3-(4-methyl)-pyridinyl, 4-(6-methyl)-pyrimidinyl, 6-(4-methyl)-pyrimidinyl, 4-pyridazinyl, 2-quinazolinyl, 4-quinazolinyl, 2-quinolinyl, 3-quinolinyl, 4-quinolinyl, 5-quinolinyl, 6-quinolinyl, 8-quinolinyl, 4-isoquinolinyl, 3-(8-methyl)-quinolinyl, 3-(1-methyl)-quinolinyl, 4-(2-methyl)-quinolinyl, 4-(2-isopropyl)-quinolinyl, 4-(6-methyl)-quinolinyl, 4-(7-methyl)-quinolinyl, 4-(8-methyl)-quinolinyl, 2-(N-methyl)-indolyl, 5-(2,4-dimethyl)-thiazolyl, or 5-(3-methyl)-oxadizolyl. In other embodiments, substituted heteroaryl$_{(C≤18)}$, such as 4-(2-trifluoromethyl)-pyridinyl, 4-(3-fluoro)-pyridinyl, 4-(2-methoxy)-pyridinyl, 4-(2-hydroxymethyl)-pyridinyl, 4-(2-acetylamino)-pyridinyl, 4-(2-fluoromethyl)-pyridinyl, 4-(2-acetamidylethyl)-pyridinyl, 4-(2-fluoromethyl)-quinolinyl, 4-(2-acetoxymethyl)-quinolinyl, 4-(2-formyl)-quinolinyl, 4-(6-fluoro)-quinolinyl, 4-(7-fluoro)-quinolinyl, 4-(8-fluoro)-quinolinyl, 4-(6,8-difluoro)-quinolinyl, 4-(6-fluoro-2-methyl)-quinolinyl, or 4-(8-fluoro-2-methyl)-quinolinyl. In still other embodiments, $R_4$ is aryl$_{(C≤12)}$ or substituted aryl$_{(C≤12)}$. In further embodiments, $R_4$ is aryl$_{(C≤12)}$, such as phenyl. In yet other embodiments, $R_4$ is substituted aryl$_{(C≤12)}$, such as 2-fluorophenyl or 4-trifluoromethylphenyl. In other embodiments, $R_4$ is cycloalkyl$_{(C≤12)}$ or substituted cycloalkyl$_{(C≤12)}$. In further embodiments, $R_4$ is cycloalkyl$_{(C≤12)}$, such as cyclohexyl. In still other embodiments, $R_4$ is:

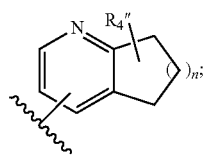

wherein:
  n is 0, 1, 2, 3, or 4; and
  $R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups.

In further embodiments, $R_4$ is:

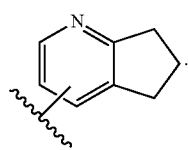

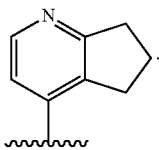 [SMILES: *c1ccnc2c1CCC2]

In yet other embodiments, $R_4$ is heterocycloalkyl$_{(C \leq 18)}$ or substituted heterocycloalkyl$_{(C \leq 18)}$. In further embodiments, $R_4$ is heterocycloalkyl$_{(C \leq 12)}$, such as morpholinyl, 4-piperidinyl, 3-(5-methyl-)1,2,3,6-tetrahydropyridinyl, or 4-N-methylpiperazinyl. In other embodiments, $R_4$ is substituted heterocycloalkyl$_{(C \leq 12)}$, such as N-t-butyloxycarbonyl-4-piperidinyl, N-acetyl-4-piperidinyl, N-t-butyloxycarbonyl-5-methyl-1,2,3,6-tetrahydropyridinyl, N-acetyl-5-methyl-1,2,3,6-tetrahydropyridinyl, or 4-N-acetylpiperazinyl. In still other embodiments, $R_4$ is hydrogen. In yet other embodiments, $R_4$ is —$X_1$—$(CH_2)_m$—$R_{4'}$; wherein:
 $X_1$ is $NR_b$, O, or S; wherein:
  $R_b$ is hydrogen, alkyl$_{(C \leq 6)}$, or substituted alkyl$_{(C \leq 6)}$;
  m is 0, 1, 2, 3, or 4; and
  $R_{4'}$ is alkyl$_{(C \leq 12)}$, cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups, provided that when $X_1$ is O, then $R_{4'}$ is not methyl.

In some embodiments, $X_1$ is $NR_b$, wherein: $R_b$ is hydrogen, alkyl$_{(C \leq 6)}$, or substituted alkyl$_{(C \leq 6)}$. In further embodiments, $R_b$ is hydrogen. In some embodiments, m is 0 or 1. In some embodiments, m is 0. In some embodiments, $R_{4'}$ is cycloalkyl$_{(C \leq 18)}$, aryl$_{(C \leq 18)}$, aralkyl$_{(C \leq 18)}$, heteroaryl$_{(C \leq 18)}$, heteroaralkyl$_{(C \leq 18)}$, heterocycloalkyl$_{(C \leq 18)}$, or a substituted version of any of these groups. In further embodiments, $R_{4'}$ is heteroaryl$_{(C \leq 12)}$ or substituted heteroaryl$_{(C \leq 12)}$. In still further embodiments, $R_{4'}$ is heteroaryl$_{(C \leq 12)}$, such as 4-pyridinyl. In other embodiments, $R_4$ is amino. In still other embodiments, $R_4$ is amido$_{(C \leq 12)}$ or substituted amido$_{(C \leq 12)}$. In further embodiments, $R_4$ is amido$_{(C \leq 12)}$, such as:

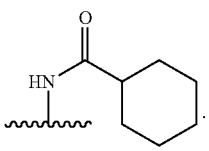 [SMILES: *NC(=O)C1CCCCC1]

In other embodiments, $R_4$ is —$X_2$—$(CH_2)_p$—$R_{4'''}$; wherein:
 $X_2$ is arenediyl$_{(C \leq 12)}$, substituted arenediyl$_{(C \leq 12)}$, heterocycloalkanediyl$_{(C \leq 12)}$, substituted heterocycloalkanediyl$_{(C \leq 12)}$, heteroarenediyl$_{(C \leq 12)}$, or substituted heteroarenediyl$_{(C \leq 12)}$;
 p is 0, 1, 2, 3, or 4; and
 $R_{4'''}$ is alkyl$_{(C \leq 8)}$, cycloalkyl$_{(C \leq 8)}$, aryl$_{(C \leq 8)}$, heteroaryl$_{(C \leq 8)}$, heterocycloalkyl$_{(C \leq 8)}$, acyl$_{(C \leq 8)}$, amido$_{(C \leq 8)}$, alkoxy$_{(C \leq 8)}$, acyloxy$_{(C \leq 8)}$, —C(O)-alkoxy$_{(C \leq 8)}$, —C(O)-alkylamino$_{(C \leq 8)}$, —C(O)-dialkylamino$_{(C \leq 8)}$, alkylsulfonyl$_{(C \leq 8)}$, arylsulfonyl$_{(C \leq 8)}$, alkoxysulfonyl$_{(C \leq 8)}$, or a substituted version of any of these groups.

In some embodiments, $X_2$ is heteroarenediyl$_{(C \leq 12)}$ or substituted heteroarenediyl$_{(C \leq 12)}$. In further embodiments, $X_2$ is heteroarenediyl$_{(C \leq 12)}$, such as pyridin-2,4-diyl or pyridine-2,5-diyl. In still other embodiments, $X_2$ is heterocycloalkanediyl$_{(C \leq 12)}$ or substituted heterocycloalkanediyl$_{(C \leq 12)}$. In further embodiments, $X_2$ is heterocycloalkanediyl$_{(C \leq 12)}$, such as piperidin-1,4-diyl, piperazin-1,4-diyl, or 1,2,3,6-tetrahydropiperidin-1,5-diyl. In some embodiments, p is 0, 1, or 2. In other embodiments, p is 0. In other embodiments, p is 1. In still other embodiments, p is 2. In some embodiments, $R_{4'''}$ is acyl$_{(C \leq 8)}$ or substituted acyl$_{(C \leq 8)}$. In further embodiments, $R_{4'''}$ is acyl$_{(C \leq 8)}$, such as acetyl. In yet other embodiments, $R_{4'''}$ is substituted acyl$_{(C \leq 8)}$. In some embodiments, $R_{4'''}$ is carboxy. In other embodiments, $R_{4'''}$ is amido$_{(C \leq 8)}$ or substituted amido$_{(C \leq 8)}$. In further embodiments, $R_{4'''}$ is amido$_{(C \leq 8)}$, such as acetamidyl. In still other embodiments, $R_{4'''}$ is cycloalkyl$_{(C \leq 8)}$ or substituted cycloalkyl$_{(C \leq 8)}$. In further embodiments, $R_{4'''}$ is cycloalkyl$_{(C \leq 8)}$, such as cyclopropyl. In yet other embodiments, $R_{4'''}$ is alkylsulfonyl$_{(C \leq 8)}$ or substituted alkylsulfonyl$_{(C \leq 8)}$. In further embodiments, $R_{4'''}$ is alkylsulfonyl$_{(C \leq 8)}$, such as —S(O)$_2$CH$_3$ or —S(O)$_2$CH$_2$CH$_3$. In other embodiments, $R_{4'''}$ is —C(O)-alkoxy$_{(C \leq 8)}$, such as —C(O)OEt. In still other embodiments, $R_{4'''}$ is —C(O)-dialkylamino$_{(C \leq 8)}$, such as —C(O)NMe$_2$.

In some embodiments, $R_5$ is aryl$_{(C \leq 12)}$, heteroaryl$_{(C \leq 12)}$, or a substituted version of either of these groups. In further embodiments, $R_5$ is aryl$_{(C \leq 12)}$ or substituted aryl$_{(C \leq 12)}$. In still further embodiments, $R_5$ is aryl$_{(C \leq 12)}$, such as phenyl, 4-methylphenyl, 3-isopropylphenyl, 4-isopropylphenyl, 1,3-biphenyl, or 1,4-biphenyl. In some embodiments, $R_5$ further comprises one or more fluorine atoms. In some embodiments, $R_5$ is substituted aryl$_{(C \leq 12)}$, such as $R_5$ is 2-fluorophenyl, 3-fluorophenyl, 4-fluorophenyl, 2,4-difluorophenyl, 4-hydroxymethylphenyl, 3-trifluoromethylphenyl, 4-trifluoromethylphenyl, 4-methoxyphenyl, 4-chlorophenyl, or 3,4-dichlorophenyl. In other embodiments, $R_5$ is cycloalkyl$_{(C \leq 12)}$, such as cyclopropyl, or substituted cycloalkyl$_{(C \leq 12)}$. In still other embodiments, $R_5$ is cycloalkoxy$_{(C \leq 12)}$, such as cyclobutyloxy, cyclopentyloxy, or cyclohexyloxy, or substituted cycloalkoxy$_{(C \leq 12)}$. In yet other embodiments, $R_5$ is alkylamino$_{(C \leq 12)}$, dialkylamino$_{(C \leq 12)}$, or a substituted version of either of these groups. In further embodiments, $R_5$ is dialkylamino$_{(C \leq 12)}$ or substituted dialkylamino$_{(C \leq 12)}$. In still further embodiments, $R_5$ is dialkylamino$_{(C \leq 8)}$, such as dimethylamino, or substituted dialkylamino$_{(C \leq 8)}$. In other embodiments, $R_5$ is alkylsulfonylamino$_{(C \leq 12)}$ or substituted alkylsulfonylamino$_{(C \leq 12)}$. In further embodiments, $R_6$ is methylsulfonylamino. In still other embodiments, $R_5$ is —$OY_1$-A; wherein:
 $Y_1$ is alkanediyl$_{(C \leq 8)}$ or substituted alkanediyl$_{(C \leq 8)}$; and
 $A_1$ is cycloalkyl$_{(C \leq 8)}$ or substituted cycloalkyl$_{(C \leq 8)}$.

In some embodiments, $Y_1$ is methylene. In some embodiments, $A_1$ is cyclobutyl. In some embodiments, $R_5$ is:

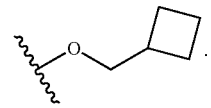 [SMILES: *OCC1CCC1]

In other embodiments, $R_5$ is —$Y_2$—C(O)NR$_c$-A$_2$; wherein:
 $Y_2$ is arenediyl$_{(C \leq 8)}$ or substituted arenediyl$_{(C \leq 8)}$;
 $R_c$ is hydrogen, alkyl$_{(C \leq 6)}$, or substituted alkyl$_{(C \leq 6)}$; and
 $A_2$ is aralkyl$_{(C \leq 12)}$ or substituted aralkyl$_{(C \leq 12)}$.

In some embodiments, $Y_2$ is arenediyl$_{(C \leq 8)}$, such as benzenediyl. In some embodiments, $R_c$ is alkyl$_{(C \leq 6)}$, such as methyl. In some embodiments, $A_2$ is aralkyl$_{(C \leq 12)}$, such as benzyl. In still other embodiments, $R_5$ is heteroaryl$_{(C \leq 12)}$ or substituted heteroaryl$_{(C \leq 12)}$. In further embodiments, $R_5$ is heteroaryl$_{(C \leq 12)}$, such as 5-(3-methyl)-oxadiazolyl, 4-(3,5-dimethyl)-isoxazolyl, furanyl, benzofuranyl, 2-thiazolyl, 5-(2-methyl)-furanyl, 3-pyridinyl, or 4-pyridinyl. In yet other embodiments, $R_5$ is hydroxy. In other embodiments, $R_5$ is $OS(O)_2C_6H_4CH_3$. In still other embodiments, $R_5$ is heterocycloalkyl$_{(C≤12)}$ or substituted heterocycloalkyl$_{(C≤12)}$. In further embodiments, $R_5$ is heterocycloalkyl$_{(C≤12)}$, such as pyrrolidinyl. In yet other embodiments, $R_5$ is alkoxy$_{(C≤12)}$ or substituted alkoxy$_{(C≤12)}$. In further embodiments, $R_5$ is alkoxy$_{(C≤12)}$, such as methoxy or isopropoxy. In other embodiments, $R_5$ is aralkyl$_{(C≤12)}$ or substituted aralkyl$_{(C≤12)}$. In further embodiments, $R_5$ is aralkyl$_{(C≤12)}$, such as benzyl.

In some embodiments, the compound is further defined as:

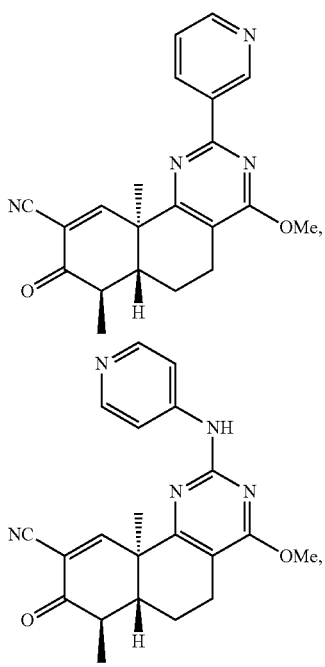

-continued

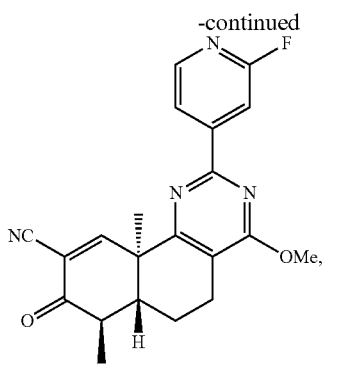

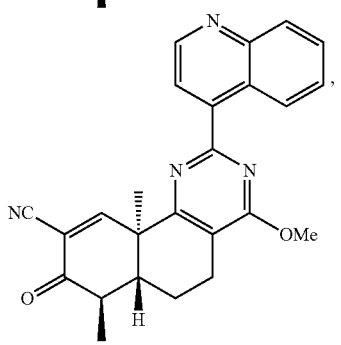

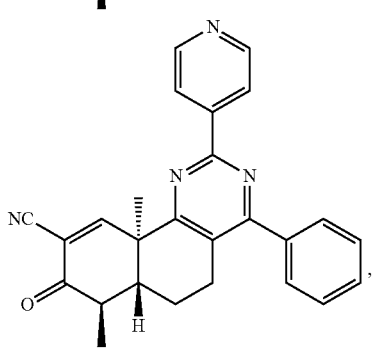

-continued
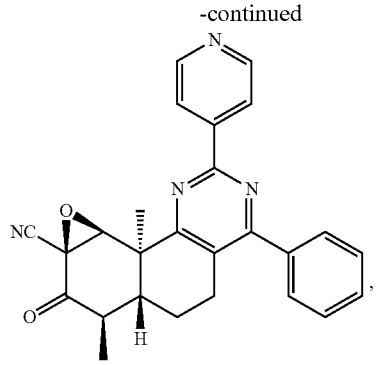
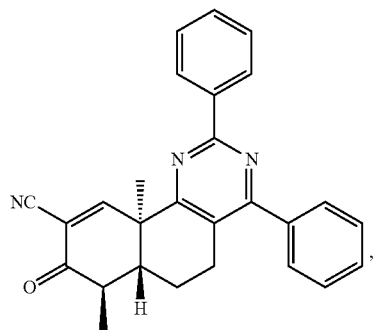
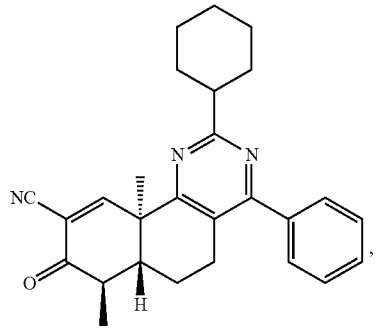
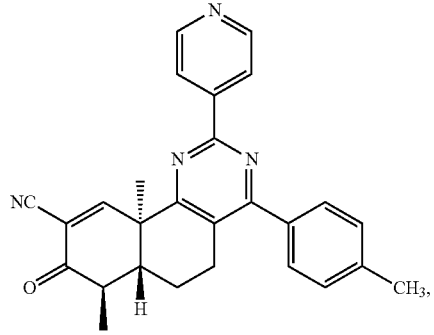
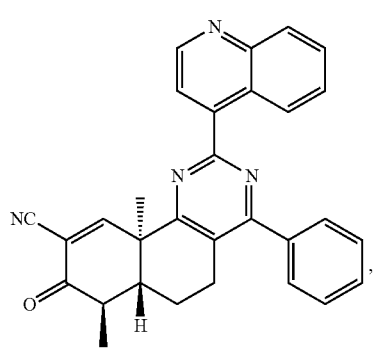
-continued
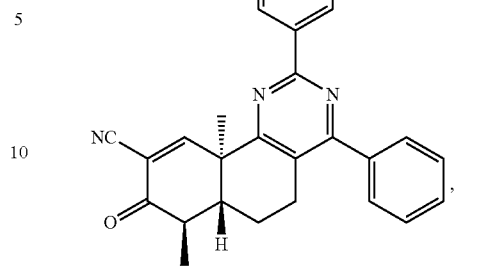
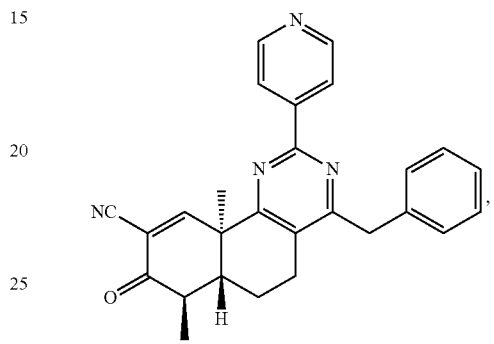
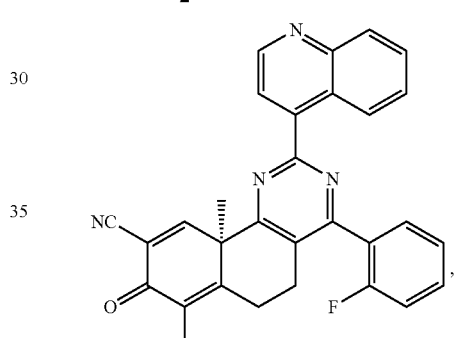
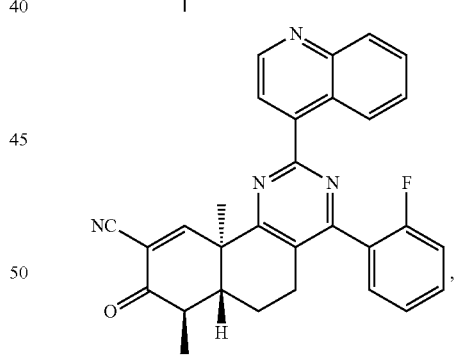
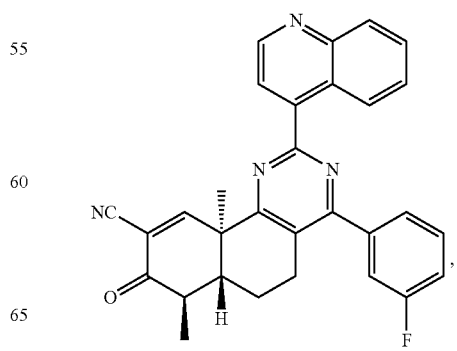

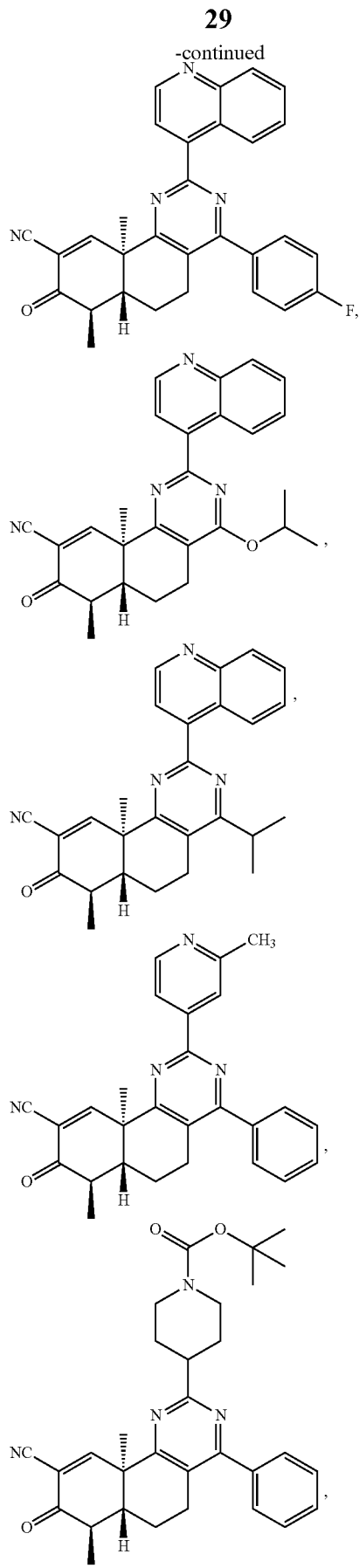
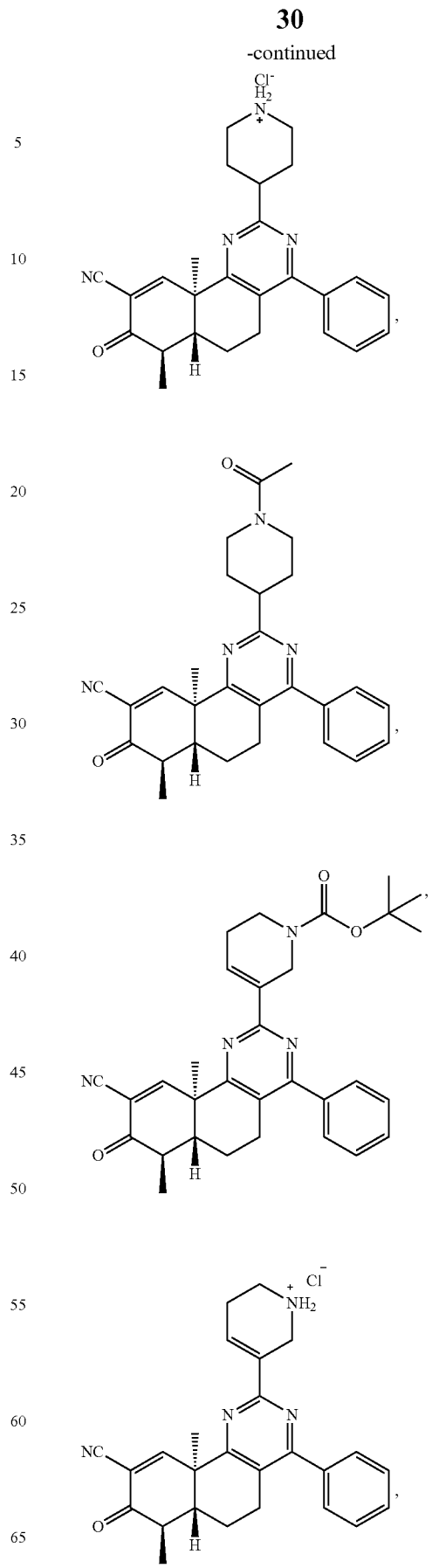

31
-continued
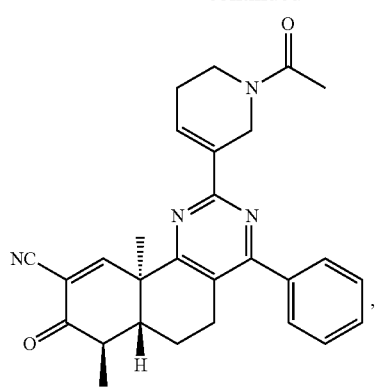
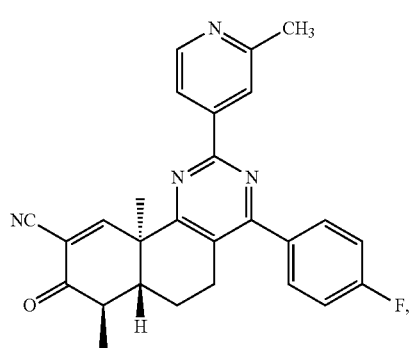
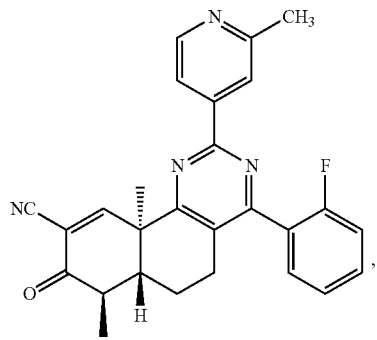
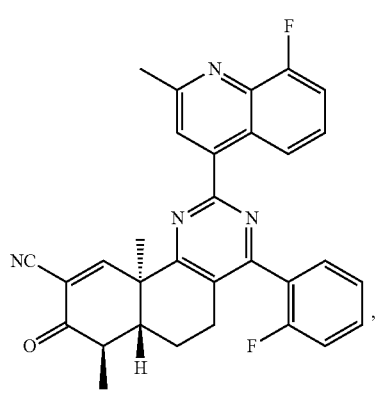
32
-continued
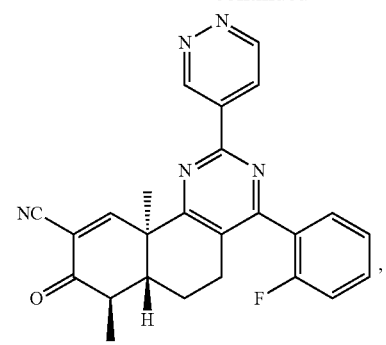
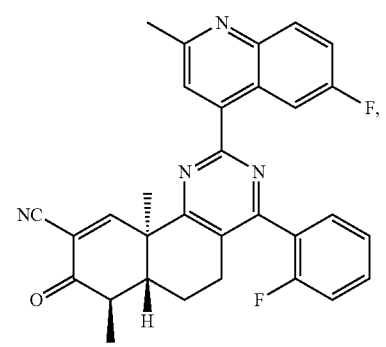
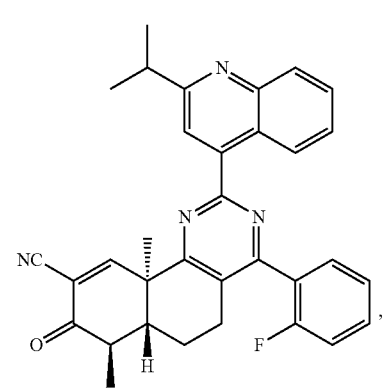
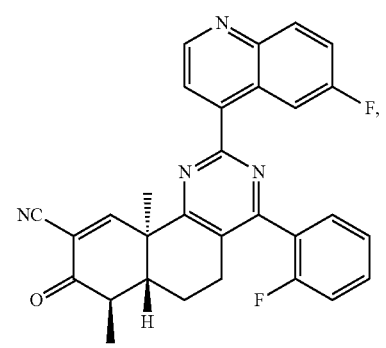

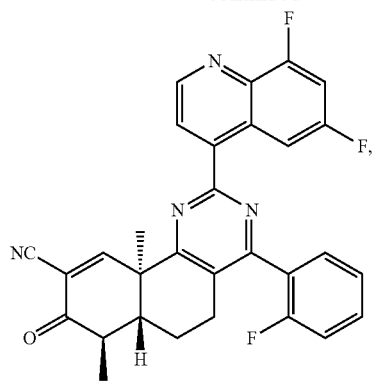
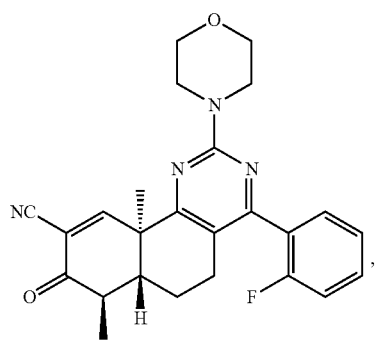
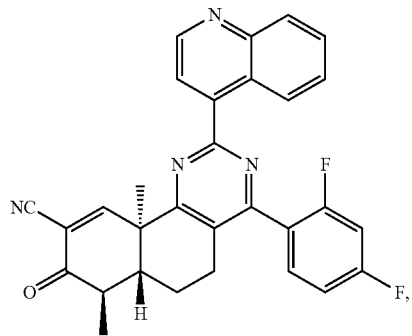
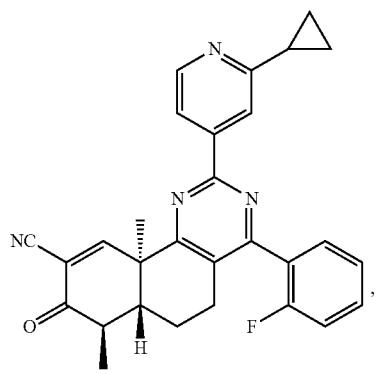
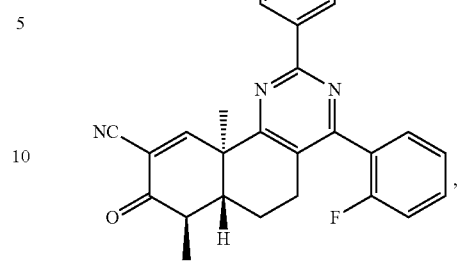
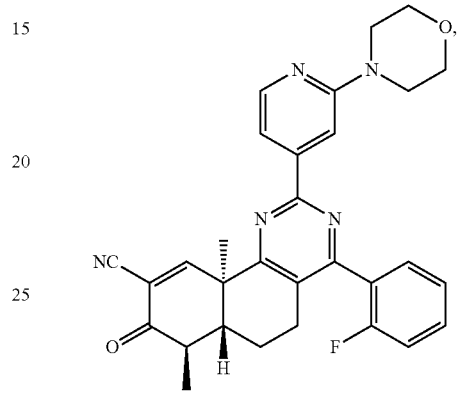
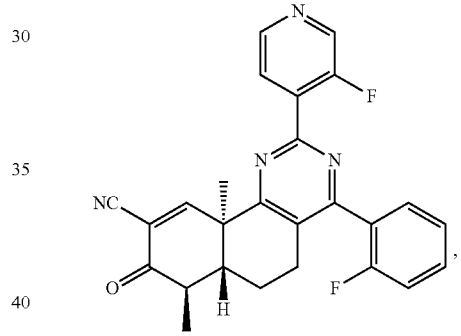
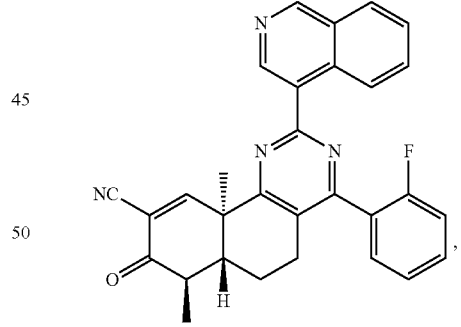
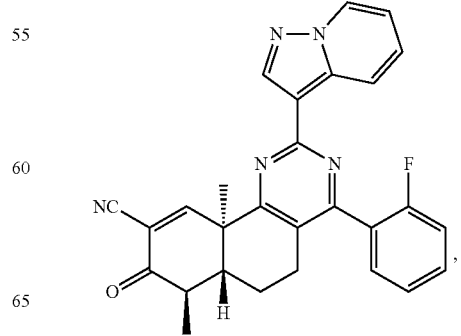

35
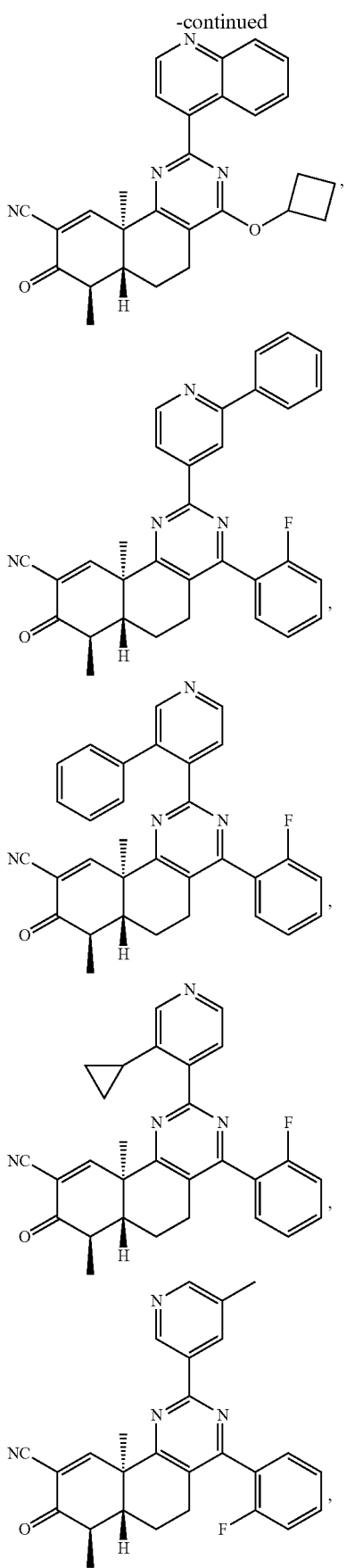
36
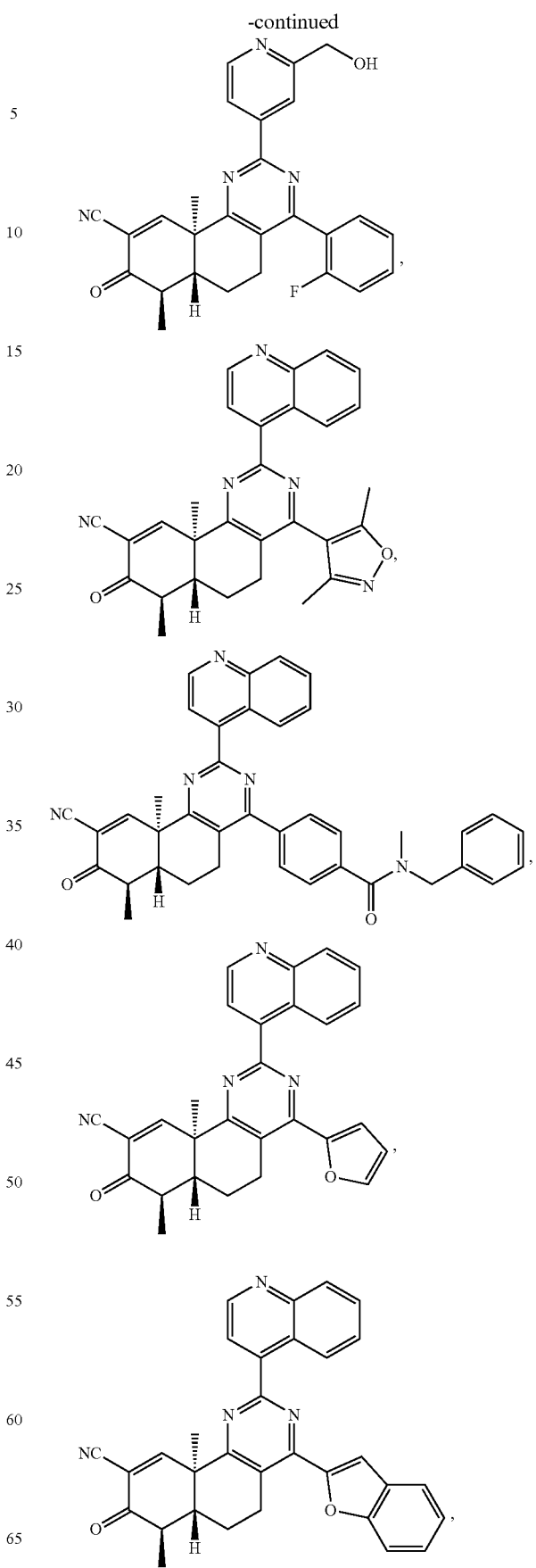

-continued
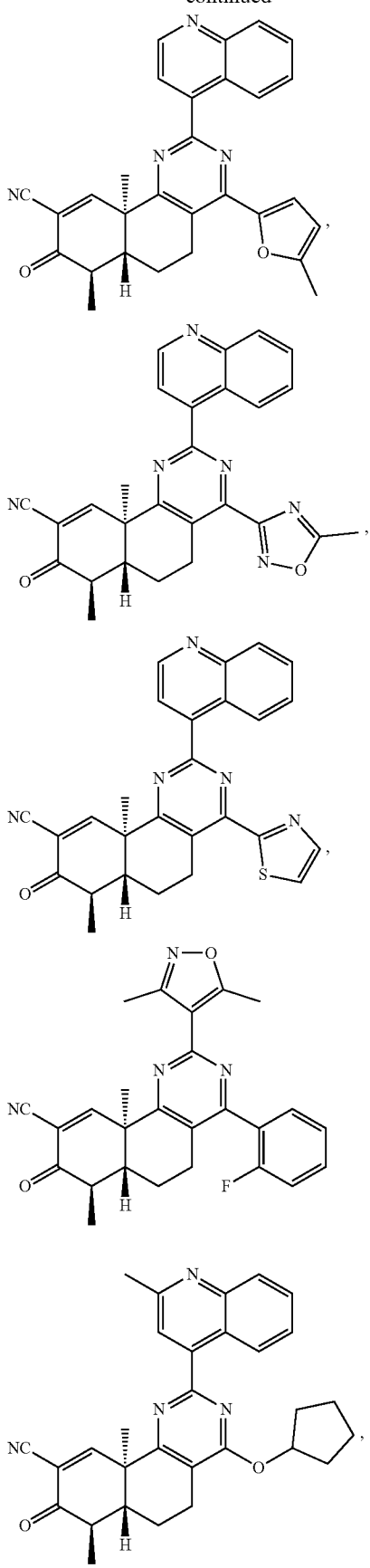
-continued
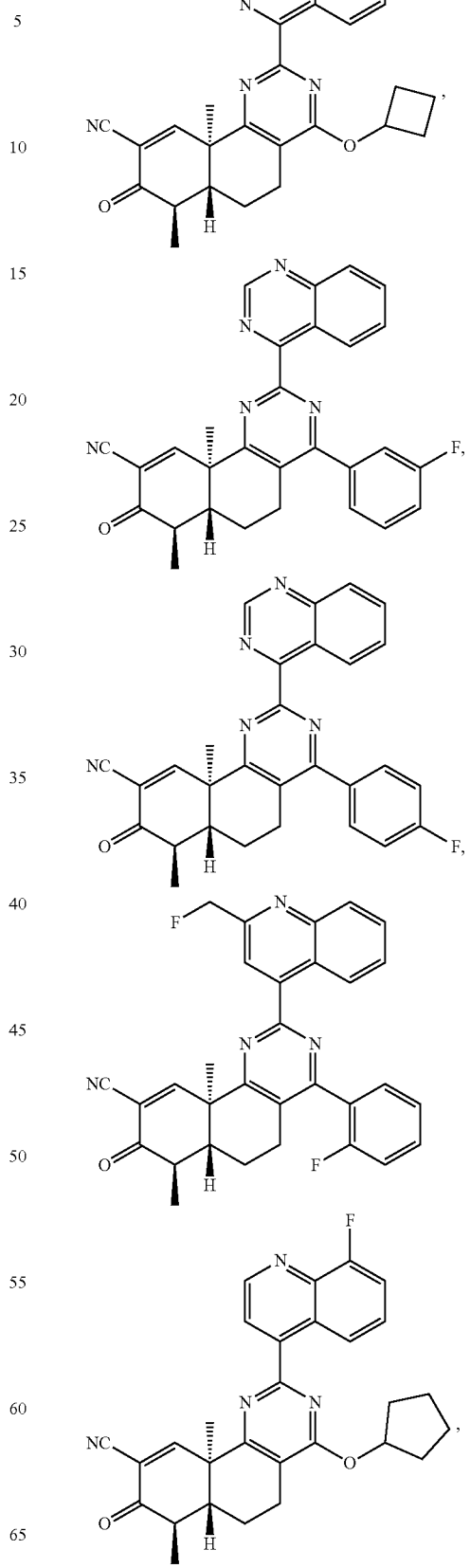

39
-continued
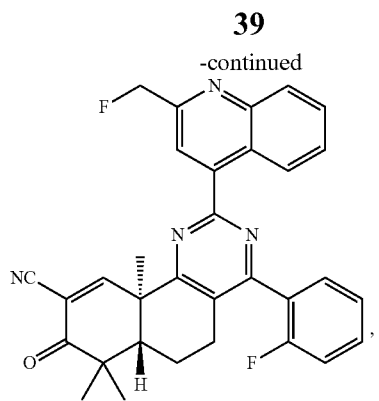
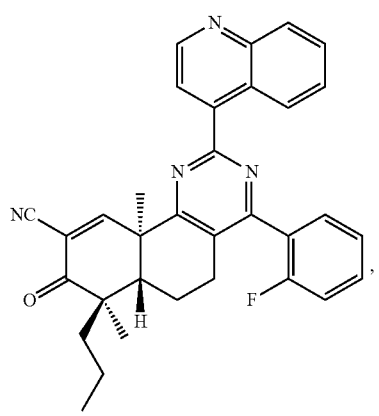
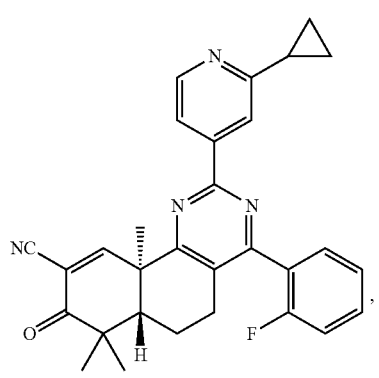
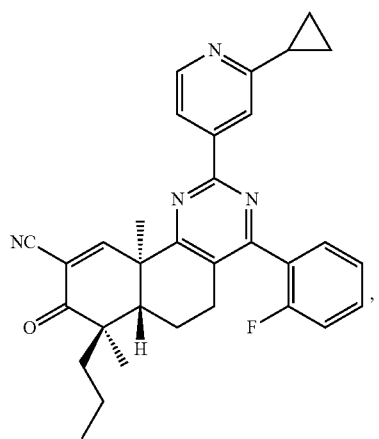
40
-continued
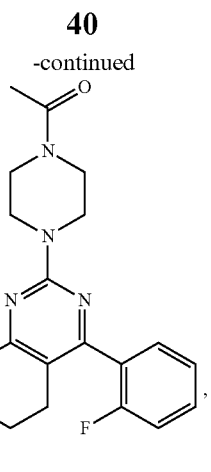
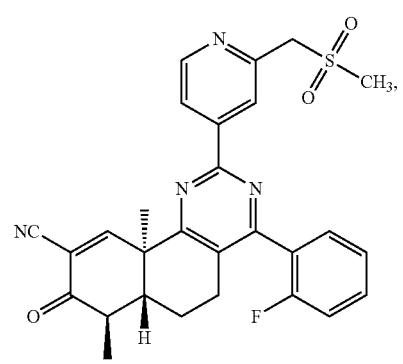
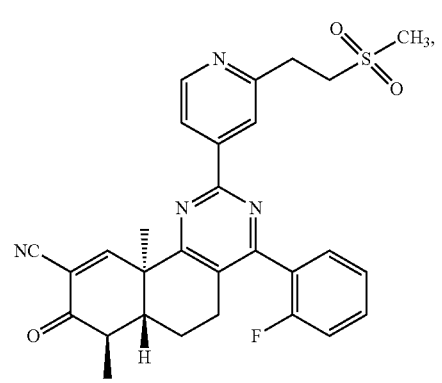
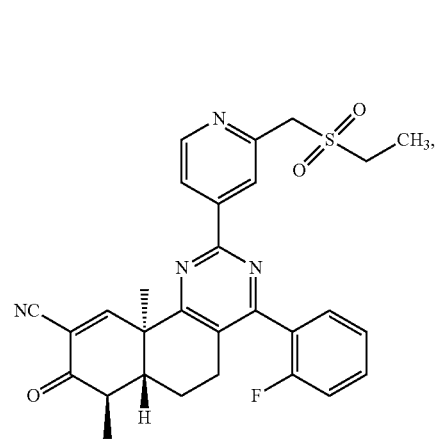

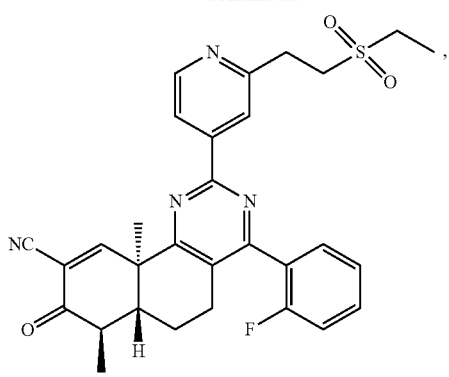
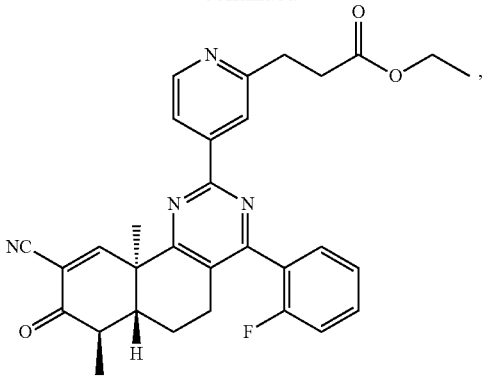
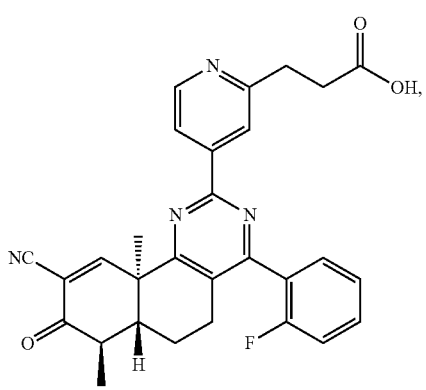
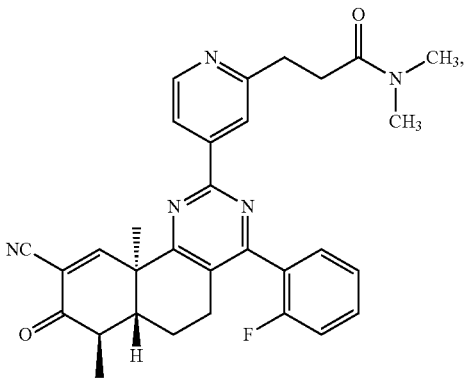
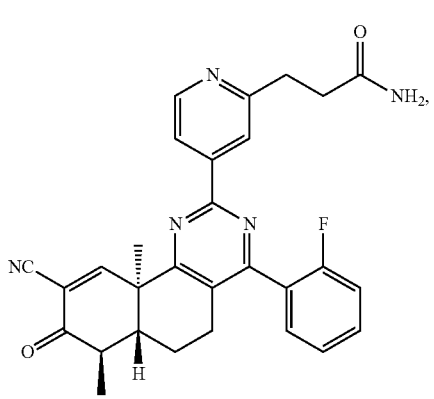
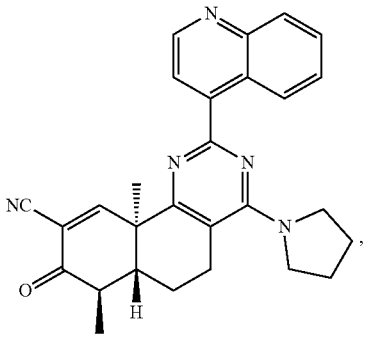
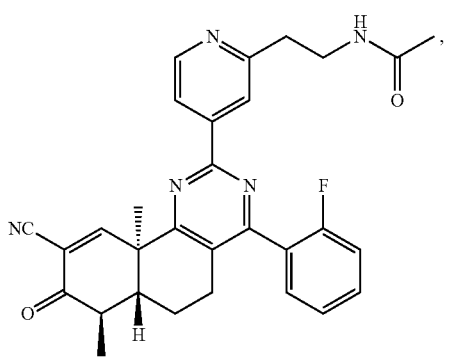
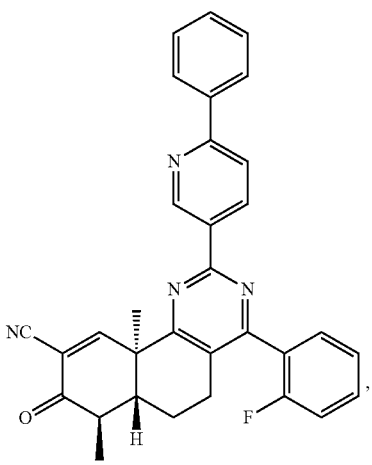

43
-continued
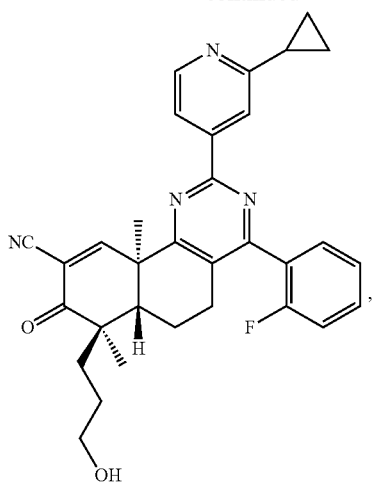
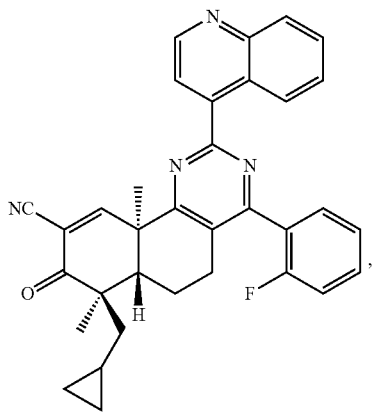
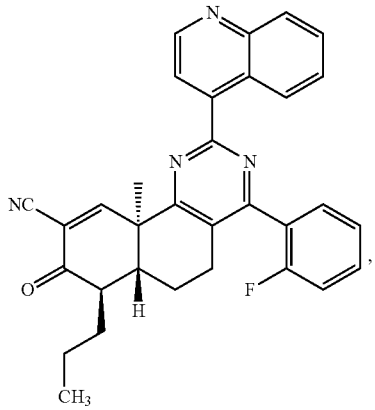
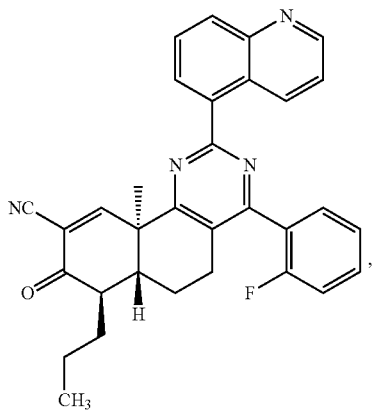
44
-continued
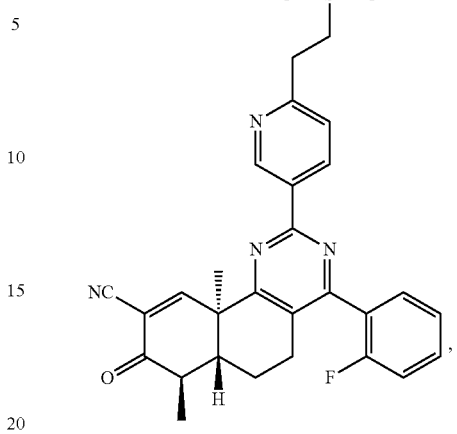
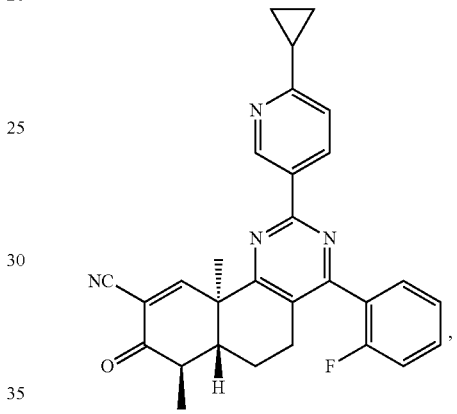
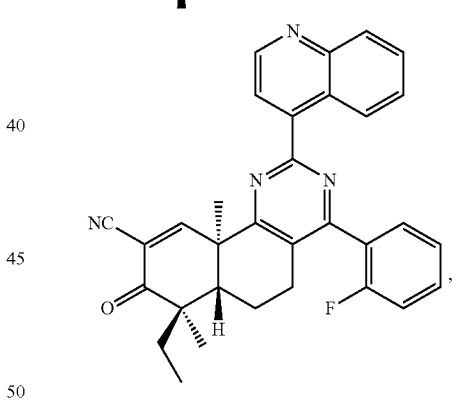
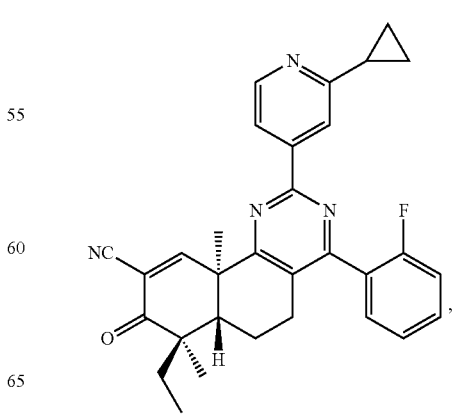

-continued
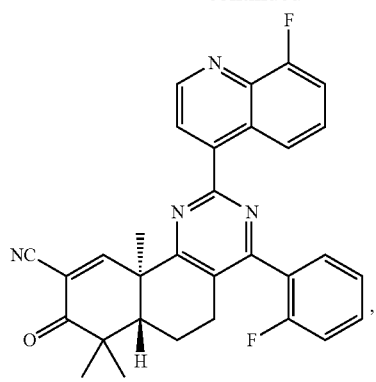
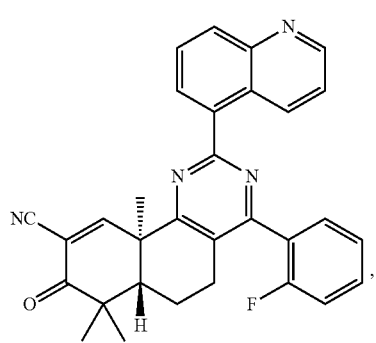
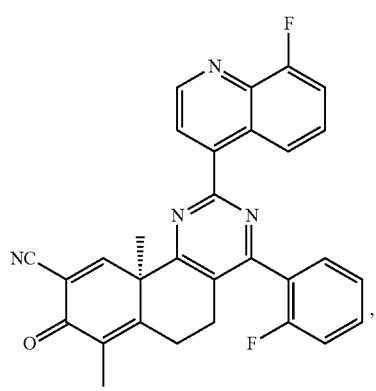
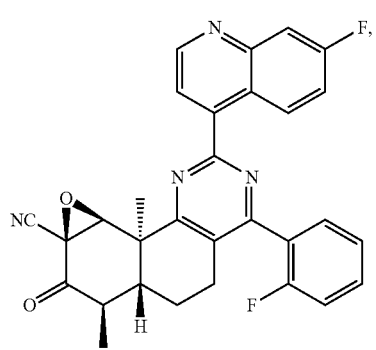
-continued
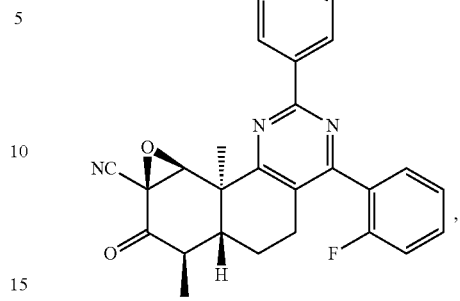
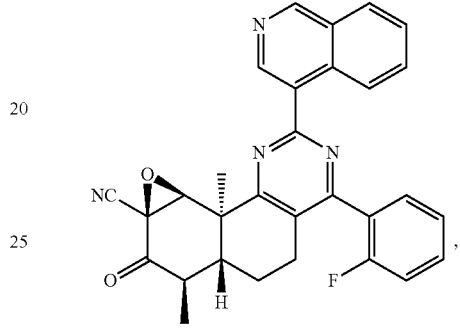
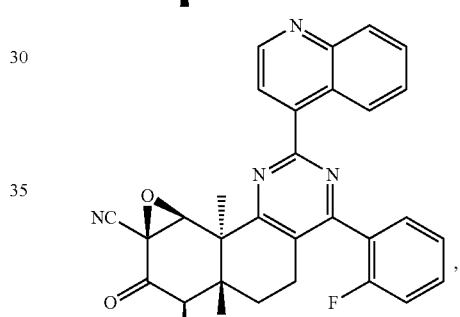
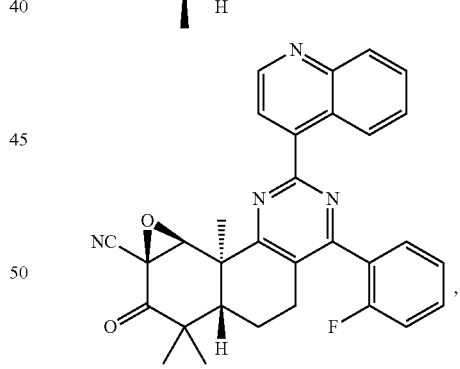
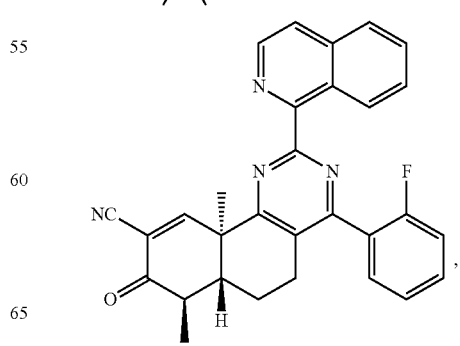

-continued
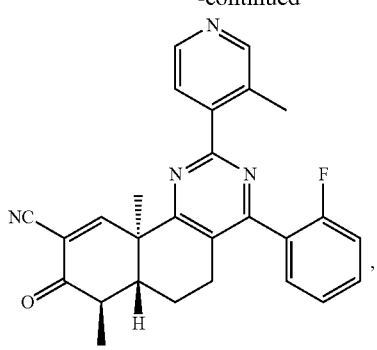
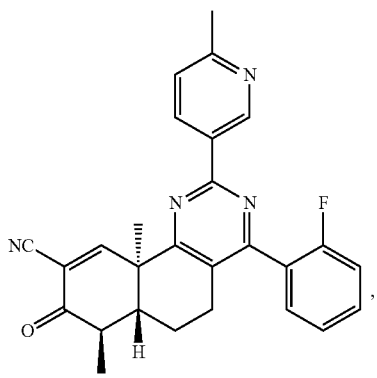
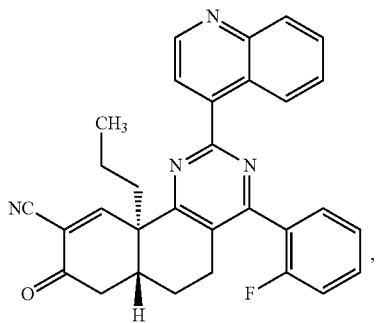
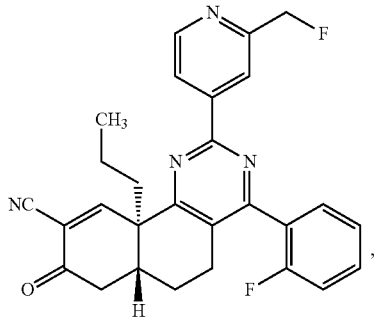
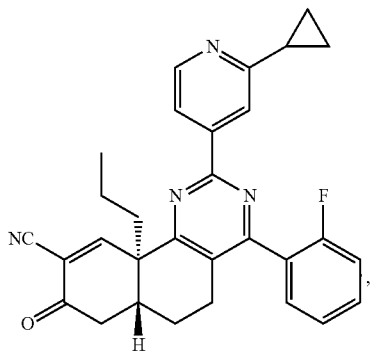
-continued
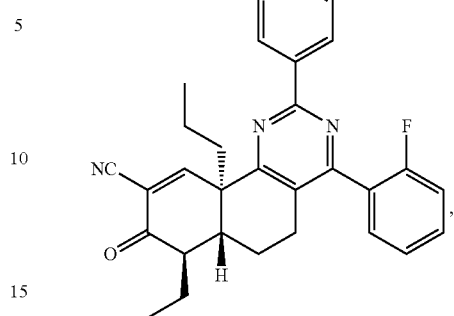
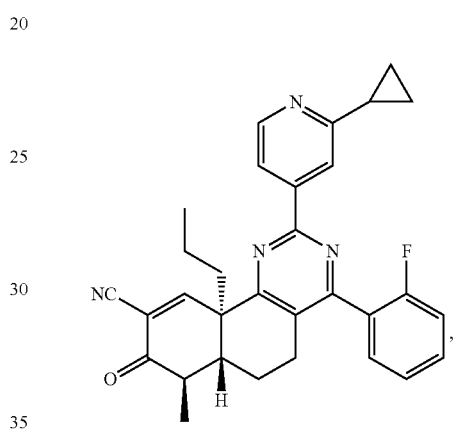
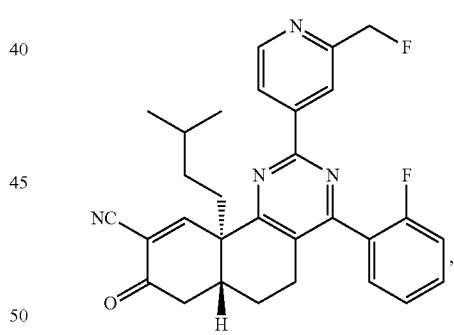
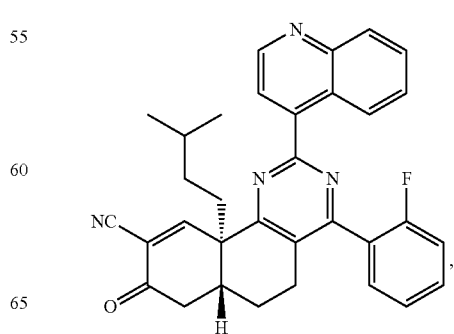

49
-continued
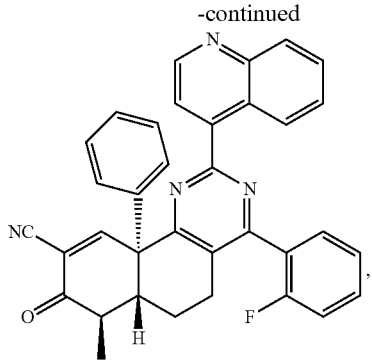
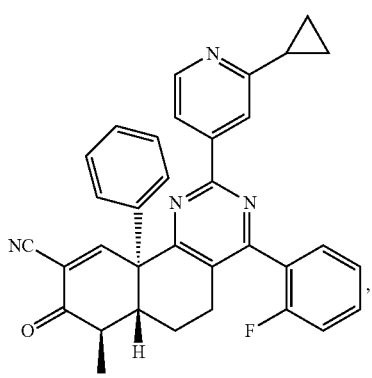
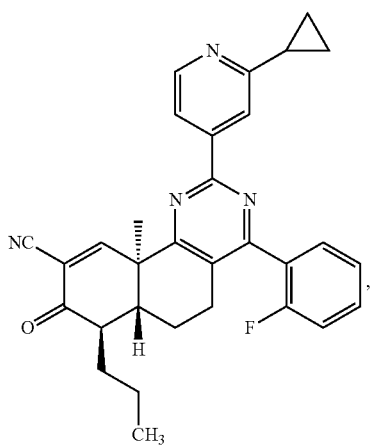
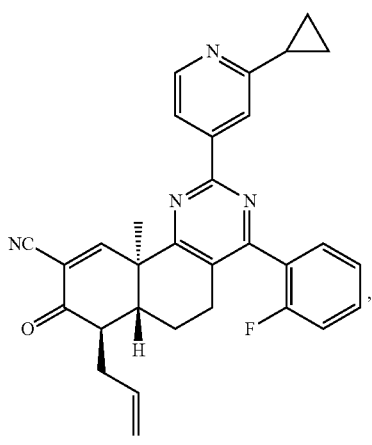
50
-continued
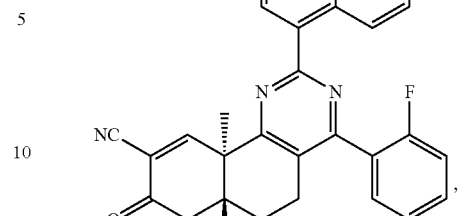
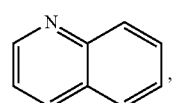
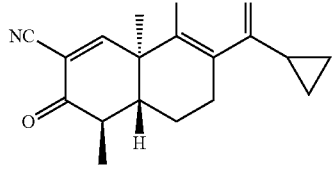
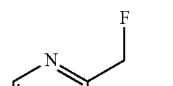
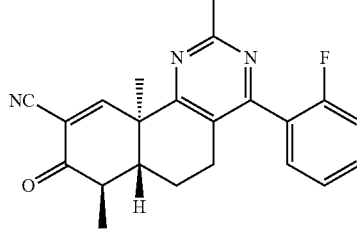
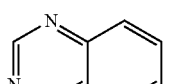
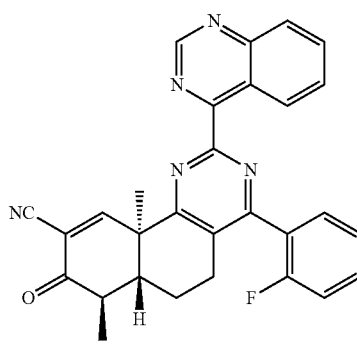

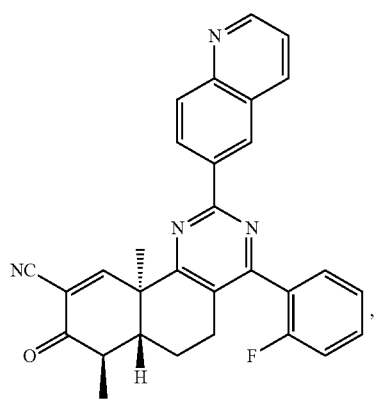
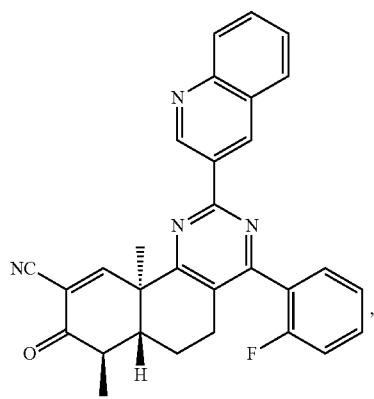
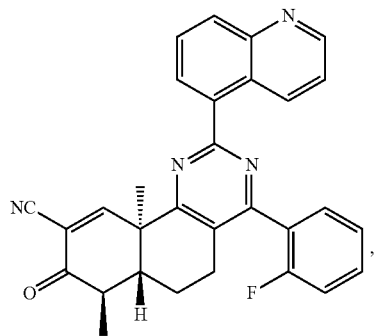
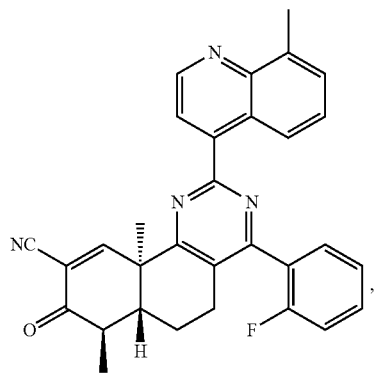
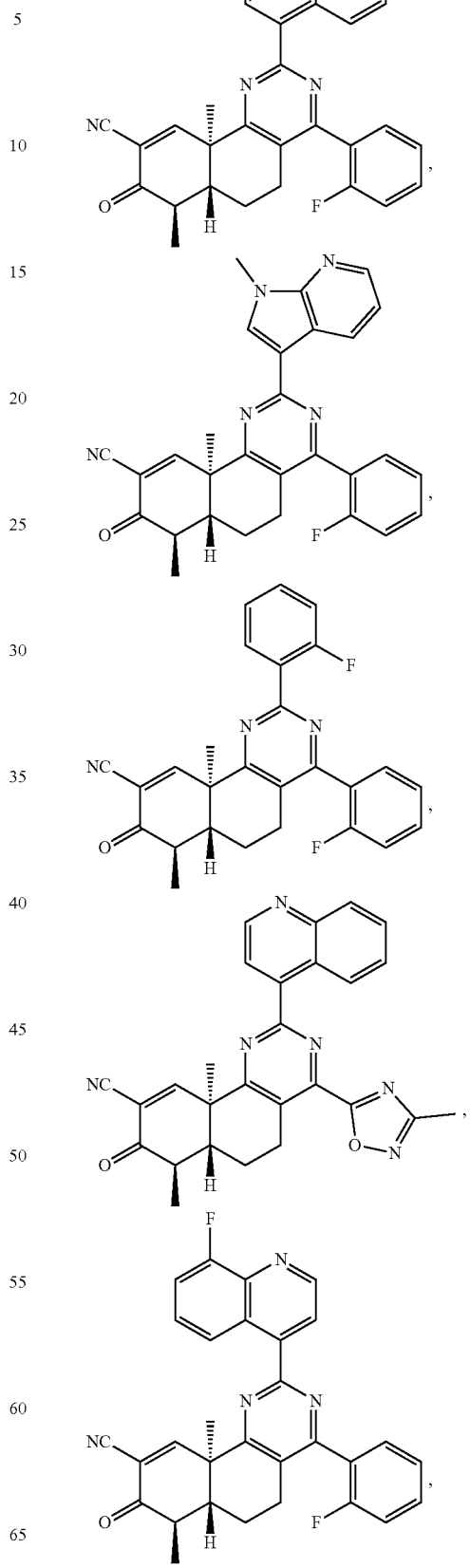

53
-continued
54
-continued
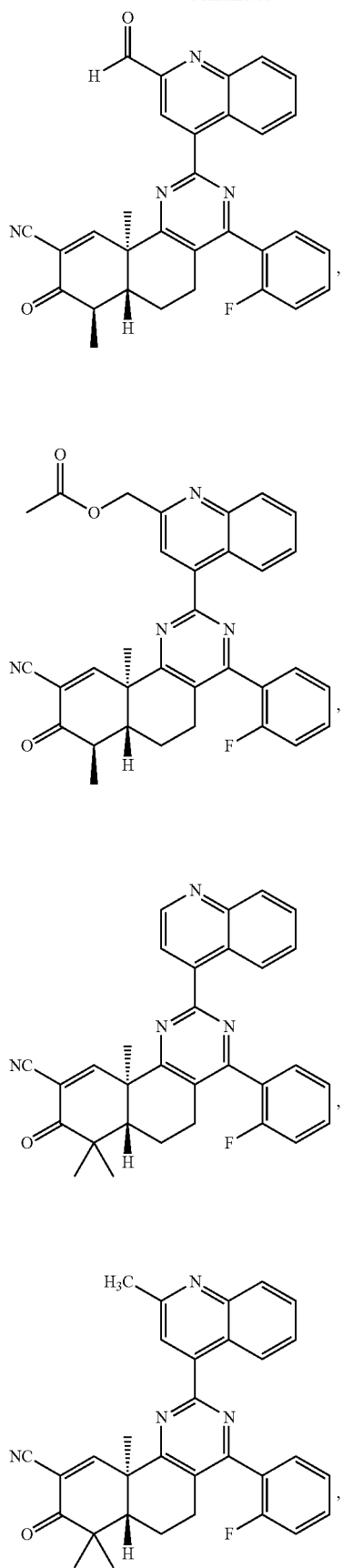
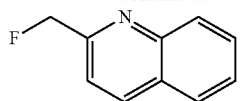
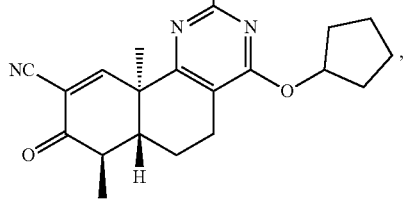
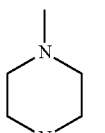
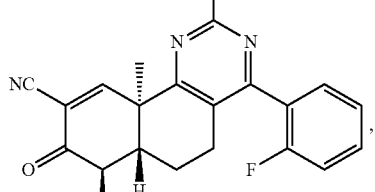
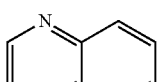
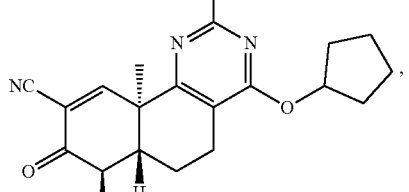
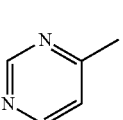
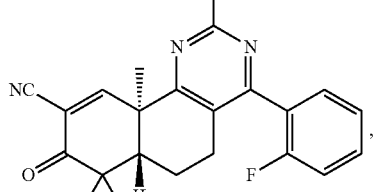
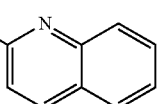
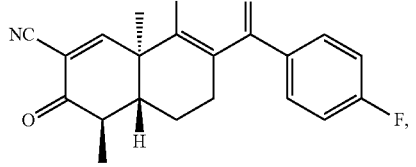

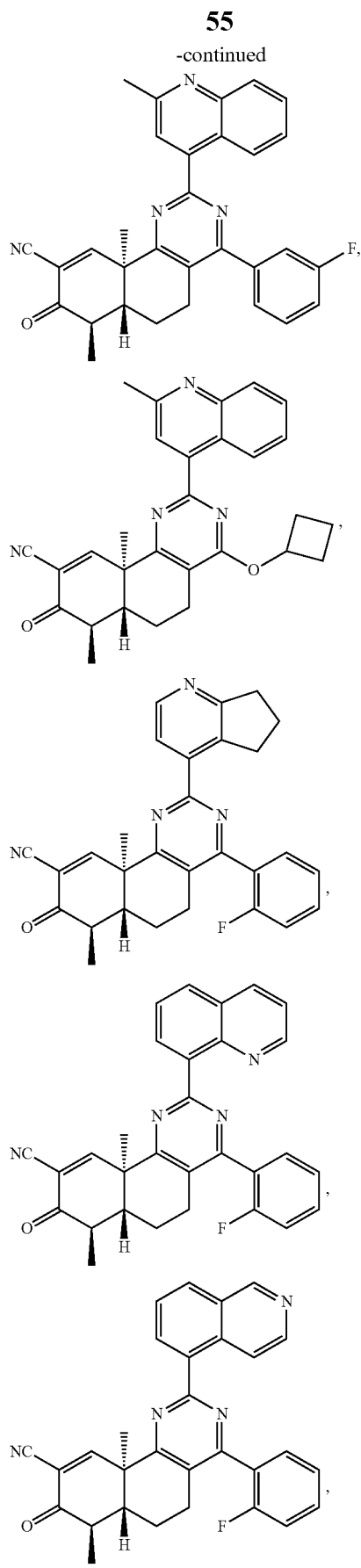
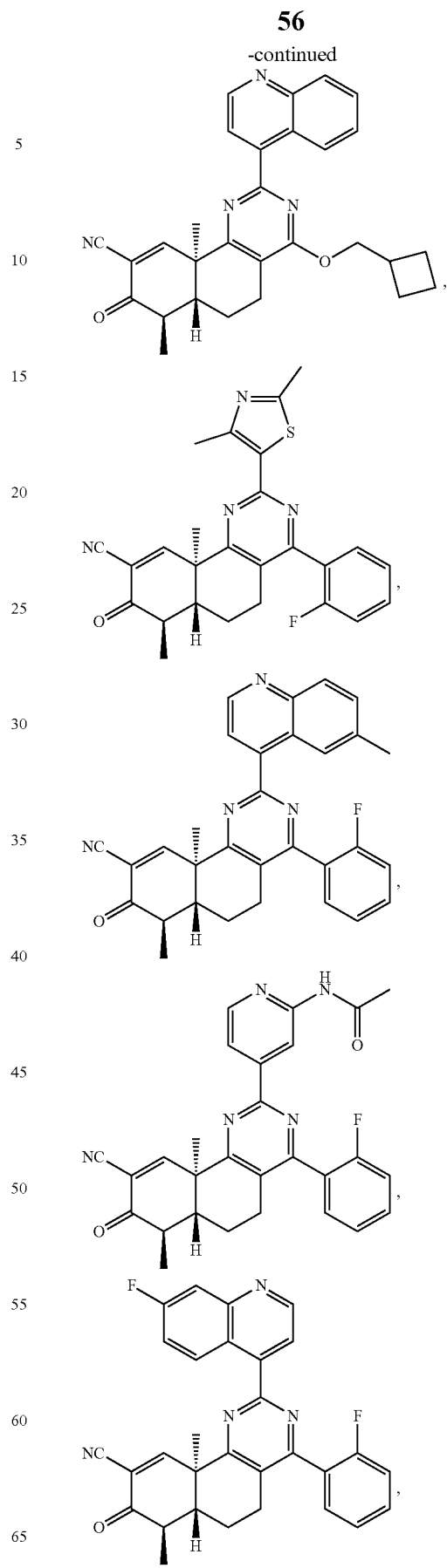

57
-continued
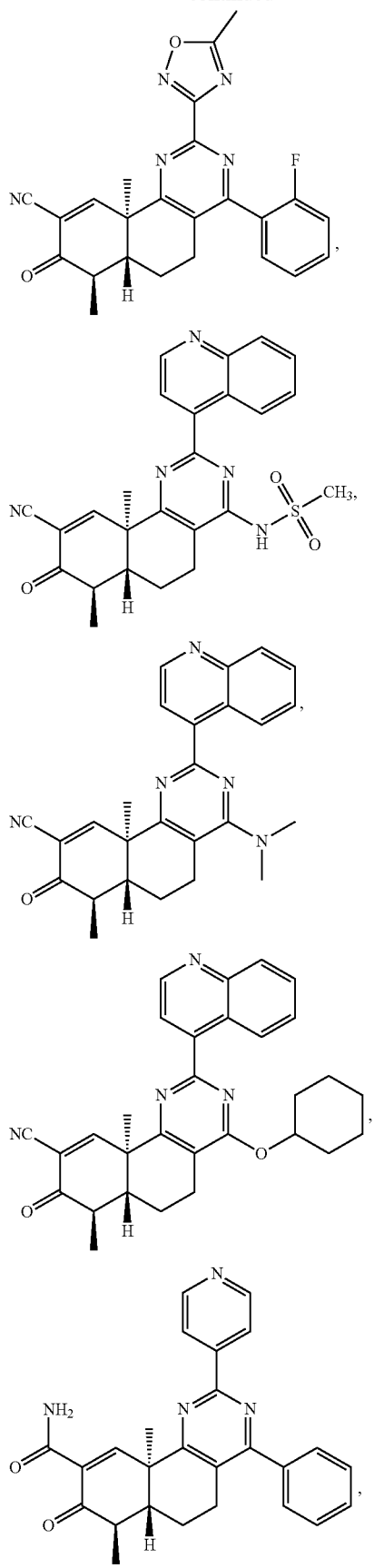
58
-continued
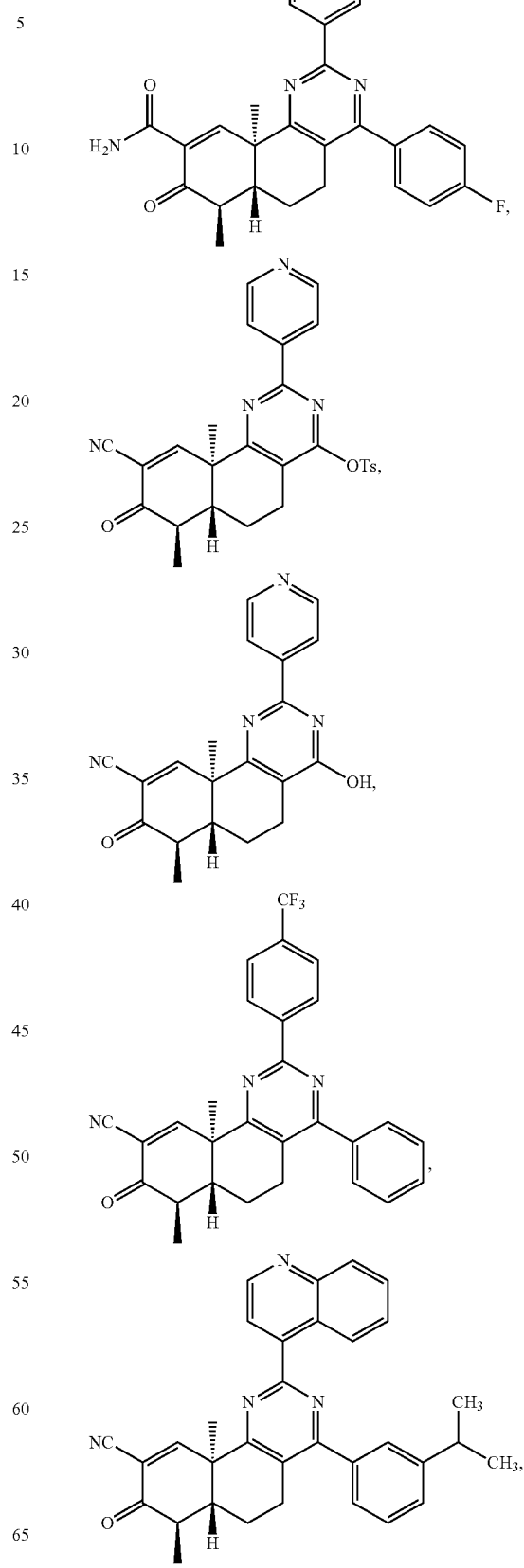

-continued

61
-continued
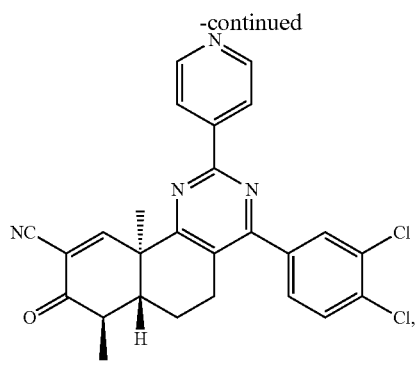
62
-continued
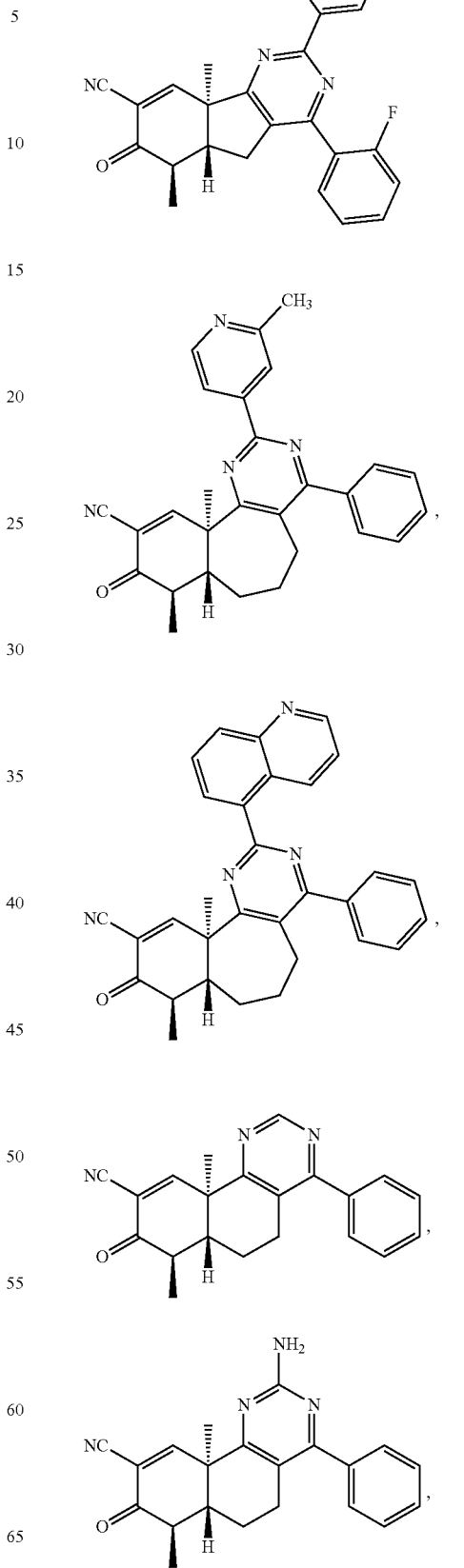

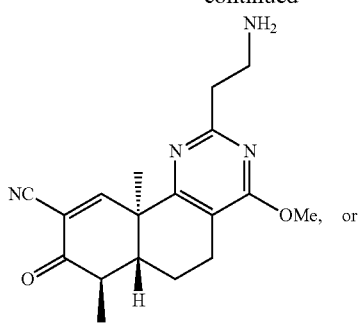
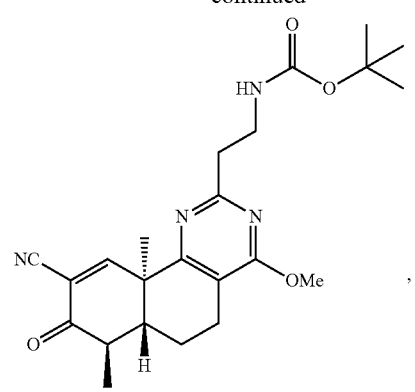
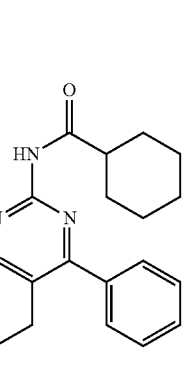
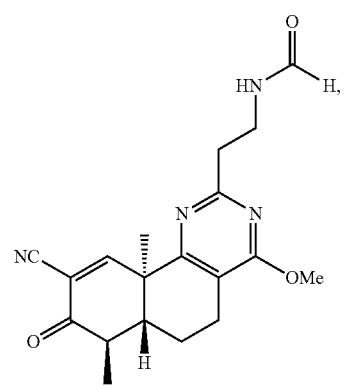
or a pharmaceutically acceptable salt thereof.
In some embodiments, the inverse agonist is a compound of the formula:
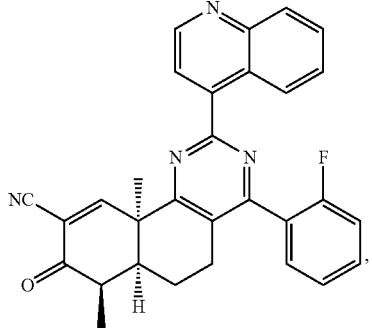
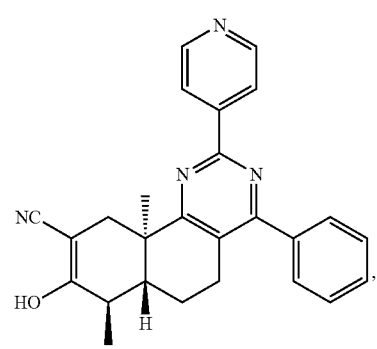
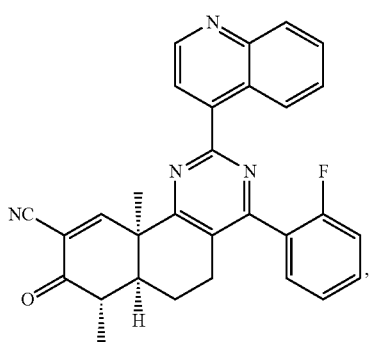
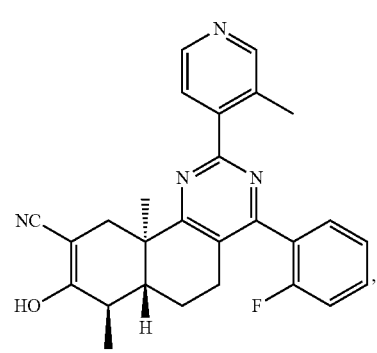

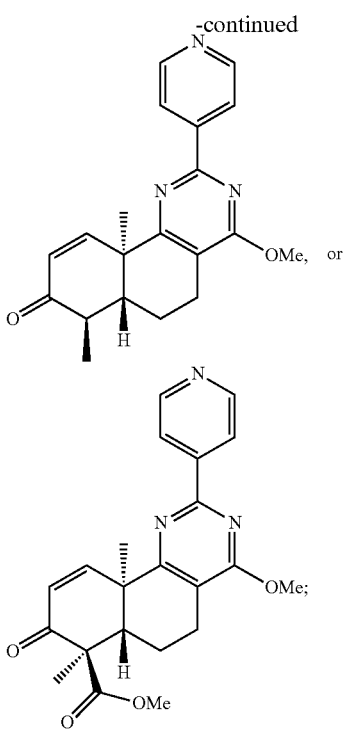

or a pharmaceutically acceptable salt thereof.

In some embodiments, the inverse agonist is a compound of the formula:

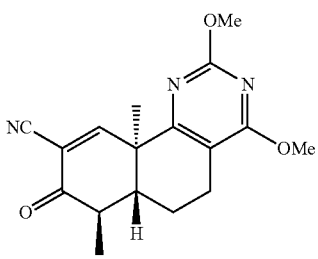 [SMILES: COc1nc(OC)c2c(n1)[C@]1(C)C=C(C#N)C(=O)[C@H](C)[C@H]1CC2]

or a pharmaceutically acceptable salt thereof.

In some embodiments, the inverse agonist is a compound of the formula:

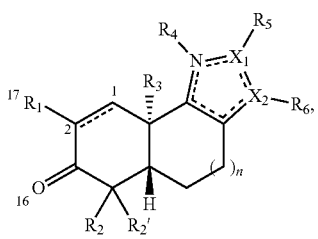

(XI)

wherein:
wherein the bond between carbon atoms 1 and 2 is an epoxidized double bond or a double bond;
n is 0, 1, or 2;
$R_1$ is cyano, fluoro, —$CF_3$, or —C(O)$R_a$, wherein:

$R_a$ is hydroxy or amino; or
alkoxy$_{(C \leq 6)}$, alkylamino$_{(C \leq 6)}$, dialkylamino$_{(C \leq 6)}$, or a substituted version of any of these groups;

$R_2$ and $R_{2'}$ are each independently hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups; or $R_2$ and $R_{2'}$ are taken together and are alkanediyl$_{(C \leq 8)}$, alkanediyl$_{(C \leq 8)}$, or a substituted version of either of these groups;

$R_3$ is alkyl$_{(C \leq 12)}$, alkenyl$_{(C \leq 12)}$, aryl$_{(C \leq 12)}$, aralkyl$_{(C \leq 12)}$, or a substituted version of any of these groups;

$R_4$ and $R_5$ are each independently absent or hydrogen; or
alkyl$_{(C \leq 12)}$, cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cycloalkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -heteroarenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cycloalkyl$_{(C \leq 12)}$, -heterocyclo-alkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or a group of the formula:

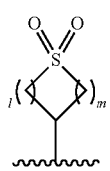

wherein l and m are each 0, 1, 2, or 3;
$R_6$ is absent, hydrogen, or amino; or
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups; and $X_1$ and $X_2$ are each independently C or N, provided that $X_2$ is C when $R_6$ is amino,
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, or diarylamino$_{(C \leq 12)}$;

or a pharmaceutically acceptable salt thereof.

In some embodiments, the compound is further defined as:

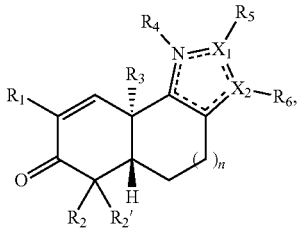

(XII)

wherein:
n is 0, 1, or 2;
$R_1$ is cyano, fluoro, —$CF_3$, or —C(O)$R_a$, wherein
  $R_a$ is hydroxy or amino; or
    alkoxy$_{(C\leq6)}$, alkylamino$_{(C\leq6)}$, dialkylamino$_{(C\leq6)}$, or a substituted version of any of these groups;
$R_2$ and $R_{2'}$ are each independently hydrogen; or
  alkyl$_{(C\leq12)}$, cycloalkyl$_{(C\leq12)}$, alkenyl$_{(C\leq12)}$, alkynyl$_{(C\leq12)}$, aryl$_{(C\leq18)}$, aralkyl$_{(C\leq18)}$, heteroaryl$_{(C\leq18)}$, heteroaralkyl$_{(C\leq18)}$, or a substituted version of any of these groups; or
  $R_2$ and $R_{2'}$ are taken together and are alkanediyl$_{(C\leq8)}$, alkenediyl$_{(C\leq8)}$, or a substituted version of either of these groups;
$R_3$ is alkyl$_{(C\leq12)}$, alkenyl$_{(C\leq12)}$, aryl$_{(C\leq12)}$, aralkyl$_{(C\leq12)}$, or a substituted version of any of these groups;
$R_4$ and $R_5$ are each independently absent or hydrogen; or
  alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cycloalkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -heteroarenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocycloalkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or
a group of the formula:

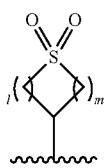

wherein l and m are each 0, 1, 2, or 3;
$R_6$ is absent, hydrogen, or amino; or
  alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups; and
$X_1$ and $X_2$ are each independently C or N, provided that $X_2$ is C when $R_6$ is amino, alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, or diarylamino$_{(C\leq12)}$;
or a pharmaceutically acceptable salt thereof.

In some embodiments, the compound is further defined as:

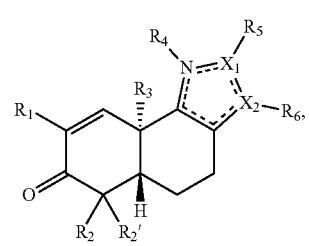

(XIII)

wherein:
$R_1$ is cyano, fluoro, —$CF_3$, or —C(O)$R_a$, wherein
  $R_a$ is hydroxy or amino; or
    alkoxy$_{(C\leq6)}$, alkylamino$_{(C\leq6)}$, dialkylamino$_{(C\leq6)}$, or a substituted version of any of these groups;
$R_2$ and $R_{2'}$ are each independently hydrogen; or
  alkyl$_{(C\leq12)}$, cycloalkyl$_{(C\leq12)}$, alkenyl$_{(C\leq12)}$, alkynyl$_{(C\leq12)}$, aryl$_{(C\leq18)}$, aralkyl$_{(C\leq18)}$, heteroaryl$_{(C\leq18)}$, heteroaralkyl$_{(C\leq18)}$, or a substituted version of any of these groups; or
  $R_2$ and $R_{2'}$ are taken together and are alkanediyl$_{(C\leq8)}$, alkenediyl$_{(C\leq8)}$, or a substituted version of either of these groups;
$R_3$ is alkyl$_{(C\leq12)}$, alkenyl$_{(C\leq12)}$, aryl$_{(C\leq12)}$, aralkyl$_{(C\leq12)}$, or a substituted version of any of these groups;
$R_4$ and $R_5$ are each independently absent or hydrogen; or
  alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cycloalkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -heteroarenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocyclo-alkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or
a group of the formula:

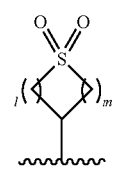

wherein l and m are each 0, 1, 2, or 3;
$R_6$ is absent, hydrogen, or amino; or alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups; and $X_1$ and $X_2$ are each independently C or N, provided that $X_2$ is C when $R_6$ is amino, alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, or diarylamino$_{(C \leq 12)}$;

or a pharmaceutically acceptable salt thereof.

In some embodiments, the compound is further defined as:

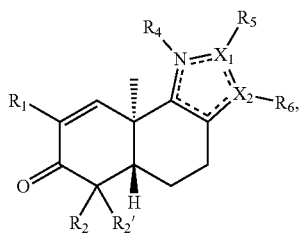

(XIV)

wherein:

$R_1$ is cyano, fluoro, —CF$_3$, or —C(O)R$_a$, wherein
$R_a$ is hydroxy or amino; or
alkoxy$_{(C \leq 6)}$, alkylamino$_{(C \leq 6)}$, dialkylamino$_{(C \leq 6)}$, or a substituted version of any of these groups;

$R_2$ and $R_2$' are each independently hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups; or
$R_2$ and $R_2$' are taken together and are alkanediyl$_{(C \leq 8)}$, alkenediyl$_{(C \leq 8)}$, or a substituted version of either of these groups;

$R_4$ and $R_5$ are each independently absent or hydrogen; or
alkyl$_{(C \leq 12)}$, cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 18)}$-heterocycloalkyl$_{(C \leq 12)}$, -arenediyl$_{(C \leq 12)}$-cycloalkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -heteroarenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cycloalkyl$_{(C \leq 12)}$, -heterocycloalkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or a group of the formula:

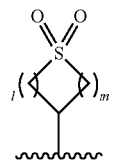

wherein l and m are each 0, 1, 2, or 3;

$R_6$ is absent, hydrogen, or amino; or
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups; and $X_1$ and $X_2$ are each independently C or N, provided that $X_2$ is C when $R_6$ is amino, alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, or diarylamino$_{(C \leq 12)}$;

or a pharmaceutically acceptable salt thereof.

In some embodiments, the compound is further defined as:

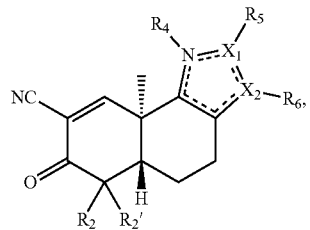

(XV)

wherein:

$R_2$ and $R_2$' are each independently hydrogen; or
alkyl$_{(C \leq 12)}$, cycloalkyl$_{(C \leq 12)}$, alkenyl$_{(C \leq 12)}$, alkynyl$_{(C \leq 12)}$, aryl$_{(C \leq 18)}$, aralkyl$_{(C \leq 18)}$, heteroaryl$_{(C \leq 18)}$, heteroaralkyl$_{(C \leq 18)}$, or a substituted version of any of these groups; or
$R_2$ and $R_2$' are taken together and are alkanediyl$_{(C \leq 8)}$, alkenediyl$_{(C \leq 8)}$, or a substituted version of either of these groups;

$R_4$ and $R_5$ are each independently absent or hydrogen; or
alkyl$_{(C \leq 12)}$, cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cycloalkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -heteroarenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cycloalkyl$_{(C \leq 12)}$, -heterocyclo-alkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or a group of the formula:

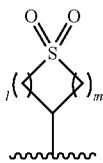

wherein l and m are each 0, 1, 2, or 3;
$R_6$ is absent, hydrogen, or amino; or
alkylamino$_{(C\leq 12)}$, dialkylamino$_{(C\leq 12)}$, cycloalkylamino$_{(C\leq 12)}$, dicycloalkylamino$_{(C\leq 12)}$, alkyl(cycloalkyl)amino$_{(C\leq 12)}$, arylamino$_{(C\leq 12)}$, diarylamino$_{(C\leq 12)}$, alkyl$_{(C\leq 12)}$, cycloalkyl$_{(C\leq 12)}$, -alkanediyl$_{(C\leq 12)}$-cycloalkyl$_{(C\leq 12)}$, -alkanediyl$_{(C\leq 18)}$-aralkoxy$_{(C\leq 18)}$, heterocycloalkyl$_{(C\leq 12)}$, aryl$_{(C\leq 18)}$, -arenediyl$_{(C\leq 12)}$-alkyl$_{(C\leq 12)}$, aralkyl$_{(C\leq 18)}$, -arenediyl$_{(C\leq 18)}$-heterocycloalkyl$_{(C\leq 12)}$, heteroaryl$_{(C\leq 18)}$, -heteroarenediyl$_{(C\leq 12)}$-alkyl$_{(C\leq 12)}$, heteroaralkyl$_{(C\leq 18)}$, acyl$_{(C\leq 12)}$, alkoxy$_{(C\leq 12)}$, or a substituted version of any of these groups; and
$X_1$ and $X_2$ are each independently C or N, provided that $X_2$ is C when $R_6$ is amino, alkylamino$_{(C\leq 12)}$, dialkylamino$_{(C\leq 12)}$, cycloalkylamino$_{(C\leq 12)}$, dicycloalkylamino$_{(C\leq 12)}$, alkyl(cycloalkyl)amino$_{(C\leq 12)}$, arylamino$_{(C\leq 12)}$, or diarylamino$_{(C\leq 12)}$;
or a pharmaceutically acceptable salt thereof.

In some embodiments, the compound is further defined as:

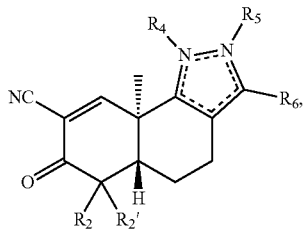

(XVI)

wherein:
$R_2$ and $R_{2'}$ are each independently hydrogen; or
alkyl$_{(C\leq 12)}$, cycloalkyl$_{(C\leq 12)}$, alkenyl$_{(C\leq 12)}$, alkynyl$_{(C\leq 12)}$, aryl$_{(C\leq 18)}$, aralkyl$_{(C\leq 18)}$, heteroaryl$_{(C\leq 18)}$, heteroaralkyl$_{(C\leq 18)}$, or a substituted version of any of these groups; or
$R_2$ and $R_{2'}$ are taken together and are alkanediyl$_{(C\leq 8)}$, alkenediyl$_{(C\leq 8)}$, or a substituted version of either of these groups;
$R_4$ and $R_5$ are each independently absent, hydrogen; or
alkyl$_{(C\leq 12)}$, cycloalkyl$_{(C\leq 12)}$, heterocycloalkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, -arenediyl$_{(C\leq 12)}$-alkyl$_{(C\leq 12)}$, -arenediyl$_{(C\leq 12)}$-aryl$_{(C\leq 12)}$, -arenediyl$_{(C\leq 12)}$-heteroaryl$_{(C\leq 12)}$, -arenediyl$_{(C\leq 12)}$-heterocycloalkyl$_{(C\leq 12)}$, -arenediyl$_{(C\leq 12)}$-cycloalkyl$_{(C\leq 12)}$, -heteroarenediyl$_{(C\leq 12)}$-alkyl$_{(C\leq 12)}$, -heteroarenediyl$_{(C\leq 12)}$-aryl$_{(C\leq 12)}$, -heteroarenediyl$_{(C\leq 12)}$-heteroarenediyl$_{(C\leq 12)}$-hetero-cycloalkyl$_{(C\leq 12)}$, -heteroarenediyl$_{(C\leq 12)}$-cycloalkyl$_{(C\leq 12)}$, -heterocyclo-alkanediyl$_{(C\leq 12)}$ -aryl$_{(C\leq 12)}$, -heterocycloalkanediyl$_{(C\leq 12)}$ -heteroaryl$_{(C\leq 12)}$, or a substituted version of any of these groups; or
a group of the formula:

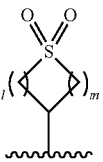

wherein l and m are each 0, 1, 2, or 3; and
$R_6$ is absent, hydrogen; or
alkylamino$_{(C\leq 12)}$, dialkylamino$_{(C\leq 12)}$, cycloalkylamino$_{(C\leq 12)}$, dicycloalkylamino$_{(C\leq 12)}$, alkyl(cycloalkyl)amino$_{(C\leq 12)}$, arylamino$_{(C\leq 12)}$, diarylamino$_{(C\leq 12)}$, alkyl$_{(C\leq 12)}$, cycloalkyl$_{(C\leq 12)}$, -alkanediyl$_{(C\leq 12)}$-cycloalkyl$_{(C\leq 12)}$, -alkanediyl$_{(C\leq 18)}$-aralkoxy$_{(C\leq 18)}$, heterocycloalkyl$_{(C\leq 12)}$, aryl$_{(C\leq 18)}$, -arenediyl$_{(C\leq 12)}$-alkyl$_{(C\leq 12)}$, aralkyl$_{(C\leq 18)}$, -arenediyl$_{(C\leq 18)}$-heterocycloalkyl$_{(C\leq 12)}$, heteroaryl$_{(C\leq 18)}$, -heteroarenediyl$_{(C\leq 12)}$-alkyl$_{(C\leq 12)}$, heteroaralkyl$_{(C\leq 18)}$, acyl$_{(C\leq 12)}$, alkoxy$_{(C\leq 12)}$, or a substituted version of any of these groups;
or a pharmaceutically acceptable salt thereof.

In some embodiments, the compound is further defined as:

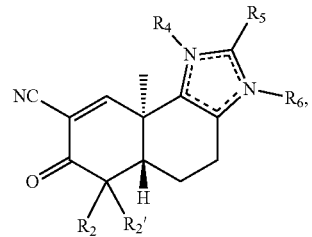

(XVII)

wherein:
$R_2$ and $R_{2'}$ are each independently hydrogen; or
alkyl$_{(C\leq 12)}$, cycloalkyl$_{(C\leq 12)}$, alkenyl$_{(C\leq 12)}$, alkynyl$_{(C\leq 12)}$, aryl$_{(C\leq 18)}$, aralkyl$_{(C\leq 18)}$, heteroaryl$_{(C\leq 18)}$, heteroaralkyl$_{(C\leq 18)}$, or a substituted version of any of these groups; or
$R_2$ and $R_{2'}$ are taken together and are alkanediyl$_{(C\leq 8)}$, alkenediyl$_{(C\leq 8)}$, or a substituted version of either of these groups;
$R_4$ and $R_5$ are each independently absent, hydrogen; or
alkyl$_{(C\leq 12)}$, cycloalkyl$_{(C\leq 12)}$, heterocycloalkyl$_{(C\leq 12)}$, aryl$_{(C\leq 12)}$, aralkyl$_{(C\leq 12)}$, heteroaryl$_{(C\leq 12)}$, heteroaralkyl$_{(C\leq 12)}$, -arenediyl$_{(C\leq 12)}$-alkyl$_{(C\leq 12)}$, -arenediyl$_{(C\leq 12)}$-aryl$_{(C\leq 12)}$, -arenediyl$_{(C\leq 12)}$-heteroaryl$_{(C\leq 12)}$, -arenediyl$_{(C\leq 12)}$-heterocycloalkyl$_{(C\leq 12)}$, -arenediyl$_{(C\leq 12)}$-cycloalkyl$_{(C\leq 12)}$, -heteroarenediyl$_{(C\leq 12)}$-alkyl$_{(C\leq 12)}$, -heteroarenediyl$_{(C\leq 12)}$-aryl$_{(C\leq 12)}$, -heteroarenediyl$_{(C\leq 12)}$-heteroaryl$_{(C\leq 12)}$, -heteroarenediyl$_{(C\leq 12)}$-hetero-cycloalkyl$_{(C\leq 12)}$, -heteroarenediyl$_{(C\leq 12)}$-cycloalkyl$_{(C\leq 12)}$, -heterocyclo-alkanediyl$_{(C\leq 12)}$ -aryl$_{(C\leq 12)}$, -heterocycloalkanediyl$_{(C\leq 12)}$ -heteroaryl$_{(C\leq 12)}$, or a substituted version of any of these groups; or a group of the formula:

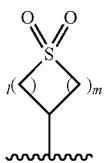

wherein l and m are each 0, 1, 2, or 3; and $R_6$ is absent, hydrogen; or alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups;

or a pharmaceutically acceptable salt thereof.

In some embodiments, the compound is further defined as:

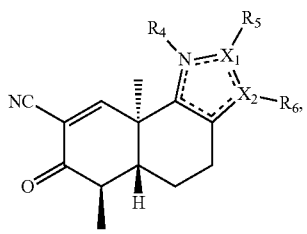

(XVIII)

wherein:

$R_4$ and $R_5$ are each independently absent, hydrogen; or alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cycloalkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -heteroarenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocyclo-alkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or a group of the formula:

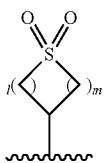

wherein l and m are each 0, 1, 2, or 3; and $R_6$ is absent, hydrogen; or alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C\leq12)}$-alkyl$_{(C\leq12)}$, heteroaralkyl$_{(C\leq18)}$, acyl$_{(C\leq12)}$, alkoxy$_{(C\leq12)}$, or a substituted version of any of these groups; and $X_1$ and $X_2$ are each independently C or N, provided that $X_2$ is C when $R_6$ is amino, alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, or diarylamino$_{(C\leq12)}$;

or a pharmaceutically acceptable salt thereof.

In some embodiments, the compound is further defined as:

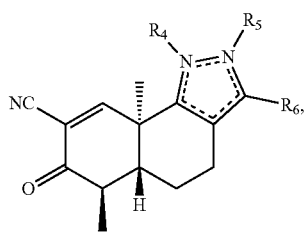

(XIX)

wherein:

$R_4$ and $R_5$ are each independently absent, hydrogen; or alkyl$_{(C\leq12)}$, cycloalkyl$_{(C\leq12)}$, heterocycloalkyl$_{(C\leq12)}$, aryl$_{(C\leq12)}$, aralkyl$_{(C\leq12)}$, heteroaryl$_{(C\leq12)}$, heteroaralkyl$_{(C\leq12)}$, -arenediyl$_{(C\leq12)}$-alkyl$_{(C\leq12)}$, -arenediyl$_{(C\leq12)}$-aryl$_{(C\leq12)}$, -arenediyl$_{(C\leq12)}$-heteroaryl$_{(C\leq12)}$, -arenediyl$_{(C\leq12)}$-heterocycloalkyl$_{(C\leq12)}$, -arenediyl$_{(C\leq12)}$-cycloalkyl$_{(C\leq12)}$, -heteroarenediyl$_{(C\leq12)}$-alkyl$_{(C\leq12)}$, -heteroarenediyl$_{(C\leq12)}$-aryl$_{(C\leq12)}$, -heteroarenediyl$_{(C\leq12)}$-heteroaryl$_{(C\leq12)}$, -heteroarenediyl$_{(C\leq12)}$-hetero-cycloalkyl$_{(C\leq12)}$, -heteroarenediyl$_{(C\leq12)}$-cycloalkyl$_{(C\leq12)}$, -heterocyclo-alkanediyl$_{(C\leq12)}$-aryl$_{(C\leq12)}$, -heterocycloalkanediyl$_{(C\leq12)}$-heteroaryl$_{(C\leq12)}$, or a substituted version of any of these groups; or a group of the formula:

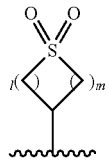

wherein l and m are each 0, 1, 2, or 3; and $R_6$ is absent, hydrogen; or alkylamino$_{(C\leq12)}$, dialkylamino$_{(C\leq12)}$, cycloalkylamino$_{(C\leq12)}$, dicycloalkylamino$_{(C\leq12)}$, alkyl(cycloalkyl)amino$_{(C\leq12)}$, arylamino$_{(C\leq12)}$, diarylamino$_{(C\leq12)}$, alkyl$_{(C\leq12)}$, cycloalkyl$_{(C\leq12)}$, -alkanediyl$_{(C\leq12)}$-cycloalkyl$_{(C\leq12)}$, -alkanediyl$_{(C\leq18)}$-aralkoxy$_{(C\leq18)}$, heterocycloalkyl$_{(C\leq12)}$, aryl$_{(C\leq18)}$, -arenediyl$_{(C\leq12)}$-alkyl$_{(C\leq12)}$, aralkyl$_{(C\leq18)}$, -arenediyl$_{(C\leq18)}$-heterocycloalkyl$_{(C\leq12)}$, heteroaryl$_{(C\leq18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups;

or a pharmaceutically acceptable salt thereof.

In some embodiments, the compound is further defined as:

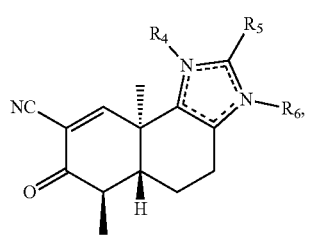

(XX)

wherein:
$R_4$ and $R_5$ are each independently absent, hydrogen; or alkyl$_{(C \leq 12)}$, cycloalkyl$_{(C \leq 12)}$, heterocycloalkyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, -arenediyl$_{(C \leq 12)}$-alkyl$_{(C \leq 12)}$, -arenediyl$_{(C \leq 12)}$-aryl$_{(C \leq 12)}$, -arenediyl$_{(C \leq 12)}$-heteroaryl$_{(C \leq 12)}$, -arenediyl$_{(C \leq 12)}$-heterocycloalkyl$_{(C \leq 12)}$, -arenediyl$_{(C \leq 12)}$-cycloalkyl$_{(C \leq 12)}$, -heteroarenediyl$_{(C \leq 12)}$-alkyl$_{(C \leq 12)}$, -heteroarenediyl$_{(C \leq 12)}$-aryl$_{(C \leq 12)}$, -heteroarenediyl$_{(C \leq 12)}$-heteroaryl$_{(C \leq 12)}$, -heteroarenediyl$_{(C \leq 12)}$-hetero-cycloalkyl$_{(C \leq 12)}$, -heteroarenediyl$_{(C \leq 12)}$-cycloalkyl$_{(C \leq 12)}$, -heterocyclo-alkanediyl$_{(C \leq 12)}$-aryl$_{(C \leq 12)}$, -heterocycloalkanediyl$_{(C \leq 12)}$-heteroaryl$_{(C \leq 12)}$, or a substituted version of any of these groups; or a group of the formula:

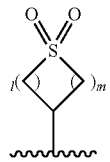

wherein l and m are each 0, 1, 2, or 3; and
$R_6$ is absent, hydrogen; or
alkylamino$_{(C \leq 12)}$, dialkylamino$_{(C \leq 12)}$, cycloalkylamino$_{(C \leq 12)}$, dicycloalkylamino$_{(C \leq 12)}$, alkyl(cycloalkyl)amino$_{(C \leq 12)}$, arylamino$_{(C \leq 12)}$, diarylamino$_{(C \leq 12)}$, alkyl$_{(C \leq 12)}$, cycloalkyl$_{(C \leq 12)}$, -alkanediyl$_{(C \leq 12)}$-cycloalkyl$_{(C \leq 12)}$, -alkanediyl$_{(C \leq 18)}$-aralkoxy$_{(C \leq 18)}$, heterocycloalkyl$_{(C \leq 12)}$, aryl$_{(C \leq 18)}$, -arenediyl$_{(C \leq 12)}$-alkyl$_{(C \leq 12)}$, aralkyl$_{(C \leq 18)}$, -arenediyl$_{(C \leq 18)}$-heterocycloalkyl$_{(C \leq 12)}$, heteroaryl$_{(C \leq 18)}$, -heteroarenediyl$_{(C \leq 12)}$-alkyl$_{(C \leq 12)}$, heteroaralkyl$_{(C \leq 18)}$, acyl$_{(C \leq 12)}$, alkoxy$_{(C \leq 12)}$, or a substituted version of any of these groups;
or a pharmaceutically acceptable salt thereof.

In some embodiments, $X_1$ and $X_2$ are both N. In other embodiments, $X_1$ and $X_2$ are not both N. In some embodiments, either $X_1$ or $X_2$ is N. In some embodiments, $X_1$ is N. In some embodiments, $X_2$ is N. In some embodiments, $R_3$ is alkyl$_{(C \leq 12)}$ or substituted alkyl$_{(C \leq 12)}$. In further embodiments, $R_3$ is alkyl$_{(C \leq 12)}$, such as methyl. In some embodiments, $R_1$ is cyano. In other embodiments, $R_1$ is —C(O)$R_a$. In some embodiments, $R_a$ is alkoxy$_{(C \leq 6)}$, such as methoxy. In other embodiments, $R_a$ is amino. In some embodiments, $R_{2'}$ is hydrogen. In some embodiments, $R_2$ is hydrogen. In some embodiments, $R_{2'}$ and $R_2$ are both hydrogen. In other embodiments, $R_2$ is alkyl$_{(C \leq 12)}$ or substituted alkyl$_{(C \leq 12)}$. In further embodiments, $R_2$ is alkyl$_{(C \leq 12)}$, such as methyl.

In some embodiments, $R_4$ is absent. In other embodiments, $R_4$ is hydrogen. In still other embodiments, $R_4$ is alkyl$_{(C \leq 12)}$ or substituted alkyl$_{(C \leq 12)}$. In further embodiments, $R_4$ is substituted alkyl$_{(C \leq 12)}$, such as $R_4$ is 2,2,2-trifluoroethyl. In still other embodiments, $R_4$ is cycloalkyl$_{(C \leq 12)}$ or substituted cycloalkyl$_{(C \leq 12)}$. In further embodiments, $R_4$ is cycloalkyl$_{(C \leq 12)}$, such as cyclohexyl. In yet other embodiments, $R_4$ is heterocycloalkyl$_{(C \leq 12)}$ or substituted heterocycloalkyl$_{(C \leq 12)}$. In further embodiments, $R_4$ is heterocycloalkyl$_{(C \leq 12)}$, such as tetrahydro-2H-pyran-4-yl or 1,1-dioxidotetrahydrothiophen-3-yl. In other embodiments, $R_4$ is:

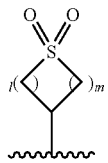

wherein:
l and m are each 0, 1, 2, or 3.

In some embodiments, l is 1 or 2. In some embodiments, m is 1 or 2. In still other embodiments, $R_4$ is aryl$_{(C \leq 18)}$, heteroaryl$_{(C \leq 18)}$, or a substituted version of either of these groups. In further embodiments, $R_4$ is aryl$_{(C \leq 18)}$ or substituted aryl$_{(C \leq 18)}$. In still further embodiments, $R_4$ is aryl$_{(C \leq 18)}$, such as phenyl, o-tolyl, p-tolyl, [1,1'-biphenyl]-4-yl, 4-isopropylphenyl, naphthalen-1-yl, 4'-methyl-[1,1'-biphenyl]-4-yl, or 2'-methyl-[1,1'-biphenyl]-4-yl. In yet other embodiments, $R_4$ is substituted aryl$_{(C \leq 18)}$, such as 4-(trifluoromethyl)phenyl, 4-cyanophenyl, 2-fluorophenyl, 4-fluorophenyl, 4-chlorophenyl, 3,4-dichlorophenyl, 4-methoxyphenyl, 4-(trifluoromethoxy)phenyl, 4-carboxyphenyl, 4'-methoxy-[1,1'-biphenyl]-4-yl, 4'-(dimethylamino)[1,1'-biphenyl]-4-yl, 2'-fluoro-[1,1'-biphenyl]-4-yl, 3'-fluoro-[1,1'-biphenyl]-4-yl, 2'-(hydroxymethyl)[1,1'-biphenyl]-4-yl, 3'-(hydroxymethyl)-[1,1'-biphenyl]-4-yl, 4'-(hydroxymethyl)-[1,1'-biphenyl]-4-yl, or 5-(3-(hydroxymethyl)phenyl. In other embodiments, $R_4$ is aralkyl$_{(C \leq 18)}$ or substituted aralkyl$_{(C \leq 18)}$. In further embodiments, $R_4$ is aralkyl$_{(C \leq 18)}$, such as benzyl. In still other embodiments, $R_4$ is -arenediyl$_{(C \leq 12)}$-heterocycloalkyl$_{(C \leq 12)}$ or substituted -arenediyl$_{(C \leq 12)}$-heterocycloalkyl$_{(C \leq 12)}$. In further embodiments, $R_4$ is -arenediyl$_{(C \leq 12)}$-heterocycloalkyl$_{(C \leq 12)}$, such as 4-morpholinophenyl. In other embodiments, $R_4$ is heteroaryl$_{(C \leq 18)}$ or substituted heteroaryl$_{(C \leq 18)}$. In further embodiments, $R_4$ is heteroaryl$_{(C \leq 18)}$, such as pyridin-4-yl, quinolin-4-yl, 5-methylpyrindin-2-yl, 6-methylpyrindin-3-yl, (pyridin-3-yl)phenyl, (pyridin-4-yl)phenyl, 4-(3,5-dimethylisoxazol-4-yl)phenyl, 4-(pyrimidin-4-yl)phenyl, 4-(pyrimidin-5-yl)phenyl, 4-(pyridin-3-yl)phenyl, 4-(pyridin-4-yl)phenyl, 5-phenylpyridin-2-yl, [3,3'-bipyridin]-6-yl, 5-cyclopropylpyridin-2-yl, 6-phenylpyridin-3-yl, 4-(6-methylpyridazin-4-yl)phenyl, 5-methyl-1,2,4-oxadiazol-3-yl, 3-methyl-1,2,4-oxadiazol-5-yl, 4-methyl-5-phenyl-4H-1,2,4-triazol-3-yl, 1-phenylpiperidin-4-yl, 4-phenyloxazol-2-yl, 4-(6-methylpyridazin-4-yl)phenyl, 4-(5-methyl-1,2,4-oxadiazol-3-yl)phenyl, 4-(3-methyl-1,2,4-oxadiazol-5-yl)phenyl, 4-(1,2,4-oxadiazol-3-yl)phenyl, 4-(pyridazin-3-yl)phenyl, 4-(5-methylpyridazin-3-yl)phenyl, 1-methyl-1H- benzo[d]imidazol-2-yl, or benzo[d]thiazol-2-yl. In still other embodiments, $R_4$ is substituted heteroaryl$_{(C≤18)}$, such as 2-fluoro-4-(pyridin-3-yl)phenyl, 5-(trifluoromethyl)pyridin-2-yl, 5-(3-fluorophenyl)pyridin-2-yl, 5-(4-fluorophenyl) pyridin-2-yl, 4-(2-(hydroxymethyl)pyridine-4-yl)phenyl, 4-(2-(fluoromethyl)pyridine-4-yl)phenyl, 5-(trifluoromethyl)benzo[d]oxazol-2-yl, 6-chlorobenzo[d]thiazol-2-yl, or 4-(5-fluoropyridin-3-yl)phenyl.

In some embodiments, $R_5$ is absent. In other embodiments, $R_5$ is hydrogen. In still other embodiments, $R_5$ is alkyl$_{(C≤12)}$ or substituted alkyl$_{(C≤12)}$. In further embodiments, $R_5$ is alkyl$_{(C≤12)}$, such as methyl. In yet other embodiments, $R_5$ is cycloalkyl$_{(C≤12)}$ or substituted cycloalkyl$_{(C≤12)}$. In further embodiments, $R_5$ is cycloalkyl$_{(C≤12)}$, such as cyclohexyl. In other embodiments, $R_5$ is heterocycloalkyl$_{(C≤12)}$ or substituted heterocycloalkyl$_{(C≤12)}$. In further embodiments, $R_5$ is heterocycloalkyl$_{(C≤12)}$, such as tetrahydro-2H-pyran-4-yl. In still other embodiments, $R_5$ is aryl$_{(C≤18)}$ or substituted aryl$_{(C≤18)}$. In further embodiments, $R_5$ is aryl$_{(C≤18)}$, such as phenyl, o-tolyl, p-tolyl, [1,1'-biphenyl]-4-yl, 4-isopropylphenyl, naphthalen-1-yl, [1,1'-biphenyl]-3-yl, or 3-isopropylphenyl. In yet other embodiments, $R_5$ is substituted aryl$_{(C≤18)}$, such as 4-chlorophenyl, 3,4-dichlorophenyl, 4-methoxyphenyl, 4-(trifluoromethoxy) phenyl, 3-bromophenyl, 3-chlorophenyl, 4-(dimethylamino) phenyl. In other embodiments, $R_5$ is aralkyl$_{(C≤18)}$ or substituted aralkyl$_{(C≤18)}$. In further embodiments, $R_5$ is aralkyl$_{(C≤18)}$, such as $R_5$ is benzyl. In still other embodiments, $R_5$ is -arenediyl$_{(C≤12)}$-heterocycloalkyl$_{(C≤12)}$ or substituted -arenediyl$_{(C≤12)}$-heterocycloalkyl$_{(C≤12)}$. In further embodiments, $R_5$ is -arenediyl$_{(C≤12)}$-heterocycloalkyl$_{(C≤12)}$, such as 3-morpholinophenyl. In yet other embodiments, $R_5$ is heteroaryl$_{(C≤18)}$ or substituted heteroaryl$_{(C≤18)}$. In further embodiments, heteroaryl$_{(C≤18)}$, such as pyridin-4-yl, quinolin-4-yl, quinolin-3-yl, quinolin-5-yl, 3-(pyridin-4-yl)phenyl, 3-(pyrimidin-5-yl)phenyl, 2-isopropylpyrimidin-5-yl, 6-cyclopropylpyridin-3-yl, 3-(1-methyl-1H-pyrazol-4-yl) phenyl, 1-methyl-1H-pyrazol-4-yl, 3-(3,5-dimethylisoxazol-4-yl)phenyl, 3-(1-methyl-1H-pyrazol-5-yl)phenyl, or 2-cyclopropylpyridin-4-yl. In other embodiments, $R_5$ is substituted heteroaryl$_{(C≤18)}$, such as 2-(trifluoromethyl)pyridin-4-yl or 3-(5-fluoropyridin-3-yl)phenyl. In still other embodiments, $R_5$ is -heteroarenediyl$_{(C≤12)}$-heterocycloalkyl$_{(C≤12)}$ or substituted -heteroarenediyl$_{(C≤12)}$-heterocycloalkyl$_{(C≤12)}$. In further embodiments, $R_5$ is -heteroarenediyl$_{(C≤12)}$-heterocycloalkyl$_{(C≤12)}$, such as 2-morpholinopyridin-4-yl.

In some embodiments, $R_6$ is hydrogen. In other embodiments, $R_6$ is aryl$_{(C≤18)}$, heteroaryl$_{(C≤18)}$, or a substituted version of either of these groups. In still other embodiments, $R_6$ is amino. In yet other embodiments, $R_6$ is alkylamino$_{(C≤12)}$ or substituted alkylamino$_{(C≤12)}$. In further embodiments, $R_6$ is alkylamino$_{(C≤12)}$, such as methylamino. In other embodiments, $R_6$ is cycloalkylamino$_{(C≤12)}$ or substituted cycloalkylamino$_{(C≤12)}$. In further embodiments, $R_6$ is cycloalkylamino$_{(C≤12)}$, such as cyclobutylamino. In still other embodiments, $R_6$ is alkyl(cycloalkyl)amino$_{(C≤12)}$ or substituted alkyl(cycloalkyl)amino$_{(C≤12)}$. In further embodiments, $R_6$ is alkyl(cycloalkyl)amino$_{(C≤12)}$, such as methyl(cyclobutyl)amino. In yet other embodiments, $R_6$ is arylamino$_{(C≤12)}$ or substituted arylamino$_{(C≤12)}$. In further embodiments, $R_6$ is arylamino$_{(C≤12)}$, such as phenylamino. In other embodiments, $R_6$ is alkyl$_{(C≤12)}$ or substituted alkyl$_{(C≤12)}$. In further embodiments, $R_6$ is alkyl$_{(C≤12)}$, such as methyl. In still other embodiments, $R_6$ is substituted alkyl$_{(C≤12)}$, such as 2-hydroxyethyl or 2-methoxyethyl. In yet other embodiments, $R_6$ is acyl$_{(C≤6)}$ or substituted acyl$_{(C≤6)}$. In further embodiments, $R_6$ is acyl$_{(C≤6)}$, such as C(O)CH$_3$. In other embodiments, $R_6$ is cycloalkyl$_{(C≤12)}$ or substituted cycloalkyl$_{(C≤12)}$. In further embodiments, $R_6$ is cycloalkyl$_{(C≤12)}$, such as cyclopropyl or cyclohexyl. In still other embodiments, $R_6$ is -alkanediyl$_{(C≤18)}$-cycloalkyl$_{(C≤18)}$ or substituted -alkanediyl$_{(C≤18)}$-cycloalkyl$_{(C≤18)}$. In further embodiments, $R_6$ is -alkanediyl$_{(C≤18)}$-cycloalkyl$_{(C≤18)}$, such as cyclobutylmethyl. In yet other embodiments, $R_6$ is aryl$_{(C≤18)}$ or substituted aryl$_{(C≤18)}$. In further embodiments, $R_6$ is aryl$_{(C≤18)}$, such as phenyl, o-tolyl, p-tolyl, or 3-isopropylphenyl. In other embodiments, $R_6$ is substituted aryl$_{(C≤18)}$, such as 2-fluorophenyl, 4-fluorophenyl, 4-(hydroxymethyl)phenyl, 3-fluorophenyl, or 4-(fluoromethyl) phenyl. In still other embodiments, $R_6$ is aralkyl$_{(C≤18)}$ or substituted aralkyl$_{(C≤18)}$. In further embodiments, $R_6$ is aralkyl$_{(C≤18)}$, such as benzyl. In yet other embodiments, $R_6$ is substituted aralkyl$_{(C≤18)}$, such as 2-fluorobenzyl, 4-fluorobenzyl, or 4-chlorobenzyl. In other embodiments, $R_6$ is -arenediyl$_{(C≤18)}$-heterocycloalkyl$_{(C≤12)}$ or substituted -arenediyl$_{(C≤18)}$-heterocycloalkyl$_{(C≤12)}$. In further embodiments, $R_6$ is -arenediyl$_{(C≤18)}$-heterocycloalkyl$_{(C≤12)}$, such as 4-morpholinophenyl. In still other embodiments, $R_6$ is heteroaryl$_{(C≤18)}$ or substituted heteroaryl$_{(C≤18)}$. In further embodiments, $R_6$ is heteroaryl$_{(C≤18)}$, such as pyridin-2-yl, pyridin-3-yl, pyridin-4-yl, 2-methyl-2H-tetrazol-5-yl, 1-methyl-1H-pyrazol-4-yl, pyrimidin-4-yl, pyrimidin-5-yl, 3-methyl-1,2,4-oxadiazol-5-yl)phenyl, pyridin-2-ylmethyl, 3-methyl-1,2,4-oxadiazol-5-yl, or 5-methyl-1,2,4-oxadiazol-3-yl. In still other embodiments, $R_6$ is heteroaralkyl$_{(C≤18)}$ or heteroaralkyl$_{(C≤18)}$. In further embodiments, $R_6$ is heteroaralkyl$_{(C≤18)}$, such as 2-pyridinylmethyl or 4-pyridinylmethyl. In yet other embodiments, $R_6$ is -alkanediyl$_{(C≤18)}$-aralkoxy$_{(C≤18)}$ or substituted -alkanediyl$_{(C≤18)}$-aralkoxy$_{(C≤18)}$. In further embodiments, $R_6$ is -alkanediyl$_{(C≤18)}$-aralkoxy$_{(C≤18)}$, such as 2-(benzyloxy)ethyl.

In some embodiments, the compound is further defined as:

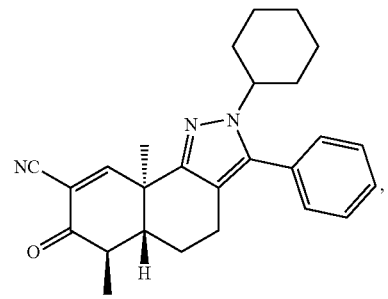

,

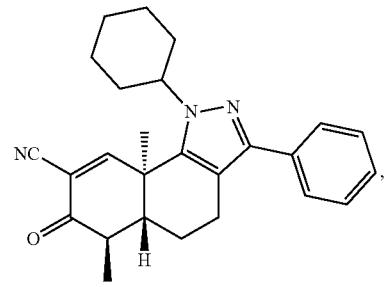

,

-continued
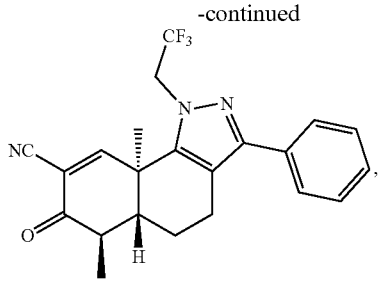
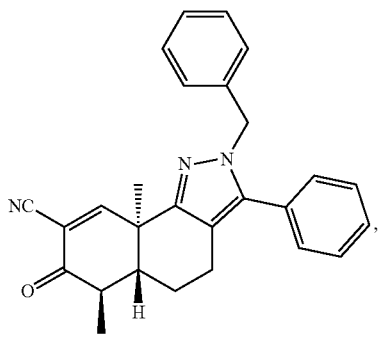
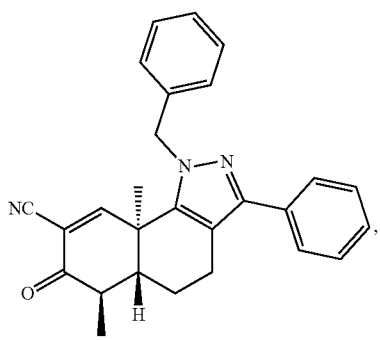
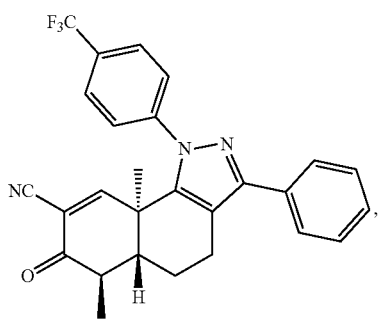
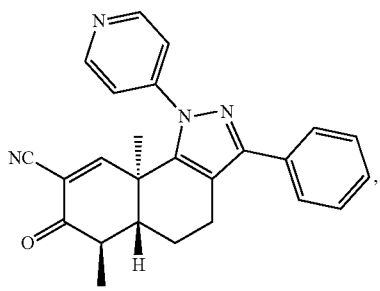
-continued
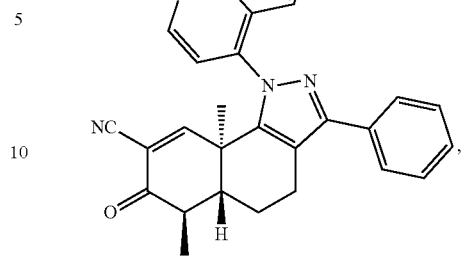
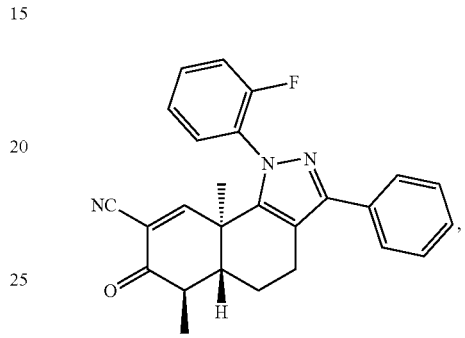
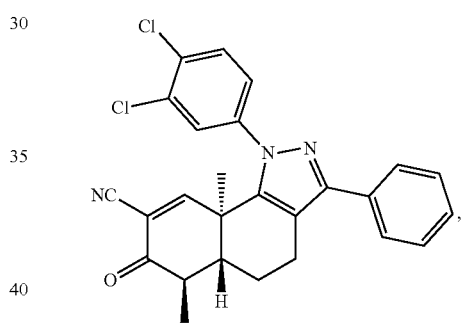
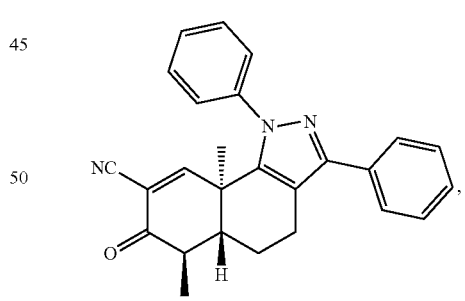
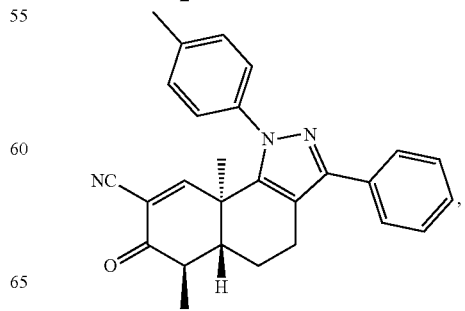

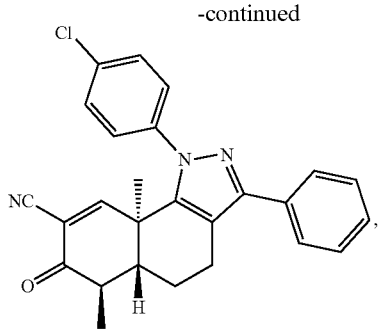
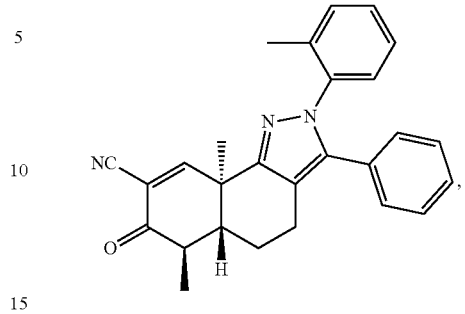
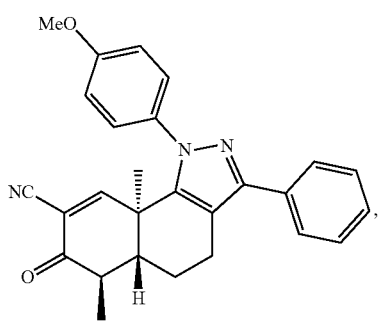
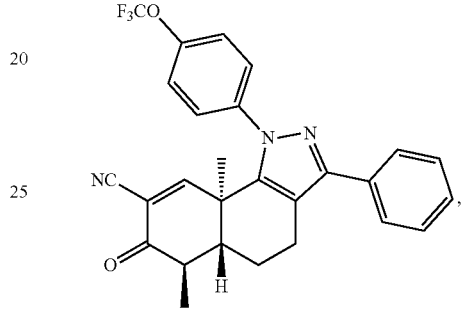
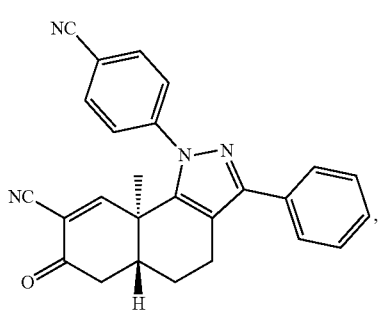
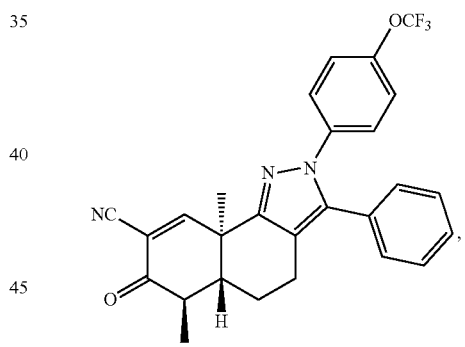
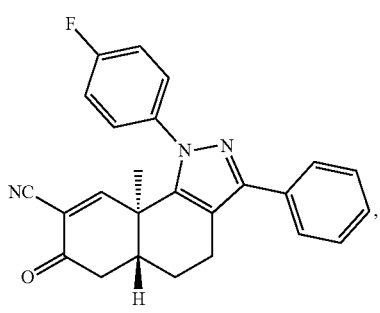
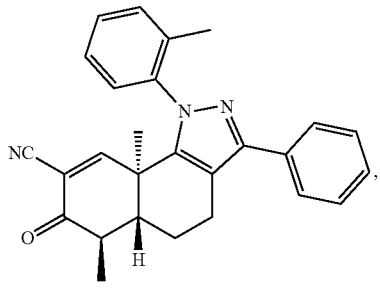
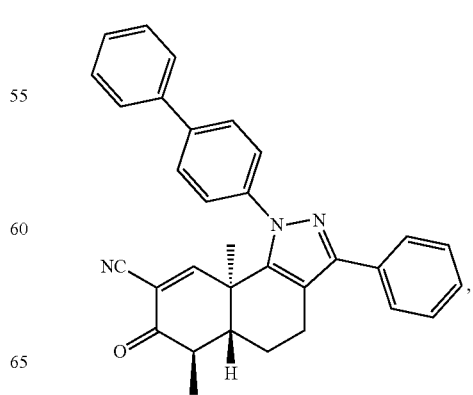

83
-continued
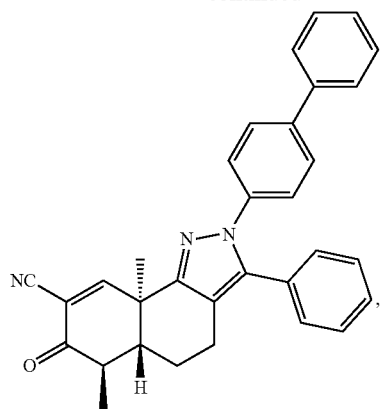
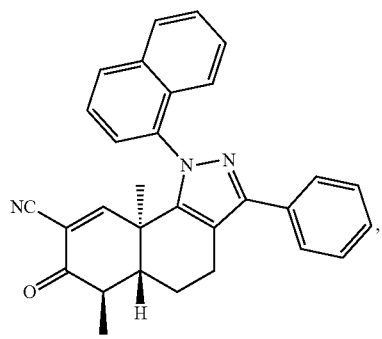
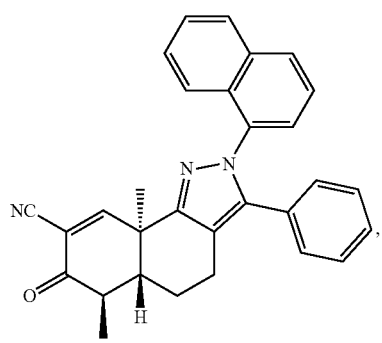
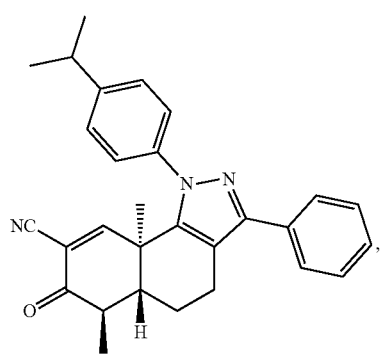
84
-continued
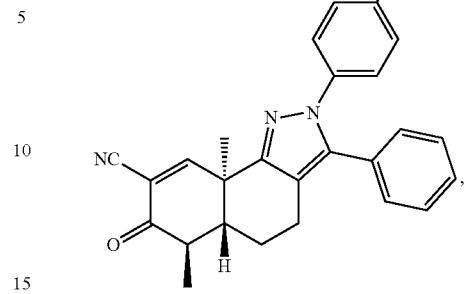
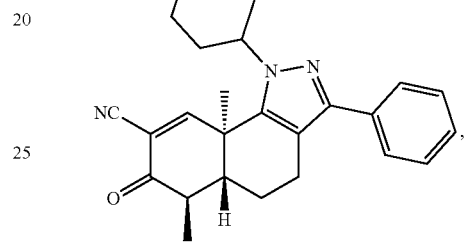
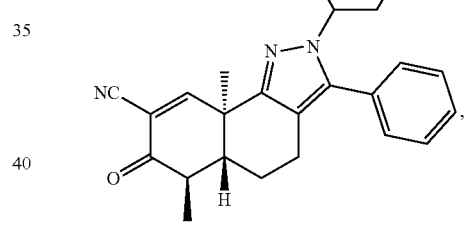
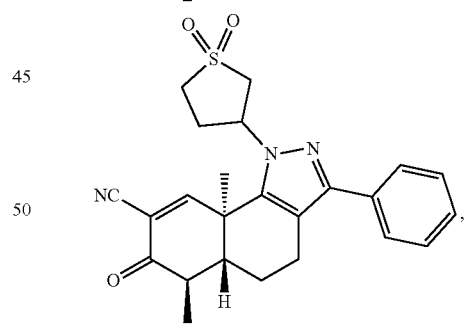
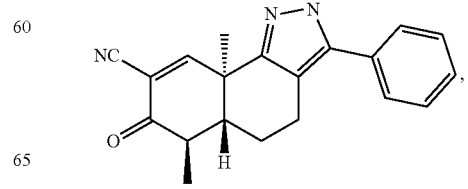

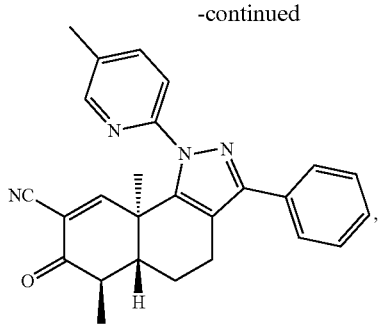
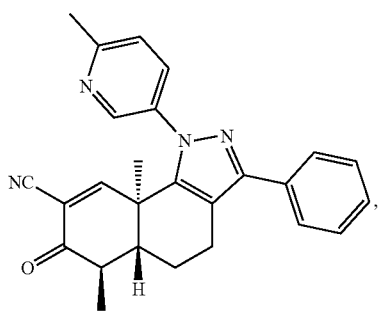
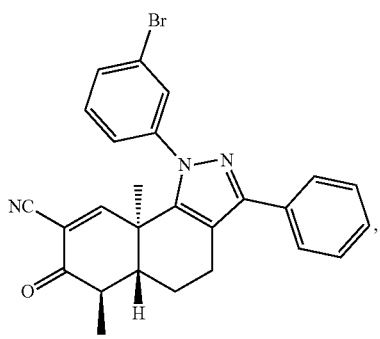
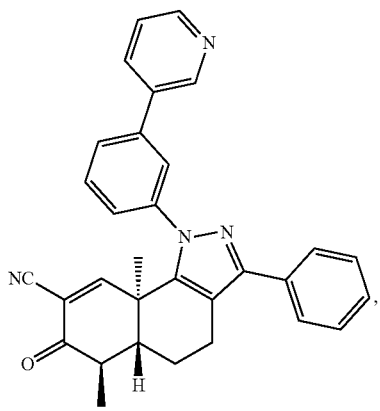
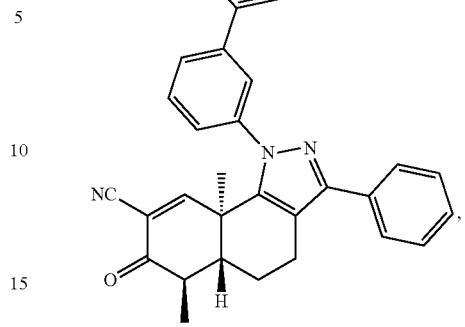
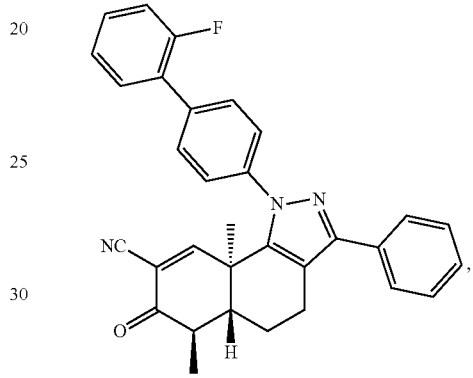
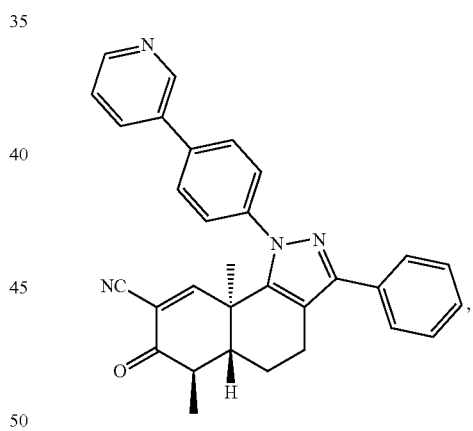
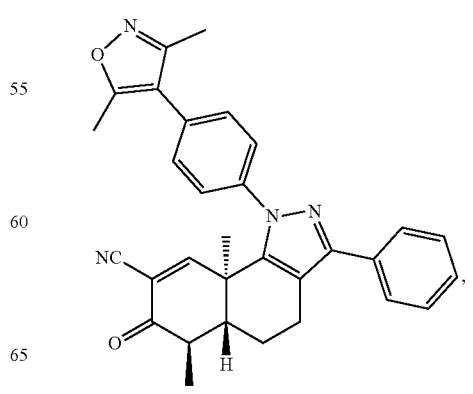

87
-continued
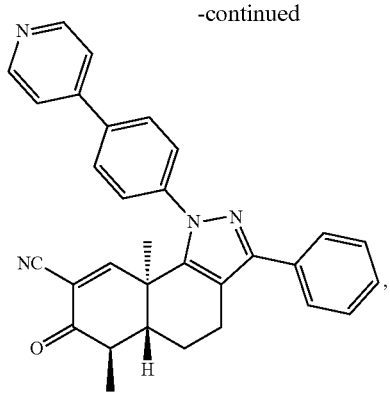
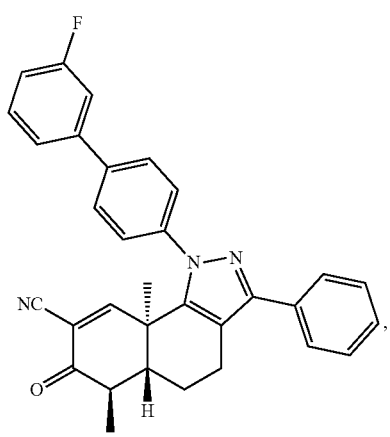
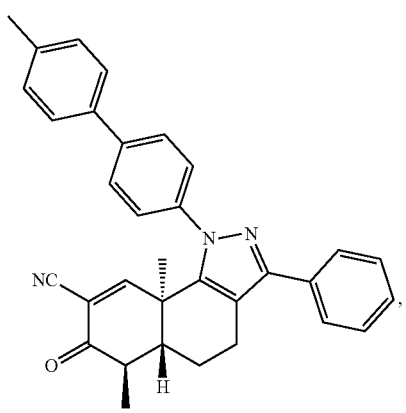
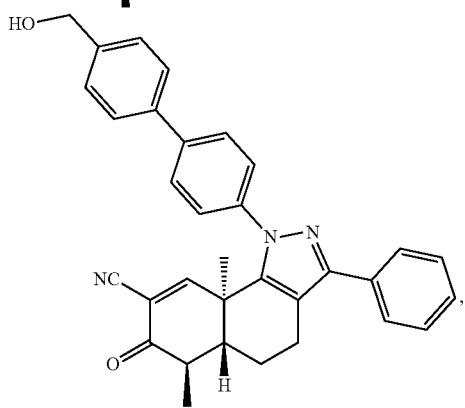
88
-continued
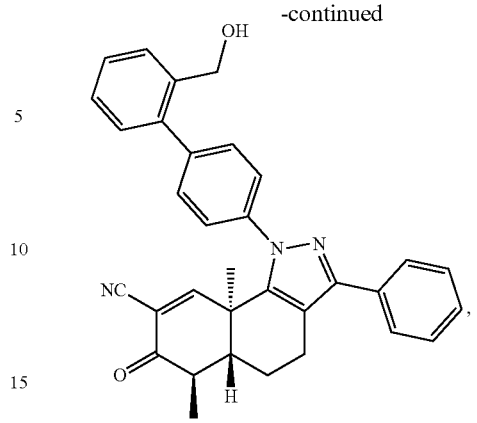
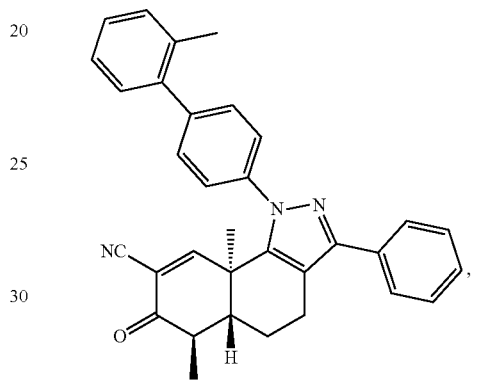
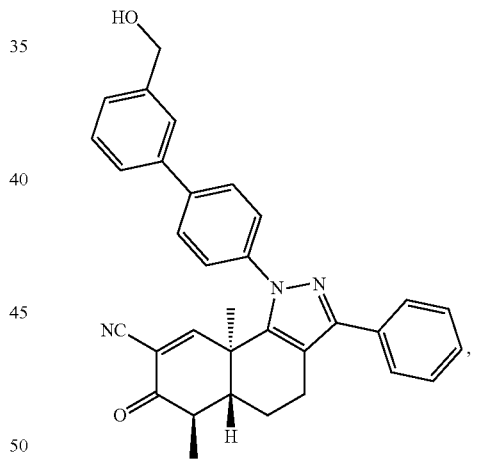
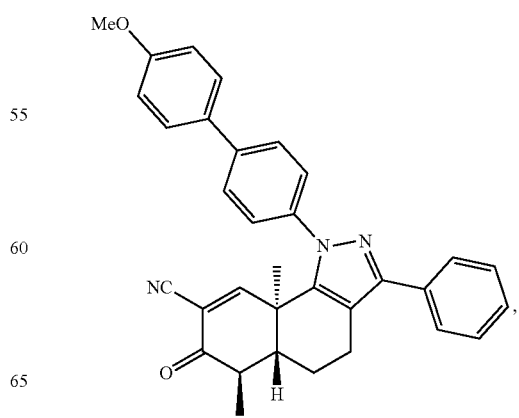

89
-continued
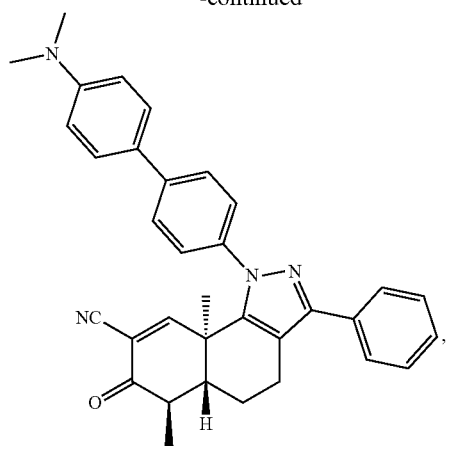
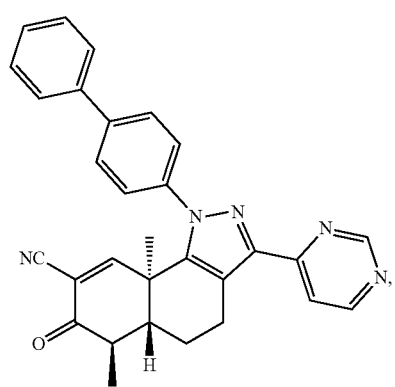
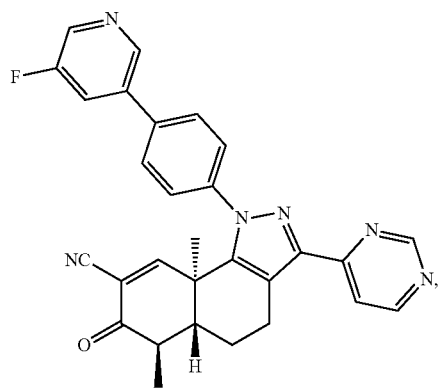
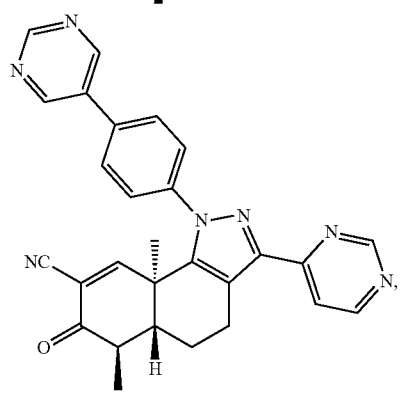
90
-continued
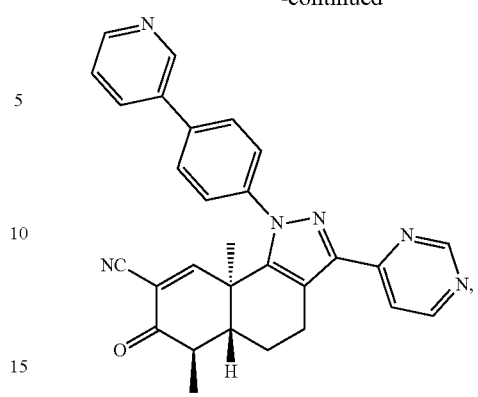
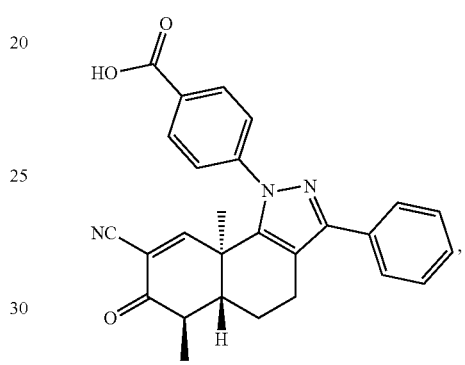
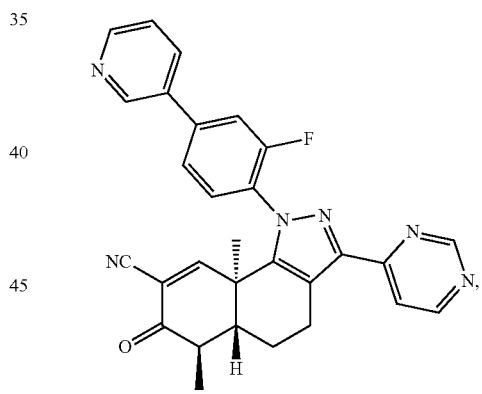
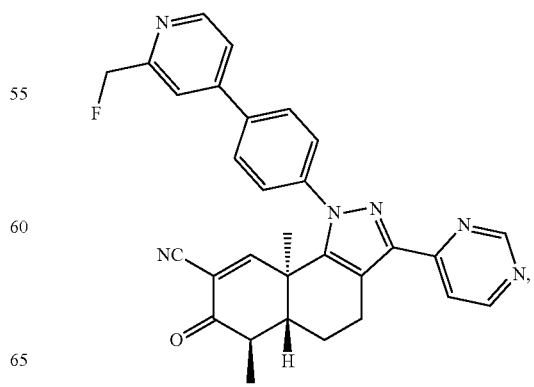

91
-continued
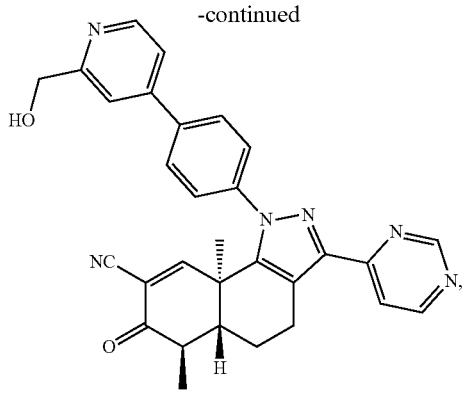
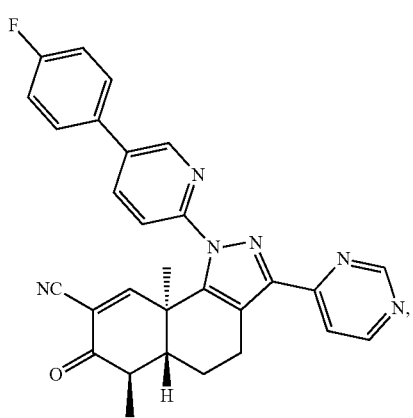
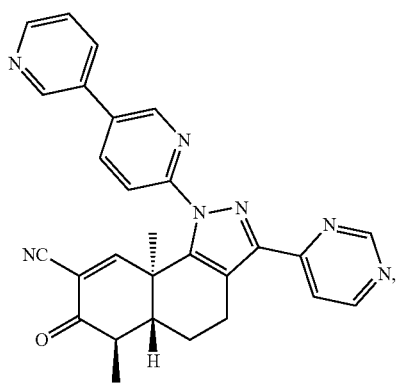
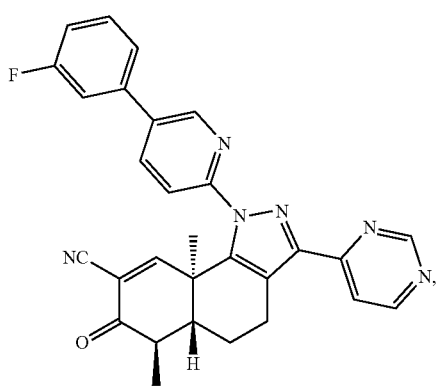
92
-continued
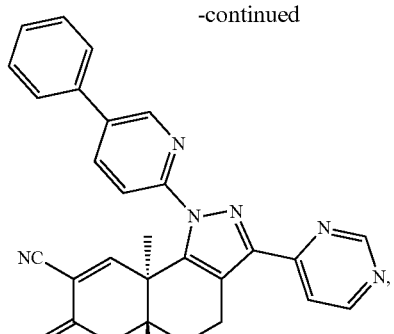
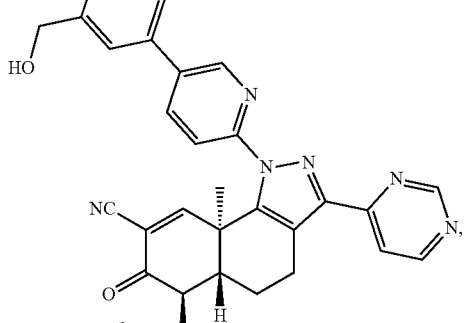
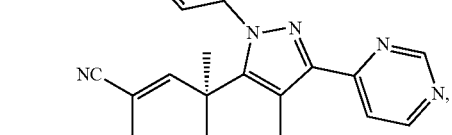
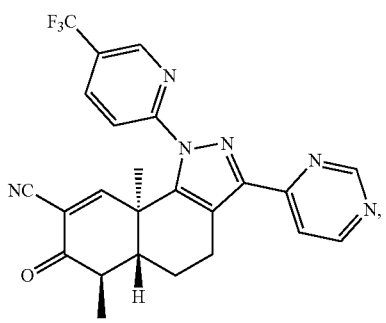

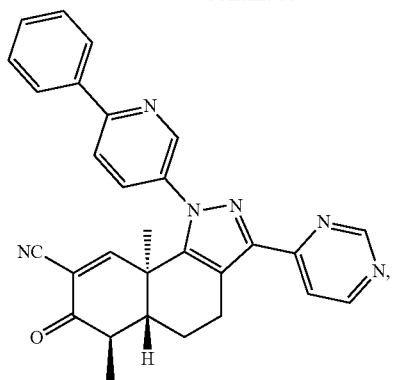
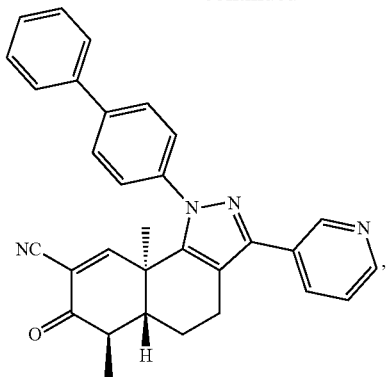
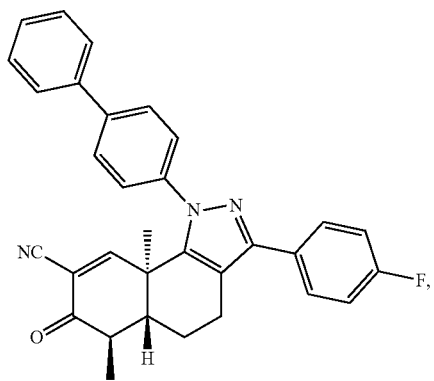
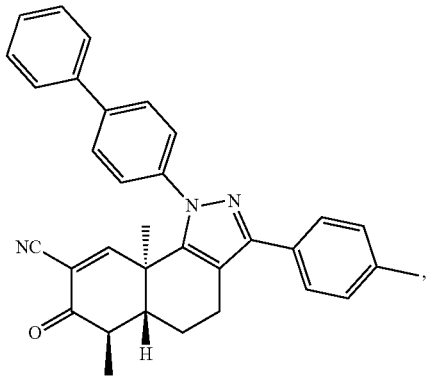
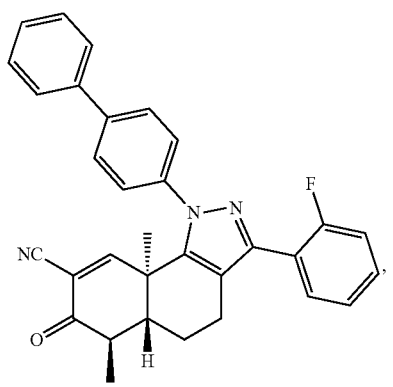
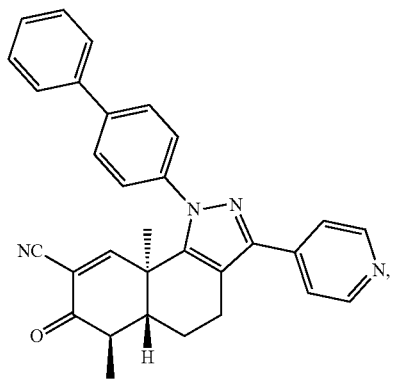
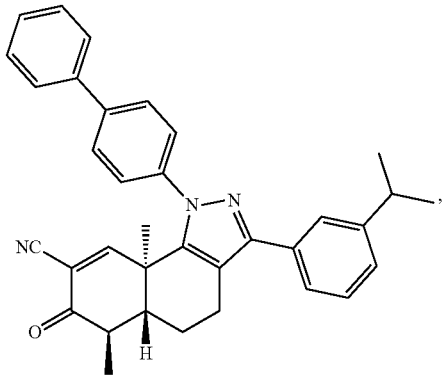

95
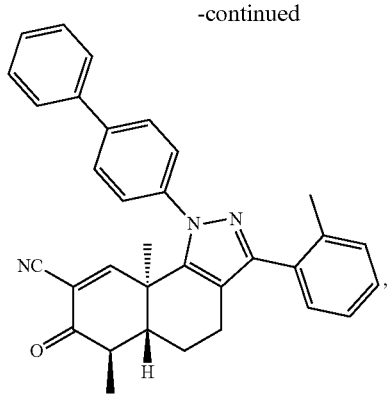
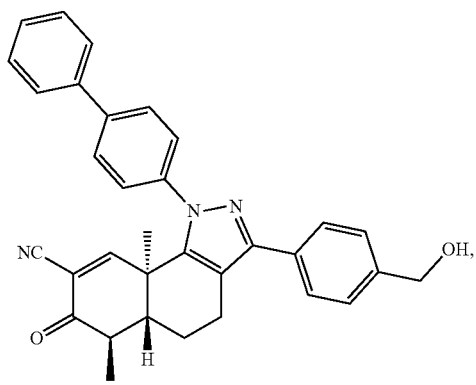
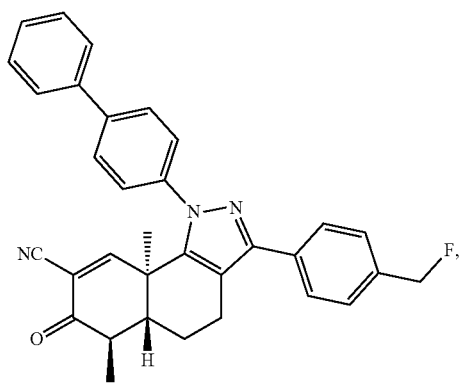
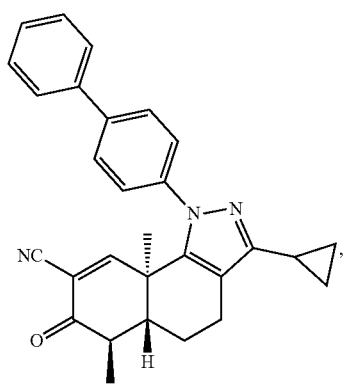
96
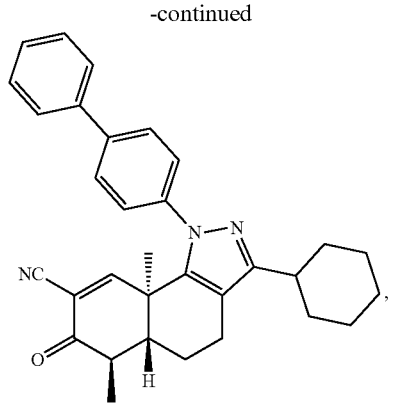
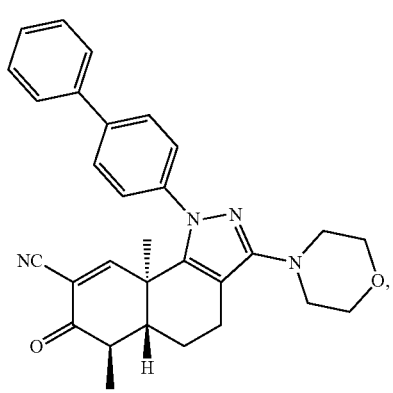
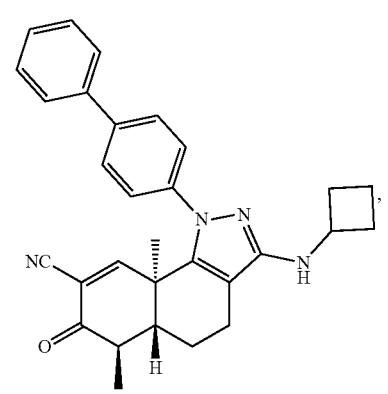
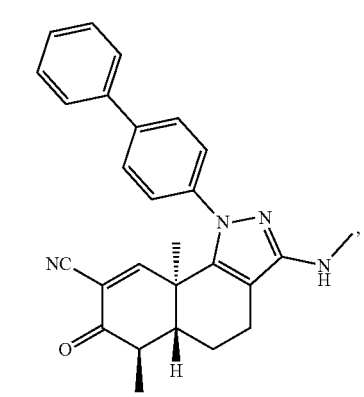

97
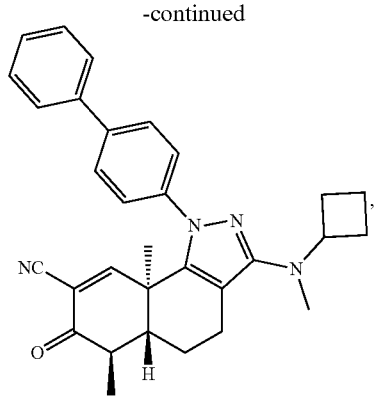
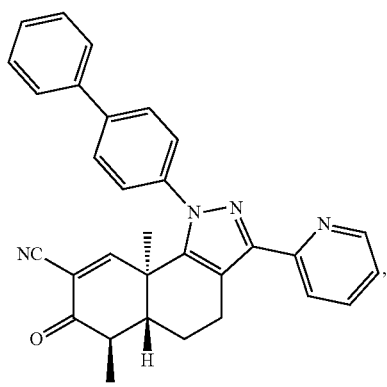
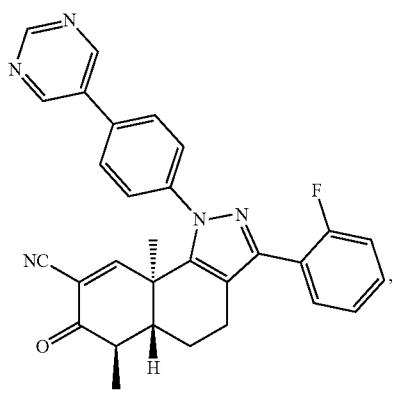
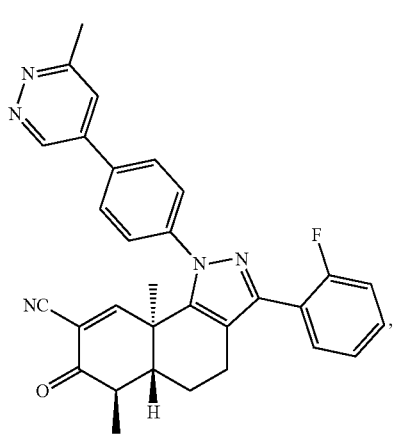
98
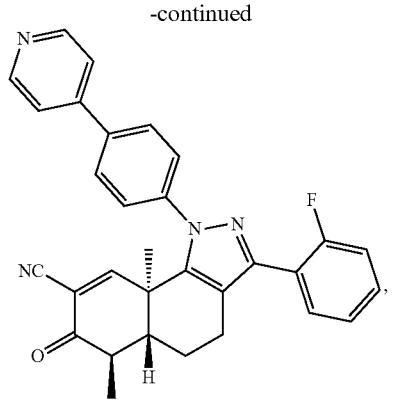
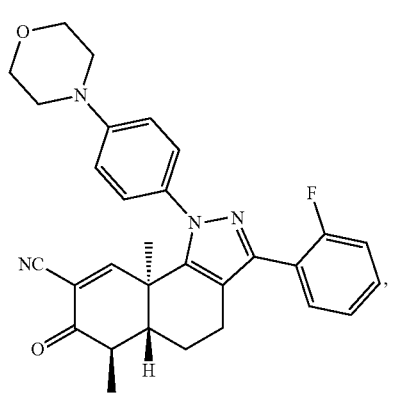
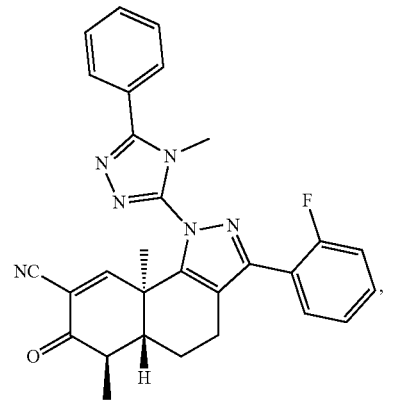
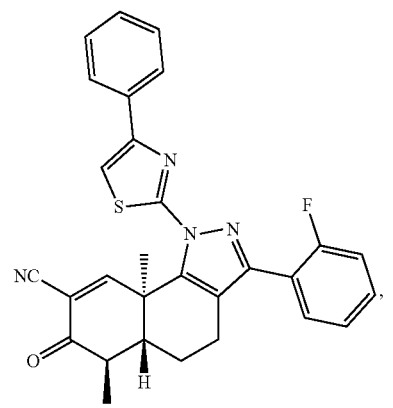

-continued
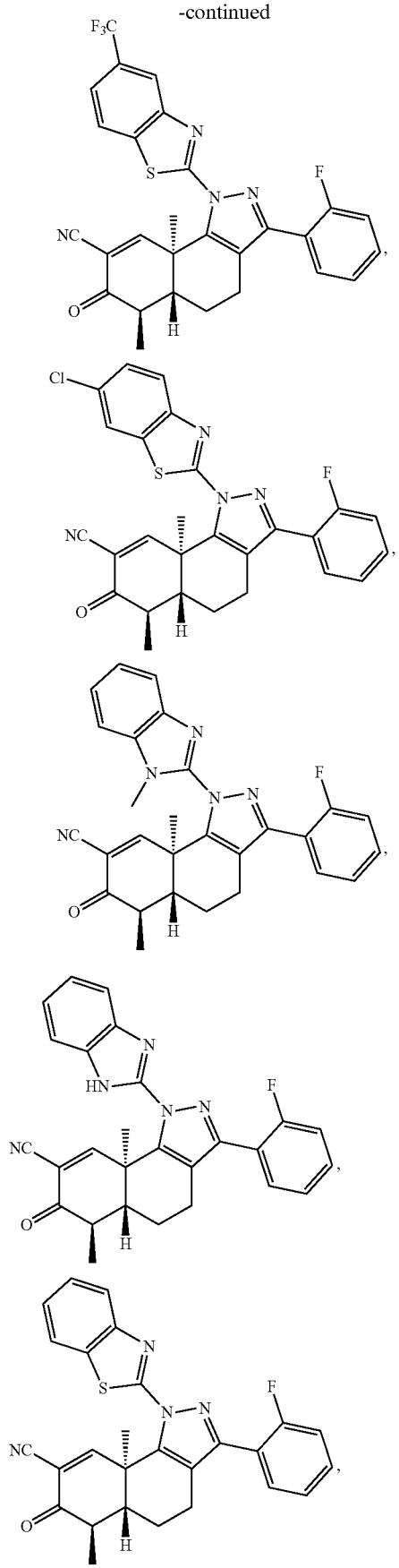
-continued
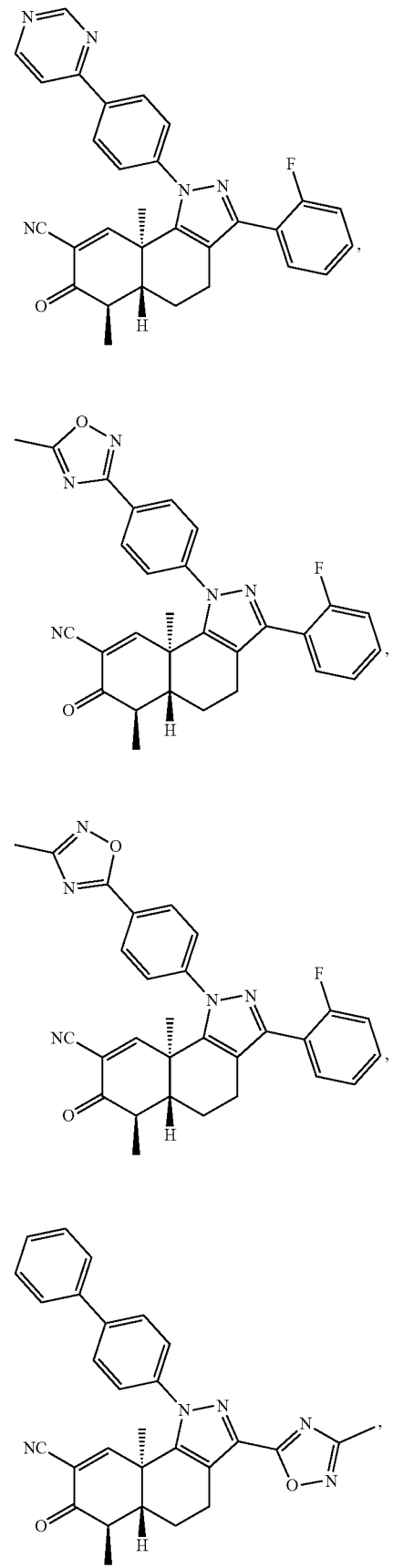

101
-continued
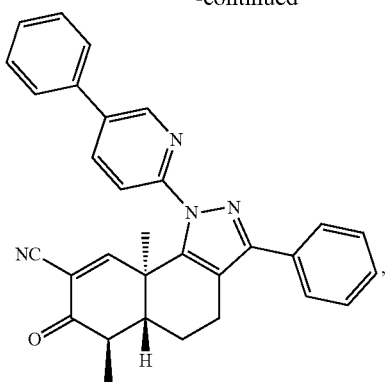
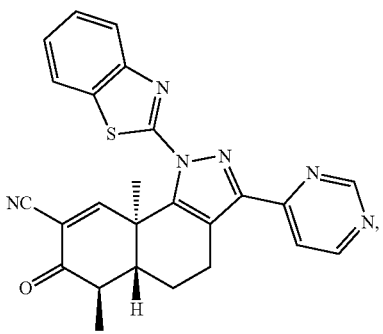
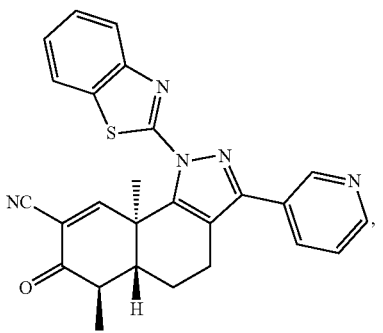
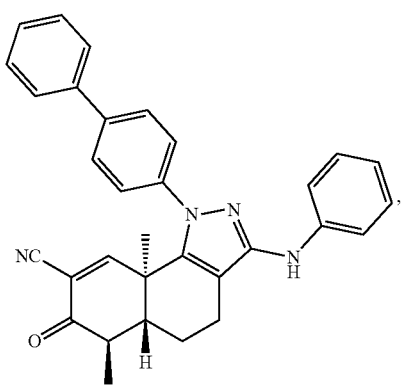
102
-continued
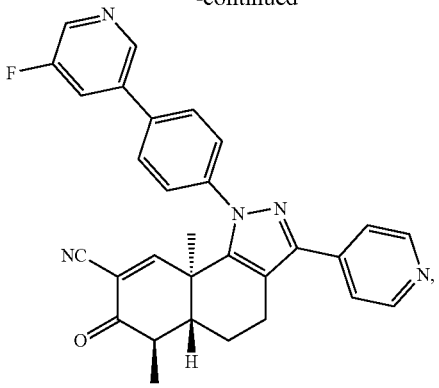
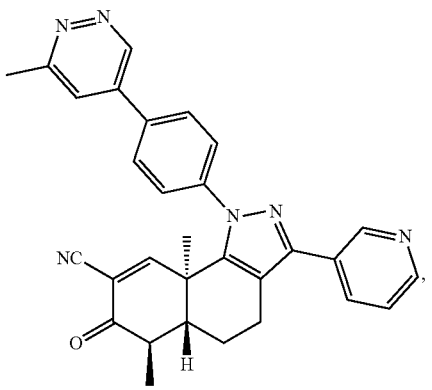
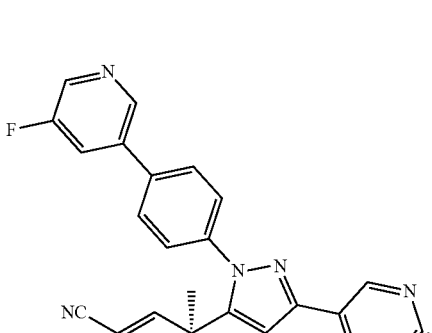
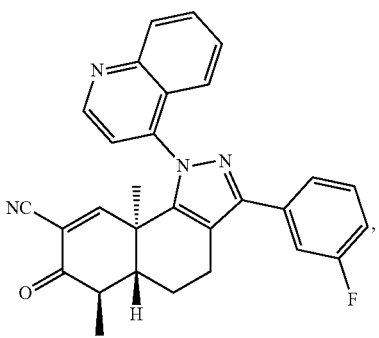

103
-continued
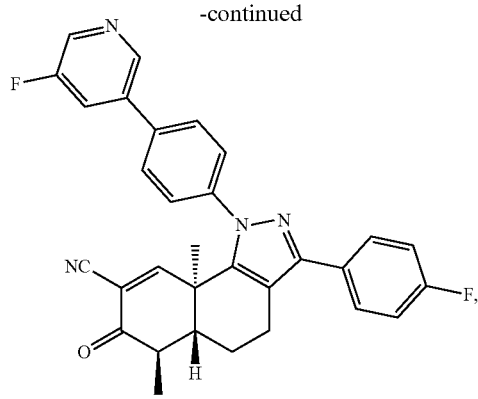
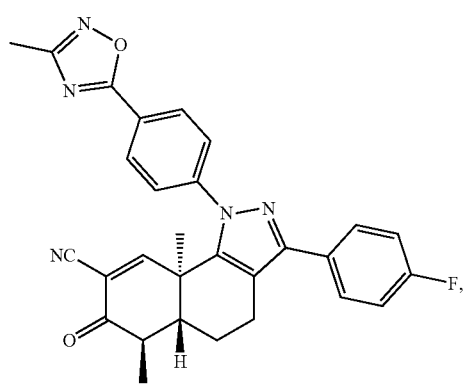
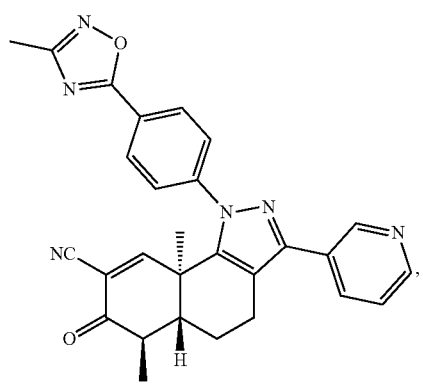
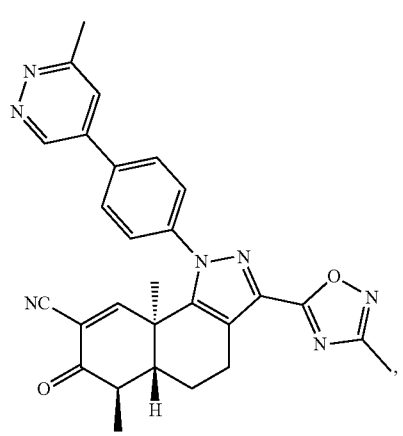
104
-continued
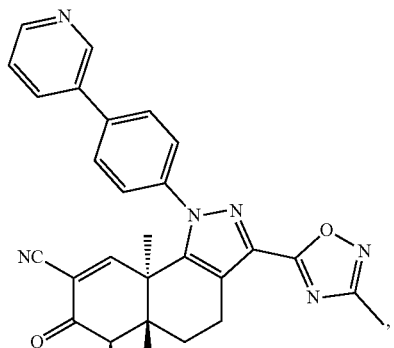
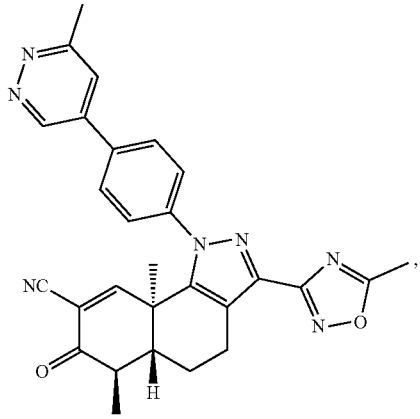
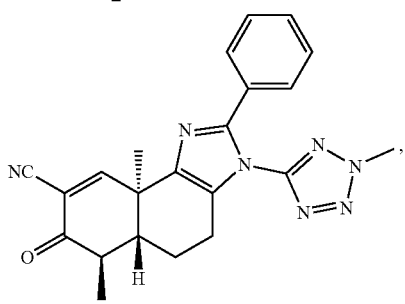
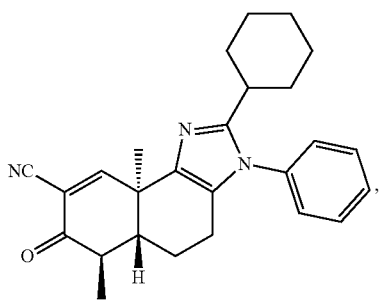

105
-continued
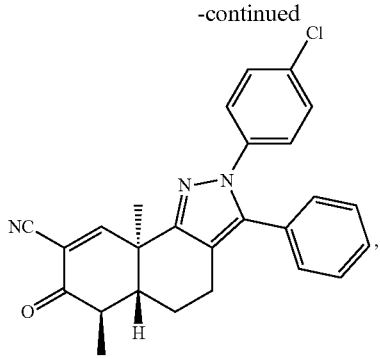
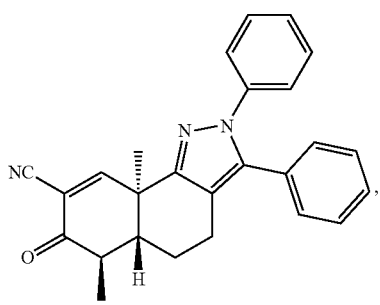
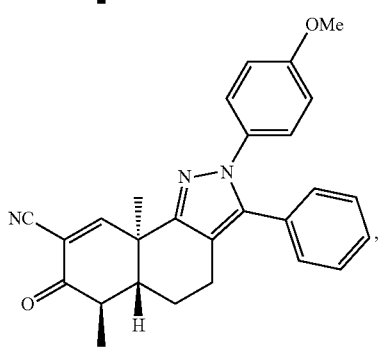
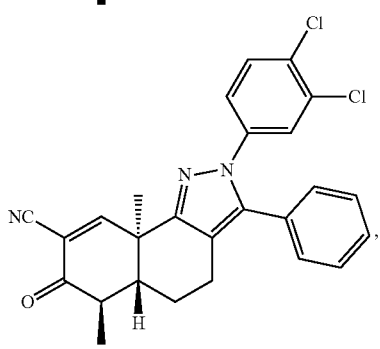
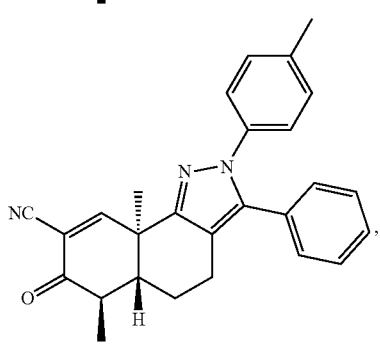
106
-continued
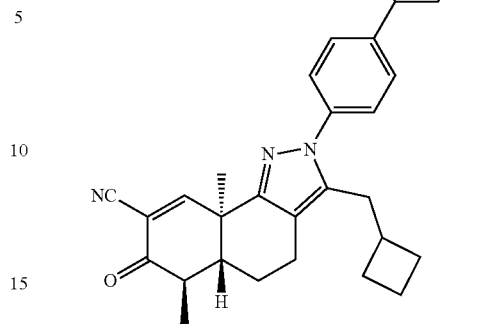
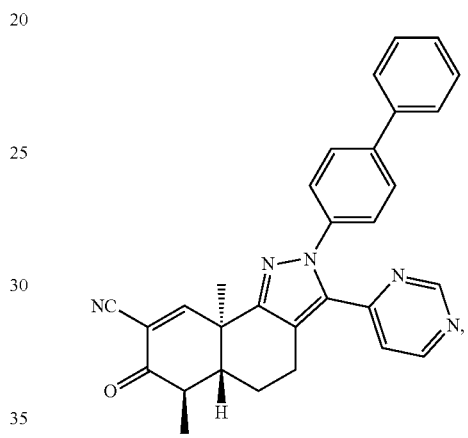
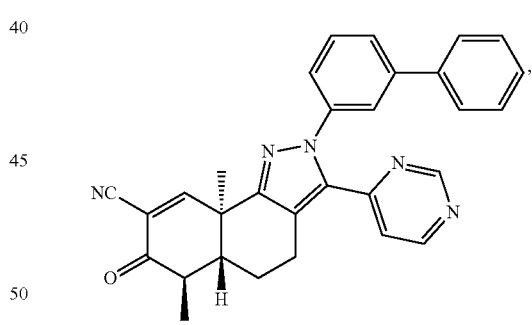
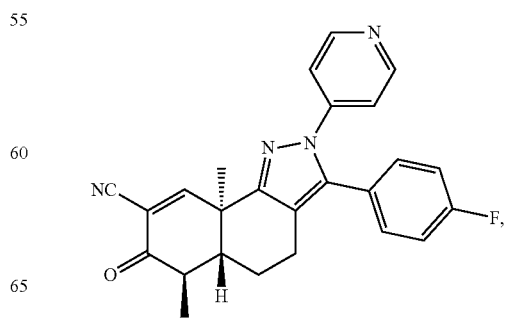

107
-continued
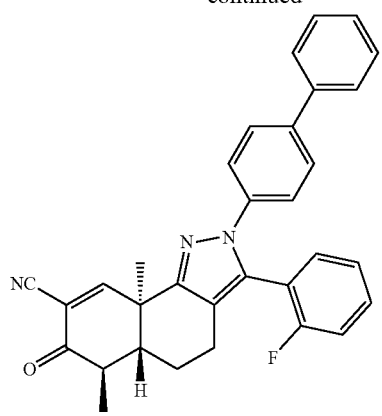
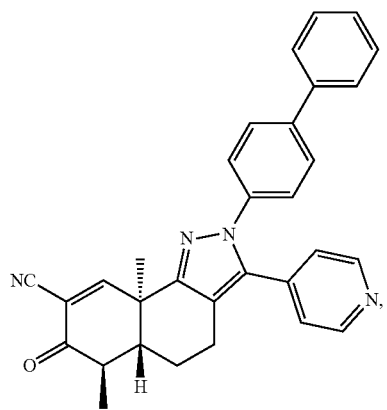
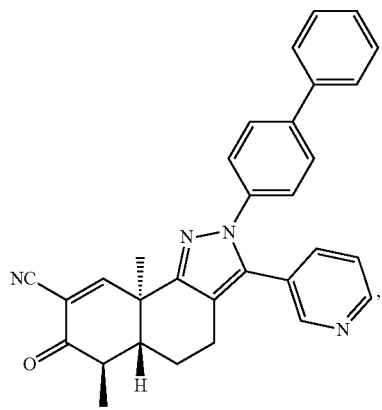
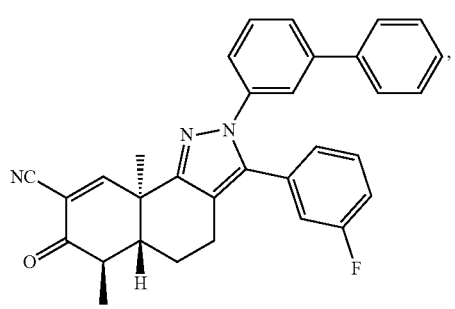
108
-continued
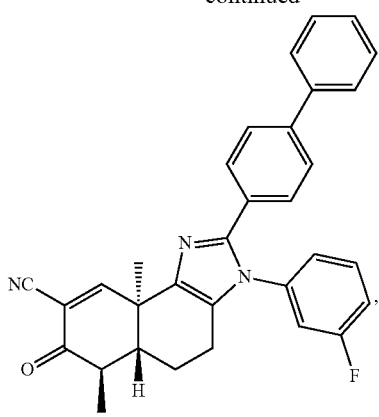
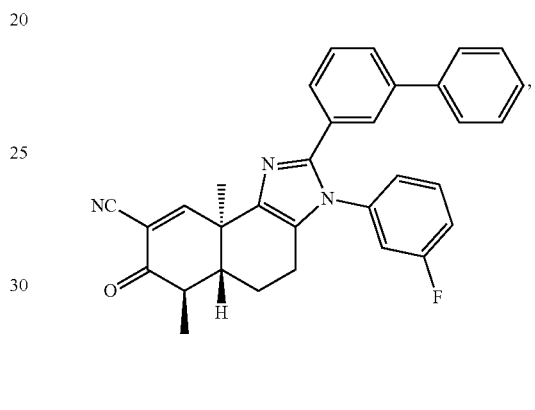
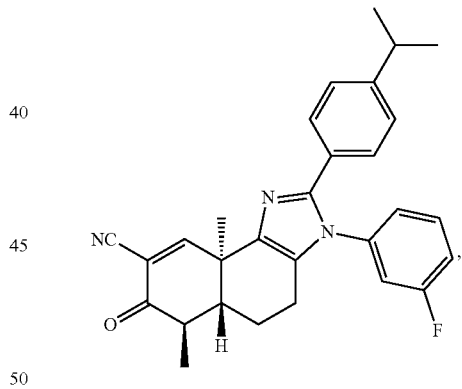
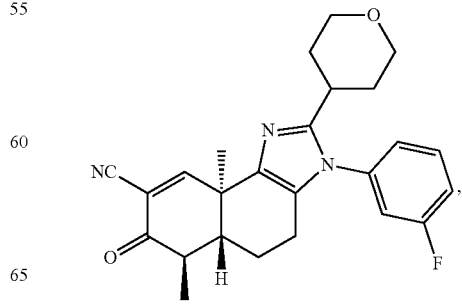

109
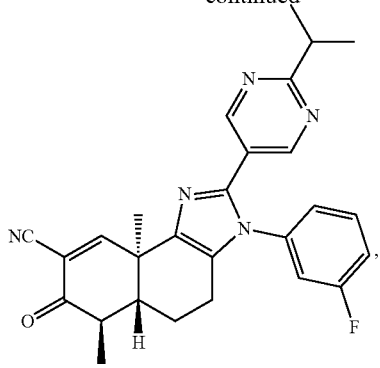
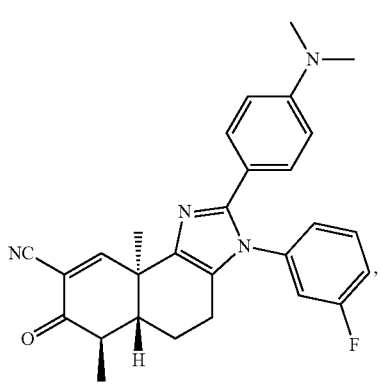
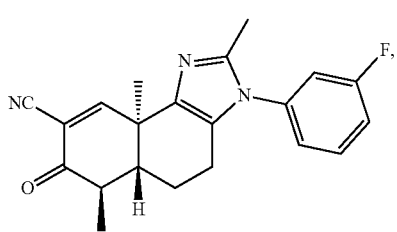
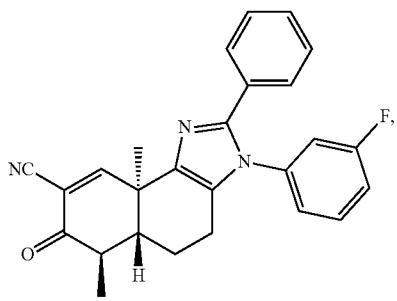
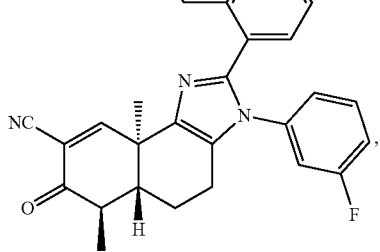
110
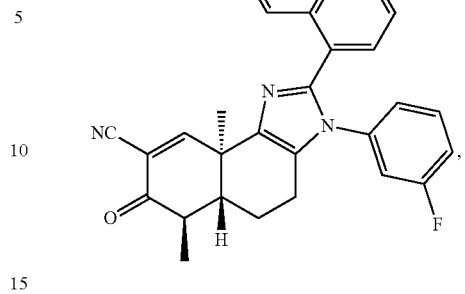
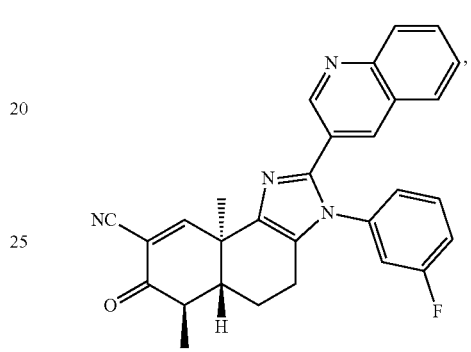
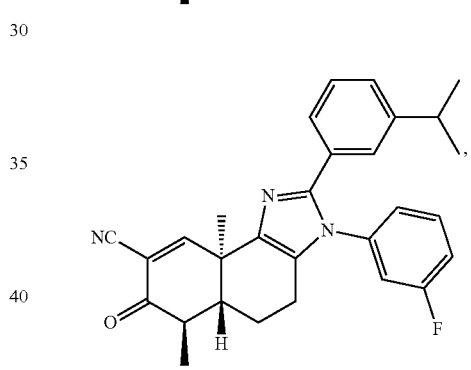
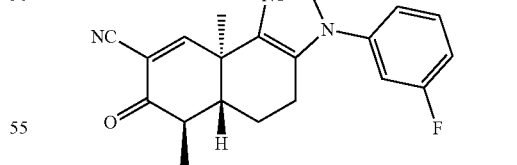
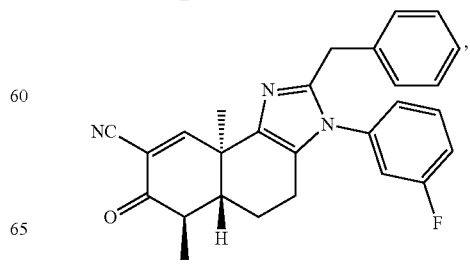

111
-continued
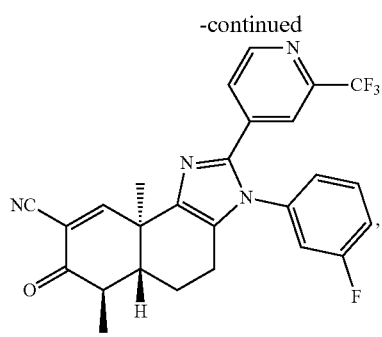
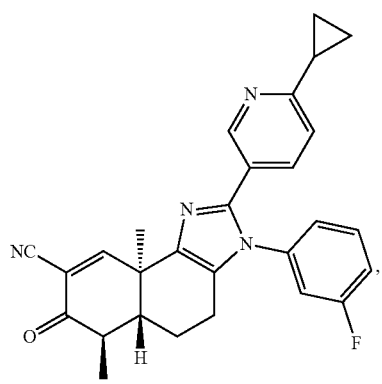
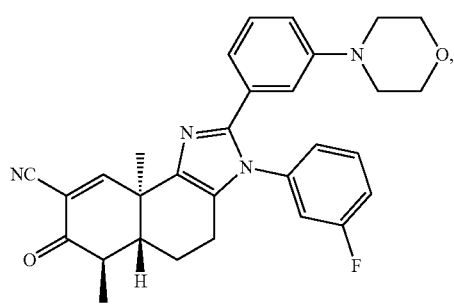
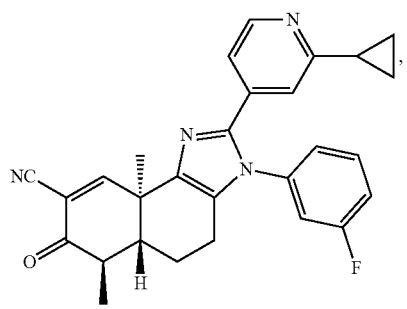
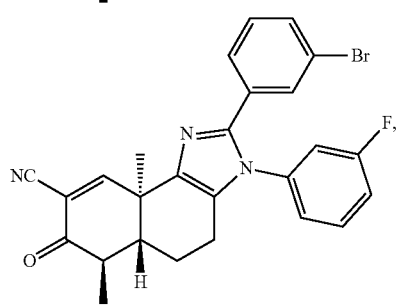
112
-continued
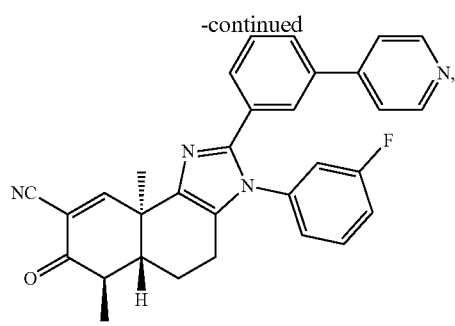
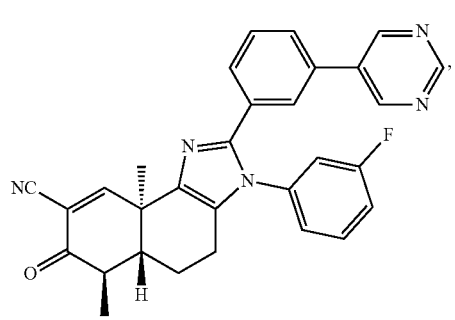
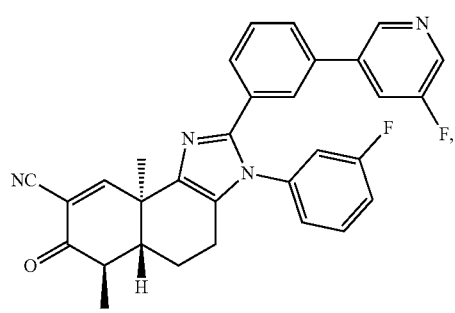
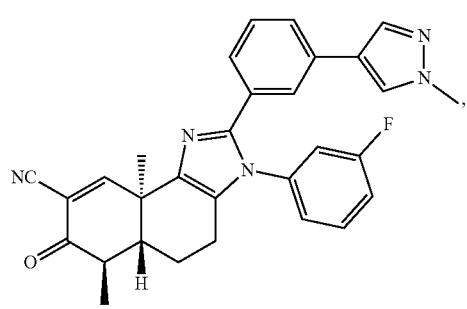
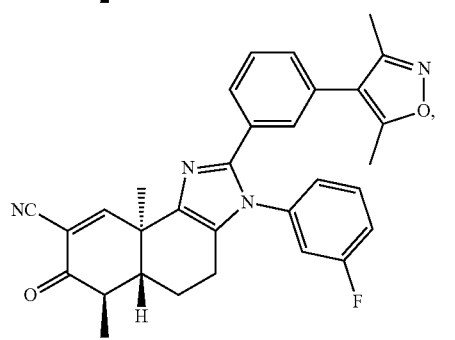

113
-continued
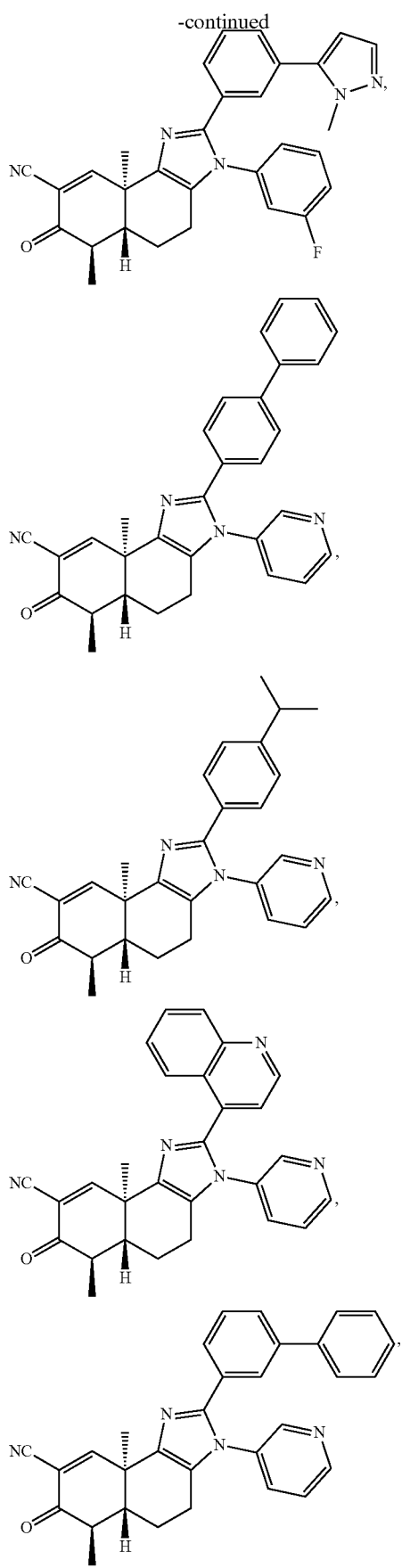
114
-continued
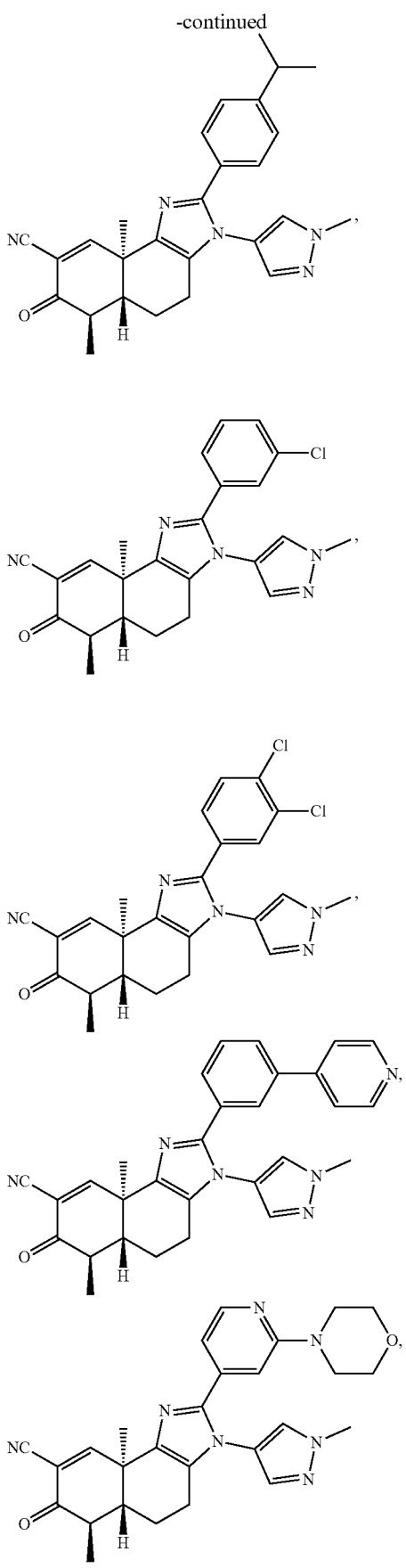

115
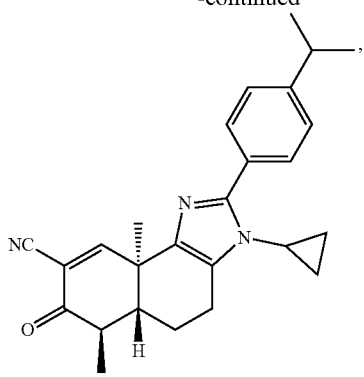
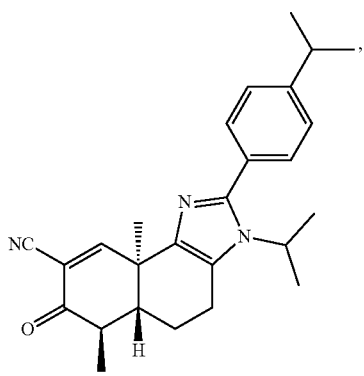
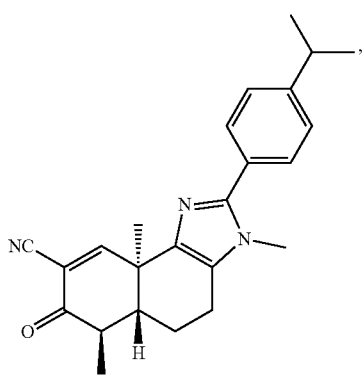
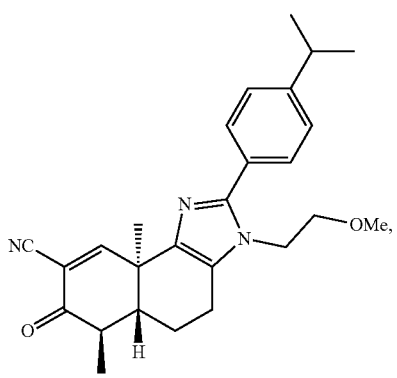
116
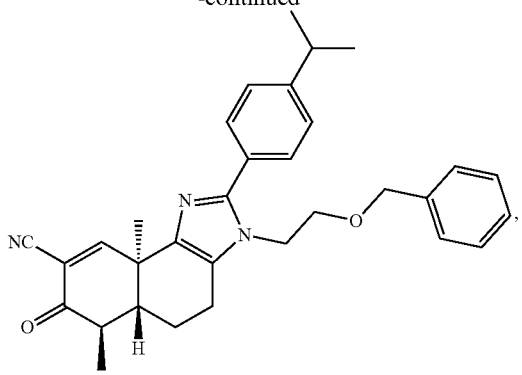
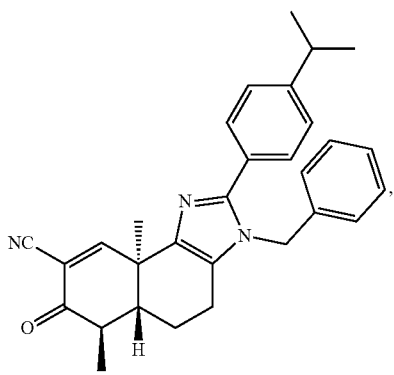
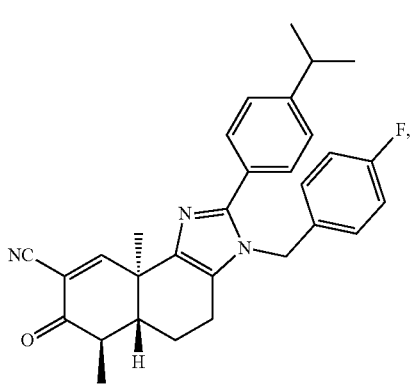
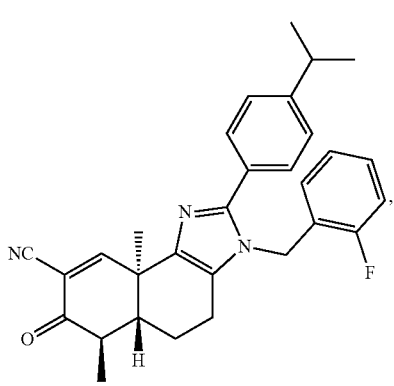

117
-continued
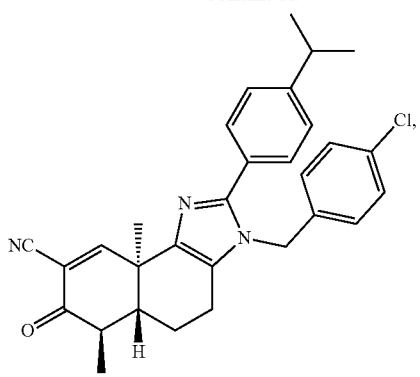
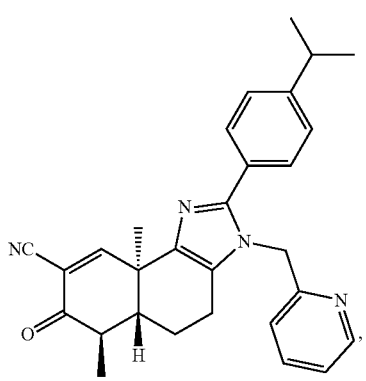
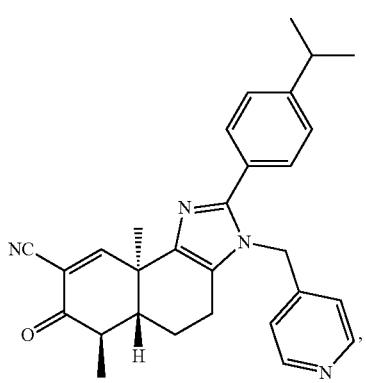
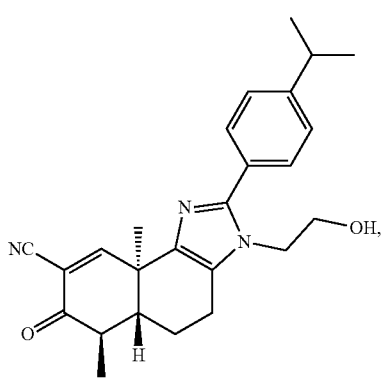
118
-continued
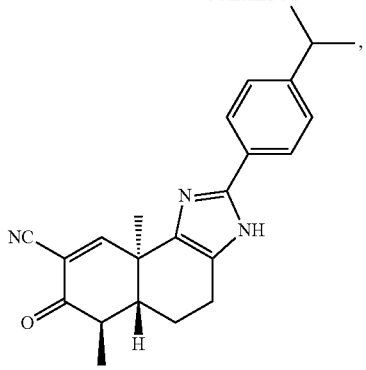
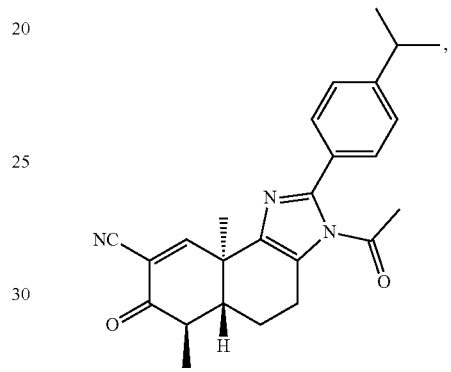
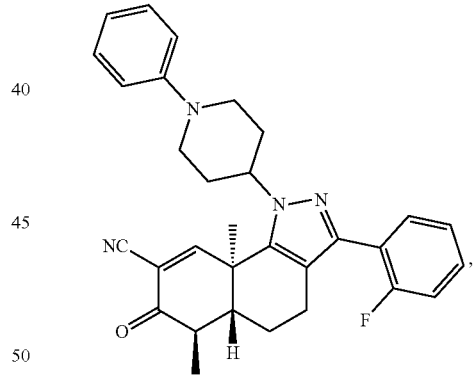
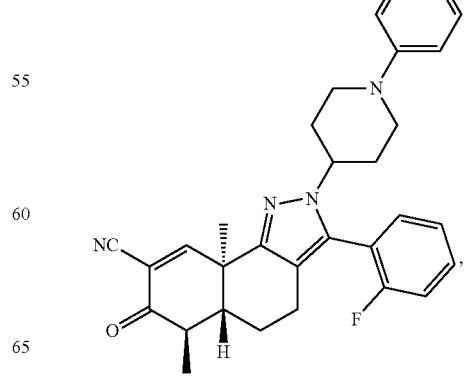

119
-continued
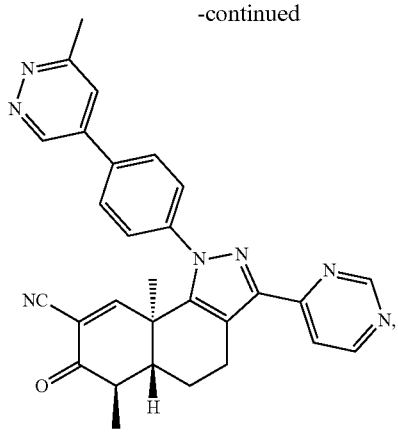
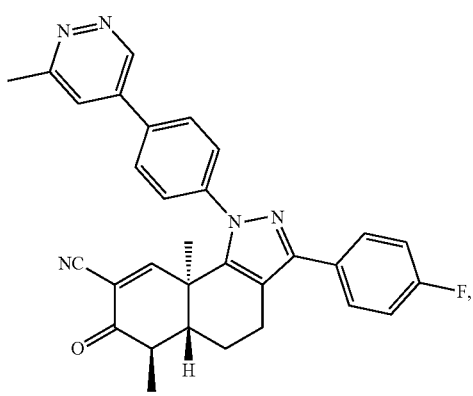
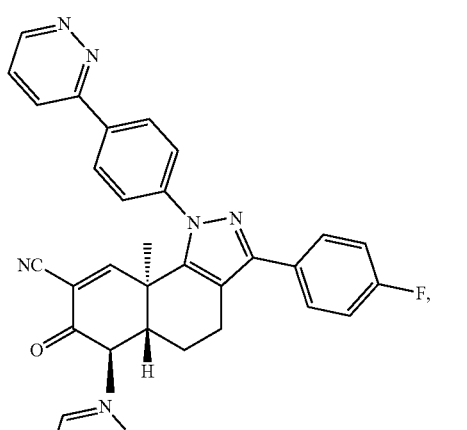
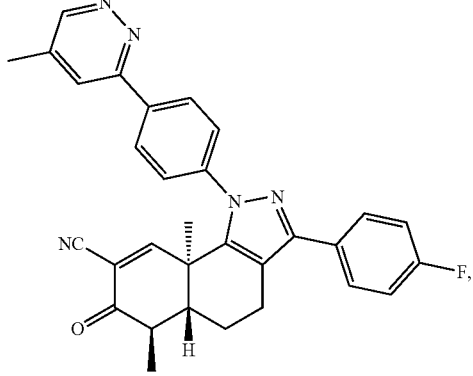
120
-continued
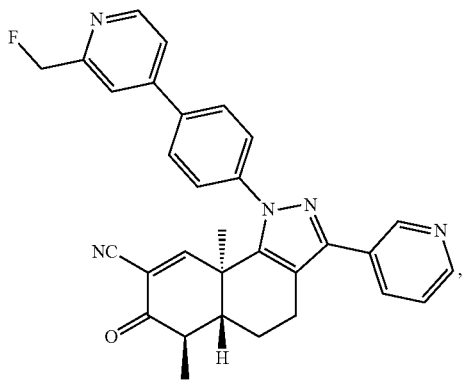
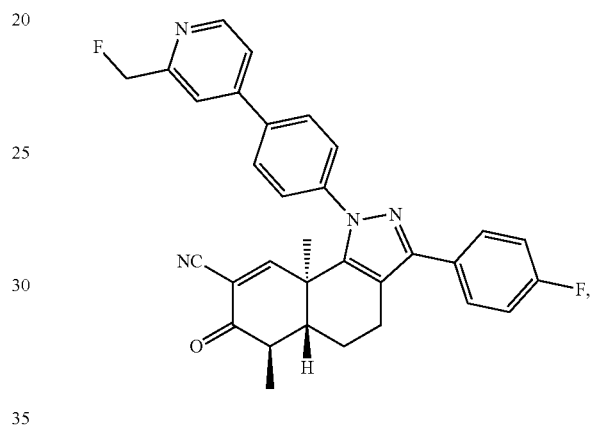
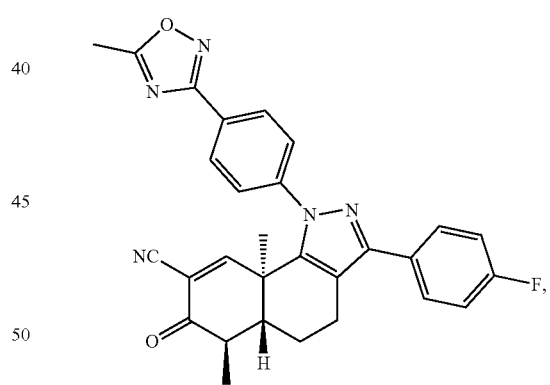
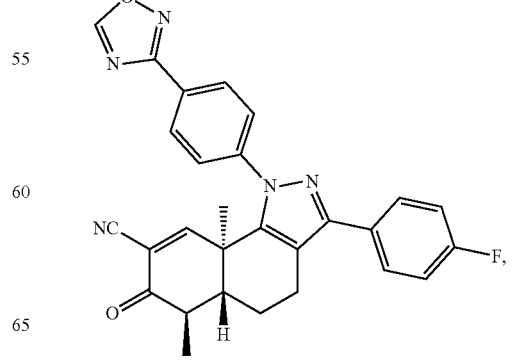

121
-continued
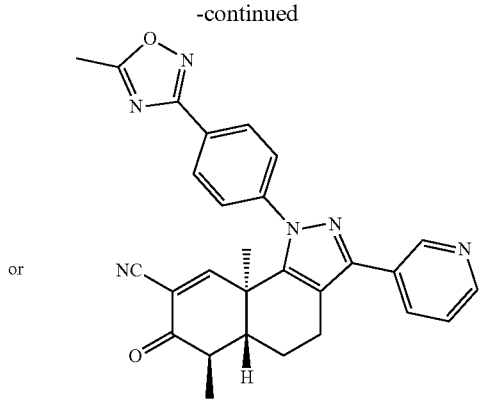
or
or a pharmaceutically acceptable salt of any of the above formulas.
In some embodiments, the compound is further defined as:
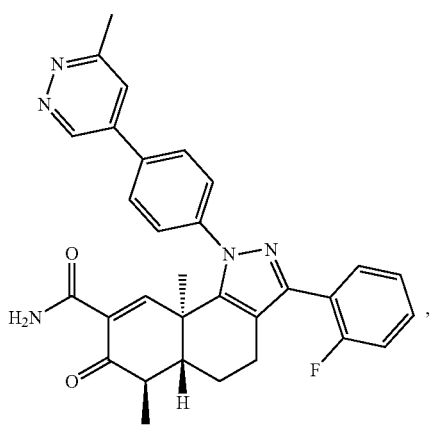
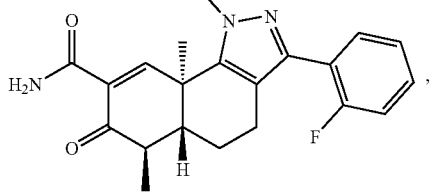
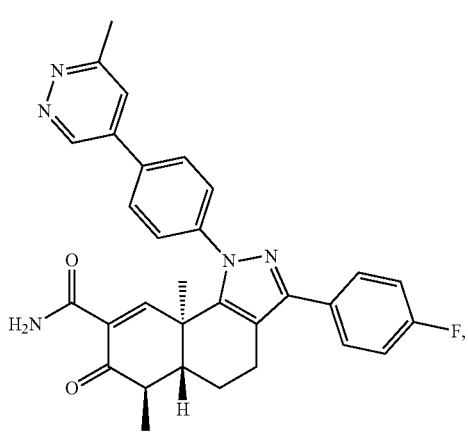
122
-continued
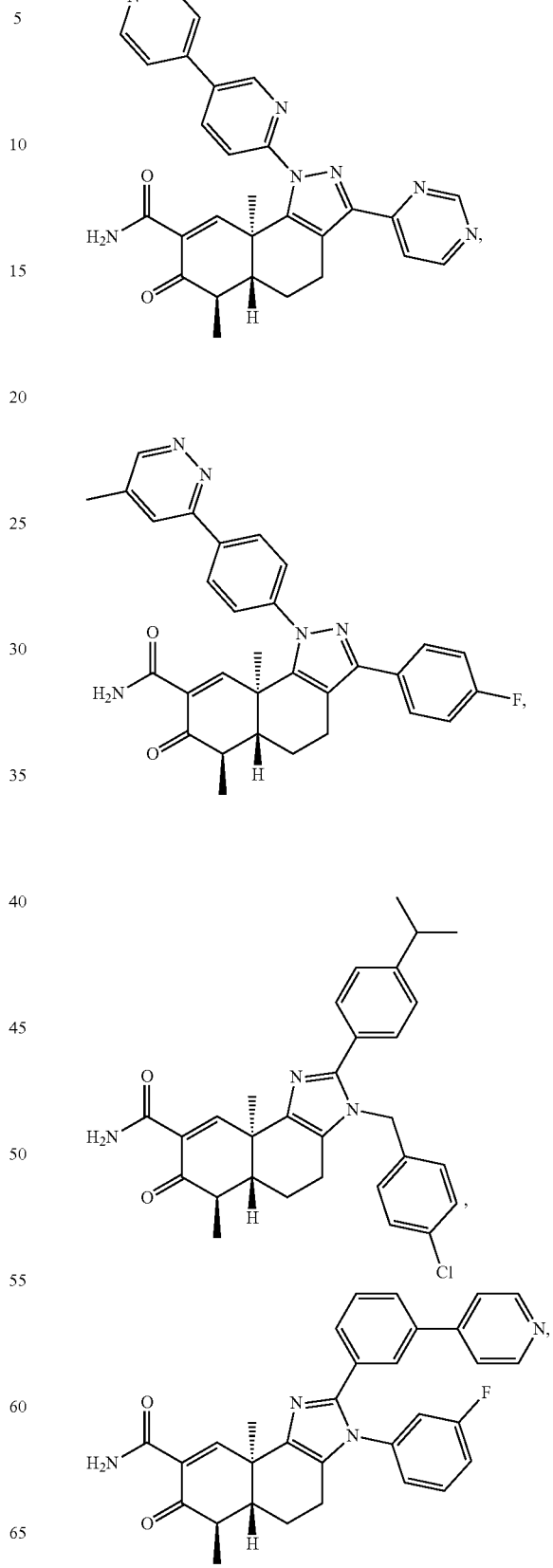

-continued

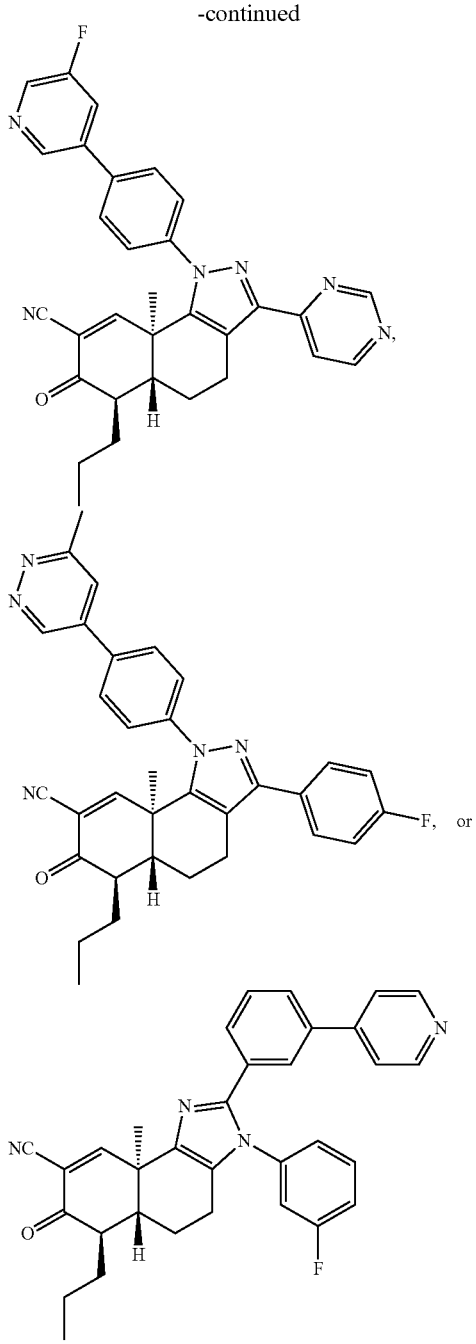

or a pharmaceutically acceptable salt of any of the above formulas.

In some embodiments, the therapeutically effective amount is a daily dose is 0.01-100 mg of inverse agonist per kg of body weight. In some embodiments, the daily dose is 0.05-30 mg of inverse agonist per kg of body weight. In some embodiments, the daily dose is 0.1-10 mg of inverse agonist per kg of body weight. In some embodiments, the daily dose is 0.1-5 mg of inverse agonist per kg of body weight. In some embodiments, the daily dose is 0.1-2.5 mg of inverse agonist per kg of body weight.

In some embodiments, the inverse agonist is administered as a single dose to the patient per day. In other embodiments, the inverse agonist is administered as two or more doses to the patient per day. In some embodiments, the inverse agonist is administered orally, intraarterially or intravenously. In some embodiments, the inverse agonist is formulated as a hard or soft capsule or a tablet.

In still another aspect, the present disclosure provides compounds of the formula:

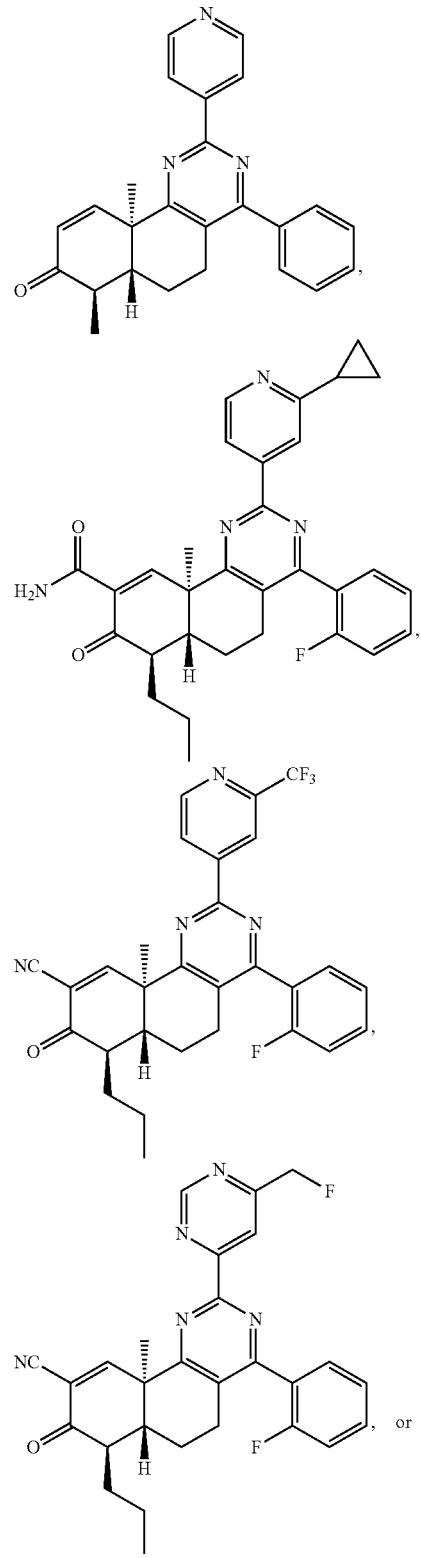

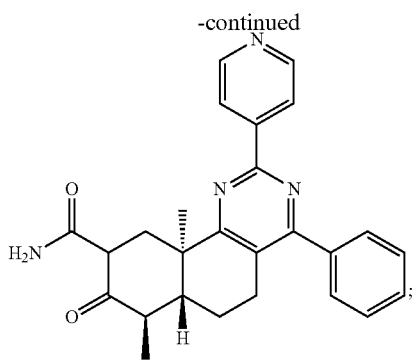

or a pharmaceutically acceptable salt thereof.

In yet another aspect, the present disclosure provides pharmaceutical compositions comprising a compound of the present disclosure and an excipient.

In some embodiments, the pharmaceutical composition is formulated for administration: orally, intraadiposally, intraarterially, intraarticularly, intracranially, intradermally, intralesionally, intramuscularly, intranasally, intraocularly, intrapericardially, intraperitoneally, intrapleurally, intraprostatically, intrarectally, intrathecally, intratracheally, intratumorally, intraumbilically, intravaginally, intravenously, intravesicularlly, intravitreally, liposomally, locally, mucosally, parenterally, rectally, subconjunctival, subcutaneously, sublingually, topically, transbuccally, transdermally, vaginally, in crèmes, in lipid compositions, via a catheter, via a lavage, via continuous infusion, via infusion, via inhalation, via injection, via local delivery, or via localized perfusion. In some embodiments, the pharmaceutical composition is formulated for oral administration. In other embodiments, the pharmaceutical composition is formulated for administration via injection such as for intraarterial administration, intramuscular administration, intraperitoneal administration, or intravenous administration. In other embodiments, the pharmaceutical composition is formulated for administration topically such as for topical administration to the skin or to the eye. In some embodiments, the pharmaceutical composition is formulated as a unit dose.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figures 1A, 1B:
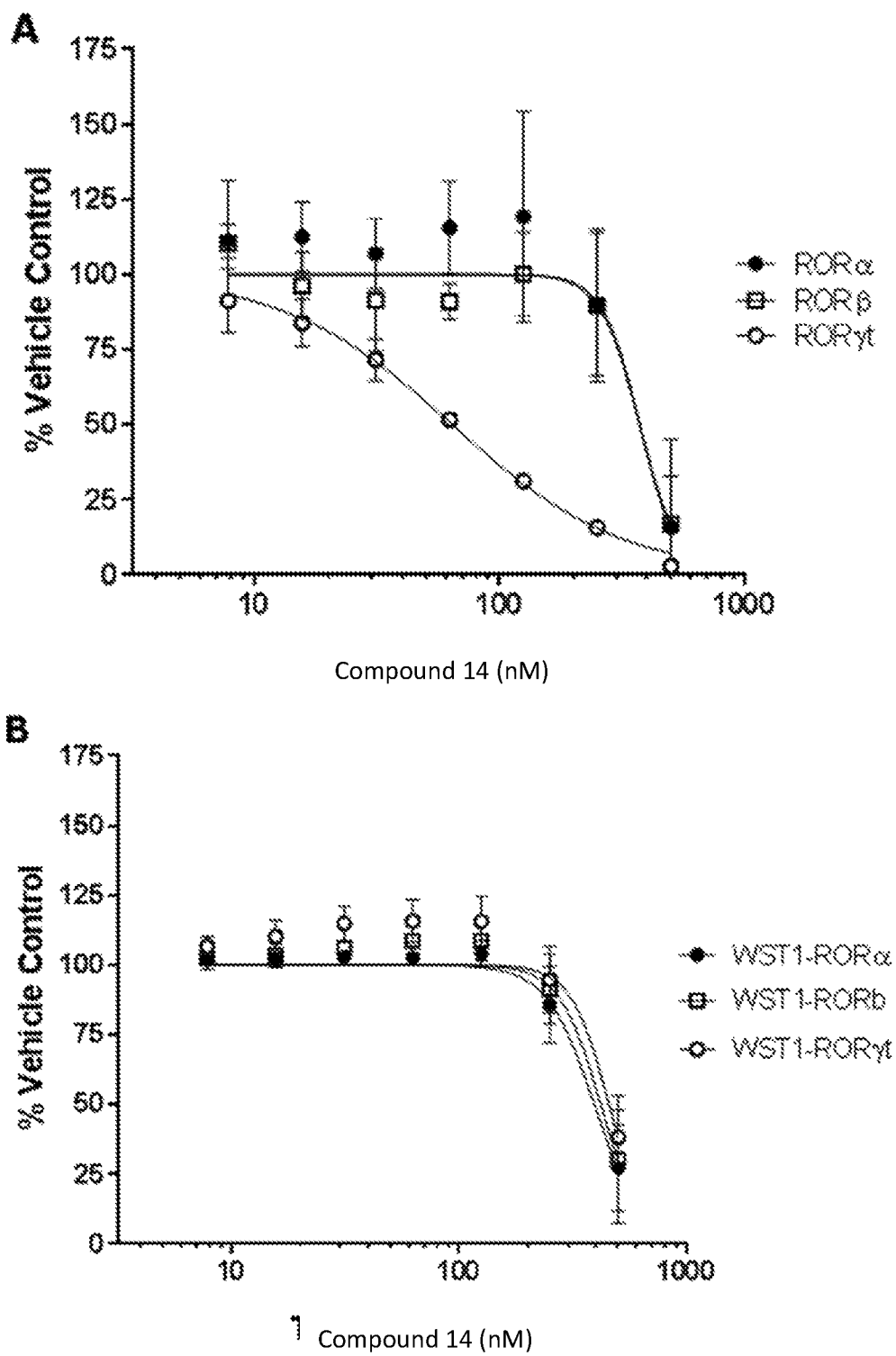
FIGS. 1A-1B show the effect of compound 14 on ROR$\alpha$, ROR$\beta$, and ROR$\gamma$t activity.

Disclosed herein are methods, compounds, and compositions that may be used to inhibit or modulate the activity of the ROR$\gamma$ nuclear receptor and/or IL-17 by covalent modification of the allosteric binding site. These methods are thus useful in the treatment of a wide variety of different indications such as autoimmune disease, metabolic diseases, cancer, and infections. These methods may be used to modulate the expression of one or more downstream compound such as interleukin-17 (IL-17) through covalent modification of the ROR$\gamma$ nuclear receptor.

I. COMPOUNDS AND SYNTHETIC METHODS

The compounds of the present invention and the compounds for use with the present invention (also referred to as "compounds of the present disclosure") are shown, for example, above, in the summary of the invention section, and in the claims below. They may be made using the synthetic methods described in PCT/US2017/000094 (WO 2018/111315) and PCT/US2019/037543, the entire contents of which are hereby incorporated by reference. These methods can be further modified and optimized using the principles and techniques of organic chemistry as applied by a person skilled in the art. Such principles and techniques are taught, for example, in Smith, *March's Advanced Organic Chemistry: Reactions, Mechanisms, and Structure*, (2013), which is incorporated by reference herein. In addition, the synthetic methods may be further modified and optimized for preparative, pilot- or large-scale production, either batch or continuous, using the principles and techniques of process chemistry as applied by a person skilled in the art. Such principles and techniques are taught, for example, in Anderson, *Practical Process Research & Development—A Guide for Organic Chemists* (2012), which is incorporated by reference herein.

All the compounds of the present invention may in some embodiments be used for the prevention and treatment of one or more diseases or disorders discussed herein or otherwise. In some embodiments, one or more of the compounds characterized or exemplified herein as an intermediate, a metabolite, and/or prodrug, may nevertheless also be useful for the prevention and treatment of one or more diseases or disorders. As such unless explicitly stated to the contrary, all the compounds of the present invention are deemed "active compounds" and "therapeutic compounds" that are contemplated for use as active pharmaceutical ingredients (APIs). Actual suitability for human or veterinary use is typically determined using a combination of clinical trial protocols and regulatory procedures, such as those administered by the Food and Drug Administration (FDA). In the United States, the FDA is responsible for protecting the public health by assuring the safety, effectiveness, quality, and security of human and veterinary drugs, vaccines and other biological products, and medical devices.

In some embodiments, the compounds of the present invention have the advantage that they may be more efficacious than, be less toxic than, be longer acting than, be more potent than, produce fewer side effects than, be more easily absorbed than, more metabolically stable than, more lipophilic than, more hydrophilic than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

Compounds of the present invention may contain one or more asymmetrically-substituted carbon or nitrogen atom and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present invention can have the S or the R configuration. In some embodiments, the present compounds may contain two or more atoms which have a defined stereochemical orientation.

Chemical formulas used to represent compounds of the present invention will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

In some embodiments, compounds of the present invention function as prodrugs or can be derivatized to function as prodrugs. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the invention contemplates prodrugs of compounds of the present invention as well as methods of delivering prodrugs. Prodrugs of the compounds employed in the invention may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a patient, cleaves to form a hydroxy, amino, or carboxylic acid, respectively.

In some embodiments, compounds of the present invention exist in salt or non-salt form. With regard to the salt form(s), in some embodiments the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will be appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present invention.

II. RORγ AND CYTOKINE IL-17

Without being bound by theory, the presence of a Michael acceptor (MA) in the A ring is important in methods of modulating the activity of RORγ/RORγt described herein. In particular, the presence of an electron-withdrawing group at C2 shows strong activity, with a CN group at C2 showing stronger activity. This relationship suggests that a cysteine dependent covalent drug:protein interaction is involved in the activity of these inhibitors and of related compounds. This mechanism of action (MOA) has been explored successfully with other protein classes, most notably with kinases, nonetheless it is rare in the nuclear hormone receptor field, and unreported in the ROR family. The chemical biology literature of NHR's provides few insights on how to triage the eight cysteines on RORγ for their proclivity towards covalent drug:protein interaction. PPARγ is the lone exception, where it has been noted that several endogenous fatty acid metabolite ligands, e.g. $PGJ_2$, bind in the orthosteric site through covalent interaction with cysteine 285 on helix H3 and thusly regulate the transcriptional activity. Interestingly, cysteine 320 on alpha helix H3 of RORγt is in the same location as cysteine 285 on PPARγ. Based on this evidence suggesting that cysteine 320 of RORγ (see SEQ ID NO: 1; and which is equivalent to cysteine 299 in RORγt (see SEQ ID NO: 2)) could be the companion residue of interest, site directed mutation of cysteine 320 to alanine and serine was used to obtain functional proteins that could be used to test this hypothesis. The activities of compounds 14 and 21 were found to be unaffected by both mutations in the full-length RORγt RORE-luciferase reporter assay in Jurkat cells, i.e., their activity was maintained in the presence of these mutations. These observations were supported by competitive binding studies monitored by mass spectrometry that demonstrated that 14 and 21 did not compete with cholesterol sulfate, a known orthosteric ligand for RORγ/RORγt. Reporter gene constructs wherein each of the remaining seven cysteine residues in the LBD were selectively mutated to a different amino acid residue were prepared. When compounds 14 and 21 were assayed against these constructs only the cysteine 476 in RORγ (cysteine 455 in RORγt) mutations led to a reduction in RORγt RORE-luciferase reporter expression in Jurkat cells versus the parent construct, demonstrating that this cysteine was the singular residue involved in covalent interactions with the Michael acceptor moiety.

```
-RORγ Protein Sequence:
                                         SEQ ID NO: 1
    MDRAPQRQHR ASRELLAAKK THTSQIEVIP

CKICGDKSSG IHYGVITCEG CKGFFRRSQR

CNAAYSCTRQ QNCPIDRTSR NRCQHCRLQK

CLALGMSRDA VKFGRMSKKQ RDSLHAEVQK

QLQQRQQQQQ EPVVKTPPAG AQGADTLTYT

LGLPDGQLPL GSSPDLPEAS ACPPGLLKAS
```

```
              GSGPSYSNNL AKAGLNGASC HLEYSPERGK

AEGRESFYST GSQLTPDRCG LRFEEHRHPG

LGELGQGPDS YGSPSFRSTP EAPYASLTEI

EHLVQSVCKS YRETCQLRLE DLLRQRSNIF

SREEVTGYQR KSMWEMWERC AHHLTEAIQY

VVEFAKRLSG FMELCQNDQI VLLKAGAMEV

VLVRMCRAYN ADNRTVFFEG KYGGMELFRA

LGCSELISSI FDFSHSLSAL HFSEDEIALY

TALVLINAHR PGLQEKRKVE QLQYNLELAF

HHHLCKTHRQ SILAKLPPKG KLRSLCSQHV

ERLQIFQHLH PIVVQAAFPP LYKELFSTET

ESPVGLSK

-RORγt Protein Sequence:
                                              SEQ ID NO: 2
              MRTQIEVIPC KICGDKSSGI

HYGVITCEGC KGFFRRSQRC NAAYSCTRQQ

NCPIDRTSRN RCQHCRLQKC LALGMSRDAV

KFGRMSKKQR DSLHAEVQKQ LQQRQQQQQE

PVVKTPPAGA QGADTLTYTL GLPDGQLPLG

SSPDLPEASA CPPGLLKASG SGPSYSNNLA

KAGLNGASCH LEYSPERGKA EGRESFYSTG

SQLTPDRCGL RFEEHRHPGL GELGQGPDSY

GSPSFRSTPE APYASLTEIE HLVQSVCKSY

RETCQLRLED LLRQRSNIFS REEVTGYQRK

SMWEMWERCA HHLTEAIQYV VEFAKRLSGF

MELCQNDQIV LLKAGAMEVV LVRMCRAYNA

DNRTVFFEGK YGGMELFRAL GCSELISSIF

DFSHSLSALH FSEDEIALYT ALVLINAHRP

GLQEKRKVEQ LQYNLELAFH HHLCKTHRQS

ILAKLPPKGK LRSLCSQHVE RLQIFQHLHP

IVVQAAFPPL YKELFSTETE SPVGLSK
```

B. Cytokine IL-17

Various reports have implicated the inflammatory cytokine IL-17 in the pathogenesis of many autoimmune diseases, including rheumatoid arthritis, psoriasis and psoriatic arthritis, inflammatory bowel diseases (including but not limited to Crohn's disease), multiple sclerosis, autoimmune nephritis, autoimmune uveitis, Type 1 diabetes, and ankylosing spondylitis. In some embodiments, the compounds provided herein may be administered to a patient in order to treat or prevent one or more of these diseases or disorders. A type of T lymphocyte known as a Th17 cell is a primary source of IL-17. There are multiple members of the IL-17 family. The first identified member, IL-17A, is commonly referred to as IL-17. IL-17 is composed of two monomers linked by disulfide bonds to form a homodimer (Miossec and Kolls, 2012). Aside from IL-17A, the other principal family member is IL-17F. Some evidence suggests that IL-17F and IL-17A, though they have many effects in common, may have different effects in certain settings such as lung inflammation. The IL-17 cytokines bind to IL-17 receptors (IL-17R) located in the membrane of select cell types. Although there are multiple subtypes of the IL-17 receptor, the IL-17RA/IL-17RC complex is required for the activity of IL-17A and IL-17F. IL-17RA has the unusual property of signaling through a pathway that involves an adaptor protein (ACT1) rather than the Janus kinase/signal transducer and activator of transcription (JAK/STAT) pathway employed by most interleukin receptors. Binding of IL-17A to IL-17RA activates the pro-inflammatory nuclear factor-kappa B (NF-κB) pathway and pro-inflammatory elements of the mitogen-activated protein kinase (MAPK) pathway such as JUN N-terminal kinase (JNK), p38 and extracellular signal-related kinase (ERK). IL-17 activity stimulates secretion of IL-6 and IL-8 from mesenchymal cells and leads to fever along with the accumulation of neutrophils in blood and tissue. In some embodiments, the compounds provided herein may be used to inhibit the secretion of IL-6 and IL-8 from mesenchymal cells. In some embodiments, the compounds provided herein may be administered to a patient in order to prevent or inhibit fever in a patient. In some embodiments, the compounds provided herein may be administered to a patient in order to prevent the accumulation of neutrophils in the blood or tissue of the patient.

Aside from its contribution to acute inflammation, IL-17 also contributes to chronic inflammation (Miossec and Kolls, 2012). In some embodiments, the compounds provided herein may be administered to a patient in order to prevent or treat chronic inflammation. IL-17 stimulates the production of matrix metalloproteinases (MMPs), which among other effects can degrade cartilage in joints. In some embodiments, the compounds provided herein may be administered to a patient in order to prevent or treat degradation of the patient's cartilage. IL-17 also increases the expression of receptor activator of NF-κB ligand (RANKL) in osteoblasts, leading to differentiation and activation of osteoclasts and bone degradation. In some embodiments, the compounds provided herein may be administered to a patient in order to prevent or treat degradation of the patient's bone. Depending on the target cell that is exposed to it, IL-17 may stimulate the production of IL-6, IL-8, IL-1, tumor necrosis factor (TNF), MMPs, nitric oxide, or several other proteins that are implicated in inflammatory conditions (e.g., tissue factor, CCL20, G-CSF and GM-CSF). In some embodiments, the compounds provided herein may be administered to a patient in order to inhibit the production of IL-6, IL-8, IL-1, tumor necrosis factor (TNF), MMPs, nitric oxide, or several other proteins that are implicated in inflammatory conditions (e.g., tissue factor, CCL20, G-CSF and GM-CSF).

Although IL-17 plays a role in the immune response to invading pathogens, excessive IL-17 activity has been implicated in pathologies associated with an excessive immune response to an infection. In some embodiments, the compounds provided herein may be administered to a patient in order to prevent or treat excessive immune response to an infection. For example, IL-17 has been implicated in the severe neuroinflammation associated with *Toxoplasma gondii* infection and increased severity of lesions associated with *Leishmania* infection. In some embodiments, the compounds provided herein may be administered to a patient in order to treat or prevent neuroinflammation, for example, neuroinflammation associated with *Toxoplasma gondii* infection. In some embodiments, the compounds provided herein may be administered to a patient in order to treat or prevent lesions associated with *Leishmania* infection. In these and other cases, IL-17 appears to play a role in perpetuating the infection, promoting an excessive inflammatory response, and inhibiting clearance of the infectious agent (Waite and Skokos, 2012). In some embodiments, the compounds provided herein may be administered to a patient in order to prevent an excessive inflammatory response and/or promote the clearance of an infectious agent.

Drugs targeting IL-17 have entered clinical trials for a wide variety of inflammatory conditions, including psoriasis, rheumatoid arthritis, ankylosing spondylitis, uveitis, Behcet's disease, psoriatic arthritis, Crohn's disease, polymyalgia rheumatica, dry eye syndrome, multiple sclerosis, graft-versus-host disease, and asthma. In some embodiments, the compounds provided herein may be administered to a patient in order to treat or prevent one or more of these diseases or disorders. Preclinical evidence also implicates IL-17 in the pathology of type 1 diabetes, and Th17 cells are elevated in patients with adult onset Still's disorder, another autoimmune disease. In some embodiments, the compounds provided herein may be administered to a patient in order to treat type 1 diabetes. In some embodiments, the compounds provided herein may be administered to a patient in order to treat or prevent adult onset Still's disorder. Activity of Th17 cells has been implicated in the development of graft-versus-host disease following allogeneic stem cell (e.g., bone marrow) transplantation (Fujiwara, et al., 2014). In some embodiments, the compounds provided herein may be administered to a patient in order to treat or prevent graft-versus-host disease, for example, following allogeneic stem cell (e.g., bone marrow) transplantation. Given the large body of evidence to date, it is likely that therapies reducing the expression of IL-17 or otherwise reducing its levels in circulation or target tissues (e.g., anti-IL17 monoclonal antibodies) could have broad applications in the treatment of autoimmune diseases and other inflammatory conditions. In some embodiments, the compounds provided herein may be administered to a patient in order to reduce the expression of IL-17 or its levels in circulation or target tissues (e.g., anti-IL17 monoclonal antibodies). In some embodiments, the compounds provided herein may be administered to a patient in order to treat autoimmune diseases or other inflammatory conditions.

Overproduction of IL-17 or elevated numbers of Th17 cells have been reported in patient studies or animal models of a large number of conditions, including autoimmune diseases, neurological disorders, cardiovascular diseases, cancer, psychiatric and neuropsychiatric disorders, acute and chronic inflammatory conditions, chronic pain syndromes, organ rejection or graft-versus-host disease, or asthma and other allergic conditions. In some embodiments, the compounds provided herein may be administered to a patient in order to treat or prevent one or more of these diseases or disorders.

Both the differentiation of Th17 cells and their production of IL-17 are regulated to a significant degree by the retinoid orphan receptor RORγt, a member of the nuclear hormone receptor family. Expression of RORγt is common to all types of Th17 cells. RORγ also regulates the production of IL-17 in other cell types, including γδ T cells, innate lymphoid cells, and lymphoid tissue inducer cells (Bronner et al., 2016). Inhibition of RORγt activity results in reduced expression of IL-17. In some embodiments, the compounds provided herein my be administered to a patient in order to inhibit RORγt activity.

Compounds and compositions provided and disclosed herein may be used to suppress IL-17 production in cultures of human T cells that are exposed to a mixture of cytokines known to induce differentiation into Th17 cells. In some embodiments, the ability to act as inverse agonists of RORγt is also demonstrated. Without wishing to be bound by any theory, it is believed that, for example, RORγt-independent mechanisms appear to contribute to the suppression of IL-17 production. Thus, the compounds and compositions provided herein may be used for inhibiting differentiation of T cells into Th17 cells, as well as inhibiting production of IL-17 by mature Th17 cells. In some of these embodiments, the net result is a reduction in IL-17 levels. In some embodiments, the compounds provided herein may be administered to a patient in order to suppress IL-17 production in one or more of the patient's tissues or organs.

III. PHARMACEUTICAL FORMULATIONS AND ROUTES OF ADMINISTRATION

In another aspect, for administration to a patient in need of such treatment, pharmaceutical formulations (also referred to as a pharmaceutical preparations, pharmaceutical compositions, pharmaceutical products, medicinal products, medicines, medications, or medicaments) comprise a therapeutically effective amount of a compound disclosed herein formulated with one or more excipients and/or drug carriers appropriate to the indicated route of administration. In some embodiments, the compounds disclosed herein are formulated in a manner amenable for the treatment of human and/or veterinary patients. In some embodiments, formulation comprises admixing or combining one or more of the compounds disclosed herein with one or more of the following excipients: lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol. In some embodiments, e.g., for oral administration, the pharmaceutical formulation may be tableted or encapsulated. In some embodiments, the compounds may be dissolved or slurried in water, polyethylene glycol, propylene glycol, ethanol, corn oil, cottonseed oil, peanut oil, sesame oil, benzyl alcohol, sodium chloride, and/or various buffers. In some embodiments, the pharmaceutical formulations may be subjected to pharmaceutical operations, such as sterilization, and/or may contain drug carriers and/or excipients such as preservatives, stabilizers, wetting agents, emulsifiers, encapsulating agents such as lipids, dendrimers, polymers, proteins such as albumin, nucleic acids, and buffers.

Pharmaceutical formulations may be administered by a variety of methods, e.g., orally or by injection (e.g. subcutaneous, intravenous, and intraperitoneal). Depending on the route of administration, the compounds disclosed herein may be coated in a material to protect the compound from the action of acids and other natural conditions which may inactivate the compound. To administer the active compound by other than parenteral administration, it may be necessary to coat the compound with, or co-administer the compound with, a material to prevent its inactivation. In some embodiments, the active compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes.

The compounds disclosed herein may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

The compounds disclosed herein can be administered orally, for example, with an inert diluent or an assailable edible carrier. The compounds and other ingredients may also be enclosed in a hard or soft-shell gelatin capsule, compressed into tablets, or incorporated directly into the patient's diet. For oral therapeutic administration, the compounds disclosed herein may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such pharmaceutical formulations is such that a suitable dosage will be obtained.

The therapeutic compound may also be administered topically to the skin, eye, ear, or mucosal membranes. Administration of the therapeutic compound topically may include formulations of the compounds as a topical solution, lotion, cream, ointment, gel, foam, transdermal patch, or tincture. When the therapeutic compound is formulated for topical administration, the compound may be combined with one or more agents that increase the permeability of the compound through the tissue to which it is administered. In other embodiments, it is contemplated that the topical administration is administered to the eye. Such administration may be applied to the surface of the cornea, conjunctiva, or sclera. Without wishing to be bound by any theory, it is believed that administration to the surface of the eye allows the therapeutic compound to reach the posterior portion of the eye. Ophthalmic topical administration can be formulated as a solution, suspension, ointment, gel, or emulsion. Finally, topical administration may also include administration to the mucosa membranes such as the inside of the mouth. Such administration can be directly to a particular location within the mucosal membrane such as a tooth, a sore, or an ulcer. Alternatively, if local delivery to the lungs is desired the therapeutic compound may be administered by inhalation in a dry-powder or aerosol formulation.

In some embodiments, it may be advantageous to formulate parenteral compositions in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical carrier. In some embodiments, the specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient. In some embodiments, active compounds are administered at a therapeutically effective dosage sufficient to treat a condition associated with a condition in a patient. For example, the efficacy of a compound can be evaluated in an animal model system that may be predictive of efficacy in treating the disease in a human or another animal.

In some embodiments, the effective dose range for the therapeutic compound can be extrapolated from effective doses determined in animal studies for a variety of different animals. In some embodiments, the human equivalent dose (HED) in mg/kg can be calculated in accordance with the following formula (see, e.g., Reagan-Shaw et al., *FASEB J.*, 22(3):659-661, 2008, which is incorporated herein by reference):

$$\text{HED (mg/kg)} = \text{Animal dose (mg/kg)} \times (\text{Animal } K_m/\text{Human } K_m)$$

Use of the $K_m$ factors in conversion results in HED values based on body surface area (BSA) rather than only on body mass. $K_m$ values for humans and various animals are well known. For example, the $K_m$ for an average 60 kg human (with a BSA of 1.6 m$^2$) is 37, whereas a 20 kg child (BSA 0.8 m$^2$) would have a $K_m$ of 25. $K_m$ for some relevant animal models are also well known, including: mice $K_m$ of 3 (given a weight of 0.02 kg and BSA of 0.007); hamster $K_m$ of 5 (given a weight of 0.08 kg and BSA of 0.02); rat $K_m$ of 6 (given a weight of 0.15 kg and BSA of 0.025) and monkey $K_m$ of 12 (given a weight of 3 kg and BSA of 0.24).

Precise amounts of the therapeutic composition depend on the judgment of the practitioner and are specific to each individual. Nonetheless, a calculated HED dose provides a general guide. Other factors affecting the dose include the physical and clinical state of the patient, the route of administration, the intended goal of treatment and the potency, stability and toxicity of the particular therapeutic formulation.

The actual dosage amount of a compound of the present disclosure or composition comprising a compound of the present disclosure administered to a patient may be determined by physical and physiological factors such as type of animal treated, age, sex, body weight, severity of condition, the type of disease being treated, previous or concurrent therapeutic interventions, idiopathy of the patient and on the route of administration. These factors may be determined by a skilled artisan. The practitioner responsible for administration will typically determine the concentration of active ingredient(s) in a composition and appropriate dose(s) for the individual patient. The dosage may be adjusted by the individual physician in the event of any complication.

In some embodiments, the therapeutically effective amount typically will vary from about 0.001 mg/kg to about 1000 mg/kg, from about 0.01 mg/kg to about 750 mg/kg, from about 100 mg/kg to about 500 mg/kg, from about 1 mg/kg to about 250 mg/kg, from about 10 mg/kg to about 150 mg/kg in one or more dose administrations daily, for one or several days (depending of course of the mode of administration and the factors discussed above). Other suitable dose ranges include 1 mg to 10,000 mg per day, 100 mg to 10,000 mg per day, 500 mg to 10,000 mg per day, and 500 mg to 1,000 mg per day. In some embodiments, the amount is less than 10,000 mg per day with a range of 750 mg to 9,000 mg per day.

In some embodiments, the amount of the active compound in the pharmaceutical formulation is from about 2 to about 75 weight percent. In some of these embodiments, the amount if from about 25 to about 60 weight percent.

Single or multiple doses of the agents are contemplated. Desired time intervals for delivery of multiple doses can be determined by one of ordinary skill in the art employing no more than routine experimentation. As an example, patients may be administered two doses daily at approximately 12-hour intervals. In some embodiments, the agent is administered once a day.

The agent(s) may be administered on a routine schedule. As used herein a routine schedule refers to a predetermined designated period of time. The routine schedule may encompass periods of time which are identical, or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may be taken orally and that the timing of which is or is not dependent upon food intake. Thus, for example, the agent can be taken every morning and/or every evening, regardless of when the patient has eaten or will eat.

IV. COMBINATION THERAPY

In addition to being used as a monotherapy, the compounds of the present invention may also find use in combination therapies. Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Non-limiting examples of such combination therapy include combination of one or more compounds of the invention with another anti-inflammatory agent, a chemotherapeutic agent, radiation therapy, an antidepressant, an antipsychotic agent, an anticonvulsant, a mood stabilizer, an anti-infective agent, an antihypertensive agent, a cholesterol-lowering agent or other modulator of blood lipids, an agent for promoting weight loss, an antithrombotic agent, an agent for treating or preventing cardiovascular events such as myocardial infarction or stroke, an antidiabetic agent, an agent for reducing transplant rejection or graft-versus-host disease, an anti-arthritic agent, an analgesic agent, an anti-asthmatic agent or other treatment for respiratory diseases, or an agent for treatment or prevention of skin disorders. Compounds of the invention may be combined with agents designed to improve a patient's immune response to cancer, including (but not limited to) cancer vaccines. See Lu et al. (2011), which is incorporated herein by reference.

V. DEFINITIONS

When used in the context of a chemical group: "hydrogen" means H; "hydroxy" means —OH; "oxo" means =O; "carbonyl" means —C(=O)—; "carboxy" means —C(=O)OH (also written as —COOH or —CO$_2$H); "halo" means independently —F, —Cl, —Br or —I; "amino" means —NH$_2$; "hydroxyamino" means —NHOH; "nitro" means —NO$_2$; imino means =NH; "cyano" means —CN; "isocyanyl" means —N=C=O; "azido" means —N$_3$; in a monovalent context "phosphate" means —OP(O)(OH)$_2$ or a deprotonated form thereof; in a divalent context "phosphate" means —OP(O)(OH)O— or a deprotonated form thereof; "mercapto" means SH; and "thio" means =S; "sulfonyl" means —S(O)$_2$—; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "" represents a single bond or a double bond. Additionally, this symbol may be used to refer to an epoxidized double bond such as the group found in the compounds described in PCT/US2013/045975 (WO 2013/188818), the entire contents of which are hereby incorporated by reference. Thus, the formula

covers, for example,

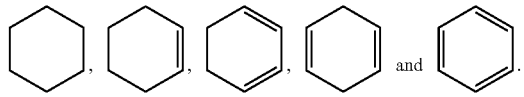

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol " ⌇⌇⌇ ", when drawn perpendicularly across a bond (e.g.,

⌇⌇⌇—CH$_3$ for methyl) indicates a point of attachment of the group. It is noted that the point of attachment is typically only identified in this manner for larger groups in order to assist the reader in unambiguously identifying a point of attachment. The symbol "◢◣" means a single bond where the group attached to the thick end of the wedge is "out of the page." The symbol "⦀⦀⦀" means a single bond where the group attached to the thick end of the wedge is "into the page". The symbol " ⌇⌇⌇ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a variable is depicted as a "floating group" on a ring system, for example, the group "R" in the formula:

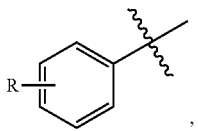

then the variable may replace any hydrogen atom attached to any of the ring atoms, including a depicted, implied, or expressly defined hydrogen, so long as a stable structure is formed. When a variable is depicted as a "floating group" on a fused ring system, as for example the group "R" in the formula:

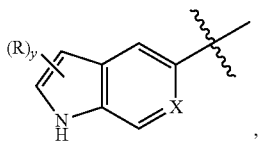

then the variable may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the R enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question. For example, it is understood that the minimum number of carbon atoms in the groups "alkyl$_{(C≤8)}$", "cycloalkanediyl$_{(C≤8)}$", "heteroaryl$_{(C≤8)}$", and "acyl$_{(C≤8)}$" is one, the minimum number of carbon atoms in the groups "alkenyl$_{(C≤8)}$", "alkynyl$_{(C≤8)}$", and "heterocycloalkyl$_{(C≤8)}$" is two, the minimum number of carbon atoms in the group "cycloalkyl$_{(C≤8)}$" is three, and the minimum number of carbon atoms in the groups "aryl$_{(C≤8)}$" and "arenediyl$_{(C≤8)}$" is six. "Cn-n'" defines both the minimum (n) and maximum (n') number of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefines" are all synonymous. When any of the chemical groups or compound classes defined herein is modified by the term "substituted", any carbon atom in the moiety replacing the hydrogen atom is not counted. Thus methoxyhexyl, which has a total of seven carbon atoms, is an example of a substituted alkyl$_{(C1-6)}$. Unless specified otherwise, any chemical group or compound class listed in a claim set without a carbon atom limit has a carbon atom limit of less than or equal to twelve.

The term "saturated" when used to modify a compound or chemical group means the compound or chemical group has no carbon-carbon double and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" signifies that the compound or chemical group so modified is an acyclic or cyclic, but non-aromatic compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" signifies that the compound or chemical group so modified has a planar unsaturated ring of atoms with 4n+2 electrons in a fully conjugated cyclic π system.

The term "alkyl" refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$, (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$— (methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" refers to the divalent group =CRR' in which R and R' are independently hydrogen, alkyl, aryl, or heteroaryl. Non-limiting examples of alkylidene groups include: =CH$_2$, =CH(CH$_2$CH$_3$), and =C(CH$_3$)$_2$. An "alkane" refers to the class of compounds having the formula HR, wherein R is alkyl as this term is defined above.

The term "cycloalkyl" refers to a monovalent saturated aliphatic group with a carbon atom as the point of attachment, said carbon atom forming part of one or more non-aromatic ring structures, no carbon-carbon double or triple bonds, and no atoms other than carbon and hydrogen. Non-limiting examples include: —CH(CH$_2$)$_2$ (cyclopropyl), cyclobutyl, cyclopentyl, or cyclohexyl (Cy). As used herein, the term does not preclude the presence of one or more alkyl groups (carbon number limitation permitting) attached to a carbon atom of the non-aromatic ring structure. The term "cycloalkanediyl" refers to a divalent saturated aliphatic group with two carbon atoms as points of attachment, no carbon-carbon double or triple bonds, and no atoms other than carbon and hydrogen. The group

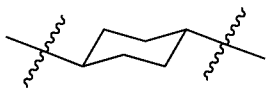 [SMILES: *C1CCC(*)CC1]

is a non-limiting example of cycloalkanediyl group. A "cycloalkane" refers to the class of compounds having the formula H—R, wherein R is cycloalkyl as this term is defined above.

The term "alkenyl" refers to a monovalent unsaturated aliphatic group with a carbon atom as the point of attachment, a linear or branched, acyclic structure, at least one nonaromatic carbon-carbon double bond, no carbon-carbon triple bonds, and no atoms other than carbon and hydrogen. Non-limiting examples include: —CH=CH$_2$ (vinyl), —CH=CHCH$_3$, —CH=CHCH$_2$CH$_3$, —CH$_2$CH=CH$_2$ (allyl), —CH$_2$CH=CHCH$_3$, and —CH=CHCH=CH$_2$. The term "alkenediyl" refers to a divalent unsaturated aliphatic group, with two carbon atoms as points of attachment, a linear or branched acyclic structure, at least one nonaromatic carbon-carbon double bond, no carbon-carbon triple bonds, and no atoms other than carbon and hydrogen. The groups —CH=CH—, —CH=C(CH$_3$)CH$_2$—, —CH=CHCH$_2$—, and —CH$_2$CH=CHCH$_2$— are non-limiting examples of alkenediyl groups. It is noted that while the alkenediyl group is aliphatic, once connected at both ends, this group is not precluded from forming part of an aromatic structure. The terms "alkene" and "olefin" are synonymous and refer to the class of compounds having the formula H—R, wherein R is alkenyl as this term is defined above. Similarly, the terms "terminal alkene" and "α-olefin" are synonymous and refer to an alkene having just one carbon-carbon double bond, wherein that bond is part of a vinyl group at an end of the molecule.

The term "alkynyl" refers to a monovalent unsaturated aliphatic group with a carbon atom as the point of attachment, a linear or branched acyclic structure, at least one carbon-carbon triple bond, and no atoms other than carbon and hydrogen. As used herein, the term alkynyl does not preclude the presence of one or more non-aromatic carbon-carbon double bonds. The groups —C≡CH, —C≡CCH$_3$, and —CH$_2$C≡CCH$_3$ are non-limiting examples of alkynyl groups. An "alkyne" refers to the class of compounds having the formula H—R, wherein R is alkynyl.

The term "aryl" refers to a monovalent unsaturated aromatic group with an aromatic carbon atom as the point of attachment, said carbon atom forming part of a one or more aromatic ring structures, each with six ring atoms that are all carbon, and wherein the group consists of no atoms other than carbon and hydrogen. If more than one ring is present, the rings may be fused or unfused. Unfused rings are connected with a covalent bond. As used herein, the term aryl does not preclude the presence of one or more alkyl, aryl, or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl (e.g., 4-phenylphenyl). The term "arenediyl" refers to a divalent aromatic group with two aromatic carbon atoms as points of attachment, said carbon atoms forming part of one or more six-membered aromatic ring structures, each with six ring atoms that are all carbon, and wherein the divalent group consists of no atoms other than carbon and hydrogen. As used herein, the term arenediyl does not preclude the presence of one or more alkyl groups (carbon number limitation permitting) attached to the first aromatic ring or any additional aromatic ring present. If more than one ring is present, the rings may be fused or unfused. Unfused rings are connected with a covalent bond. Non-limiting examples of arenediyl groups include:

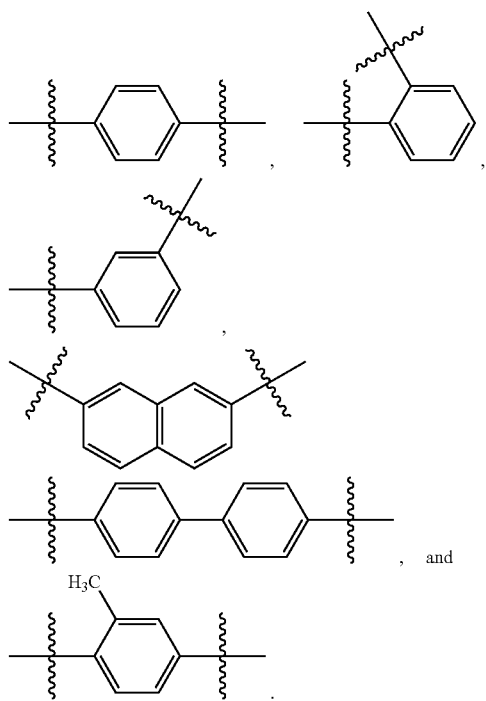

An "arene" refers to the class of compounds having the formula HR, wherein R is aryl as that term is defined above. Benzene and toluene are non-limiting examples of arenes.

The term "aralkyl" refers to the monovalent group -alkanediyl-aryl, in which the terms alkanediyl and aryl are each used in a manner consistent with the definitions provided above. Non-limiting examples are: phenylmethyl (benzyl, Bn) and 2-phenyl-ethyl.

The term "heteroaryl" refers to a monovalent aromatic group with an aromatic carbon atom or nitrogen atom as the point of attachment, said carbon atom or nitrogen atom forming part of one or more aromatic ring structures, each with three to eight ring atoms, wherein at least one of the ring atoms of the aromatic ring structure(s) is nitrogen, oxygen or sulfur, and wherein the heteroaryl group consists of no atoms other than carbon, hydrogen, aromatic nitrogen, aromatic oxygen and aromatic sulfur. If more than one ring is present, the rings are fused. The term heteroaryl does not preclude the presence of one or more alkyl, cycloalkyl, heterocycloalkyl, aryl, or aralkyl groups (carbon number limitation permitting) attached to one or more ring atoms. Non-limiting examples of heteroaryl groups include benzthiazolyl, benzimidazolyl, furanyl, imidazolyl (Im), indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. A "heteroarene" refers to the class of compounds having the formula H—R, wherein R is heteroaryl. Pyridine and quinoline are non-limiting examples of heteroarenes.

The term "heteroarenediyl" refers to a divalent aromatic group, with two aromatic carbon atoms, two aromatic nitrogen atoms, or one aromatic carbon atom and one aromatic nitrogen atom as the two points of attachment, said atoms forming part of one or more aromatic ring structures, each with three to eight ring atoms, wherein at least one of the ring atoms of the aromatic ring structure(s) is nitrogen, oxygen or sulfur, and wherein the divalent group consists of no atoms other than carbon, hydrogen, aromatic nitrogen, aromatic oxygen and aromatic sulfur. If more than one ring is present, the rings are fused; however, the term heteroarenediyl does not preclude the presence of one or more alkyl or aryl groups (carbon number limitation permitting) attached to one or more ring atoms. Non-limiting examples of heteroarenediyl groups include:

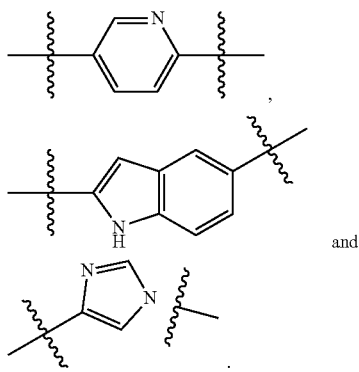

and

The term "heteroaralkyl" refers to the monovalent group -alkanediyl-heteroaryl, in which the terms alkanediyl and heteroaryl are each used in a manner consistent with the definitions provided above. Non-limiting examples are: pyridinylmethyl and 2-quinolinyl-ethyl.

The term "heterocycloalkyl" refers to a monovalent non-aromatic group with a carbon atom or nitrogen atom as the point of attachment, said carbon atom or nitrogen atom forming part of one or more non-aromatic ring structures, each with three to eight ring atoms, wherein at least one of the ring atoms of the non-aromatic ring structure(s) is nitrogen, oxygen or sulfur, and wherein the heterocycloalkyl group consists of no atoms other than carbon, hydrogen, nitrogen, oxygen and sulfur. If more than one ring is present, the rings are fused. As used herein, the term does not preclude the presence of one or more alkyl or cycloalkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkyl groups include aziridinyl, azetidinyl, pyrrolidinyl, piperidinyl, piperazinyl, morpholinyl, thiomorpholinyl, tetrahydrofuranyl, tetrahydrothiofuranyl, tetrahydropyranyl, pyranyl, oxiranyl, and oxetanyl. The term "N-heterocycloalkyl" refers to a heterocycloalkyl group with a nitrogen atom as the point of attachment. N-pyrrolidinyl is an example of such a group.

The term "heterocycloalkanediyl" refers to a divalent cyclic group, with two carbon atoms, two nitrogen atoms, or one carbon atom and one nitrogen atom as the two points of attachment, said atoms forming part of one or more ring structure(s) wherein at least one of the ring atoms of the non-aromatic ring structure(s) is nitrogen, oxygen or sulfur, and wherein the divalent group consists of no atoms other than carbon, hydrogen, nitrogen, oxygen and sulfur. If more than one ring is present, the rings are fused. As used herein, the term heterocycloalkanediyl does not preclude the presence of one or more alkyl groups (carbon number limitation permitting) attached to one or more ring atoms. Also, the term does not preclude the presence of one or more double bonds in the ring or ring system, provided that the resulting group remains non-aromatic. Non-limiting examples of heterocycloalkanediyl groups include:

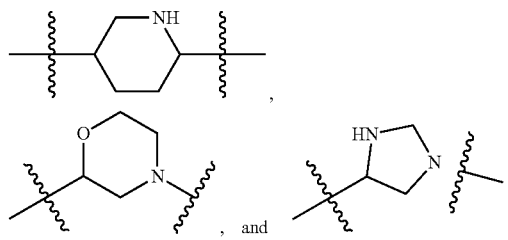

, and

.

The term "acyl" refers to the group —C(O)R, in which R is a hydrogen, alkyl, cycloalkyl, or aryl as those terms are defined above. The groups, —CHO, —C(O)CH$_3$ (acetyl, Ac), —C(O)CH$_2$CH$_3$, —C(O)CH(CH$_3$)$_2$, —C(O)CH(CH$_2$)$_2$, —C(O)C$_6$H$_5$, and —C(O)C$_6$H$_4$CH$_3$ are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkyl group, as defined above, attached to a —CHO group.

The term "alkoxy" refers to the group —OR, in which R is an alkyl, as that term is defined above. Non-limiting examples include: —OCH$_3$ (methoxy), —OCH$_2$CH$_3$ (ethoxy), —OCH$_2$CH$_2$CH$_3$, —OCH(CH$_3$)$_2$ (isopropoxy), or OC(CH$_3$)$_3$ (tert-butoxy). The terms "cycloalkoxy", "alkenyloxy", "alkynyloxy", "aryl oxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group.

The term "alkylamino" refers to the group —NHR, in which R is an alkyl, as that term is defined above. Non-limiting examples include: —NHCH$_3$ and —NHCH$_2$CH$_3$. The term "dialkylamino" refers to the group —NRR', in which R and R' can be the same or different alkyl groups.

Non-limiting examples of dialkylamino groups include: —N(CH$_3$)$_2$ and —N(CH$_3$)(CH$_2$CH$_3$). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC$_6$H$_5$. The terms "dicycloalkylamino", "dialkenylamino", "dialkynylamino", "diarylamino", "diaralkylamino", "diheteroarylamino", "diheterocycloalkylamino", and "dialkoxyamino", refers to groups, defined as —NRR', in which R and R' are both cycloalkyl, alkenyl, alkynyl, aryl, aralkyl, heteroaryl, heterocycloalkyl, and alkoxy, respectively. Similarly, the term alkyl(cycloalkyl)amino refers to a group defined as —NRR', in which R is alkyl and R' is cycloalkyl. The term "amido" (acylamino), when used without the "substituted" modifier, refers to the group —NHR, in which R is acyl, as that term is defined above. A non-limiting example of an amido group is —NHC(O)CH$_3$.

The terms "alkylsulfonyl" refers to the group: —S(O)$_2$R, in which R is an alkyl, as that term is defined above. The terms "cycloalkylsulfonyl", "alkenylsulfonyl", "alkynylsulfonyl", "aryl sulfonyl", "aralkylsulfonyl", "heteroarylsulfonyl", "heterocycloalkylsulfonyl", and "alkoxysulfonyl" are defined in an analogous manner, wherein R is a cycloalkyl, alkenyl, alkynyl, aryl, aralkyl, heteroaryl, heterocycloalkyl, and alkoxy group, respectively, as those terms are defined above.

When a chemical group is used with the "substituted" modifier, one or more hydrogen atom has been replaced, independently at each instance, by —OH, —F, —Cl, —Br, —I, —NH$_2$, —NO$_2$, —CO$_2$H, —C(O)H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$CH$_3$, —S(O)$_2$OH, or —S(O)$_2$NH$_2$. For example, the following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups. Non-limiting examples of substituted aralkyls are: (3-chlorophenyl)-methyl, and 2-chloro-2-phenyl-eth-1-yl. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups. The groups —NHC(O)OCH$_3$ and —NHC(O)NHCH$_3$ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects or patients.

An "active ingredient" (AI) or active pharmaceutical ingredient (API) (also referred to as an active compound, active substance, active agent, pharmaceutical agent, agent, biologically active molecule, or a therapeutic compound) is the ingredient in a pharmaceutical drug that is biologically active.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating or preventing a disease, is an amount sufficient to effect such treatment or prevention of the disease.

An "excipient" is a pharmaceutically acceptable substance formulated along with the active ingredient(s) of a medication, pharmaceutical composition, formulation, or drug delivery system. Excipients may be used, for example, to stabilize the composition, to bulk up the composition (thus often referred to as "bulking agents," "fillers," or "diluents" when used for this purpose), or to confer a therapeutic enhancement on the active ingredient in the final dosage form, such as facilitating drug absorption, reducing viscosity, or enhancing solubility. Excipients include pharmaceutically acceptable versions of antiadherents, binders, coatings, colors, disintegrants, flavors, glidants, lubricants, preservatives, sorbents, sweeteners, and vehicles. The main excipient that serves as a medium for conveying the active ingredient is usually called the vehicle. Excipients may also be used in the manufacturing process, for example, to aid in the handling of the active substance, such as by facilitating powder flowability or non-stick properties, in addition to aiding in vitro stability such as prevention of denaturation or aggregation over the expected shelf life. The suitability of an excipient will typically vary depending on the route of administration, the dosage form, the active ingredient, as well as other factors.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

As used herein, the term "IC$_{50}$" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human patients are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio. One example of compounds which are pharmaceutically acceptable include those compounds, materials, compositions, and/or dosage forms have been designated by the United States Food and Drug Administration (US FDA) as having a status of generally regarded as safe (GRAS).

"Pharmaceutically acceptable salts" means salts of compounds disclosed herein which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

A "pharmaceutically acceptable carrier," "drug carrier," or simply "carrier" is a pharmaceutically acceptable substance formulated along with the active ingredient medication that is involved in carrying, delivering and/or transporting a chemical agent. Drug carriers may be used to improve the delivery and the effectiveness of drugs, including for example, controlled-release technology to modulate drug bioavailability, decrease drug metabolism, and/or reduce drug toxicity. Some drug carriers may increase the effectiveness of drug delivery to the specific target sites. Examples of carriers include: liposomes, microspheres (e.g., made of poly(lactic-co-glycolic) acid), albumin microspheres, synthetic polymers, nanofibers, protein-DNA complexes, protein conjugates, erythrocytes, virosomes, and dendrimers.

A "pharmaceutical drug" (also referred to as a pharmaceutical, pharmaceutical preparation, pharmaceutical composition, pharmaceutical formulation, pharmaceutical product, medicinal product, medicine, medication, medicament, or simply a drug, agent, or preparation) is a composition used to diagnose, cure, treat, or prevent disease, which comprises an active pharmaceutical ingredient (API) (defined above) and optionally contains one or more inactive ingredients, which are also referred to as excipients (defined above).

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Non-limiting examples of suitable esters that may be converted in vivo into hydroxy compounds include acetates, citrates, lactates, phosphates, tartrates, malonates, oxalates, salicylates, propionates, succinates, fumarates, maleates, methylene-bis-β-hydroxynaphthoate, gentisates, isethionates, di-p-toluoyltartrates, methanesulfonates, ethanesulfonates, benzenesulfonates, p-toluenesulfonates, cyclohexylsulfamates, quinates, and esters of amino acids. Similarly, a compound comprising an amine group may be administered as an amide that is converted by hydrolysis in vivo to the amine compound.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease or symptom thereof in a subject or patient that is experiencing or displaying the pathology or symptomatology of the disease.

The term "unit dose" refers to a formulation of the compound or composition such that the formulation is prepared in a manner sufficient to provide a single therapeutically effective dose of the active ingredient to a patient in a single administration. Such unit dose formulations that may be used include but are not limited to a single tablet, capsule, or other oral formulations, or a single vial with a syringeable liquid or other injectable formulations.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials & Methods

RORγ LBD-GAL4 Assay. The RORγ assay system was purchased from Indigo Biosciences (State College, PA, USA). The assay utilizes a human cell line engineered to provide high level expression of a hybrid form of the Human RAR-related Orphan Receptor Gamma (RORγ). The N-terminal DNA binding domain (DBD) of the native RORγ receptor was substituted with the yeast GAL4-DBD to generate the GAL4-RORγ hybrid nuclear receptor. The reporter cell line is transfected with a plasmid that encodes the beetle luciferase gene under the control of the GAL4 upstream activating sequence (UAS). The GAL4-RORγ hybrid is constitutively active providing measurable levels of basal Luciferase activity. To assess the RORγ inverse-agonist activity of the test compounds, reporter cells were plated in 96-well plates in triplicate and were treated with DMSO (vehicle) or different concentrations of test compounds at 37° C. with 5% $CO_2$ in a humidified atmosphere for 23 hours. After that, luciferin was added to the wells and luciferase activity was determined by measuring the luminescence signal using a BMG Pherastar microplate reader. Values from test compound samples were normalized to those from DMSO-treated samples.

Full-length RORgt activity in Jurkat Cells. RORγt transcriptional activity was assessed by transfecting human Jurkat T lymphocytes with each full-length human ROR isoform expression construct together with a 5×-RORE luciferase reporter construct and assaying luciferase activity. Expression plasmids consisting of human ROR isoform cDNA in a pReceiver-M02 vector were purchased from GeneCopoeia. Specific constructs included: RORA, transcript variant 1 (Catalog #EX-T3100-M02-B); RORB (Catalog #EX-Z5728-M02-B); and RORC, transcript variant 2 (Catalog #EX-T6988-M02-B). The pReceiver-M02 empty vector (Catalog #EX-NEG-M02) was used as control. p5×RORE_sluc3.3 luciferase reporter plasmid was synthesized at Blue Heron Biotech, LLC, by inserting 5 copies of the ROR response element sequence (5'-AAAGTAGGTCA-3' (SEQ. NO. 3) in XhoI/HindIII restriction sites of the pNL3.3[secNLuc/minP] vector (Promega).

Jurkat cells (Human peripheral blood T lymphocytes) were cultured in RPMI 1640 medium (Life Technologies) supplemented with 10% dilapidated FBS (Gemini Bio-Products) and 1% penicillin-streptomycin in a humidified atmosphere at 37° C. with 5% $CO_2$. Cells were seeded in a 75 $cm^2$ flask at a density of 0.3×106 cells/mL of growth media. After 18 h, cells were re-seeded into 25 $cm^2$ flasks at a density of 0.6×106 cells/mL. Cells were transfected using Lipofectamine LTX with Plus reagent according to the manufacturer's protocol, with 0.8 μg p5×RORE_sluc3.3 luciferase reporter plasmid and 0.8 μg of pReceiverM02 control, pRORA, pRORB, or pRORC plasmids (1.6 μg plasmid DNA in total) in a total volume of 250 μL Opti-MEM per mL of cell suspension. 6 h after transfection, cells were diluted with growth medium and plated in 96-well plates at a density of 5×104 cells per well in 190 μL medium. Immediately following plating, transfected cells were treated for 18 h with vehicle (DMSO) or compounds at concentrations ranging from 0 to 500 nM in a two-fold dilution series. Final DMSO concentration in each well was 0.1%. Three replicate wells were tested for each treatment condition.

NanoLuc luciferase activity was measured using the Nano-Glo Luciferase Assay System (Promega) according to the manufacturer's protocol. Briefly, after shaking the 96-well plates on an orbital shaker at 100 RPM for 2 min and centrifuging at 250×g RPM at room temperature for 5 min, 60 μL of media was removed from each well and transferred to the corresponding well of a 96-well V-bottom plate. Ten (10) μL of this media was transferred to duplicate wells of a 384-well Small Volume HiBase plate, resulting in a total of six luciferase activity measurements for each concentration of the test compound. NanoLuc assay reagent (10 μL) was added to each well. After shaking the 384-well plate at 500 RPM for 2 min and incubating at room temperature for an additional 3 min, the luminescence signal was measured on a PHERAstar FS microplate reader (BMG Labtech).

After removing the aliquot of medium for the luciferase assay, 14 μL (10% of remaining volume) WST-1 reagent was added to each well of the 96-well plate and incubated at 37°

C. with 5% $CO_2$ for 30 min. Molecular Devices SpectraMax M2e plate reader was used to measure absorbance of the formazan dye at 450 nm and background at 650 nm.

IL-17 Release from Th17-polarized Primary Human T-Cells. Primary human cryopreserved CD4+ T Cells (Lonza) were thawed according to the manufacturer's recommendations and plated either in Lymphocyte Growth Medium-3 (LGM-3) or X-VIVO 20 media (Lonza) in 96-well tissue culture plates at a density of ~$2\times10^5$ cells per well, and allowed to recover for approximately 4 hours at 37° C. with 5% $CO_2$ in a humidified atmosphere. After the recovery step, DMSO (vehicle) or test compound at doses ranging from 2 to 500 nM or 4 to 1000 nM in a three-fold dilution series was added to the cells. Three replicate wells were tested for each treatment condition. Final DMSO concentration in each well was 0.1%. Immediately after treatment, CD4+ T cells were activated by adding Dynabeads Human T-Activator CD3/CD28 (Life Technologies; bead-to-cell ratio of 1:2.5) and differentiated into Th17 cells by adding a mixture of the following cytokines: transforming growth factor-β (TGF-β, 5 ng/mL), IL-6 (20 ng/mL), IL-23 (20 ng/mL), and IL-1β (10 ng/mL). Undifferentiated control cells received only cytokine IL-2 (50 ng/mL). All human recombinant cytokines were purchased from R&D Systems. Following a 45-hour incubation at 37° C. with 5% $CO_2$ in a humidified atmosphere, the plates were centrifuged for 3 minutes at 250×g, and half of the supernatant was transferred to a new plate to be used in the IL-17A assay. The concentration of IL-17A in the supernatant was measured using the Homogeneous Time-Resolved Fluorescence (HTRF) assay (Cisbio Bioassays) according to the manufacturer's protocol. The assay was performed at room temperature in low volume, solid white 384-well plates (Greiner Bio-One). Samples and standards (serially-diluted human recombinant IL-17A (0 to 5,000 µg/mL concentration range; Cisbio Bioassays) were incubated with the anti-human IL-17A antibody conjugates (the HTRF donor and acceptor pair) for 16 hours and fluorescence was measured using a Pherastar FS microplate reader (BMG Labtech) in the HTRF mode (excitation at 337 nm and emission at 665 nm and 620 nm). IL-17A levels were assessed in duplicate aliquots of supernatant from each well resulting in a total of six readings per test condition. The 665 nm/620 nm signal ratio was calculated and the concentration of IL-17A in each sample was determined by interpolation from the standard curve. The amount of IL-17A from test compound treated samples were normalized to that of the vehicle-treated samples, set to 100%. Data were analyzed using GraphPad Prism (GraphPad Software, La Jolla California USA). Concentrations of test compound were transformed by taking the logarithm of each concentration used. The $IC_{50}$ values for compound mediated reduction in IL-17A levels and cell viability were determined by non-linear regression analysis using the log (inhibitor) vs. normalized response with variable slope equation.

Naïve T cell differentiation and intracellular staining. Naïve CD4+ T cells were isolated from cryopreserved human PBMCs (ZenBio) using an EasySep human naïve CD4+ T cell isolation kit (StemCell Technologies). The purity of cells (CD4+CD45RA+≥95%) was verified by flow cytometry. Naïve cells ($2\times10^5$ cells/well) were cultured in X-VIVO 20 media (Lonza) in 24-well tissue culture plates pre-coated with anti-CD3 antibody (1 µg/mL). Immediately following plating (day 0), cells were treated with vehicle (DMSO) or compound 14 at indicated concentrations. Cells were activated with anti-CD28 antibody (1 µg/mL) and cultured for 6 days under either neutral (Th0) or Th17-polarizing (Th17) conditions (TGF-β (5 ng/mL), IL-6 (20 ng/mL), IL-1β (10 ng/mL), IL-23 (20 ng/mL), anti-IL-4 antibody (1 µg/mL), and anti-IFN-γ antibody (1 µg/mL)). All cytokines were from R&D Systems, and all antibodies were from Biolegend. On day 5, cells were resuspended in the same media and reactivated by re-plating in new 24-well plates coated with anti-CD3 antibody (1 µg/mL). On day 6, cells were restimulated with Cell Stimulation Cocktail (eBioscience) in the presence of BD GolgiStop™ Protein Transport Inhibitor for the last 5 h, stained with Fixable Viability Dye eFluor 520 followed by fixation with BD Fixation buffer, permeabilized with BD Perm/Wash buffer and stained with AF647 antihuman IL-17A antibody. Data were acquired using a BD Accuri™ C6 or C6 Plus flow cytometer (BD Biosciences) and analyzed using FlowJo Software (Tree Star Inc). Lymphocytes were gated based on forward vs. side scatter (FSC vs. SSC) plot. Dead cells were subsequently excluded from analysis based on Fixable Viability Dye eFluor520 staining. At least 20,000 events per sample were analyzed.

RNA Extraction, Quantitative RT-PCR.

For qPCR analysis, human naïve T-cells were differentiated under Th-17 condition for six days as described under Naïve T cell differentiation and intracellular staining protocol. Total RNA was extracted using RNeasy kits including the optional DNaseI digestion (Qiagen). Following cDNA synthesis, Real Time quantitative PCR was performed on a 7900HT Real Time PCR System (Applied Biosystems).

Example 1: Activity of RORγ/RORγt Inhibitors

Screening a series of tricyclic compounds in a RORγt-LBD-GAL4 reporter assay, identified the tricyclic pyrimidine 1 with inhibitory activity ($IC_{50}$=608 nM) (Table 1).

Sequential introduction of C-12 phenyl and 4-pyridyl groups afforded compound 3 a 9-fold increase in activity relative to 1, with an $IC_{50}$ of 68 nM. Compound 3 was characterized further in a phenotypic assay where the amount of IL-17A produced by Th17 polarized human CD4+ T cells was measured. Consistent with the essential role that RORγt plays in controlling IL-17A expression, potent suppression of IL-17A secretion from human CD4+ T-cells treated with compound 3 ($IC_{50}$=76 nM) was observed. The combination of an alkyl substituted C-12 pyridyl ring with a fluoro phenyl C-14 substituent, afforded compounds 12-16 which were quite potent in the RORγt GAL4 transcriptional assay as well as in the IL-17 phenotypic assay (Table 1). Further modification of the A ring, B ring, C4 and C10 was carried out to determine the effects of these changes on the potency in the RORγt GAL4 transcriptional assay as well as in the IL-17 phenotypic assay (Tables 2 and 3).

TABLE 1

Activity of Compound with Modifications at the C12 and C14 Positions of the Pyrimidine Ring.

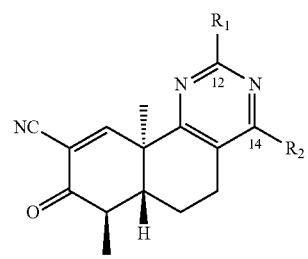

TABLE 1-continued

| Compd | $R_1$ | $R_2$ | CD4+ T-cell IL17 $IC_{50}$ (μM) | GAL4 Luc $IC_{50}$ (μM) |
|---|---|---|---|---|
| 1 | H | Phenyl | 0.071 | 0.613 |
| 2 | Phenyl | Phenyl | 0.030 | 0.162 |
| 3 | 4'-Pyridyl | Phenyl | 0.076 | 0.067 |
| 4 | 4'-Pyridyl | 4'-Pyridyl | 0.128 | 0.254 |
| 5 | 4'-Pyridyl | 3'-Pyridyl | 0.154 | 0.212 |
| 6 | 4'-Pyridyl | 4'-hydroxy-methylphenyl | 0.201 | 0.203 |
| 7 | 4'-Pyridyl | Methoxy | 0.461 | 0.163 |
| 8 | 4'-Pyridyl | Benzyl | 0.132 | 0.160 |
| 9 | Morpholine | 2'-F-Phenyl | 0.097 | 0.136 |
| 10 | N'-Acetyl piperazine | 2'-F-Phenyl | 0.104 | 0.141 |
| 11 | N'-Methyl piperazine | 2'-F-Phenyl | 0.236 | 0.314 |
| 12 | 3'-Methyl-4'-Pyridyl | 2'-F-Phenyl | 0.048 | 0.060 |
| 13 | 2'-Methyl-4'-Pyridyl | 2'-F-Phenyl | 0.046 | 0.060 |
| 14 | 3'-Methyl-4'-Pyridyl | 4'-F-Phenyl | 0.040 | 0.058 |
| 15 | 3'-Fluoromethyl-4'-Pyridyl | 2'-F-Phenyl | 0.035 | 0.074 |
| 16 | 3'-Cyclopropyl-4'-Pyridyl | 2'-F-Phenyl | 0.031 | 0.097 |

TABLE 2

Activity of Compound with Modifications at C4, C10 and the B-ring

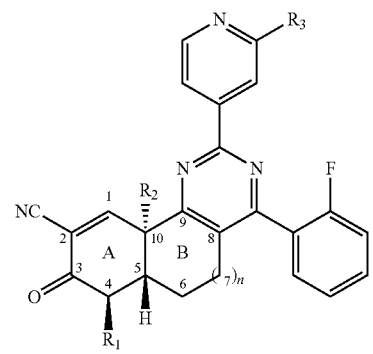

| Compd | $R_1$ | $R_2$ | B-ring (n) | CD4+ T-Cells IL17 $IC_{50}$ (μM) | GAL4 Luciferase Reporter $IC_{50}$ (μM) | $R_3$ |
|---|---|---|---|---|---|---|
| 16 | $CH_3$ | $CH_3$ | cyclohexyl (n = 1) | 0.031 | 0.097 | 3'-Cyclopropyl |
| 17 | $CH_3$ | Phenyl | cyclohexyl (n = 1) | 0.046 | 0.475 | 3'-Cyclopropyl |
| 18 | $CH_3$ | n-Propyl | cyclohexyl (n = 1) | 0.026 | 0.140 | 3'-Cyclopropyl |
| 19 | H | iso-Pentyl | cyclohexyl (n = 1) | 0.071 | 0.402 | 3'-Fluoromethyl |
| 20 | Allyl | $CH_3$ | cyclohexyl (n = 1) | 0.020 | 0.072 | 3'-Cyclopropyl |
| 21 | n-Propyl | $CH_3$ | cyclohexyl (n = 1) | 0.012 | 0.082 | 3'-Cyclopropyl |
| 22 | n-Propyl | $CH_3$ | cyclohexyl (n = 1) | 0.012 | 0.092 | 3'-$CF_3$ |
| 23 | n-Propyl | $CH_3$ | cyclohexyl (n = 1) | 0.017 | 0.051 | 3'-$CH_2F$ |
| 24 | $CH_3$ | $CH_3$ | cyclopentyl (n = 0) | 0.140 | 0.334 | 3'-$CH_2F$ |
| 25 | $CH_3$ | $CH_3$ | cyclopentyl (n = 0) | 0.117 | 0.524 | 3'-Cyclopropyl |
| 26 | $CH_3$ | $CH_3$ | cycloheptyl (n = 2) | 0.076 | 0.068 | 3'-$CH_3$ |

TABLE 3

Activity of Compound with Modifications at the Michael Acceptor A-ring

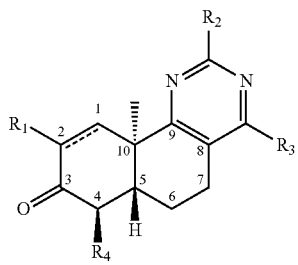

| Compd | $R_1$ | C1, C2 bond | CD4+ T-cells IL17 IC$_{50}$ (µM) | GAL4 Luc Reporter IC$_{50}$ (µM) | $R_2$ | $R_3$ | $R_4$ |
|---|---|---|---|---|---|---|---|
| 3 | CN | unsaturated | 0.076 | 0.068 | 4'-Pyridyl | Phenyl | Methyl |
| 27 | CONH$_2$ | unsaturated | 0.181 | 0.337 | 4'-Pyridyl | Phenyl | Methyl |
| 14 | CN | unsaturated | 0.04 | 0.058 | 3'-Methyl-4'-Pyridyl | p-Fluorophenyl | Methyl |
| 28 | CONH$_2$ | unsaturated | 0.107 | 0.295 | 3'-Methyl-4'-Pyridyl | p-Fluorophenyl | Methyl |
| 21 | CN | unsaturated | 0.012 | 0.082 | 3'-cyclopropyl-4'-Pyridyl | o-Fluorophenyl | n-propyl |
| 29 | CONH$_2$ | unsaturated | 0.036 | 0.293 | 3'-cyclopropyl-4'-Pyridyl | o-Fluorophenyl | n-propyl |
| 30 | H | unsaturated | 0.328 | 0.310 | 4'-Pyridyl | Phenyl | Methyl |
| 31 | CN | saturated | 0.476 | 0.643 | 4'-Pyridyl | Phenyl | Methyl |
| 32 | CONH$_2$ | saturated | >2 | 5.39 | 4'-Pyridyl | Phenyl | Methyl |
| 33 | CN | saturated | 0.154 | 1.24 | 3'-cyclopropyl-4'-Pyridyl | o-Fluorophenyl | n-propyl |

The relationship between biological activity and the A-ring Michael acceptor is consistent with a covalent drug: protein interaction, most likely involving one of the 8 free cysteines in the RORγ/RORγt LBD. While this mechanism of action (MOA) has been exploited successfully against other protein classes, most notably with kinases, it is rare in the nuclear receptor (NR) field, especially in the ROR family of NRs. The chemical biology literature of NRs provides few insights on how to identify the specific cysteine in the LBD of RORγ/RORγt central to the inverse agonism observed. PPARγ was the lone exception, where several endogenous fatty acid metabolite ligands (e.g. PGJ$_2$), have been shown to bind in the orthosteric site, ligate Cysteine 285 on alpha helix H3, and regulate the NR's transcriptional activity. Interestingly, Cysteine 320 on alpha helix H3 of RORγt occupies precisely the same location relative to the RORγt orthosteric site, as Cysteine 285 does on PPARγ. With this in mind, full-length human RORγt constructs were generated where Cysteine 320 (Cysteine 299 in RORγt) was mutated to Alanine as well as Serine, and the activity of compounds 14 and 21 in full-length RORγt RORE-luciferase reporter assays in Jurkat cells was assessed using these mutants. Compounds 14 and 21 were found to be refractory to both mutations, displaying similar activity against the wild-type and mutant RORγt proteins (Table 4). Supportive of these results, compounds 14 and 21 were found not to compete with cholesterol sulfate, a known orthosteric RORγt ligand, in competitive binding experiments using the RORγt LBD.

TABLE 4

Effect of Cysteine Mutations in Human RORγ on Inhibitory Activity of Selected Compounds

| RORγ (RORγt)[a] | RORγt IC$_{50}$ (nM) | |
|---|---|---|
| | Compound 14 | Compound 21 |
| Wild Type | 35.7 +/− 13.1 | 39.5 +/− 9.5 |
| C320S (C299S) | 36.7 +/− 13.4 | 58.3 +/− 20.9 |
| C320A (C299A) | 43.7 +/− 11.8 | 64.1 +/− 24.0 |
| C476S (C455S) | ND | ND |
| C476A (C455A) | ND | ND |
| C393S (C372S) | 60.4 +/− 25.2 | 48.7 +/− 20.0 |
| C285S (C264S) | 37.6 +/− 17.2 | 28.1 +/− 9.7 |
| C455S (C434S) | 37.5 +/− 17.9 | 52.6 +/− 18.5 |
| C278S (C257S) | 41.3 +/− 14.9 | 46.5 +/− 13.8 |
| C366S (C345S) | 39.0 +/− 7.6 | 50.3 +/− 12.3 |
| C345S (C324S) | 33.9 +/− 14.8 | 37.4 +/− 11.3 |

ND—IC$_{50}$ value could not be determined because RORγt was not inhibited at concentrations that did not affect cellular viability
[a]Residue numbering is according to full-length human RORγ with human RORγt numbering shown in brackets Next, expression plasmids serially mutating the seven remaining free cysteine residues on RORγ to serine and/or alanine were generated. In subsequent reporter gene assays, only mutation of Cysteine 476 affected the ability of compounds 14 and 21 to inhibit RORγ (Table 4). In addition, the binding of compound 21 to Cysteine 476 was confirmed by hydrogen/deuterium exchange (HDX) mass spectrometry (MS).

Cysteine 476 resides on alpha helix H11 of RORγ and coincidentally is on the periphery of the allosteric site previously described by Merck and Eindhoven. In binding experiments, compound 21 and MRL-871, a known allosteric modulator of RORγ, were found to be mutually competitive. Moreover, no complex was observed in which MRL-871 and compound 21 were simultaneously bound to RORγt. However, the binding of MRL-871 was not affected by the presence of the C476S mutation. In addition, MRL-871 displayed similar activity against the wild-type and C476S mutant RORγt protein. Taken together these data support a MOA where compound 12 binds to an allosteric site through a specific covalent interaction with Cysteine 476, thereby inhibiting the transcriptional activity of RORγ/RORγt.

Cysteine 476 is strictly conserved among all three ROR isoforms: alpha, beta, and gamma. Nonetheless, it is rarely found in the remaining 45 human NRs, occurring only in the orphan receptors nerve growth factor1B (NGF1B), testicular receptor2 (NR2C2), and nuclear receptor related1 (NR4A2) receptors. The inhibitory activity of compound 14 was evaluated against a panel of seventeen human NRs from the NR1 subfamily and found no appreciable activity at concentrations that did not affect cell viability. Furthermore, compounds 14 and 21 showed good ROR isoform selectivity, inhibiting RORγ/RORγt activity without measurable effects on RORα or RORβ activity at concentrations that did not affect cell viability (see FIGS. 1A-1B for data using compound 14).

Towards the goal of developing a predictive model consistent with the observed potency, selectivity and MOA of this drug class, molecular dynamics (MD) simulations were utilized. A covalent docking protocol was developed within MOE and applied to compound 21 using the MRL-871/RORγt protein crystal structure.

Figure 2A:
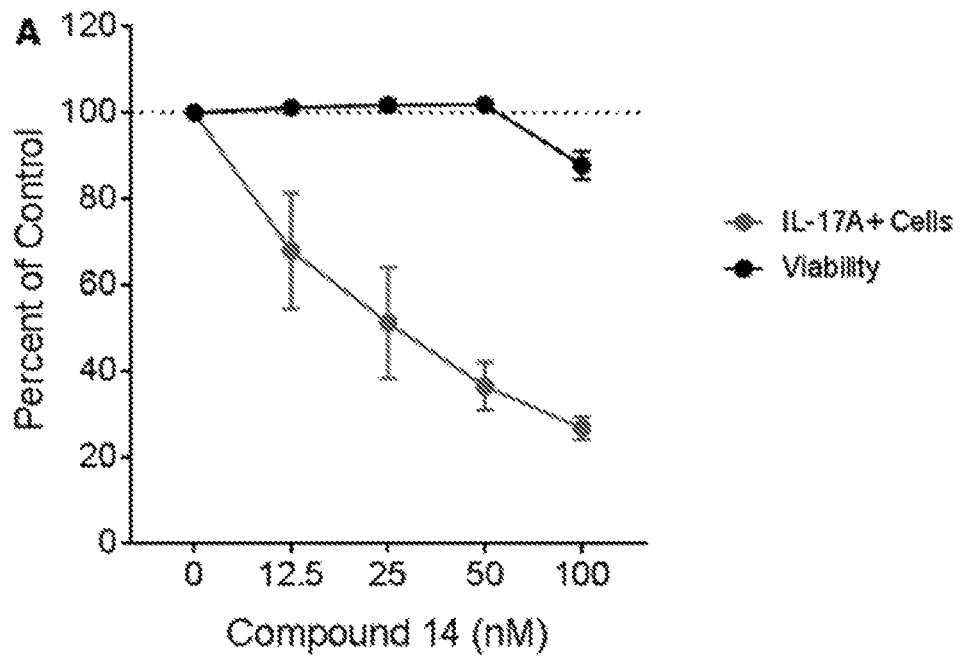
FIGS. 2A-2D show the effect of compound 14 on Th17 cell differentiation (A) and suppression of TH17 signature genes (B-D).
Figure 2B:
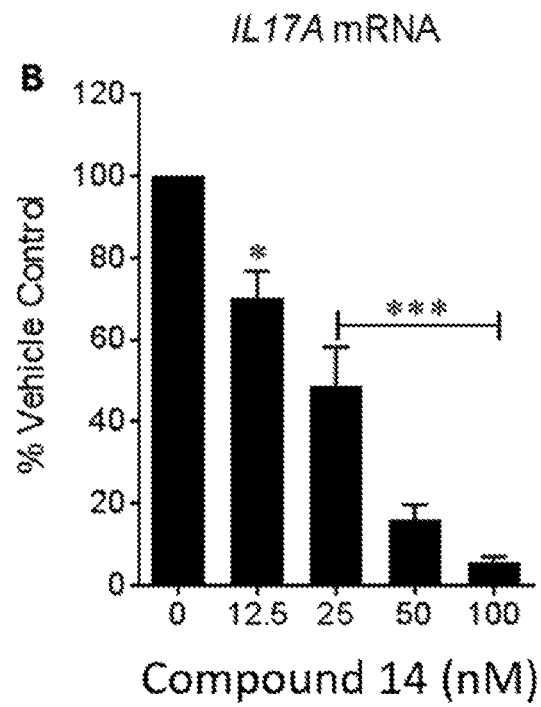
Figure 2C:
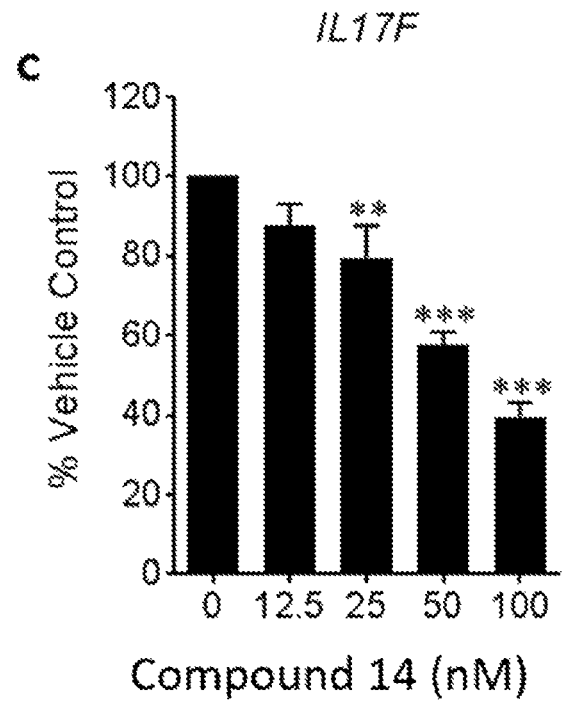
Figure 2D:
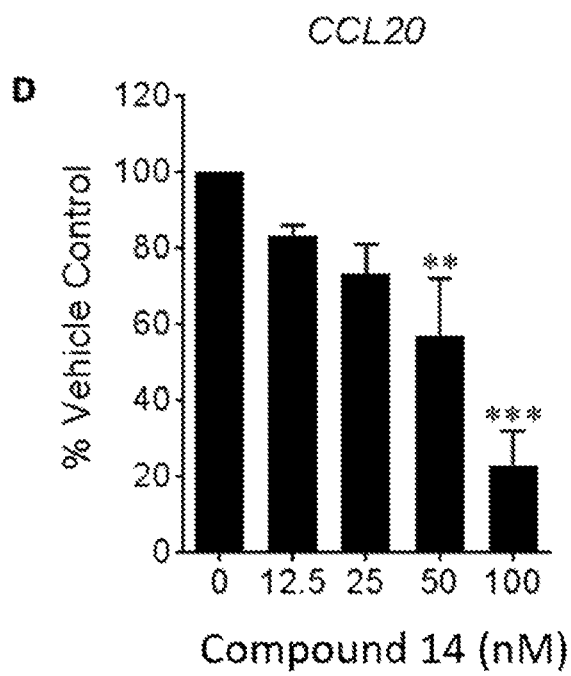

The biological activity of compound 14 was further characterized by assessing its ability to inhibit Th17 differentiation of human naïve CD4+ T cells cultured in vitro under Th17-polarizing conditions. Compound 14 potently inhibited Th17 differentiation, as measured by the percentage of IL-17A-expressing cells, with an average $IC_{50}$ value of 30 nM (FIG. 2A). Compound 14 also significantly reduced the expression of key Th17 signature genes, including IL17A, IL17F, and CCL20 (FIGS. 2B-6D). Under the Th17 differentiating protocol used for these experiments, compound 14 reduced cell viability by 10-15% at the highest concentration (FIG. 2A).

Figure 3A:
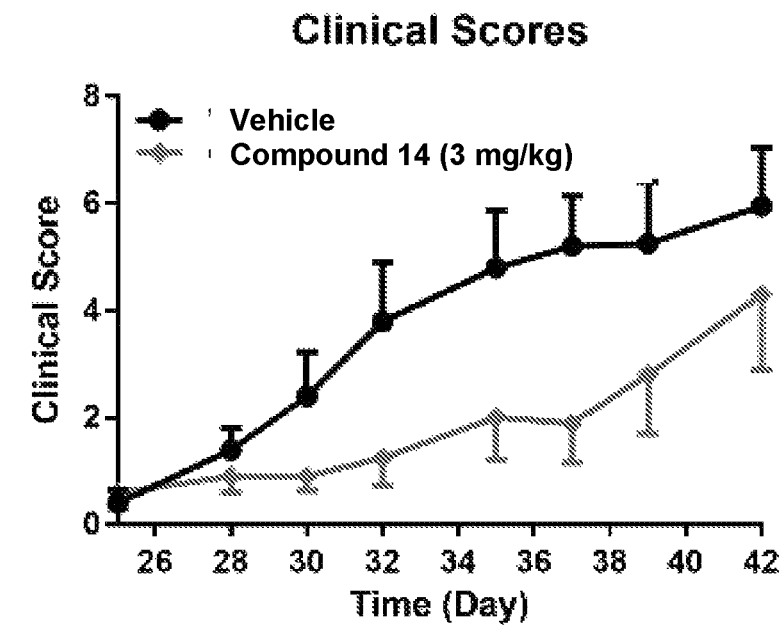
FIGS. 3A-3B show activity of compound 14 in the mCIA model dosed orally at 3 mg/kg.
Figure 3B:
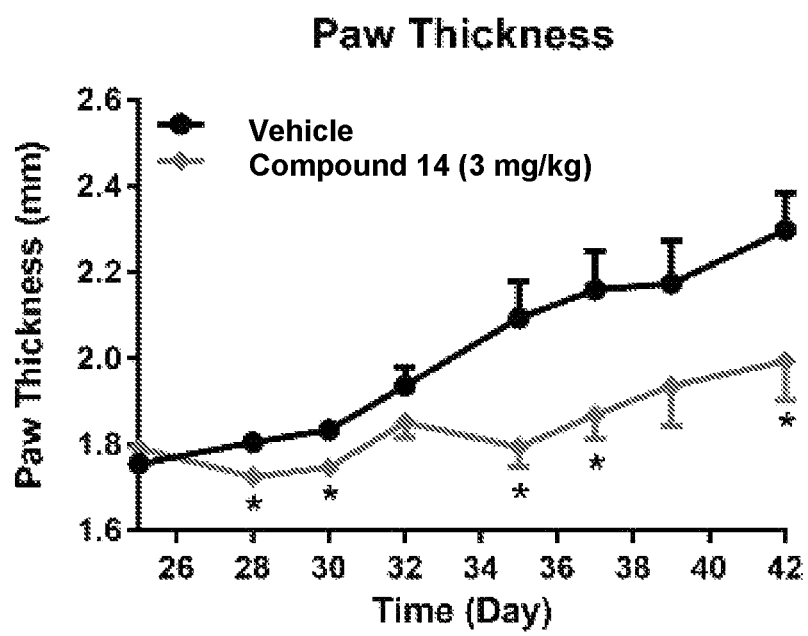

Compound 14 was evaluated for oral bioavailability, and consistent with its physicochemical properties, compound 14 easily achieves therapeutic systemic exposures after a single oral dosing to mice. Compound 14 was then evaluated for pharmacological activity in the collagen-induced rheumatoid arthritis (CIA) mouse model, as RORγt has been shown to be important in the pathophysiology of this model (Park, 2014) and in patients with rheumatoid arthritis (Paradowska-Gorycka, 2016). The study was conducted and progression of disease severity evaluated as previously described (Scales, 2016). Compound 14 significantly decreased both the clinical scores and paw thickness measurements, starting as early as one week after starting treatment and continuing until termination of the study on Day 42 (FIGS. 3A-3B). Collectively, these data provide in vivo proof of concept for this series of compounds.

Example 2: Compound Synthesis and Characterization

General Information

Unless otherwise stated, commercially reagents were used as received, and all reactions were run under nitrogen atmosphere. All solvents were of HPLC or ACS grade. Nuclear magnetic resonance (NMR) spectra were recorded on a Varian Inova-400 spectrometer at operating frequencies of 400 MHz ($^1$H NMR). Chemical shifts (δ) are given in ppm relative to residual solvent (usually chloroform δ 7.26 ppm for $^1$H NMR), and coupling constants (J) in Hz. Multiplicity is tabulated as s for singlet, d for doublet, t for triplet, q for quadruplet, and m for multiplet. Mass spectra were recorded on Agilent 6120 mass spectrometer.

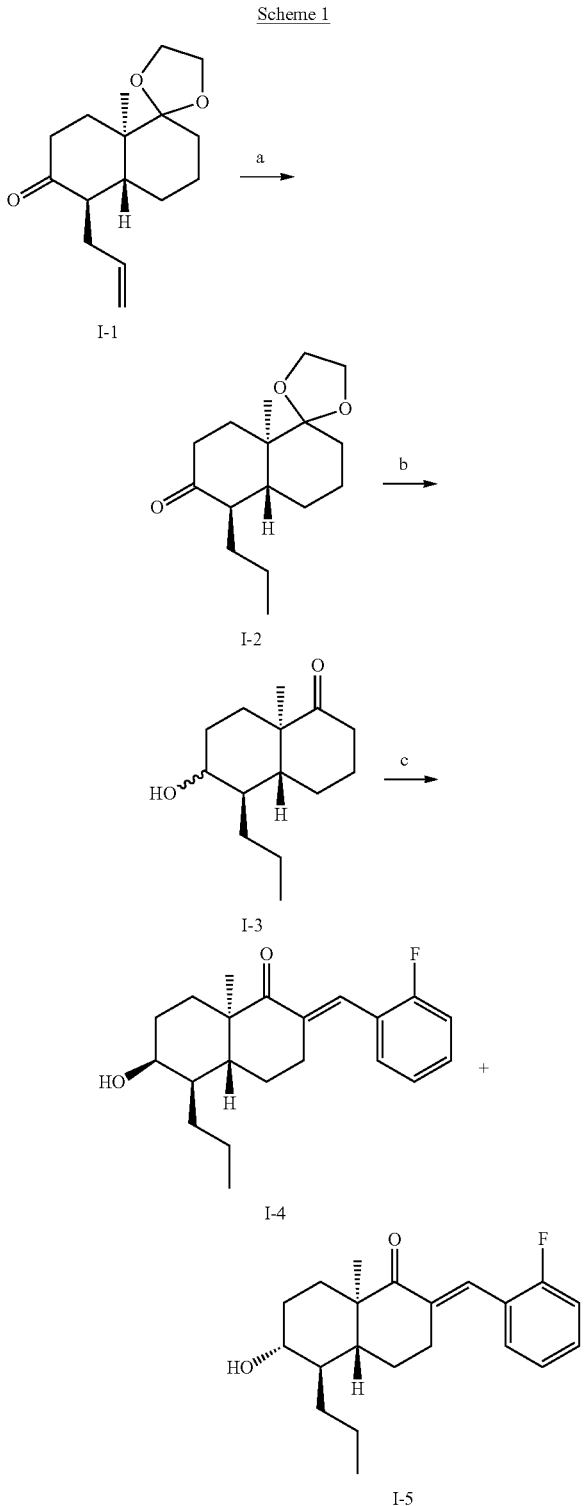

Reagents and conditions: a) 10% Pd/C, H$_2$, EtOH, rt, 78%; b) NaBH$_4$, EtOH, 0° C.-rt; 3N aq. HCl, 0° C.-rt, 91%; c) 2-F—PhCHO, KF on alumina, EtOH, rt, 31% for I-4; 50% for compound I-5.

Scheme 2
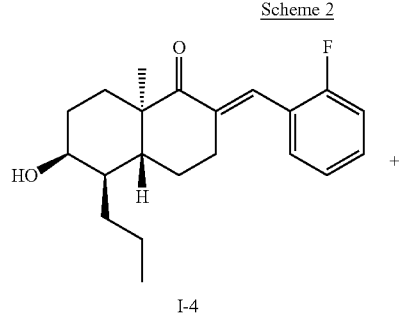
I-4
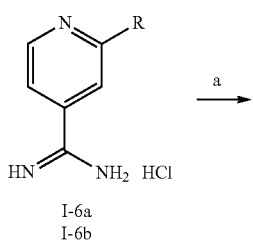
I-6a
I-6b
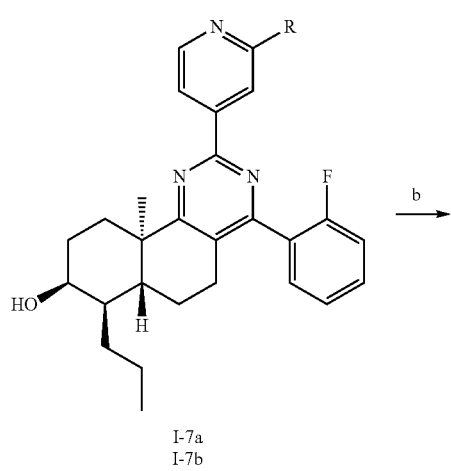
I-7a
I-7b
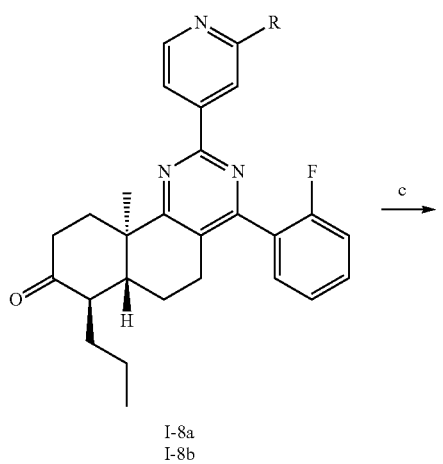
I-8a
I-8b
-continued
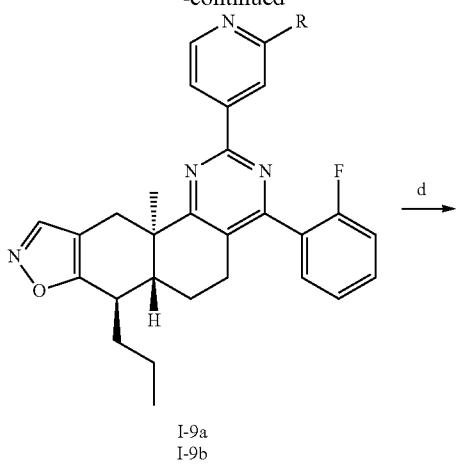
I-9a
I-9b
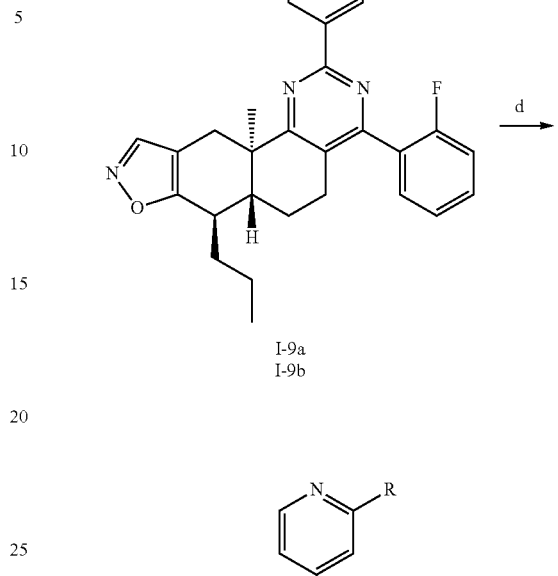
I-10a
I-10b
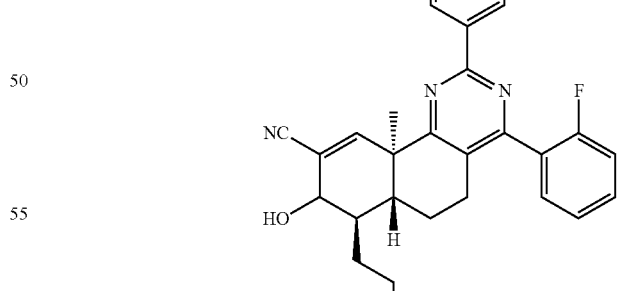
a 22 R = CF$_3$
b 23 R = CH$_2$F
Reagents and conditions: a) K$_2$CO$_3$, EtOH, 100° C.; MnO$_2$, CH$_2$Cl$_2$, rt, 45% for I-7a; 56% for I-7b; b) Dess-Martin periodinane, CH$_2$Cl$_2$, rt, 91% for I-8a; 92% for I-8b; c) HCO$_2$Et, NaOMe, MeOH, 0° C; 6N aq. HCl, NH$_2$OH•HCl, EtOH, 55° C., 74 for I-9a; 84% for I-9b; d) NaOMe, MeOH, 55° C., 83% for I-10a; 89% for I-10b; e) 1,3-dibromo-5,5-dimethylhydantoin, DMF, 0° C.; pyridine, 55° C., 91% for 22; 89% for 23.

Scheme 3

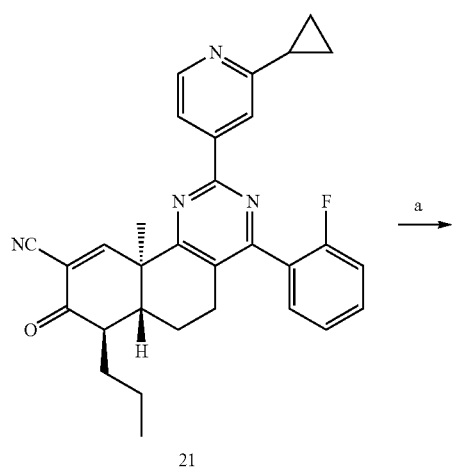

21

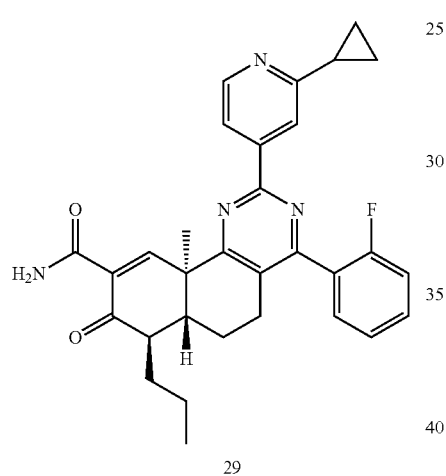

29

Reagents and conditions: a) hydrido(dimethylphosphinous acid-kP)[hydrogenbis(dimethylphosphinito-kP)]platinum(II), EtOH, H₂O, reflux, 45%.

Scheme 4

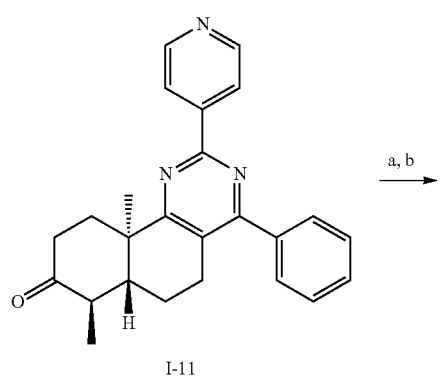

I-11

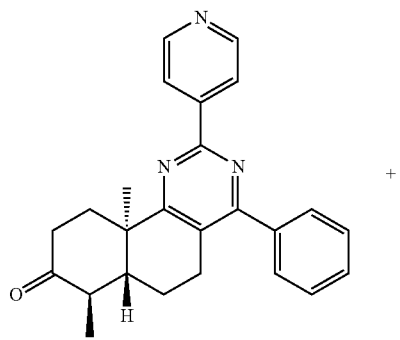

30

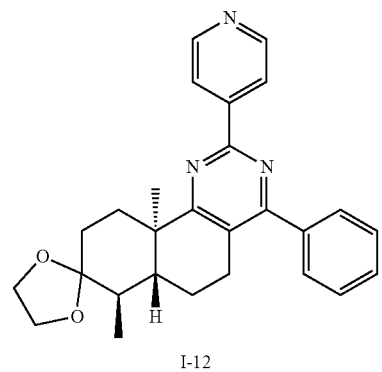

I-12

Reagents and conditions: a) 2-iodoxybenzoic acid, DMSO, 80-85° C.; b) ethylene glycol, p-TsOH, rt, 30% from I-11.

Scheme 5

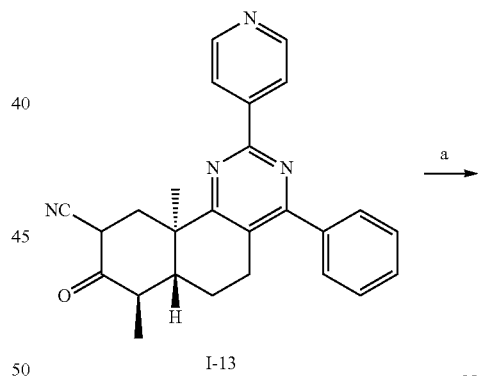

I-13

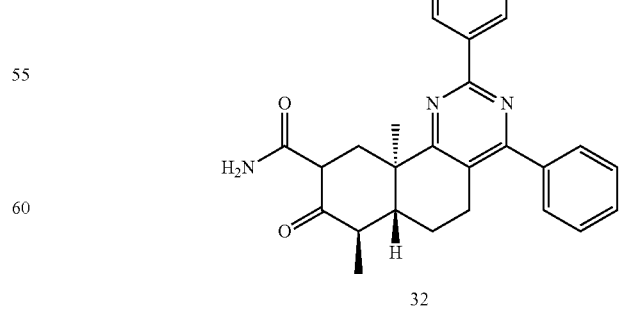

32

Reagents and conditions: a) hydrido(dimethylphosphinous acid-kP)[hydrogenbis(dimethylphosphinito-kP)]platinum(II), EtOH, H₂O, reflux, 22%.

Compound I-2: To a solution of compound I-1 (20 g, 71.87 mmol) in EtOH (200 mL) was added 10% wet Pd/C (2 g). The mixture was stirred at 20° C. for 16 h under hydrogen (15 Psi) and filtered. The filtrate was concentrated to give compound I-2 (15.8 g, 78% yield) as a colorless oil. m/z=267 (M+1).

Compound I-3: To a solution of compound I-2 (5.022 g, 18.85 mmol) in EtOH (50 mL) was added $NaBH_4$ (357 mg, 9.38 mmol) at 0° C. in 1 portion. After the mixture was stirred at 0° C. for 3 h, additional amount of $NaBH_4$ (100 mg, 2.62 mmol) was added. The mixture was stirred at ambient temperature for 30 min. TLC indicated the starting material was completely consumed. The mixture was cooled to 0° C. 3 N aq. HCl (80 mL, 240 mmol) was added. The mixture was stirred at room temperature for 20 h and concentrated. The residue was extracted with EtOAc (2×30 mL). The combined organic extracts were dried with $Na_2SO_4$, filtered, and concentrated. The residue was purified by column chromatography (silica gel, eluting with 0% to 40% EtOAc in hexanes) to give compound I-3 (3.850 g, 91% yield) as viscous oil. Compound I-3 is 1.6/1 mixture of diastereomers (determined by $^1H$ NMR).

Compound I-4 and I-5: To a solution of compound I-3 (1.011 g, 4.51 mmol) in EtOH (15 mL) were added 2-fluorobenzaldehyde (697 mg, 5.62 mmol) and potassium fluoride on alumina (5.5 mmol/g, 1.23 g, 6.765 mmol) sequentially at room temperature. The mixture was stirred at room temperature under $N_2$ for 20 h, diluted with EtOAc (30 mL), and filtered through a pad of Celite®. The filter cake was washed with EtOAc. The filtrate was concentrated, and the residue was partitioned between EtOAc (50 mL) and water (20 mL). The aqueous phase was extracted with EtOAc (30 mL). The combined organic extracts were dried with $Na_2SO_4$ and concentrated. The residue was purified by column chromatography (silica gel, eluting with 0 to 40% EtOAc in hexanes) to give compound I-4 (459 mg, 31% yield) and compound I-5 (743 mg, 50% yield) as white solids. Compound I-4: m/z=331 (M+1); Compound I-5: m/z=331 (M+1).

Compound I-7a: A mixture of compound I-4 (152 mg, 0.46 mmol), compound I-6a (156 mg, 0.69 mmol) and $K_2CO_3$ (191 mg, 1.38 mmol) in EtOH (4 mL) was heated in a sealed vial at 100° C. for 48 h. After cooled to room temperature, the mixture was diluted with EtOAc (20 mL) and washed with water (3×15 mL) and brine (15 mL). The organic extract was dried with $Na_2SO_4$, filtered, and concentrated. The crude product was dissolved in $CH_2Cl_2$ (4 mL), and treated with $MnO_2$ (88%, 0.36 g, 3.65 mmol) at room temperature. The mixture was stirred at room temperature for 20 h and purified by column chromatography (silica gel, eluting with 0-50% EtOAc in hexanes) to give compound I-7a (103 mg, 45% yield) as a light yellow solid. m/z=500 (M+1).

Compound I-7b: Following the same procedure as described for the synthesis of compound I-7a, compound I-7b (light yellow solid; 119 mg, 56% yield) was synthesized from compound I-4 (152 mg, 0.46 mmol) and compound I-6b (131 mg, 0.69 mmol). m/z=464 (M+1).

Compound I-8a: Compound I-7a (96.0 mg, 0.19 mmol) and Dess-Martin periodinane (163 mg, 0.38 mmol) in $CH_2Cl_2$ (2 mL) was stirred at room temperature for 3 h. The mixture was treated with 10% aq. $Na_2SO_3$ (5 mL) and sat. aq. $NaHCO_3$ (5 mL), stirred at room temperature for 10 min, and extracted with t-butyl methyl ether (2×15 mL). The combined organic extracts were washed with sat. aq. $NaHCO_3$, dried with $Na_2SO_4$, filtered, and concentrated. The residue was purified by column chromatography (silica gel, eluting with 0-35% EtOAc in hexanes) to give compound I-8a (87 mg, 91% yield) as a white solid. m/z=498 (M+1).

Compound I-8b: Following the same procedure as described for the synthesis of compound I-8a, compound I-8b (white solid; 105 mg, 92% yield) was synthesized from compound I-7b (115 mg, 0.25 mmol). m/z=462 (M+1).

Compound I-9a: To a mixture of compound I-8a (85 mg, 0.17 mmol) in ethyl formate (0.42 mL, 5.1 mmol) at 0° C. under $N_2$ was added sodium methoxide (4.37 M in MeOH, 0.39 mL, 1.7 mmol). The mixture was stirred at ambient temperature for 2 h and then cooled to 0° C. 6 N aq. HCl (0.28 mL, 1.7 mmol), EtOH (1.7 mL), and hydroxylamine hydrochloride (22 mg, 0.32 mmol) were added sequentially. The mixture was heated at 55° C. for 16 h, and then cooled to room temperature. The mixture was diluted with sat. aq. $NaHCO_3$ (5 mL) and extracted with EtOAc (20 mL). The organic extract was washed with water (10 mL), dried with $Na_2SO_4$, filtered, and concentrated. The residue was purified by column chromatography (silica gel, eluting with 0 to 40% EtOAc in hexanes) to give compound I-9a (66 mg, 74% yield) as a light yellow solid. m/z=523 (M+1).

Compound I-9b: Following the same procedure as described for the synthesis of compound I-9a, compound I-9b (white solid; 91 mg, 84% yield) was synthesized from compound I-8b (103 mg, 0.22 mmol). m/z=487 (M+1).

Compound I-10a: To a solution of compound I-9a (63 mg, 0.12 mmol) in MeOH (1.2 mL) at room temperature under $N_2$ was added sodium methoxide (4.37 M, 55 µL, 0.24 mmol). The mixture was stirred at 55° C. for 1.5 h, cooled to room temperature, treated with 10% aq. $NaH_2PO_4$ (5 mL), and extracted with EtOAc (30 mL). The organic extract was washed with water (10 mL), dried with $MgSO_4$, filtered, and concentrated. The residue was purified by column chromatography (silica gel, eluting with 0 to 50% EtOAc in hexanes) to give compound I-10a (52 mg, 83% yield) as a white solid. m/z=523 (M+1).

Compound I-10b: Following the same procedure as described for the synthesis of compound I-10a, compound I-10b (white solid; 77 mg, 89% yield) was synthesized from compound I-9b (87 mg, 0.18 mmol). m/z=487 (M+1).

Compound 22: Compound I-10a (52 mg, 0.10 mmol) in DMF (0.36 mL) was cooled to 0° C. under $N_2$. 1,3-dibromo-5,5-dimethylhydantoin (14 mg, 0.050 mmol) in DMF (0.14 mL) was added. The solution was stirred at 0° C. for 1 h. Pyridine (24 µL, 0.30 mmol) was added. The mixture was heated at 55° C. for 4 h, cooled to room temperature, diluted with EtOAc (20 mL), and washed with water (3×15 mL). The organic extract was dried with $Na_2SO_4$, filtered, and concentrated. The residue was purified by column chromatography (silica gel, eluting 0 to 50% EtOAc in hexanes) to give compound 22 (47 mg, 91% yield) as an off-white solid. m/z=521 (M+1); $^1H$ NMR (400 MHz, $CDCl_3$) δ 8.94 (s, 1H), 8.91 (d, J=5.0 Hz, 1H), 8.70 (dd, J=1.5, 0.8 Hz, 1H), 8.57 (dd, J=5.1, 1.5 Hz, 1H), 7.54 (m, 1H), 7.45 (td, J=7.4, 1.8 Hz, 1H), 7.35 (td, J=7.5, 1.1 Hz, 1H), 7.23 (m, 1H), 2.93-2.77 (m, 2H), 2.61 (ddd, J=13.1, 5.0, 3.2 Hz, 1H), 2.46 (td, J=12.8, 2.5 Hz, 1H), 2.14-2.06 (m, 2H), 1.81 (m, 1H), 1.69 (m, 1H), 1.55 (s, 3H), 1.35 (m, 1H), 1.22 (m, 1H), 0.93 (t, J=7.3 Hz, 3H).

Compound 23: Following the same procedure as described for the synthesis of compound 22, compound 23 (off-white solid; 68 mg, 89% yield) was synthesized from compound I-10b (77 mg, 0.16 mmol). m/z=485 (M+1); $^1H$ NMR (400 MHz, $CDCl_3$) δ 8.98 (s, 1H), 8.76 (d, J=5.2 Hz, 1H), 8.48 (s, 1H), 8.31 (ddd, J=5.1, 1.7, 0.8 Hz, 1H), 7.52 (m, 1H), 7.45 (td, J=7.4, 1.8 Hz, 1H), 7.34 (td, J=7.5, 1.1 Hz, 1H), 7.22 (ddd, J=9.7, 8.5, 1.1 Hz, 1H), 5.60 (d, J=46.9 Hz, 2H), 2.93-2.73 (m, 2H), 2.60 (ddd, J=13.1, 5.0, 3.2 Hz, 1H), 2.46 (td, J=12.8, 2.5 Hz, 1H), 2.15-2.05 (m, 2H), 1.82 (m, 1H), 1.69 (m, 1H), 1.54 (s, 3H), 1.34 (m, 1H), 1.19 (m, 1H), 0.93 (t, J=7.2 Hz, 3H).

Compound 29: A mixture of compound 21 (70 mg, 0.14 mmol) and hydrido(dimethylphosphinous acid-kP)[hydrogen bis(dimethylphosphinito-kP)]platinum(II) (6.1 mg, 14 µmol) in EtOH (1 mL) and water (1 mL) were heated at 90° C. for 4 h open to the air. After cooled to room temperature, the mixture was concentrated. The residue was extracted with EtOAc (2×15 mL). The organic extract was dried with $Na_2SO_4$, filtered, and concentrated. The residue was purified by column chromatography (silica gel, eluting with 0 to 100% EtOAc in hexanes) to give impure product, which was purified again by column chromatography (silica gel, eluting with 0 to 50% acetone in hexanes) to give compound 29 (33 mg, 45% yield) as a white solid. m/z=511 (M+1); $^1$H NMR (400 MHz, $CDCl_3$) δ 9.47 (s, 1H), 8.58 (d, J=5.1 Hz, 1H), 8.50 (d, J=5.1 Hz, 1H), 8.24 (s, 1H), 8.13 (dd, J=5.1, 1.6 Hz, 1H), 7.53-7.42 (m, 2H), 7.32 (t, J=7.5 Hz, 1H), 7.20 (t, J=9.1 Hz, 1H), 5.68 (d, J=4.5 Hz, 1H), 2.89-2.70 (m, 2H), 2.62 (ddd, J=12.9, 5.2, 3.4 Hz, 1H), 2.42 (td, J=12.8, 2.5 Hz, 1H), 2.19 (m, 1H), 2.14-1.99 (m, 2H), 1.91-1.63 (m, 2H), 1.50 (s, 3H), 1.43-1.13 (m, 2H), 1.10 (m, 2H), 1.02 (m, 2H), 0.93 (t, J=7.3 Hz, 3H).

Compound 30: A solution of compound I-11 (225 mg, 0.59 mmol) and 2-iodoxybenzoic acid (657 mg, 2.35 mmol) in DMSO (5 mL) was heated at 80-85° C. under nitrogen for 20 h. The reaction mixture was cooled to room temperature and diluted with t-butyl methyl ether (50 mL). The mixture was stirred for 10 min and filtered through a pad of Celite®. The filter cake was washed with t-butyl methyl ether (2×25 mL). The filtrate was washed with water (3×50 mL). The organic extract was dried with $Na_2SO_4$, filtered, and concentrated. The residue was purified by column chromatography (silica gel, eluting with 0 to 70% EtOAc in hexanes) to give a mixture of compound I-11 and compound 30 (150 mg).

The mixture of compound I-11 and compound 30 (72 mg, 0.19 mmol) in ethylene glycol (1 mL) was treated with p-toluenesulfonic acid monohydrate (35.7 mg, 0.19 mmol) at at room temperature. The mixture was stirred at room temperature for 30 min, compound I-11 was converted to compound I-12. The mixture was diluted with $CH_2Cl_2$ (20 mL), poured into sat. aq. $NaHCO_3$ (20 mL), and stirred for 5 min. The organic layer was separated. The aqueous layer was extracted with $CH_2Cl_2$ (20 mL). The combined organic extracts were dried with $Na_2SO_4$, filtered, and concentrated. The residue was purified by column chromatography (silica gel, eluting with 0 to 50% acetone in hexanes) to give compound 30 (32 mg, 30% yield from I-11) as a white solid. m/z=382 (M+1); $^1$H NMR (400 MHz, $CDCl_3$) δ 8.76 (m, 2H), 8.38 (m, 2H), 8.28 (d, J=10.1 Hz, 1H), 7.63-7.58 (m, 2H), 7.55-7.49 (m, 3H), 6.12 (d, J=10.1 Hz, 1H), 3.06-2.89 (m, 2H), 2.53 (dq, J=13.5, 6.8 Hz, 1H), 2.21 (td, J=12.7, 2.7 Hz, 1H), 2.11 (m, 1H), 1.75 (m, 1H), 1.47 (s, 3H), 1.27 (d, J=6.7 Hz, 3H).

Compound 32: A mixture of compound I-13 (35 mg, 0.086 mmol) and hydrido(dimethylphosphinous acid-kP) [hydrogen bis(dimethylphosphinito-kP)]platinum(II) (3.5 mg, 8.6 µmmol) in EtOH (1 mL) and water (1 mL) were heated at 90° C. for 4 h open to the air. After cooled to room temperature, the mixture was concentrated. The residue was extracted with EtOAc. The organic extract was dried with $Na_2SO_4$, filtered, and concentrated. The residue was purified by column chromatography (silica gel, eluting 0 to 100% EtOAc in hexanes) to give impure product, which was purified again by column chromatography (silica gel, eluting 0 to 50% acetone in hexanes) to give compound 32 (mixture of tautomers, 8 mg, 22% yield) as a white solid. m/z=427 (M+1); $^1$H NMR (400 MHz, $CDCl_3$) δ major tautomer: 8.73 (m, 2H), 8.32 (m, 2H), 7.65-7.59 (m, 2H), 7.54-7.48 (m, 3H), 4.78 (bs, 2H), 3.06 (d, J=14.5 Hz, 1H), 2.99-2.80 (m, 2H), 2.39 (dd, J=14.6, 2.6 Hz, 1H), 2.29 (m, 1H), 2.05 (m, 1H), 1.69 (ddd, J=12.9, 11.0, 2.3 Hz, 1H), 1.50 (m, 1H), 1.32 (d, J=6.8 Hz, 3H), 1.28 (s, 3H).

All of the compounds, compositions, and methods disclosed and claimed herein can be made and executed without undue experimentation in light of the present disclosure. While the disclosure may have focused on several embodiments or may have been described in terms of preferred embodiments, it will be apparent to those of skill in the art that variations and modifications may be applied to the compounds, compositions, and methods without departing from the spirit, scope, and concept of the invention. All variations and modifications apparent to those skilled in the art are deemed to be within the spirit, scope, and concept of the invention as defined by the appended claims.

REFERENCES

The following references to the extent that they provide exemplary procedural or other details supplementary to those set forth herein, are specifically incorporated herein by reference.

PCT/US2013/045975 (WO 2013/188818)
PCT/US2017/000094 (WO 2018/111315)
PCT/US2019/037543
Anderson, *Practical Process Research & Development—A Guide for Organic Chemists*, 2$^{nd}$ ed., Academic Press, New York, 2012.
Bronner, et al., *Expert Opin. Ther. Pat.*, 1:101-112, 2017.
Coltart and Danishefsky, *Org. Lett.*, 5:1289, 2003.
Fujiwara, et al., *J. Immunol.*, 193(5):2565-73, 2014.
*Handbook of Pharmaceutical Salts: Properties, and Use*, Stahl and Wermuth Eds., Verlag Helvetica Chimica Acta, 2002.
Lu et al., *J. Clin. Invest.*, 121(10):4015-29, 2011.
Miosse and Kolls, *Nature Reviews*, 11(10):763-776, 2012.
Reagan-Shaw et al., *FASEB J.*, 22(3):659-661, 2008.
Smith, *March's Advanced Organic Chemistry: Reactions, Mechanisms, and Structure*, 7$^{th}$ Ed., Wiley, 2013.
Waite and Skokos, *International Journal of Inflammation*, 2012:1-10, 2011.

What is claimed is:

1. A method of treating a disease or disorder, wherein the disease or disorder is an autoimmune disease, in a patient in need thereof, comprising administering to the patient a therapeutically effective amount of a cysteine-dependent inverse agonist of nuclear receptor RORγ/RORγt, wherein the cysteine-dependent inverse agonist binds via the formation of a covalent bond between the inverse agonist and a cysteine of the patient's nuclear receptor RORγ/RORγt, and wherein the inverse agonist comprises a group of the formula:

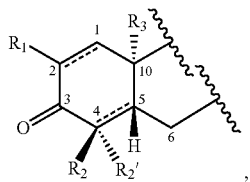

wherein:
the bond between carbon atoms 4 and 5 is a single bond or a double bond;

$R_1$ is cyano, heteroaryl$_{(C \leq 8)}$, substituted heteroaryl$_{(C \leq 8)}$, —CF$_3$, or —C(O)R$_a$; wherein:
  $R_a$ is hydroxy, amino, or alkoxy$_{(C \leq 8)}$, alkylamino$_{(C \leq 8)}$, dialkylamino$_{(C \leq 8)}$, alkylsulfonylamino$_{(C \leq 8)}$, or a substituted version of any of these groups;

$R_2$ is hydrogen or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, or a substituted version of any of these groups, or -alkanediyl$_{(C \leq 8)}$-cycloalkyl$_{(C \leq 12)}$ or a substituted version of this group;

$R_{2'}$ is absent, hydrogen, or alkyl$_{(C \leq 12)}$, cycloalkyl$_{(C \leq 12)}$, alkenyl$_{(C \leq 12)}$, alkynyl$_{(C \leq 12)}$, aryl$_{(C \leq 12)}$, aralkyl$_{(C \leq 12)}$, heteroaryl$_{(C \leq 12)}$, heteroaralkyl$_{(C \leq 12)}$, acyl$_{(C \leq 12)}$, or a substituted version of these groups; provided that when the bond between carbon atoms 4 and 5 is a double bond then $R_{2'}$ is absent; and $R_3$ is alkyl$_{(C \leq 12)}$, alkenyl$_{(C \leq 12)}$, aryl$_{(C \leq 12)}$, aralkyl$_{(C \leq 12)}$, or a substituted version of any of these groups;

provided that when carbon atoms 4 and 5 are joined by a double bond, then $R_{2'}$ and the hydrogen atom at carbon atom 5 are absent.

2. The method of claim 1, wherein the therapeutically effective amount is sufficient to modulate the activity of the nuclear receptor RORγ/RORγt in the patient.

3. The method of claim 1, wherein the inverse agonist binds to cysteine 476 of the nuclear receptor RORγ in the patient.

4. The method of claim 3, wherein the inverse agonist selectively binds to cysteine 476 of the nuclear receptor RORγ in the patient.

5. The method of claim 3, wherein the inverse agonist preferentially binds to cysteine 476 of the nuclear receptor RORγ relative to the orthosteric binding pocket in the ligand binding domain (LBD) of RORγ/RORγt in the patient.

6. The method of claim 1, wherein the inverse agonist does not bind to any significant extent to the orthosteric binding pocket in the ligand binding domain (LBD) of RORγ/RORγt in the patient.

7. The method of claim 1, wherein the inverse agonist inhibits activity of the nuclear receptor RORγ/RORγt without significantly affecting activity of the nuclear receptor RORα or the nuclear receptor RORβ in the patient.

8. The method of claim 1, wherein the method modulates the function of the nuclear receptor RORγ in the patient.

9. The method of claim 1, wherein the method suppresses interleukin-17A production in the patient.

10. The method of claim 1, wherein the method selectively inhibits T helper 17 (Th17) cell differentiation in the patient.

11. The method of claim 1, wherein the inverse agonist's RORγt-LBD-GAL4 reporter assay $IC_{50}$ activity is less than 1 μM.

12. The method of claim 1, wherein the inverse agonist's suppression of IL-17A secretion from human CD4+ T-cells assay $IC_{50}$ activity is less than 500 nM.

13. The method of claim 1, wherein the formula is further defined as:

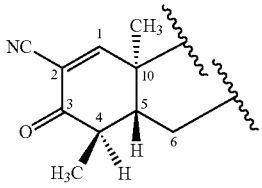

14. The method of claim 1, wherein the inverse agonist is a compound of the formula:

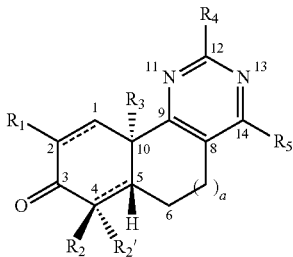

wherein:
the bond between carbon atoms 4 and 5 is a single bond or a double bond;
a is 0, 1, or 2;
$R_1$ is cyano, heteroaryl$_{(C≤8)}$, substituted heteroaryl$_{(C≤8)}$, —CF$_3$, or —C(O)R$_a$; wherein:
  $R_a$ is hydroxy, amino, or alkoxy$_{(C≤8)}$, alkylamino$_{(C≤8)}$, dialkylamino$_{(C≤8)}$, alkylsulfonylamino$_{(C≤8)}$, or a substituted version of any of these groups;

$R_2$ is hydrogen or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of any of these groups, or -alkanediyl$_{(C≤8)}$-cycloalkyl$_{(C≤12)}$ or a substituted version of this group;

$R_{2'}$ is absent, hydrogen, or alkyl$_{(C≤12)}$, cycloalkyl$_{(C≤12)}$, alkenyl$_{(C≤12)}$, alkynyl$_{(C≤12)}$, aryl$_{(C≤12)}$, aralkyl$_{(C≤12)}$, heteroaryl$_{(C≤12)}$, heteroaralkyl$_{(C≤12)}$, acyl$_{(C≤12)}$, or a substituted version of these groups; provided that when the bond between carbon atoms 4 and 5 is a double bond then $R_{2'}$ is absent;

$R_3$ is alkyl$_{(C≤12)}$, alkenyl$_{(C≤12)}$, aryl$_{(C≤12)}$, aralkyl$_{(C≤12)}$, or a substituted version of any of these groups;

$R_4$ is hydrogen, amino, alkyl$_{(C≤18)}$, substituted alkyl$_{(C≤18)}$, cycloalkyl$_{(C≤18)}$, substituted cycloalkyl$_{(C≤18)}$, aryl$_{(C≤18)}$, substituted aryl$_{(C≤18)}$, aralkyl$_{(C≤18)}$, substituted aralkyl$_{(C≤18)}$, heteroaryl$_{(C≤18)}$, substituted heteroaryl$_{(C≤18)}$, heteroaralkyl$_{(C≤18)}$, substituted heteroaralkyl$_{(C≤18)}$, heterocycloalkyl$_{(C≤18)}$, substituted heterocycloalkyl$_{(C≤18)}$, amido$_{(C≤18)}$, substituted amido$_{(C≤18)}$, or —X$_1$—(CH$_2$)$_m$—R$_{4'}$;

wherein:
$X_1$ is NR$_b$, O, or S; wherein:
  $R_b$ is hydrogen, alkyl$_{(C≤6)}$, or substituted alkyl$_{(C≤6)}$;
m is 0, 1, 2, 3, or 4; and
$R_{4'}$ is alkyl$_{(C≤12)}$, cycloalkyl$_{(C≤12)}$, aryl$_{(C≤18)}$, aralkyl$_{(C≤18)}$, heteroaryl$_{(C≤18)}$, heteroaralkyl$_{(C≤8)}$, heterocycloalkyl$_{(C≤8)}$, or a substituted version of any of these groups; or

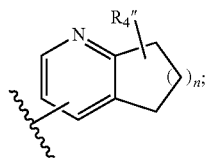

wherein:
n is 0, 1, 2, 3, or 4; and
$R_{4''}$ is —H, —OH, —F, —Cl, —Br, —I, —NH$_2$, —NO$_2$, —CN, —SH, —S(O)$_2$OH, or —S(O)$_2$NH$_2$, or alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, alkylamino$_{(C≤8)}$, dialkylamino$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; or —X$_2$—(CH$_2$)$_p$—R$_{4'''}$;

wherein:
$X_2$ is arenediyl$_{(C≤12)}$, substituted arenediyl$_{(C≤12)}$, heterocycloalkanediyl$_{(C≤12)}$, substituted heterocycloalkanediyl$_{(C≤12)}$, heteroarenediyl$_{(C≤12)}$, or substituted heteroarenediyl$_{(C≤12)}$;
p is 0, 1, 2, 3, or 4; and
$R_{4'''}$ is alkyl$_{(C≤8)}$, cycloalkyl$_{(C≤8)}$, aryl$_{(C≤8)}$, heteroaryl$_{(C≤8)}$, heterocycloalkyl$_{(C≤8)}$, acyl$_{(C≤8)}$, amido$_{(C≤8)}$, alkoxy$_{(C≤8)}$, acyloxy$_{(C≤8)}$, —C(O)-alkoxy$_{(C≤8)}$, —C(O)-alkylamino$_{(C≤8)}$, —C(O)-dialkyl-amino$_{(C≤8)}$, alkylsulfonyl$_{(C≤8)}$, arylsulfonyl$_{(C≤8)}$, alkoxysulfonyl$_{(C≤8)}$, or a substituted version of any of these groups; and $R_5$ is amino, hydroxy, —OS(O)$_2$C$_6$H$_4$CH$_3$, alkyl$_{(C≤12)}$, alkoxy$_{(C≤12)}$, cycloalkyl$_{(C≤12)}$, cycloalkoxy$_{(C≤12)}$, aryl$_{(C≤12)}$, aralkyl$_{(C≤12)}$, heteroaryl$_{(C≤12)}$, heteroaralkyl$_{(C≤12)}$, heterocycloalkyl$_{(C≤12)}$, acyl$_{(C≤12)}$, acyloxy$_{(C≤12)}$, alkylamino$_{(C≤12)}$, dialkylamino$_{(C≤12)}$, alkylsulfonylamino$_{(C≤12)}$, or a substituted version of any of the last fourteen groups, or

—OY$_1$-A$_1$;

wherein:
Y$_1$ is alkanediyl$_{(C≤8)}$ or substituted alkanediyl$_{(C≤8)}$; and
A$_1$ is cycloalkyl$_{(C≤8)}$ or substituted cycloalkyl$_{(C≤8)}$; or —Y$_2$—C(O)NR$_c$-A$_2$;

wherein:
Y$_2$ is arenediyl$_{(C≤8)}$ or substituted arenediyl$_{(C≤8)}$;
R$_c$ is hydrogen, alkyl$_{(C≤6)}$, or substituted alkyl$_{(C≤6)}$; and
A$_2$ is aralkyl$_{(C≤12)}$ or substituted aralkyl$_{(C≤12)}$; or -A$_3$R$_d$;

wherein:
A$_3$ is —O— or —NR$_e$—, wherein
R$_e$ is hydrogen, alkyl$_{(C≤6)}$, or substituted alkyl$_{(C≤6)}$; and
R$_d$ is acyl$_{(C≤12)}$, or substituted acyl$_{(C≤12)}$;

provided that when carbon atoms 4 and 5 are joined by a double bond, then R$_{2'}$ and the hydrogen atom at carbon atom 5 are absent;

or a pharmaceutically acceptable salt thereof.

15. The method of claim 14, wherein the compound is further defined as:

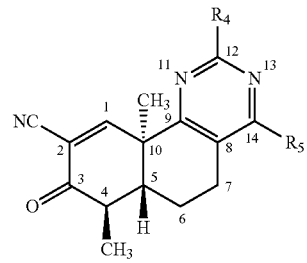

(IX)

wherein:
R$_4$ is heteroaryl$_{(C≤18)}$ or substituted heteroaryl$_{(C≤18)}$; and
R$_5$ is aryl$_{(C≤12)}$ or substituted aryl$_{(C≤12)}$;
or a pharmaceutically acceptable salt thereof.

16. The method of claim 1, wherein the autoimmune disease is Crohn's disease.

17. The method of claim 1, wherein the autoimmune disease is rheumatoid arthritis.

18. The method of claim 1, wherein the autoimmune disease is lupus.

19. The method of claim 1, wherein the autoimmune disease is psoriasis.

20. The method of claim 1, wherein the inverse agonist further comprises a core comprising three fused rings.

* * * * *

SEQUENCE LISTING

<160> NUMBER OF SEQ ID NOS: 2

<210> SEQ ID NO 1
<211> LENGTH: 518
<212> TYPE: PRT

<213> ORGANISM: Homo sapiens

<400> SEQUENCE: 1

```
Met Asp Arg Ala Pro Gln Arg Gln His Arg Ala Ser Arg Glu Leu Leu
1               5                   10                  15

Ala Ala Lys Lys Thr His Thr Ser Gln Ile Glu Val Ile Pro Cys Lys
            20                  25                  30

Ile Cys Gly Asp Lys Ser Ser Gly Ile His Tyr Gly Val Ile Thr Cys
        35                  40                  45

Glu Gly Cys Lys Gly Phe Phe Arg Arg Ser Gln Arg Cys Asn Ala Ala
    50                  55                  60

Tyr Ser Cys Thr Arg Gln Gln Asn Cys Pro Ile Asp Arg Thr Ser Arg
65                  70                  75                  80

Asn Arg Cys Gln His Cys Arg Leu Gln Lys Cys Leu Ala Leu Gly Met
                85                  90                  95

Ser Arg Asp Ala Val Lys Phe Gly Arg Met Ser Lys Lys Gln Arg Asp
            100                 105                 110

Ser Leu His Ala Glu Val Gln Lys Gln Leu Gln Gln Arg Gln Gln Gln
        115                 120                 125

Gln Gln Glu Pro Val Val Lys Thr Pro Pro Ala Gly Ala Gln Gly Ala
    130                 135                 140

Asp Thr Leu Thr Tyr Thr Leu Gly Leu Pro Asp Gly Gln Leu Pro Leu
145                 150                 155                 160

Gly Ser Ser Pro Asp Leu Pro Glu Ala Ser Ala Cys Pro Pro Gly Leu
                165                 170                 175

Leu Lys Ala Ser Gly Ser Gly Pro Ser Tyr Ser Asn Asn Leu Ala Lys
            180                 185                 190

Ala Gly Leu Asn Gly Ala Ser Cys His Leu Glu Tyr Ser Pro Glu Arg
        195                 200                 205

Gly Lys Ala Glu Gly Arg Glu Ser Phe Tyr Ser Thr Gly Ser Gln Leu
    210                 215                 220

Thr Pro Asp Arg Cys Gly Leu Arg Phe Glu Glu His Arg His Pro Gly
225                 230                 235                 240

Leu Gly Glu Leu Gly Gln Gly Pro Asp Ser Tyr Gly Ser Pro Ser Phe
                245                 250                 255

Arg Ser Thr Pro Glu Ala Pro Tyr Ala Ser Leu Thr Glu Ile Glu His
            260                 265                 270

Leu Val Gln Ser Val Cys Lys Ser Tyr Arg Glu Thr Cys Gln Leu Arg
        275                 280                 285

Leu Glu Asp Leu Leu Arg Gln Arg Ser Asn Ile Phe Ser Arg Glu Glu
    290                 295                 300

Val Thr Gly Tyr Gln Arg Lys Ser Met Trp Glu Met Trp Glu Arg Cys
305                 310                 315                 320

Ala His His Leu Thr Glu Ala Ile Gln Tyr Val Val Glu Phe Ala Lys
                325                 330                 335

Arg Leu Ser Gly Phe Met Glu Leu Cys Gln Asn Asp Gln Ile Val Leu
            340                 345                 350

Leu Lys Ala Gly Ala Met Glu Val Val Leu Val Arg Met Cys Arg Ala
        355                 360                 365

Tyr Asn Ala Asp Asn Arg Thr Val Phe Phe Glu Gly Lys Tyr Gly Gly
    370                 375                 380

Met Glu Leu Phe Arg Ala Leu Gly Cys Ser Glu Leu Ile Ser Ser Ile
385                 390                 395                 400
```

```
Phe Asp Phe Ser His Ser Leu Ser Ala Leu His Phe Ser Glu Asp Glu
                405                 410                 415

Ile Ala Leu Tyr Thr Ala Leu Val Leu Ile Asn Ala His Arg Pro Gly
                420                 425                 430

Leu Gln Glu Lys Arg Lys Val Glu Gln Leu Gln Tyr Asn Leu Glu Leu
                435                 440                 445

Ala Phe His His His Leu Cys Lys Thr His Arg Gln Ser Ile Leu Ala
                450                 455                 460

Lys Leu Pro Pro Lys Gly Lys Leu Arg Ser Leu Cys Ser Gln His Val
465                 470                 475                 480

Glu Arg Leu Gln Ile Phe Gln His Leu His Pro Ile Val Val Gln Ala
                485                 490                 495

Ala Phe Pro Pro Leu Tyr Lys Glu Leu Phe Ser Thr Glu Thr Glu Ser
                500                 505                 510

Pro Val Gly Leu Ser Lys
                515

<210> SEQ ID NO 2
<211> LENGTH: 497
<212> TYPE: PRT
<213> ORGANISM: Homo sapiens

<400> SEQUENCE: 2

Met Arg Thr Gln Ile Glu Val Ile Pro Cys Lys Ile Cys Gly Asp Lys
1               5                   10                  15

Ser Ser Gly Ile His Tyr Gly Val Ile Thr Cys Glu Gly Cys Lys Gly
                20                  25                  30

Phe Phe Arg Arg Ser Gln Arg Cys Asn Ala Ala Tyr Ser Cys Thr Arg
                35                  40                  45

Gln Gln Asn Cys Pro Ile Asp Arg Thr Ser Arg Asn Arg Cys Gln His
            50                  55                  60

Cys Arg Leu Gln Lys Cys Leu Ala Leu Gly Met Ser Arg Asp Ala Val
65                  70                  75                  80

Lys Phe Gly Arg Met Ser Lys Lys Gln Arg Asp Ser Leu His Ala Glu
                85                  90                  95

Val Gln Lys Gln Leu Gln Gln Arg Gln Gln Gln Gln Glu Pro Val
                100                 105                 110

Val Lys Thr Pro Pro Ala Gly Ala Gln Gly Ala Asp Thr Leu Thr Tyr
                115                 120                 125

Thr Leu Gly Leu Pro Asp Gly Gln Leu Pro Leu Gly Ser Ser Pro Asp
            130                 135                 140

Leu Pro Glu Ala Ser Ala Cys Pro Pro Gly Leu Leu Lys Ala Ser Gly
145                 150                 155                 160

Ser Gly Pro Ser Tyr Ser Asn Asn Leu Ala Lys Ala Gly Leu Asn Gly
                165                 170                 175

Ala Ser Cys His Leu Glu Tyr Ser Pro Glu Arg Gly Lys Ala Glu Gly
                180                 185                 190

Arg Glu Ser Phe Tyr Ser Thr Gly Ser Gln Leu Thr Pro Asp Arg Cys
                195                 200                 205

Gly Leu Arg Phe Glu Glu His Arg His Pro Gly Leu Gly Glu Leu Gly
            210                 215                 220

Gln Gly Pro Asp Ser Tyr Gly Ser Pro Ser Phe Arg Ser Thr Pro Glu
225                 230                 235                 240

Ala Pro Tyr Ala Ser Leu Thr Glu Ile Glu His Leu Val Gln Ser Val
                245                 250                 255
```

```
Cys Lys Ser Tyr Arg Glu Thr Cys Gln Leu Arg Leu Glu Asp Leu Leu
            260             265             270

Arg Gln Arg Ser Asn Ile Phe Ser Arg Glu Glu Val Thr Gly Tyr Gln
        275             280             285

Arg Lys Ser Met Trp Glu Met Trp Glu Arg Cys Ala His His Leu Thr
        290             295             300

Glu Ala Ile Gln Tyr Val Val Glu Phe Ala Lys Arg Leu Ser Gly Phe
305             310             315             320

Met Glu Leu Cys Gln Asn Asp Gln Ile Val Leu Leu Lys Ala Gly Ala
            325             330             335

Met Glu Val Val Leu Val Arg Met Cys Arg Ala Tyr Asn Ala Asp Asn
            340             345             350

Arg Thr Val Phe Phe Glu Gly Lys Tyr Gly Gly Met Glu Leu Phe Arg
            355             360             365

Ala Leu Gly Cys Ser Glu Leu Ile Ser Ser Ile Phe Asp Phe Ser His
        370             375             380

Ser Leu Ser Ala Leu His Phe Ser Glu Asp Glu Ile Ala Leu Tyr Thr
385             390             395             400

Ala Leu Val Leu Ile Asn Ala His Arg Pro Gly Leu Gln Glu Lys Arg
            405             410             415

Lys Val Glu Gln Leu Gln Tyr Asn Leu Glu Leu Ala Phe His His His
            420             425             430

Leu Cys Lys Thr His Arg Gln Ser Ile Leu Ala Lys Leu Pro Pro Lys
        435             440             445

Gly Lys Leu Arg Ser Leu Cys Ser Gln His Val Glu Arg Leu Gln Ile
    450             455             460

Phe Gln His Leu His Pro Ile Val Val Gln Ala Ala Phe Pro Pro Leu
465             470             475             480

Tyr Lys Glu Leu Phe Ser Thr Glu Thr Glu Ser Pro Val Gly Leu Ser
            485             490             495

Lys
```